United States Patent
Ma et al.

(10) Patent No.: US 11,098,022 B2
(45) Date of Patent: Aug. 24, 2021

(54) NITROGEN-CONTAINING COMPOUND, ELECTRONIC COMPONENT AND ELECTRONIC DEVICE

(71) Applicant: Shaanxi Lighte Optoelectronics Material Co., Ltd., Shaanxi (CN)

(72) Inventors: Tiantian Ma, Shaanxi (CN); Qiqi Nie, Shaanxi (CN)

(73) Assignee: SHAANXI LIGHTE OPTOELECTRONICS MATERIAL CO. LTD., Shaanxi (CN)

( * ) Notice: Subject to any disclaimer, the term of this patent is extended or adjusted under 35 U.S.C. 154(b) by 0 days.

(21) Appl. No.: 17/025,569

(22) Filed: Sep. 18, 2020

(65) Prior Publication Data

US 2021/0130313 A1  May 6, 2021

(30) Foreign Application Priority Data

Oct. 31, 2019 (CN) .......................... 201911054970.9
Nov. 15, 2019 (CN) .......................... 201911121665.7

(51) Int. Cl.
*C07C 211/54* (2006.01)
*C07C 211/61* (2006.01)
(Continued)

(52) U.S. Cl.
CPC .......... *C07D 307/91* (2013.01); *C07C 211/54* (2013.01); *C07D 209/82* (2013.01);
(Continued)

(58) Field of Classification Search
CPC .... H01L 51/006; C07C 211/54; C07C 211/61
See application file for complete search history.

(56) References Cited

FOREIGN PATENT DOCUMENTS

| CN | 105555913 A | 5/2016 |
|----|-------------|--------|
| CN | 105829279 A | 8/2016 |

(Continued)

OTHER PUBLICATIONS

SciFinder Search (Mar. 8, 2021).*

(Continued)

*Primary Examiner* — Vu A Nguyen
(74) *Attorney, Agent, or Firm* — Tucker Ellis LLP

(57) ABSTRACT

The present disclosure provides a nitrogen-containing compound as shown in Formula I, an electronic component, and an electronic device, which belongs to the technical field of the organic materials. The nitrogen-containing compound can improve the performance of electronic components.

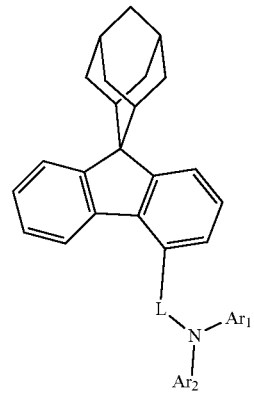

formula I

8 Claims, 2 Drawing Sheets

(51) Int. Cl.
    *H01L 51/00*     (2006.01)
    *H01L 51/50*     (2006.01)
    *H01L 51/42*     (2006.01)
    *C07D 307/91*     (2006.01)
    *C07D 333/76*     (2006.01)
    *C07D 209/82*     (2006.01)

(52) U.S. Cl.
    CPC .......... *C07D 333/76* (2013.01); *H01L 51/006* (2013.01); *H01L 51/0052* (2013.01); *H01L 51/0072* (2013.01); *H01L 51/0073* (2013.01); *H01L 51/0074* (2013.01)

(56) References Cited

FOREIGN PATENT DOCUMENTS

| CN | 107459466 | A | * | 12/2017 |
|---|---|---|---|---|
| CN | 107459466 | A | | 12/2017 |
| CN | 108083969 | A | | 5/2018 |
| CN | 110128279 | A | | 8/2019 |
| CN | 110183333 | A | | 8/2019 |
| CN | 110240546 | A | | 9/2019 |
| CN | 111138297 | A | | 5/2020 |
| EP | 2578572 | A4 | | 11/2013 |
| KR | 20190035567 | A | | 4/2019 |
| KR | 20200037732 | A | | 4/2020 |
| WO | 2017099466 | A1 | | 6/2017 |
| WO | 2017111389 | A1 | | 6/2017 |
| WO | 2020050623 | A1 | | 3/2020 |

OTHER PUBLICATIONS

Bin Huang et al: "Organic Small Molecules Host Materials for Blue Phosphorescent Organic Light-Emitting Diodes", Chinese Journal of Organic Chemistry; published in 2013; pp. 1395-1406.

First Office Action Search Report regarding CN App. No. 201911121665.7; dated Jun. 17, 2020.

* cited by examiner

NITROGEN-CONTAINING COMPOUND, ELECTRONIC COMPONENT AND ELECTRONIC DEVICE

CROSS-REFERENCE OF RELATED APPLICATIONS

The present disclosure claims the priority of the inventions having the Chinese patent application No. CN201911054970.9, the filing date of Oct. 31, 2019, and the title of "Nitrogen-containing compound, electronic component and electronic device", and the Chinese patent application No. CN 201911121665.7, the filing date of Nov. 15, 2019, and the title of "Nitrogen-containing compound, electronic component and electronic device", whose entire contents are specifically incorporated into this disclosure by reference in their entirety.

TECHNICAL FIELD

The present disclosure relates to the technical field of organic materials, in particular to a nitrogen-containing compound, electronic component and electronic device.

BACKGROUND ART

With the development of electronic technology and the advancement of materials science, the application range of electronic components for realizing electroluminescence or photoelectric conversion becomes more and more extensive. Such electronic component, such as organic electroluminescent device or photoelectric conversion device, usually includes a cathode and an anode disposed opposite to each other, and a functional layer disposed between the cathode and the anode. The functional layer is composed of multiple organic or inorganic film layers, and generally includes an energy conversion layer, a hole transporting layer disposed between the energy conversion layer and the anode, and an electron transporting layer disposed between the energy conversion layer and the cathode.

For example, when the electronic component is an organic electroluminescent device, it generally includes an anode, a hole transporting layer, an electroluminescent layer as an energy conversion layer, an electron transporting layer, and a cathode, which are sequentially stacked. When a voltage is applied to between anode and cathode, the two electrodes generate an electric field. Under the action of the electric field, the electrons on the cathode side move to the electroluminescent layer, and the holes on the anode side also move to the light emitting layer. The electrons and the holes combine in the electroluminescent layer to form excitons, and the excitons are in an excited state and release energy outwards, which in turn makes the organic light-emitting layer emit light outward. In order to improve the performance of electronic components that realize electroluminescence or photoelectric conversion, an electron blocking layer may also be provided between the energy conversion layer and the hole transporting layer.

In electronic components that realize electroluminescence or photoelectric conversion, the hole transport performance of the film layer disposed between the anode and the energy conversion layer has an important influence on the performance of the electronic component. As recited in Chinese Patent Application CN201710407382.3, Korea Patent Application KR1020180113731 and other patent documents, the fluorene group-containing compound can be used for the hole transporting layer. However, the performance of the existing hole transporting layer materials containing fluorene group needs to be further improved.

SUMMARY

The object of the present disclosure is to provide a nitrogen-containing compound, an electronic component and an electronic device to improve the performance of the electronic component and the electronic device.

In order to achieve the above-mentioned object of the invention, the present disclosure adopts the following technical solutions:

According to the first aspect of the present disclosure, there is provided a nitrogen-containing compound having a structure shown in Formula I:

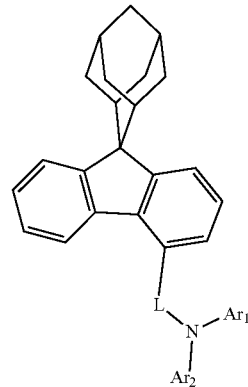

Formula I wherein, L is selected from a single bond, a substituted or unsubstituted arylene group having 6 to 20 carbon atoms;

$Ar_1$ and $Ar_2$ are the same or different, and are each independently selected from the following substituted or unsubstituted groups: an aryl group having 6 to 20 carbon atoms, and a heteroaryl group having 1 to 20 carbon atoms;

the substituents of $Ar_1$, $Ar_2$ and L are the same or different, and are each independently selected from the group consisting of deuterium, nitro, hydroxy, an alkyl, a cycloalkyl, an alkenyl, an alkynyl, a heterocycloalkyl, an alkoxy, an alkylamino, an arylamino, an alkylthio, and an arylsilyl.

According to the second aspect of the present disclosure, there is provided an electronic component including an anode and a cathode disposed opposite to each other, and a functional layer disposed between the anode and the cathode, wherein the functional layer comprises an electron blocking layer including the above-mentioned nitrogen-containing compound. According to an embodiment of the present disclosure, the electronic component is an organic electroluminescence device. According to another embodiment of the present disclosure, the electronic component is a solar cell.

According to the third aspect of the present disclosure, there is provided an electronic device comprising the above-mentioned electronic component.

The nitrogen-containing compound provided in the present disclosure introduces the adamantyl structure at the side of the fluorene to increase the electron density of the entire conjugated system of the fluorene ring and the nitrogen-containing compound through the super-conjugation effect, which can enhance the hole conductivity as well as the electronic tolerance of the nitrogen-containing compound, and also improve the luminous efficiency and life of organic electroluminescent device, improve the conversion efficiency and life of photoelectric conversion device, and thereby improve the life and efficiency of electronic component used for photoelectric conversion or electro-optic conversion. Moreover, in some embodiments, the adamantyl group is introduced between the branches of the triarylamine, which is originally a near-plane structure, rather than at the end, the large steric hindrance of the adamantyl group can finely adjust the bonding angle and conjugation degree of the amine and each aryl group, thereby obtaining HOMO value suitable for the material of the adjacent layer, which reduces the operating voltage of the organic electroluminescent device, and increases the open circuit voltage of the photoelectric conversion device. In addition, the introduction of adamantyl can also increase the molecular weight of the nitrogen-containing compound and reduce the molecular symmetry, can increase the glass transition temperature and evaporation temperature of the nitrogen-containing compound of the present disclosure, and can control the crystallinity of the nitrogen-containing compound, so that the nitrogen-containing compound can be used in mass production, it has better physical and thermal stability, which facilitates the mass production stability of the organic electroluminescent device and photoelectric conversion device.

In particular, the 4-position of the fluorene group in the nitrogen-containing compound of the present disclosure is connected to the amine, which greatly increases the steric hindrance of the arylamine structure, thereby increasing the twist angle between the plane of fluorene and the plane of the arylamine (especially the plane of triarylamine), and reducing the degree of conjugation. Thus, the energy band width and triplet energy level of the nitrogen-containing compound are improved, so that the nitrogen-containing compound is particularly suitable for electron blocking layers (also known as hole auxiliary layer, second hole transporting layer, etc.). When the nitrogen-containing compound is used as the electron blocking layer in the organic electroluminescent device (especially blue light device) and the electron blocking layer in the photoelectric conversion device, the efficiency and life of the organic electroluminescent device and photoelectric conversion device are significantly improved.

BRIEF DESCRIPTION OF THE DRAWINGS

The above and other features and advantages of the present disclosure will become more apparent by describing in detail exemplary embodiments thereof with reference to the drawings.

Figure 1:
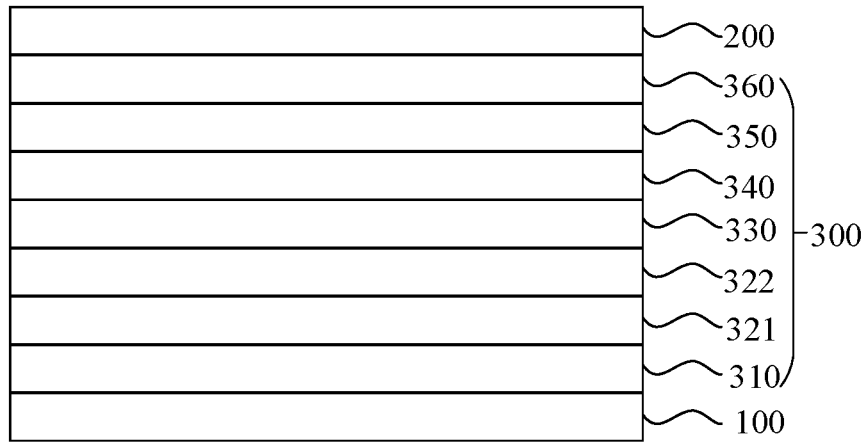
FIG. 1 is a schematic structural diagram of an organic electroluminescent device according to an embodiment of the present disclosure.

The reference symbols of the main elements in the figure are as follows:

100, anode;
200, cathode;
300, functional layer;
310, hole injecting layer;
321, hole transporting layer;
322, electron blocking layer;
330, organic electroluminescent layer;
340, hole blocking layer;
350, electron transporting layer;
360, electron injecting layer;
370, photoelectric conversion layer;
400, electronic device; and
500, electronic device.

DETAILED DESCRIPTION

Exemplary embodiments will now be described more fully with reference to the drawings. However, the exemplary embodiments can be implemented in various forms, and should not be construed as being limited to the examples set forth herein; on the contrary, providing these embodiments makes the present disclosure more comprehensive and complete, and will fully convey the concept of the exemplary embodiments to those skilled in the art. The described features, structures, or characteristics may be combined in one or more embodiments in any suitable manner. In the following description, many specific details are provided to give a full understanding of the embodiments of the present disclosure.

In the figures, the area and layer thickness may be exaggerated for clarity. The same reference symbols in the figures denote the same or similar structures, and thus their detailed description will be omitted.

In the present disclosure, since adamantane has a three-dimensional structure, it will show different plane shapes in the structure diagram of the compound due to the different drawing angles. The ring structure formed on 9,9-dimethylfluorene is all adamantine, and the connection location is the same. For example,

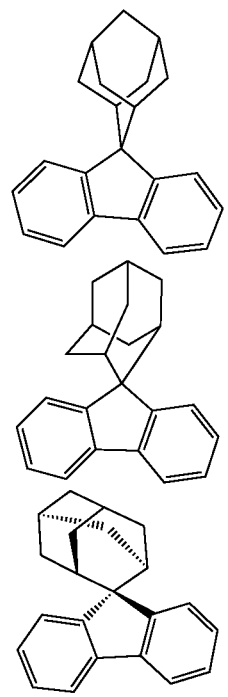

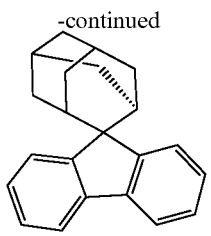

all have the same structure.

The present disclosure provides a nitrogen-containing compound having a structure shown in Formula I:

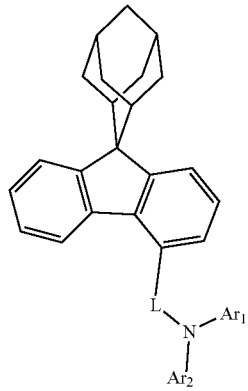

Formula I wherein, L is selected from a single bond, and a substituted or unsubstituted arylene group having 6 to 20 carbon atoms;

$Ar_1$ and $Ar_2$ are the same or different, and are each independently selected from the following substituted or unsubstituted groups: an aryl group having 6 to 20 carbon atoms, and a heteroaryl group having 1 to 20 carbon atoms;

the substituents of $Ar_1$, $Ar_2$ and L are the same or different, and are each independently selected from the group consisting of deuterium, nitro, hydroxy, an alkyl, a cycloalkyl, an alkenyl, an alkynyl, a heterocycloalkyl, an alkoxy, an alkylamino, an arylamino, an alkylthio, and arylsilyl.

Alternatively, neither $Ar_1$ nor $Ar_2$ is spirobifluorenyl.

Alternatively, the substituents of L, $Ar_1$ and $Ar_2$ are each independently selected from the group consisting of deuterium, a heteroaryl having 3 to 18 carbon atoms, an aryl group having 6 to 18 carbon atoms, a haloaryl groups having 6 to 20 carbon atoms, a trialkylsilyl groups having 3 to 12 carbon atoms, an arylsilyl groups having 8 to 12 carbon atoms, an alkyl group having 1 to 10 carbon atoms, a haloalkyl group having 1 to 10 carbon atoms, an alkenyl group having 2 to 6 carbon atoms, an alkynyl group having 2 to 6 carbon atoms, a cycloalkyl group having 3 to 10 carbon atoms, and a heterocycloalkyl group having 2 to 10 carbon atoms, a cycloalkenyl group having 5 to 10 carbon atoms, a heterocyclic alkenyl group having 4 to 10 carbon atoms, an alkoxy group having 1 to 10 carbon atoms, an alkylthio group having 1 to 10 carbon atoms, an aryloxy group having 6 to 18 carbon atoms, an arylthio group having 6 to 18 carbon atoms, and a phosphoryloxy group having 6 to 18 carbon atoms.

In the present disclosure, the number of carbon atoms of L, $Ar_1$ and $Ar_2$ refers to all the number of carbon atoms. For example, if L is selected from a substituted arylene group having 12 carbon atoms, all the carbon atoms of the arylene group and the substituents thereon are 12.

In the present disclosure, the expressions "each . . . independently" and " . . . each independently" and " . . . independently selected from" can be interchangeable, and should be interpreted broadly. They may mean that in different groups, specific options expressed between the same symbols do not affect each other, or it can mean that in the same group, specific options expressed between the same symbols do not affect each other. For example,

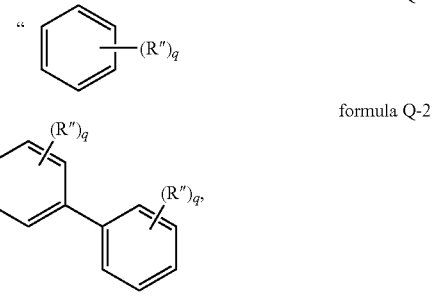

wherein each q is independently 0, 1, 2, or 3, and each R" is independently selected from hydrogen, deuterium, fluorine, and chlorine", means that: formula Q-1 represents that there are q substituents R" on the benzene ring, each R" may be the same or different, and the options of each R" do not affect each other; formula Q-2 represents that there are q substitutions R" on each benzene ring of the biphenyl. The number q of the R" substituents on the two benzene rings may be the same or different, each R" may be the same or different, and the options of each R" do not affect each other.

In the present disclosure, the term "substituted or unsubstituted" means that the functional group described after the term may or may not have a substituent (hereinafter, the substituent is referred to as Rc for convenience of description). For example, "substituted or unsubstituted aryl group" refers to an aryl group having a substituent Rc or an unsubstituted aryl group. Among them, the above substituent Rc can be, for example, deuterium, halogen group, cyano group, a heteroaryl group having 3 to 20 carbon atoms, an aryl group having 6 to 20 carbon atoms, a trialkylsilyl group having 3 to 12 carbon atoms, a triarylsilyl group having 18 to 24 carbon atoms, an alkyl group having 1 to 10 carbon atoms, a haloalkyl group having 1 to 10 carbon atoms, an alkenyl having 2 to 6 carbon atoms, an alkynyl group having 2 to 6 carbon atoms, a cycloalkyl group having 3 to 10 carbon atoms, a heterocycloalkyl group having 2 to 10 carbon atoms, a cycloalkenyl group having 5 to 10 carbon atoms, a heterocyclicalkenyl group having 4 to 10 carbon atoms, an alkoxy having 1 to 10 carbon atoms, an alkylamine group having 1 to 10 carbon atoms, an alkylthio group having 1 to 10 carbon atoms, an aryloxy group having 6 to 18 carbon atoms, an arylthio group having 6 to 18 carbon atoms, a phosphoryloxy group having 6 to 18 carbon atoms, an alkylsulfonyl group having 6 to 18 carbon atoms, a trialkylphosphine group having 3 to 18 carbon atoms and a trialkylboryl group having 3 to 18 carbon atoms.

In the present disclosure, the number of carbon atoms of the substituted or unsubstituted functional group refers to the total number of carbon atoms. For example, if $L_1$ is a substituted arylene group having 12 carbon atoms, the total number of carbon atoms of the arylene group and the substituents thereon is 12.

In the present disclosure, when no specific definition is provided otherwise, "hetero" means that at least one hetero atom such as B, N, O, S, or P, etc. is included in one functional group and the remaining atoms are carbon and hydrogen. The unsubstituted alkyl group may be a "saturated alkyl group" without any double or triple bonds. The unsubstituted alkyl group may be a branched, linear, or cyclic alkyl group.

In the present disclosure, the alkyl group having 1 to 10 carbon atoms may include a linear alkyl group having 1 to 10 carbon atoms and a branched alkyl group having 3 to 10 carbon atoms. The number of carbon atoms may be, for example, 1, 2, 3, 4, 5, 6, 7, 8, 9, or 10. Specific examples of alkyl groups having 1 to 10 carbon atoms include, but are not limited to, methyl, ethyl, n-propyl, isopropyl, n-butyl, isobutyl, t-butyl, n-pentyl, isopentyl, neopentyl, n-hexyl, n-heptyl, n-octyl, 2-ethylhexyl, nonyl, decyl, 3,7-dimethyloctyl, etc.

In the present disclosure, the number of carbon atoms of the cycloalkyl group may be, for example, 3, 5, 6, 7, 8, 9, or 10. Specific examples of cycloalkyl having 3 to 10 carbon atoms include, but are not limited to, cyclopentyl, cyclohexyl, and adamantyl.

In the present disclosure, "alkenyl" refers to a hydrocarbon group containing one or more double bonds in a linear or branched hydrocarbon chain. The alkenyl group can be unsubstituted or substituted. An alkenyl group can have 1 to 20 carbon atoms. Whenever it appears herein, a numerical range such as "1 to 20" refers to each integer in a given range. For example, "1 to 20 carbon atoms" means that an alkenyl group can contain 1 carbon atom, 2 carbon atoms, 3 carbon atoms, 4 carbon atoms, 5 carbon atoms, 6 carbon atoms, 7 carbon atoms, 8 carbon atoms, 9 carbon atoms, 10 carbon atoms, 11 carbon atoms, 12 carbon atoms, 13 carbon atoms, 14 carbon atoms, 15 carbon atoms, 16 carbon atoms, 17 carbon atoms, 18 carbon atoms, 19 carbon atoms or 20 carbon atoms. For example, the alkenyl group may be vinyl, butadiene, or 1,3,5-hexatriene.

In the present disclosure, the halogen group may be, for example, fluorine, chlorine, bromine, or iodine.

In the present disclosure, specific examples of fluoroalkyl include, but are not limited to, trifluoromethyl.

In the present disclosure, aryl refers to an optional functional group or substituent derived from an aromatic carbocycle. The aryl group may be a monocyclic aryl group (such as a phenyl group) or a polycyclic aryl group. In other words, the aryl group may be a monocyclic aryl group, a condensed ring aryl group, two or more monocyclic aryl groups conjugatedly connected by a carbon-carbon bond, a monocyclic aryl group and a fused ring aryl group conjugatedly connected through a carbon-carbon bond, two or more fused ring aryl groups conjugatedly connected through a carbon-carbon bond. That is, unless otherwise specified, two or more aromatic groups conjugatedly connected through a carbon-carbon bond may also be regarded as aryl groups of the present disclosure. Among them, the fused ring aryl group may include, for example, a bicyclic fused aryl group (e.g., naphthyl), a tricyclic fused aryl group (e.g., phenanthrenyl, fluorenyl, anthracenyl), and the like. The aryl group does not contain a heteroatom such as B, N, O, S, P, Se, and Si, etc. For example, in the present disclosure, biphenyl, terphenyl and the like are aryl groups. Examples of aryl groups may include, but are not limited to, phenyl, naphthyl, fluorenyl, anthracenyl, phenanthrenyl, biphenyl, terphenyl, tetraphenyl, pentaphenyl, benzo[9,10] phenanthryl, pyrene, benzofluoranthene, chrysyl, etc. In the present disclosure, the arylene group refers to a divalent group formed by the aryl group further losing a hydrogen atom.

In the present disclosure, the substituted aryl refers to one or more hydrogen atoms in the aryl group being replaced by other groups. For example, at least one hydrogen atom is substituted with a deuterium atom, F, Cl, I, CN, hydroxyl, nitro, a branched alkyl, a linear alkyl, a cycloalkyl, an alkoxy, or other groups. It can be understood that the substituted aryl group having 18 carbon atoms means that the total number of carbon atoms of the aryl group and the substituents on the aryl group is 18. For example, 9,9-diphenylfluorenyl has 25 carbon atoms.

In the present disclosure, the fluorenyl group may be substituted, and the substituted fluorenyl group may be

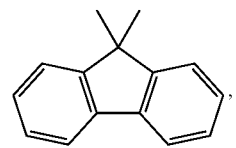, and may be

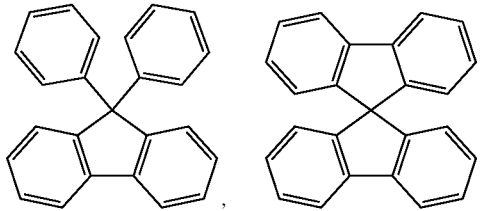, and

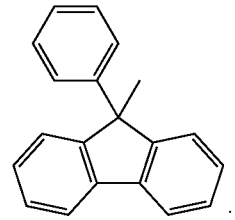 [SMILES: CC1(c2ccccc2)c2ccccc2-c2ccccc21].

In the present disclosure, the heteroaryl group refers to a monovalent aromatic ring containing at least one heteroatom in the ring or a derivative thereof. The heteroatom may be at least one of B, O, N, P, Si, Se, and S. The heteroaryl group may be a monocyclic heteroaryl group or a polycyclic heteroaryl group. In other words, the heteroaryl group may be a single aromatic ring system or multiple aromatic ring systems conjugatedly connected through a carbon-carbon bond, and any of the aromatic ring system is an aromatic monocyclic ring or an aromatic condensed ring. Exemplarily, the heteroaryl group may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyazinyl, isoquinolinyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazine, silylfluorenyl, dibenzofuranyl, and N-arylcarbazole group (e.g., N-phenylcarbazolyl), N-heteroarylcarbazolyl (e.g., N-pyridylcarbazolyl), N-alkylcarbazolyl (e.g., N-methylcarbazolyl), etc., not limited to these. Among them, thienyl, furyl, phenanthrolinyl, etc. are heteroary groups of a single aromatic ring system, and N-arylcarbazolyl and N-heteroarylcarbazolyl are heteroary groups of multiple aromatic ring systems conjugatedly connected through carbon-carbon bonds. In the present disclosure, the heteroarylene group refers to a divalent group formed by the heteroaryl group further losing a hydrogen atom.

In the present disclosure, the substituted heteroaryl group may refers to heteroaryl group where one or more hydrogen atoms in the heteroaryl group are replaced by a group such as deuterium atom, halogen group, —CN, an aryl group, a heteroaryl group, a trialkylsilyl, an alkyl, a cycloalkyl, an alkoxy, and an alkylthio group and the like. Specific examples of the aryl substituted heteroaryl include, but are not limited to, phenyl substituted dibenzofuranyl, phenyl substituted dibenzothienyl, phenyl substituted pyridyl, and the like. It should be understood that the number of carbon atoms of the substituted heteroaryl group refers to the total number of carbon atoms of the heteroaryl group and the substituents on the heteroaryl group.

In the present disclosure, the interpretation of aryl can be applied to arylene, and the interpretation of heteroaryl can also be applied to heteroarylene.

In the present disclosure, the unpositioned connecting bond refers to a single bond "$\dashv$" extending from the ring system, which means that one end of the connecting bond can be connected to any position in the ring system through which the bond penetrates, and the other end is connected to the rest of the compound molecule.

For example, as shown in the following formula (f), the naphthyl group represented by the formula (f) is connected to other positions of the molecule through two unpositioned connecting bonds penetrating the bicyclic ring, meaning that it includes any possible connection modes shown in formula (f-1) to formula (f-10).

formula (f)

formula (f-1)

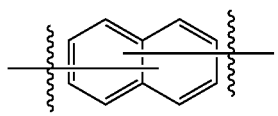

formula (f-2)

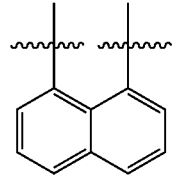

formula (f-3)

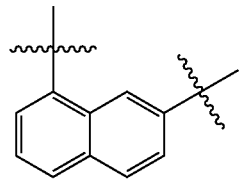

formula (f-4)

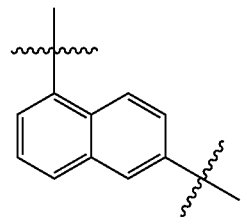

formula (f-5)

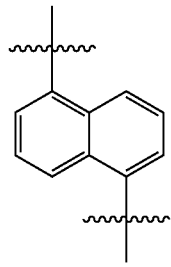

formula (f-6)

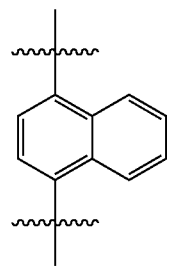

formula (f-7)

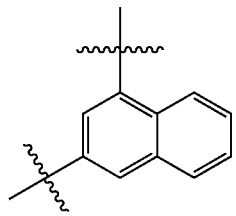

formula (f-8)

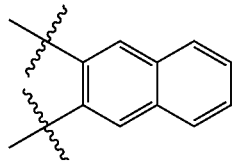

formula (f-9)

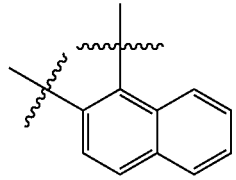

formula (f-10)

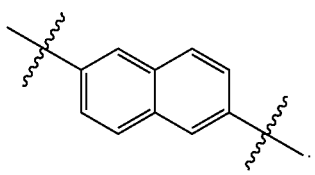

For another example, as shown in the following formula (X'), the phenanthrene represented by the formula (X') is connected to the other position of the molecule through a unpositioned connecting bond extending from the middle of one side of the benzene ring, meaning that it includes any possible connection modes as shown in formula (X'-1) ~formula (X'-4).

(X')

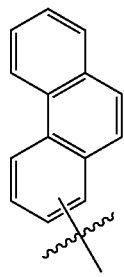

(X'-1)

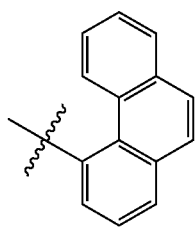

(X'-2)

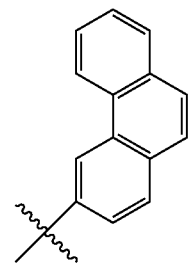

(X'-3)

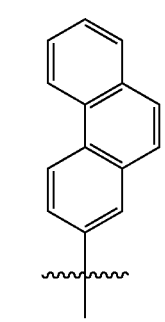

(X'-4)

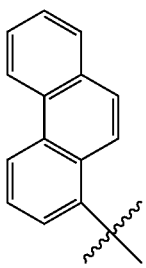

The unpositioned substituent in the present disclosure refers to a substituent connected by a single bond extending from the center of the ring system, which means that the substituent can be connected at any possible position in the ring system. For example, as shown in the following formula (Y), the substituent R' in the formula (Y) is connected to the quinoline ring through an unpositioned connecting bond, meaning that it includes, for example, any possible connection modes shown in the formula (Y-1)~formula (Y-7).

formula (Y)

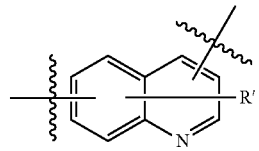

formula (Y-1)

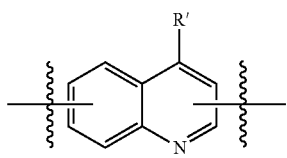

formula (Y-2)

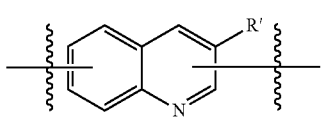

formula (Y-3)

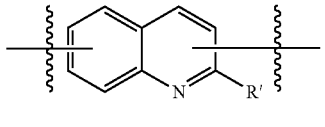

formula (Y-4)

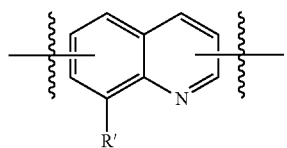

formula (Y-5)

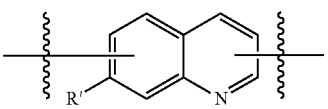

formula (Y-6)

formula (Y-7)

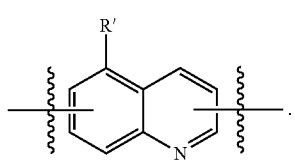

The nitrogen-containing compound provided in the present disclosure introduces the adamantyl structure at the side of the fluorene to increase the electron density of the conjugated system of the fluorene ring and the entire nitrogen-containing compound through the super-conjugation effect, which can enhance the hole conductivity of the nitrogen-containing compound as well as the electronic tolerance. The adamantyl group is introduced between the branches of the triarylamine, which is originally a near-plane structure, rather than at the end. The large steric hindrance of the adamantyl group can finely adjust the bonding angle and conjugation degree of the amine and each aryl group, thereby obtaining HOMO value suitable for the material of the adjacent layer. In addition, the introduction of adamantyl can also increase the molecular weight of the nitrogen-containing compound and reduce the molecular symmetry, can increase the glass transition temperature and evaporation temperature of the compound of the present disclosure, and can control the crystallinity of the nitrogen-containing compound. When the nitrogen compound is used in mass production, it has better physical and thermal stability. The 4-position of the fluorene group in the nitrogen-containing compound of the present disclosure is connected to the amine, which greatly increases the steric hindrance of the arylamine structure, thereby increasing the twist angle between the plane of fluorene and the plane of the arylamine (especially the plane of triarylamine), and reducing the degree of conjugation. Thus, the energy band width and triplet energy level of the nitrogen-containing compound are improved, so that the nitrogen-containing compound is particularly suitable for electron blocking layers (also known as hole auxiliary layer, second hole transporting layer, etc.).

These characteristics of the nitrogen-containing compound of the present disclosure enable it to be used in the preparation of organic electroluminescence device and photoelectric conversion device, especially suitable for preparing the electron blocking layer of organic electroluminescence device and photoelectric conversion device, so as to improve the efficiency and lifespan of the organic electroluminescence device and the photoelectric conversion device, reduce the operating voltage of the organic electroluminescence device, increase the open circuit voltage of the photoelectric conversion device, and improve the mass production stability of the photoelectric conversion device and the organic electroluminescence device.

Alternatively, L is selected from the group consisting of a single bond, a substituted or unsubstituted phenylene, a substituted or unsubstituted naphthylene, a substituted or unsubstituted biphenylene, a substituted or unsubstituted terphenylene, and a substituted or unsubstituted dimethylfluorene.

Alternatively, L is selected from a substituted or unsubstituted phenanthrene.

Alternatively, L is selected from a single bond or the group consisting of a group represented by the formula j-1 to a group represented by the formula j-7:

formula j-1

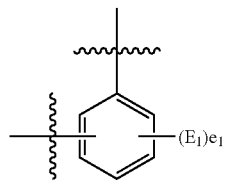

formula j-2

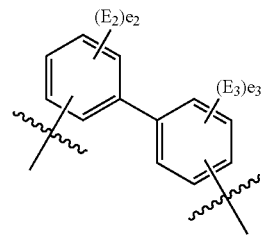

formula j-3

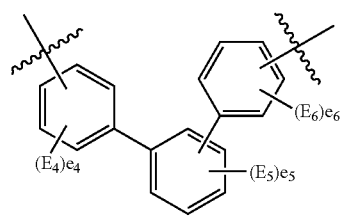

formula j-4

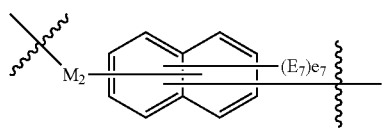

formula j-5

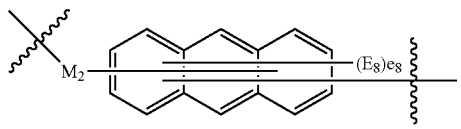

formula j-6

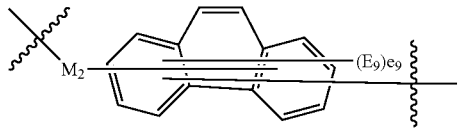

formula j-7

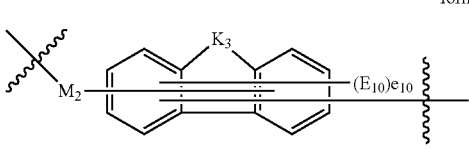

wherein, $M_2$ is selected from a single bond or

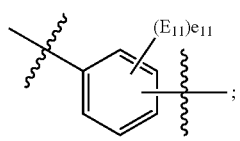

;

$E_1$~$E_{11}$ are each independently selected from: hydrogen, a heteroaryl group having 3 to 20 carbon atoms, an aryl groups having 6 to 20 carbon atoms, an arylsilyl group having 8 to 12 carbon atoms, an alkyl group having 1 to 10 carbon atoms, an alkenyl group having 2 to 6 carbon atoms, an alkynyl group having 2 to 6 carbon atoms, a cycloalkyl group having 3 to 10 carbon atoms, a heterocycloalkyl having 2 to 10 carbon atoms, an alkoxy having 1 to 10 carbon atoms, and an alkylthio group having 1 to 10 carbon atoms;

$e_r$ is the number of substituents $E_r$, r is any integer from 1 to 11; when r is selected from 1, 2, 3, 4, 5 or 6, $e_r$ is selected from 1, 2, 3 or 4; when r is selected from 7 or 10, $e_r$ is selected from 1, 2, 3, 4, 5 or 6; when r is selected from 8 or 9, $e_r$ is selected from 1, 2, 3, 4, 5, 6, 7 or 8; when $e_r$ is greater than 1, any two $E_r$ are the same or different;

$K_3$ is selected from $C(E_{12}E_{13})$; wherein $E_{12}$ and $E_{13}$ are each independently selected from: phenyl, an alkyl having 1 to 10 carbon atoms, an alkenyl having 2 to 6 carbon atoms, an alkynyl group having 2 to 6 carbon atoms, a cycloalkyl group having 3 to 10 carbon atoms, and a heterocycloalkyl group having 2 to 10 carbon atoms.

Alternatively, L is selected from a single bond or the group consisting of the following groups:

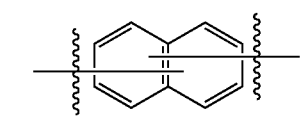

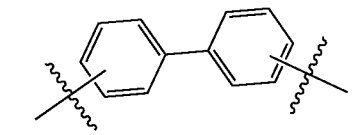

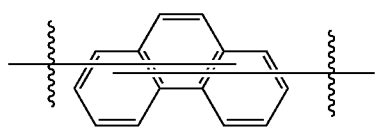

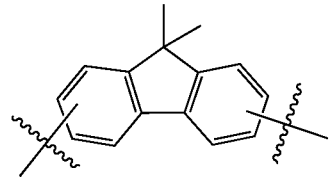

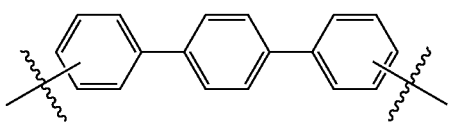

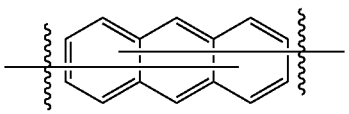

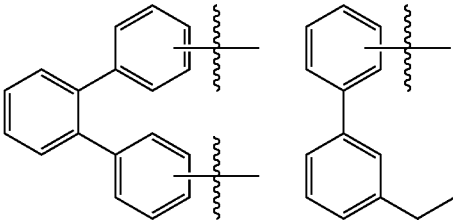

Alternatively, L is selected from a single bond or the group consisting of the following groups:

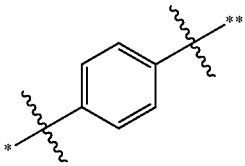

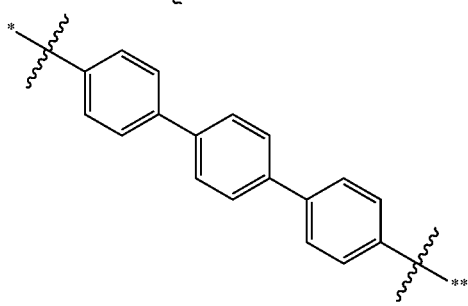

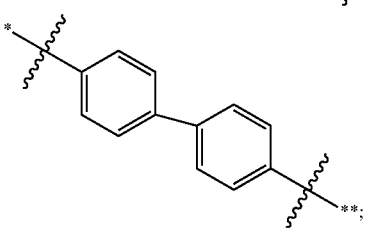

wherein, * represents the position for L connecting with group
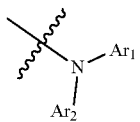
** represents the position for L connecting with group
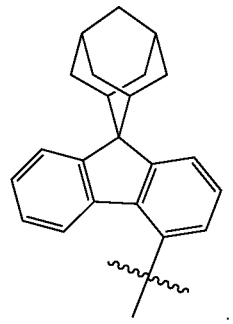 [SMILES: *c1cccc2c1-c1ccccc1C21C2CC3CC(C2)CC1C3]
Alternatively, L is selected from a single bond or the group consisting of the following groups:
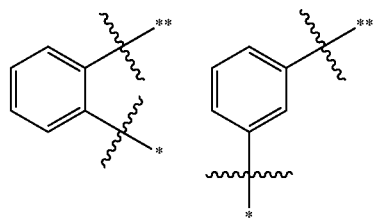
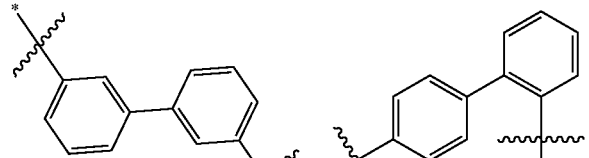
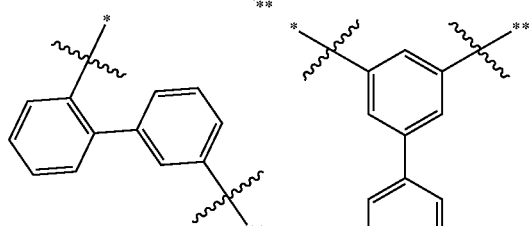
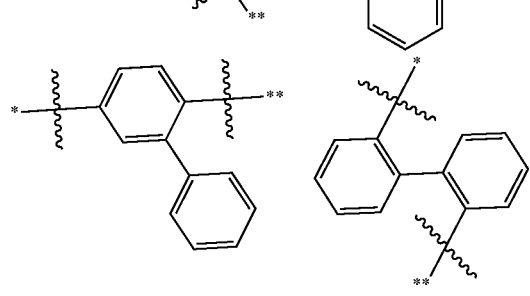
-continued
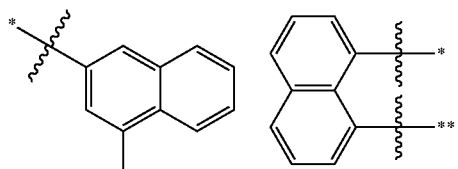
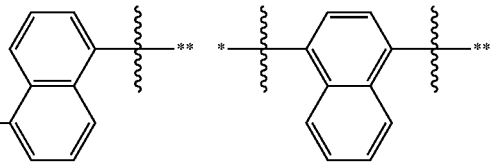
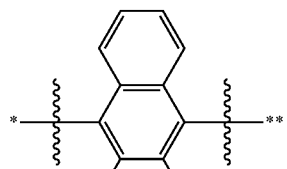
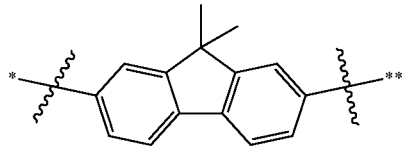
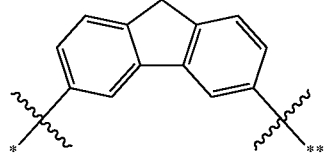
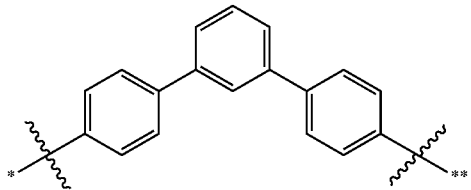
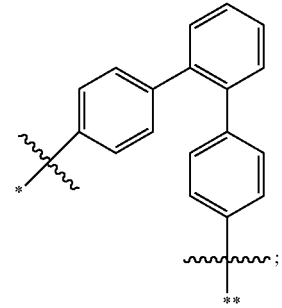

wherein, * represents the position for L connecting with group
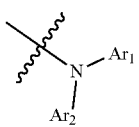
** represents the position for L connecting with group
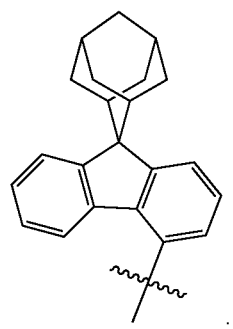 [SMILES: *c1cccc2c1-c1ccccc1C21C2CC3CC(C2)CC1C3]
Alternatively, $Ar_1$ and $Ar_2$ are each independently selected from the group consisting of the following groups:
formula i-1
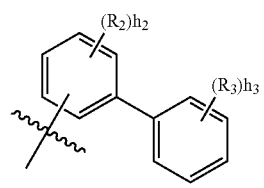
formula i-2
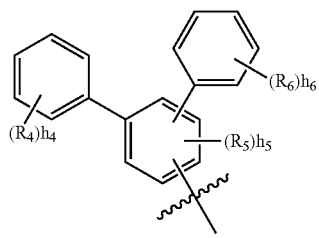
formula i-3
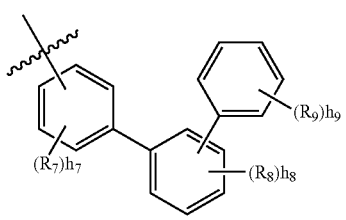
formula i-4
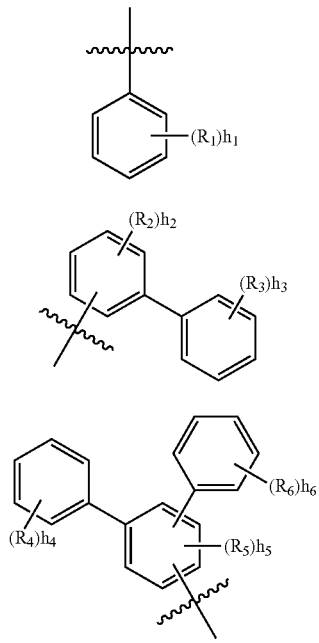
formula i-5
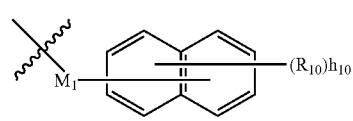
formula i-6
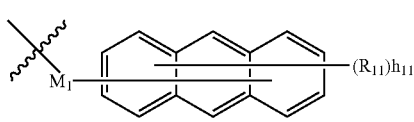
formula i-7
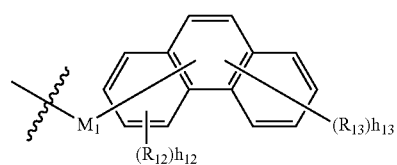
formula i-8
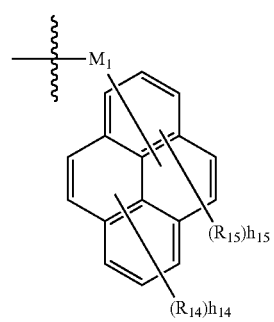
formula i-9
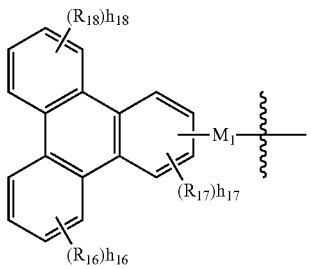
formula i-10
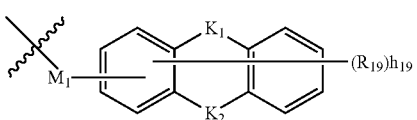
formula i-11
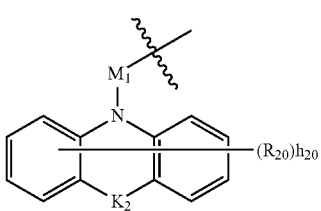
formula i-12
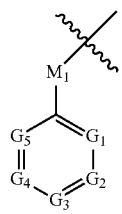

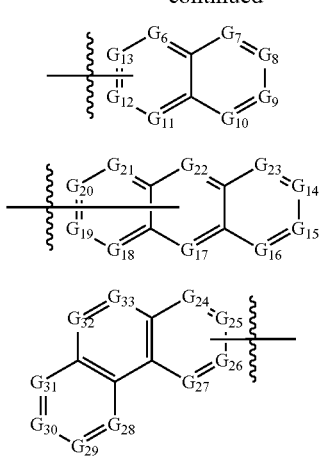

formula i-13 formula i-14 formula i-15 wherein, $M_1$ is selected from a single bond or

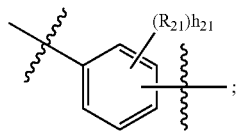

$G_1$~$G_5$ are each independently selected from N or $C(F_1)$, and at least one of $G_1$~$G_5$ is selected from N; when two or more of $G_1$~$G_5$ are selected from $C(F_1)$, any two $F_1$ are the same or different;

$G_6$~$G_{13}$ are each independently selected from N or $C(F_2)$, and at least one of $G_6$~$G_{13}$ is selected from N; when two or more of $G_6$~$G_{13}$ are selected from $C(F_2)$, any two $F_2$ are the same or different;

$G_{14}$~$G_{23}$ are each independently selected from N or $C(F_3)$, and at least one of $G_{14}$~$G_{23}$ is selected from N; when two or more of $G_{14}$~$G_{23}$ are selected from $C(F_3)$, any two $F_3$ are the same or different;

$G_{24}$~$G_{33}$ are each independently selected from N or $C(F_4)$, and at least one of $G_{24}$~$G_{33}$ is selected from N; when two or more of $G_{24}$~$G_{33}$ are selected from $C(F_4)$, any two $F_4$ are the same or different;

$R_1$ is selected from the group consisting of hydrogen, deuterium, an arylsilyl group having 8 to 12 carbon atoms, an alkyl group having 1 to 10 carbon atoms, an alkenyl group having 2 to 6 carbon atoms, an alkynyl group having 2 to 6 carbon atoms, a cycloalkyl group having 3 to 10 carbon atoms, a heterocycloalkyl group having 2 to 10 carbon atoms, an alkoxy group having 1 to 10 carbon atoms, and an alkylthio group having 1 to 10 carbon atoms;

$R_2$~$R_9$, $R_{21}$ are each independently selected from the group consisting of hydrogen, deuterium, a heteroaryl group having 3-10 carbon atoms, an arylsilyl group having 8-12 carbon atoms, an alkyl group having 1-10 carbon atoms, an alkenyl group having 2 to 6 carbon atoms, an alkynyl group having 2 to 6 carbon atoms, a cycloalkyl group having 3 to 10 carbon atoms, a heterocycloalkyl group having 2 to 10 carbon atoms, an alkoxy group having 1 to 10 carbon atoms and an alkylthio group having 1 to 10 carbon atoms;

$R_{10}$~$R_{20}$, $F_1$~$F_4$ are each independently selected from the group consisting of hydrogen, deuterium, an aryl group having 6-12 carbon atoms, a heteroaryl group having 3-10 carbon atoms, an arylsilyl group having 8-12 carbon atoms, an alkyl group having 1-10 carbon atoms, an alkenyl group having 2 to 6 carbon atoms, an alkynyl group having 2 to 6 carbon atoms, a cycloalkyl group having 3 to 10 carbon atoms, a heterocycloalkyl group having 2 to 10 carbon atoms, an alkoxy group having 1 to 10 carbon atoms and an alkylthio group having 1 to 10 carbon atoms;

$h_k$ is the number of substituents $R_k$, k is any integer from 1 to 21; wherein, when k is selected from 5 or 17, $h_k$ is selected from 1, 2 or 3; when k is selected from 2, 7, 8, 12, 15, 16, 18, or 21, $h_k$ is selected from 1, 2, 3, or 4; when k is selected from 1, 3, 4, 6, 9, or 14, $h_k$ is selected from 1, 2, 3, 4 or 5; when k is 13, $h_k$ is selected from 1, 2, 3, 4, 5 or 6; when k is selected from 10 or 19, $h_k$ is selected from 1, 2, 3, 4, 5, 6 or 7; when k is selected from 20, $h_k$ is selected from 1, 2, 3, 4, 5, 6, 7 or 8; when k is 11, $h_k$ is selected from 1, 2, 3, 4, 5, 6, 7, 8 or 9; when $h_k$ is greater than 1, any two $R_k$ are the same or different;

$K_1$ is selected from O, S, Se, $N(R_{22})$, $C(R_{23}R_{24})$, $Si(R_{25}R_{26})$; wherein, $R_{22}$~$R_{26}$ are each independently selected from: phenyl, an alkyl group having 1-10 carbon atoms, an alkenyl group having 2 to 6 carbon atoms, an alkynyl group having 2 to 6 carbon atoms, a cycloalkyl group having 3 to 10 carbon atoms, and a heterocycloalkyl group having 2 to 10 carbon atoms;

$K_2$ is selected from a single bond, O, S, Se, $N(R_{27})$, $C(R_{28}R_{29})$, $Si(R_{30}R_{31})$; wherein, $R_{27}$~$R_{31}$ are each independently selected from: phenyl, an alkyl group having 1 to 10 carbon atoms, an alkenyl group having 2 to 6 carbon atoms, an alkynyl group having 2 to 6 carbon atoms, a cycloalkyl group having 3 to 10 carbon atoms, and a heterocycloalkyl group having 2 to 10 carbon atoms.

Alternatively, $Ar_1$ and $Ar_2$ are the same or different, and are each independently selected from: a substituted or unsubstituted aryl group having 6 to 20 carbon atoms, and a substituted or unsubstituted heteroaryl group having 7 to 20 carbon atoms.

Alternatively, $Ar_1$ and $Ar_2$ are the same or different, and are each independently selected from: an unsubstituted aryl group having 6 to 20 carbon atoms, a substituted aryl group having 15 to 20 carbon atoms, and a unsubstituted heteroaryl having 12 to 18 carbon atoms.

Alternatively, $Ar_1$ and $Ar_2$ are the same or different, and are each independently selected from the group consisting of the following groups:

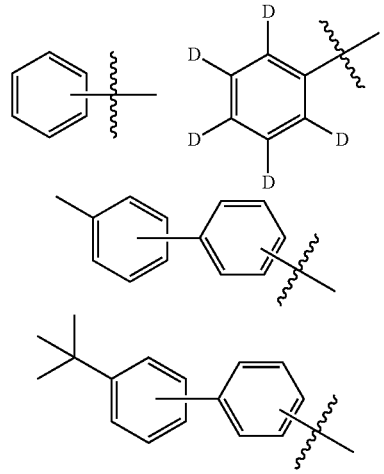

-continued
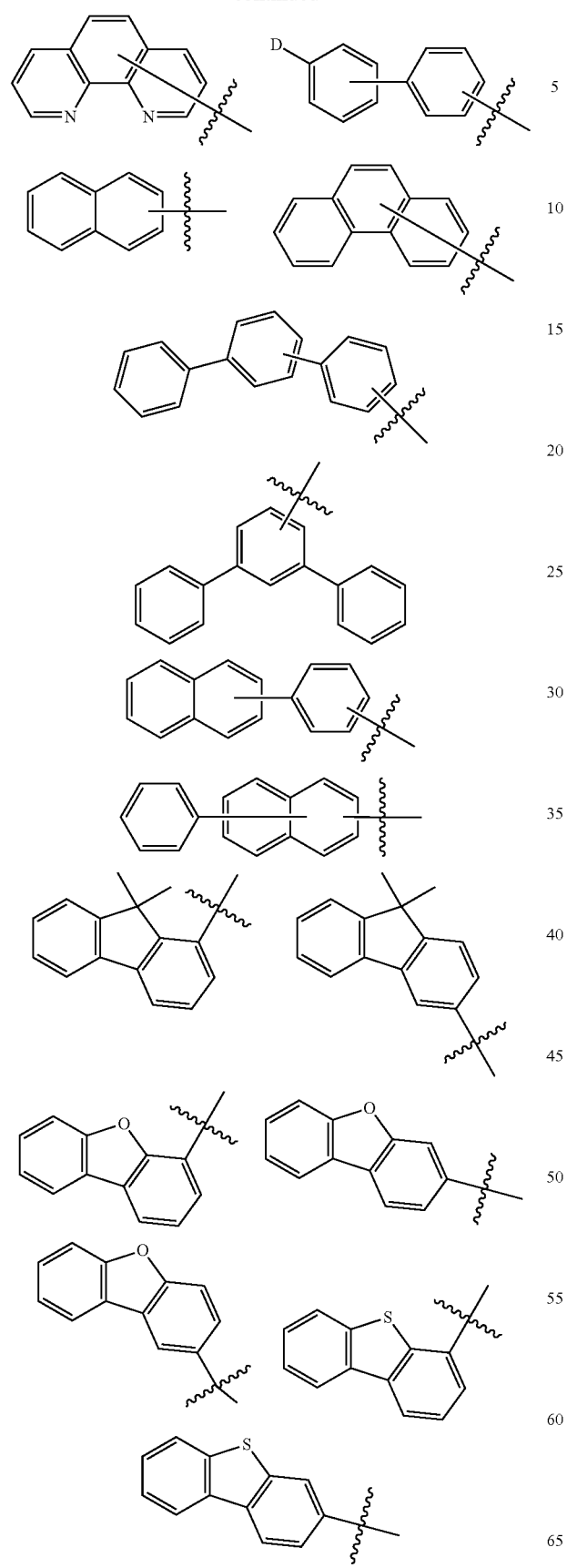
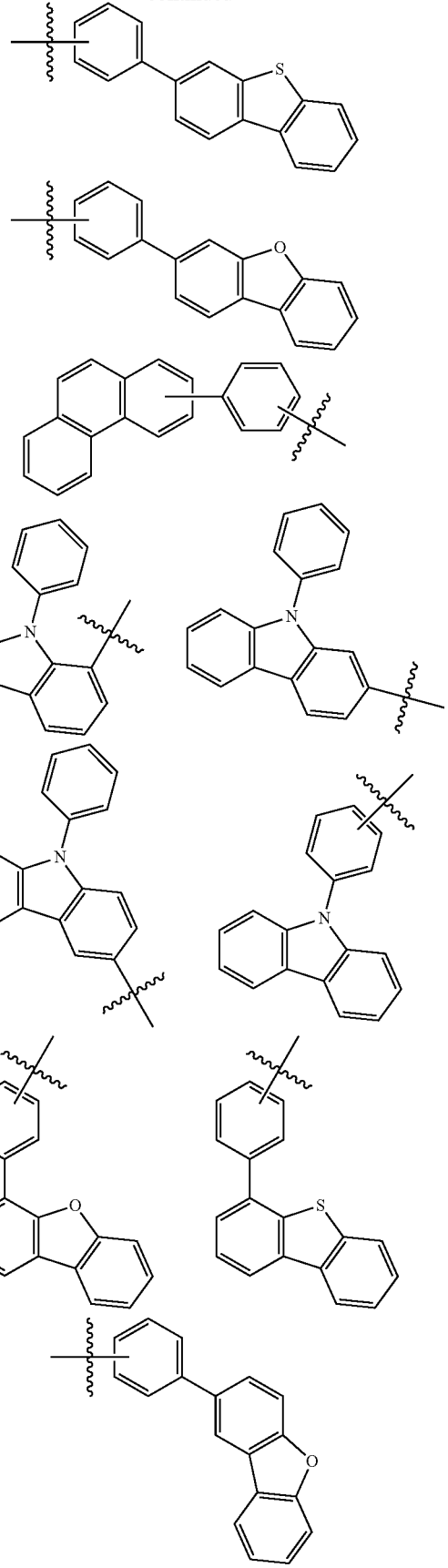

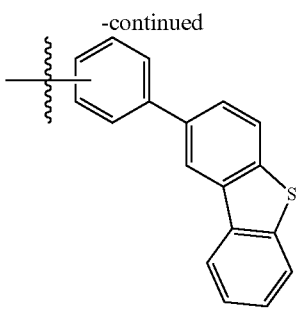
Alternatively, $Ar_1$ and $Ar_2$ are the same or different, and are each independently selected from the group consisting of the following groups:
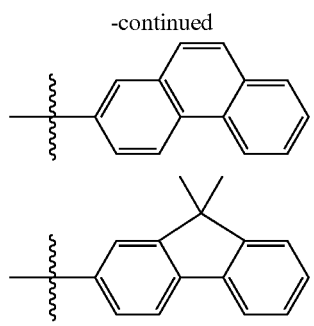
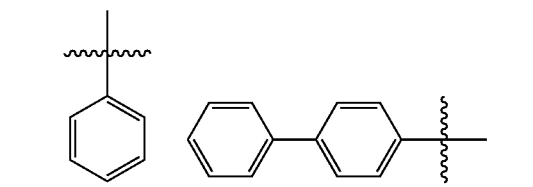
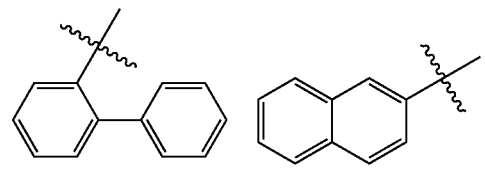
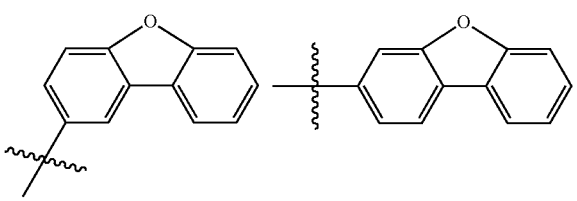
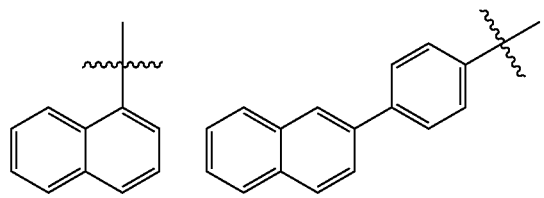
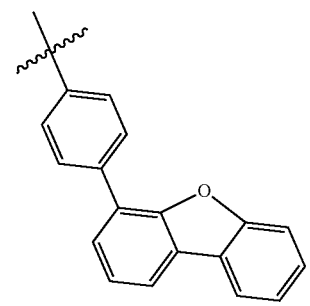
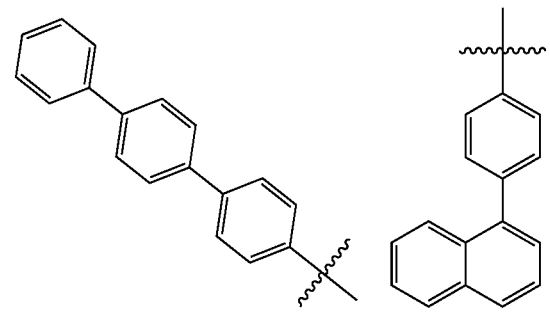
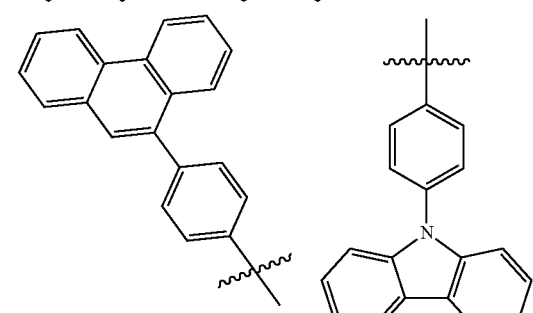
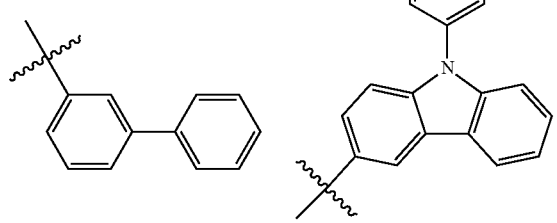
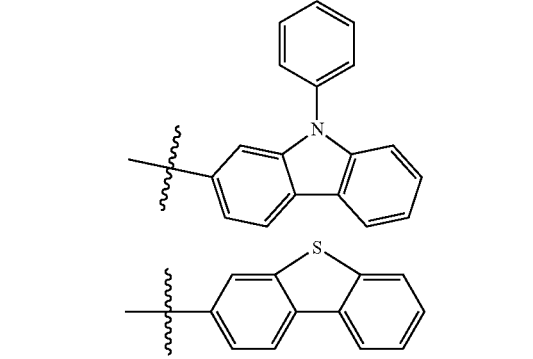
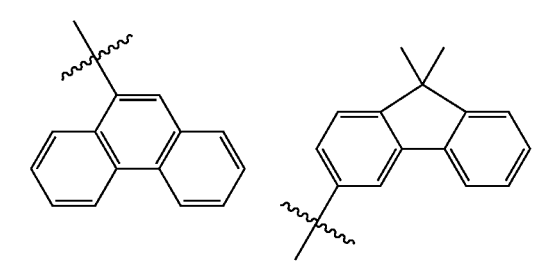

-continued
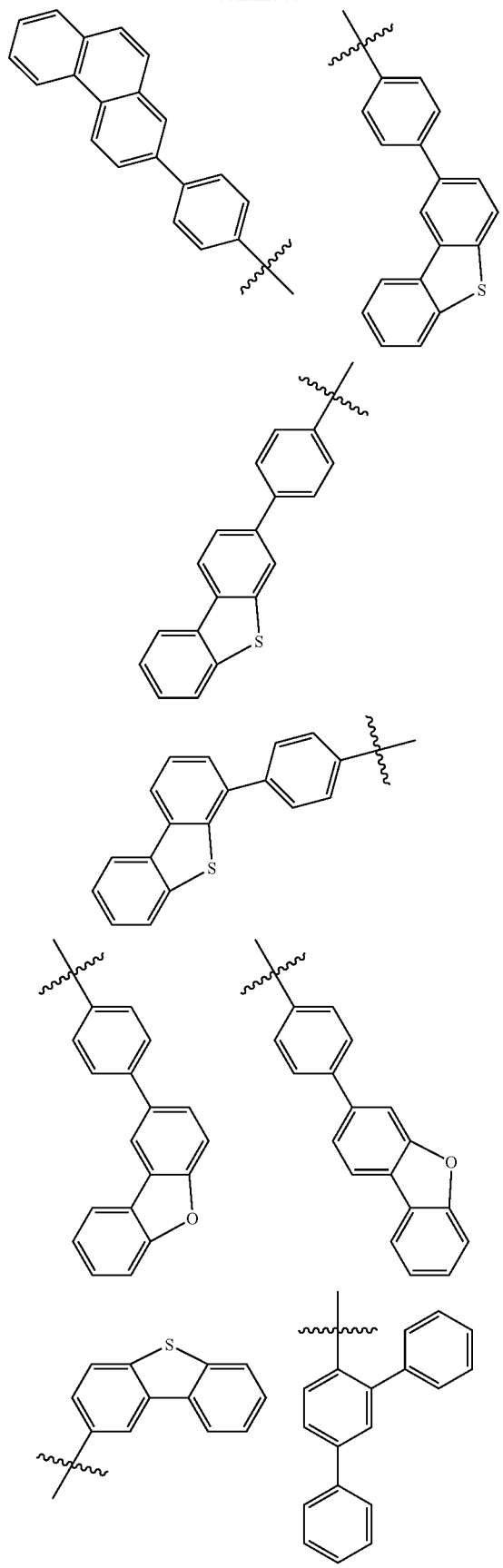
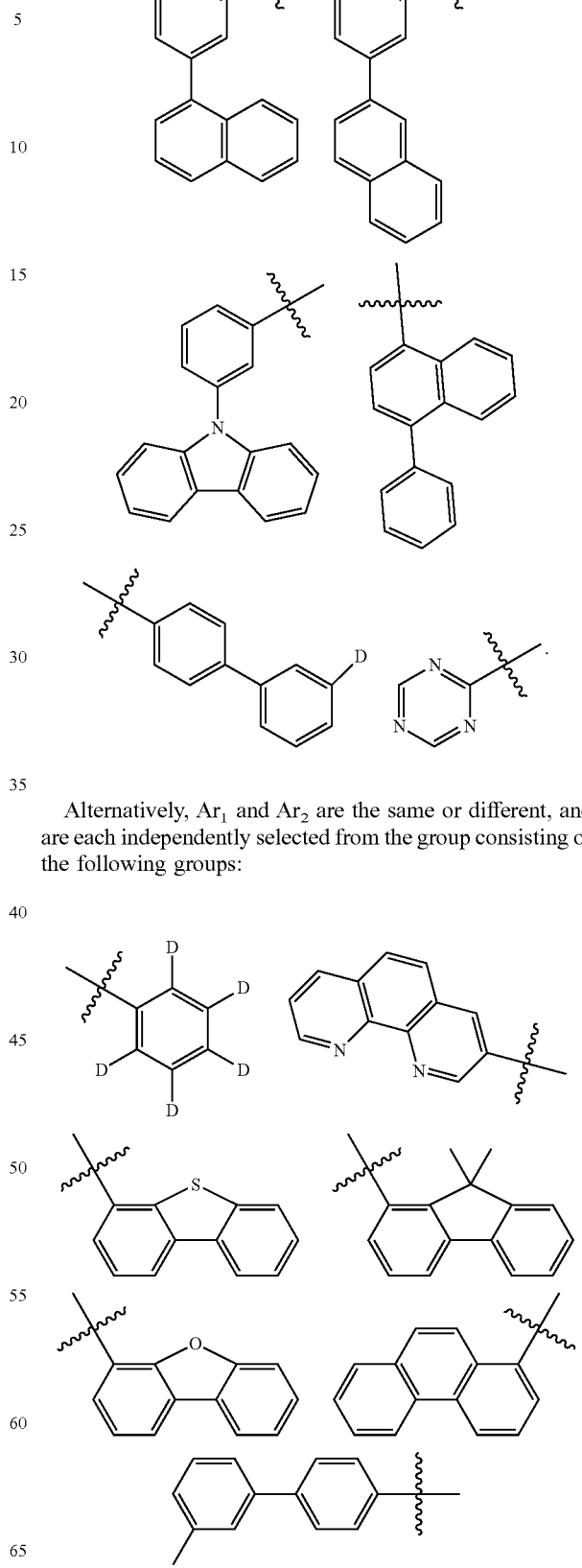
Alternatively, Ar₁ and Ar₂ are the same or different, and are each independently selected from the group consisting of the following groups:

-continued
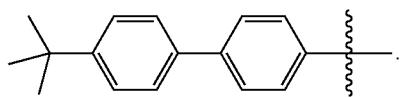
Alternatively, the nitrogen-containing compound is selected from the group consisting of the following compounds:
1
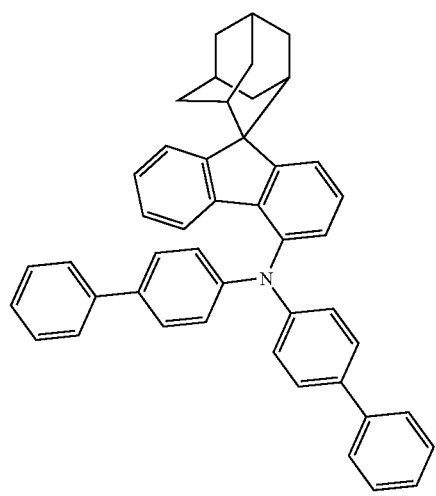
2
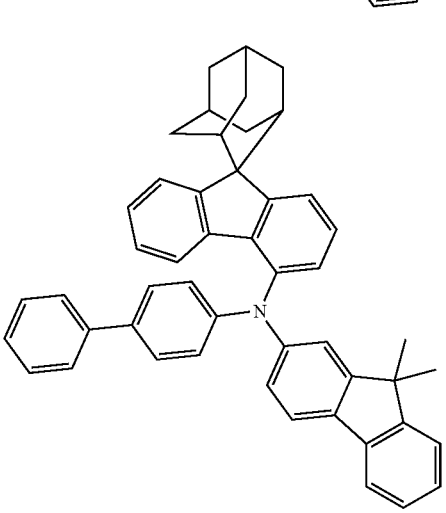
3
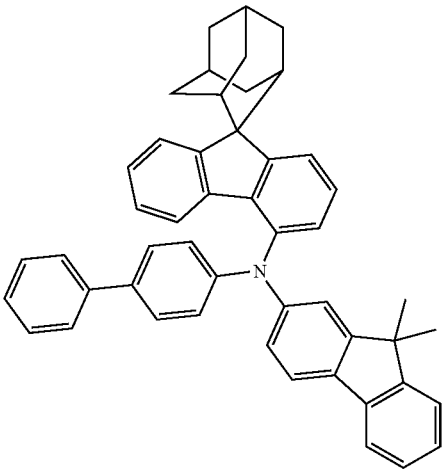
-continued
4
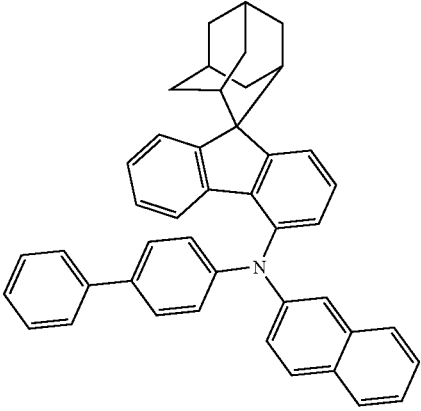
5
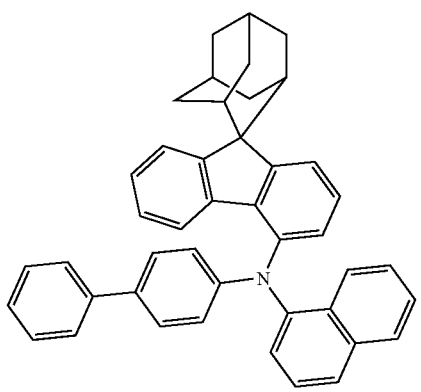
6
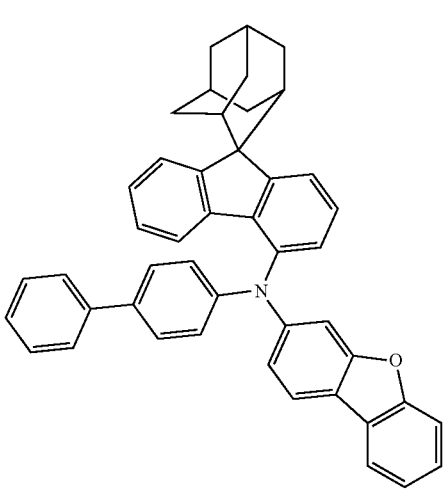

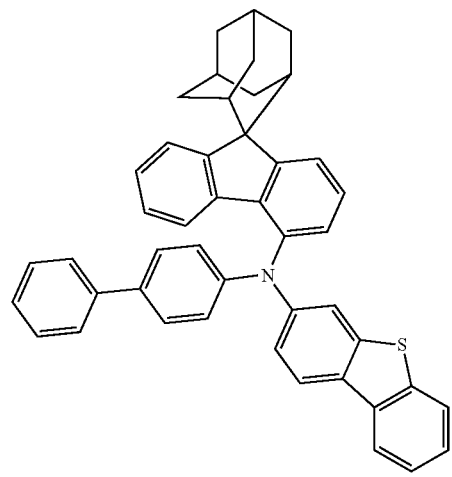
7
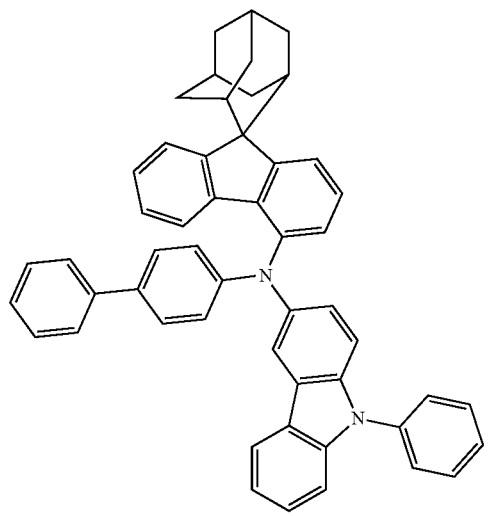
10
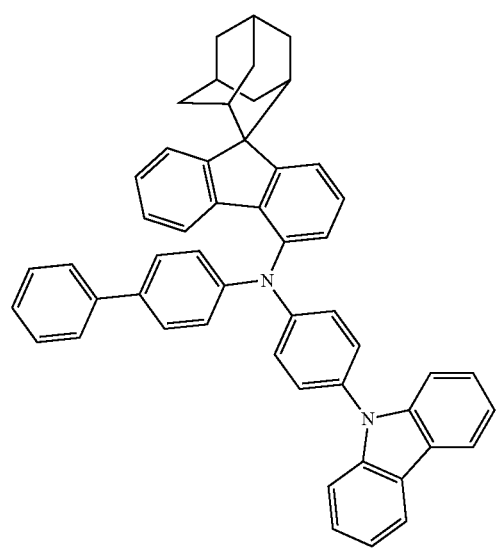
8
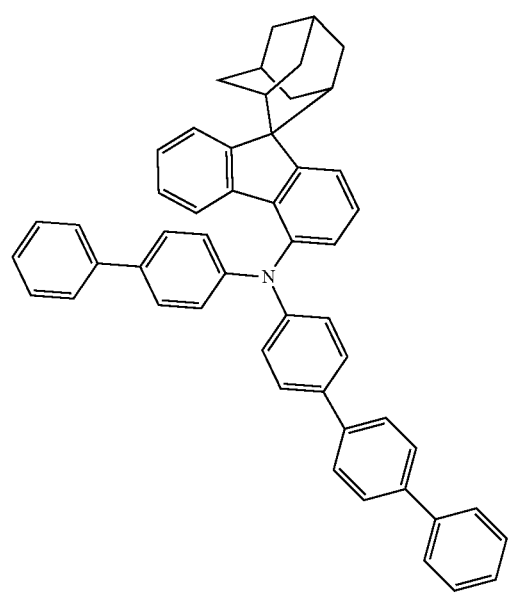
11
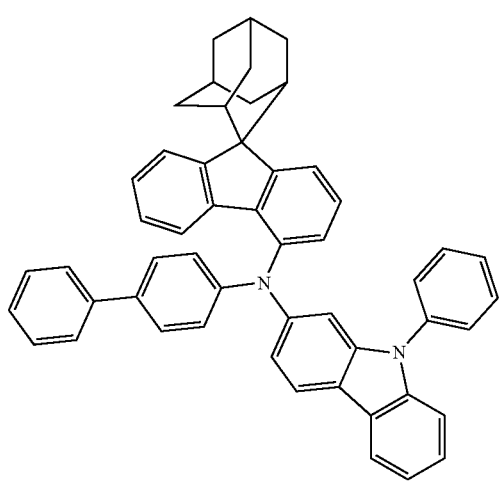
9
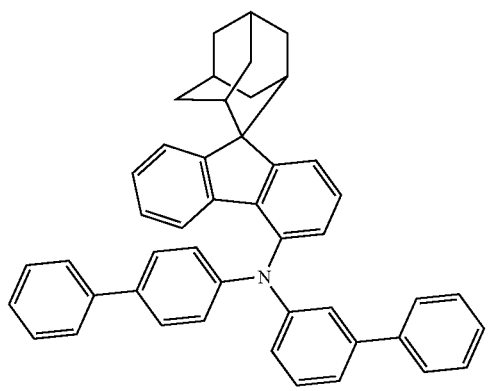
12

13
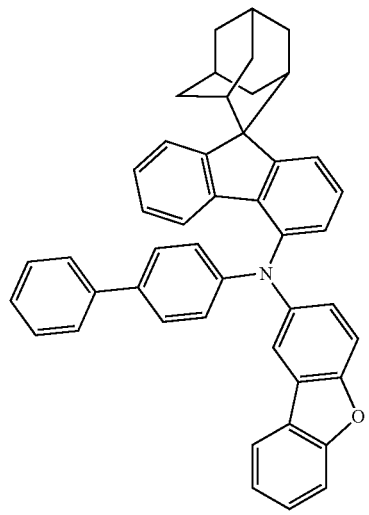
14
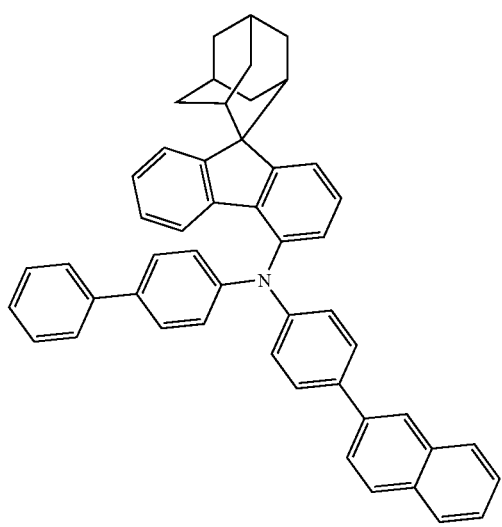
15
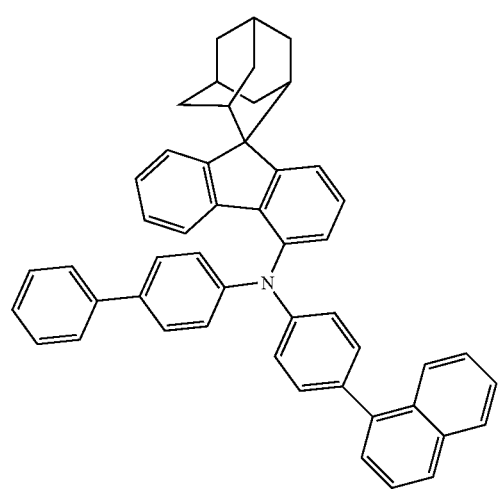
16
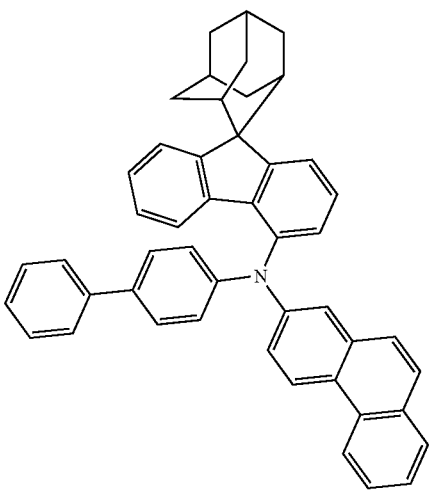
17
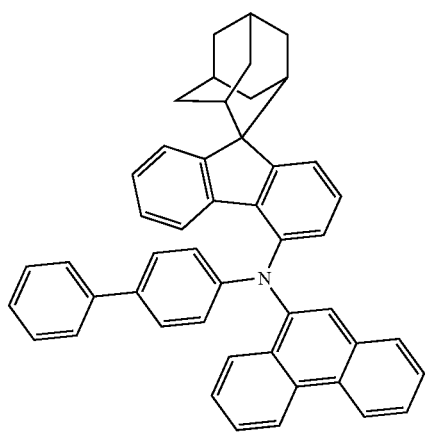
18
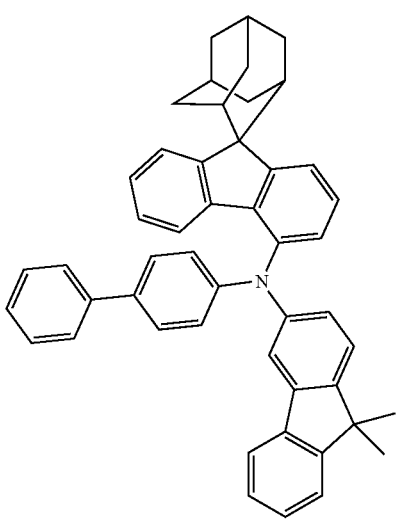

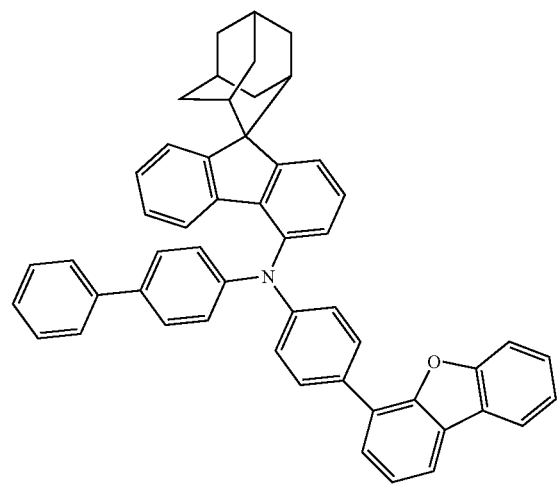
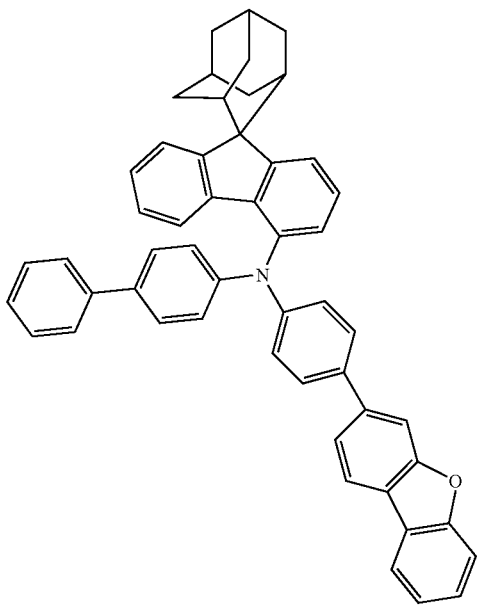
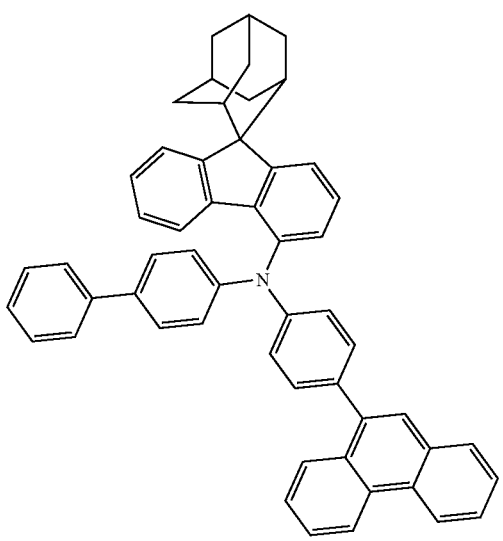
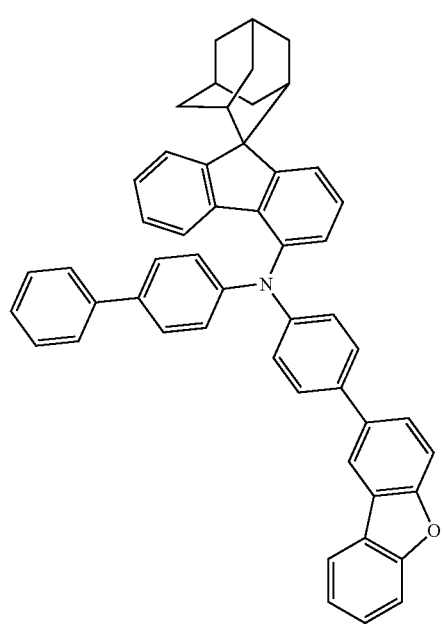
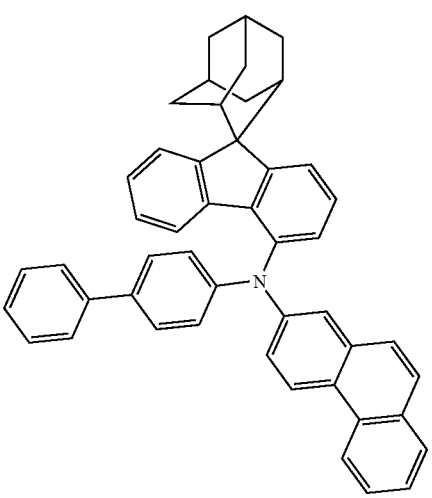

24
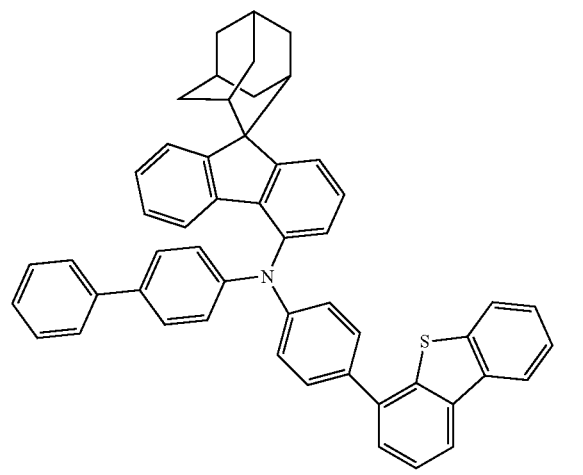
25
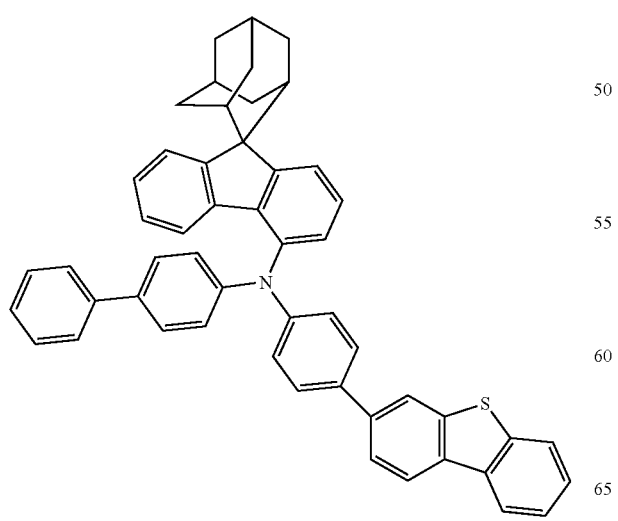
26
27
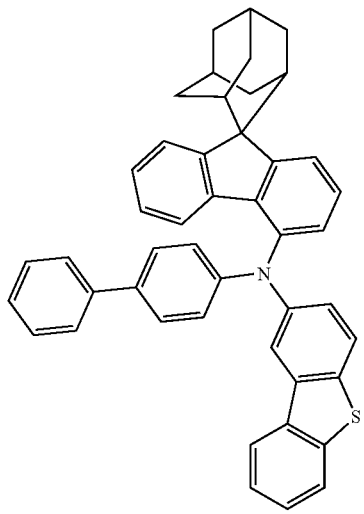
28
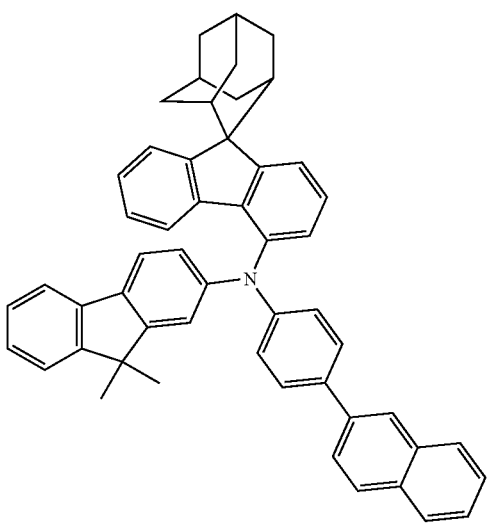
29
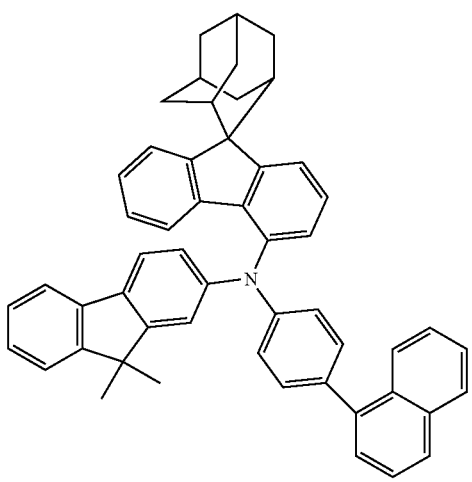

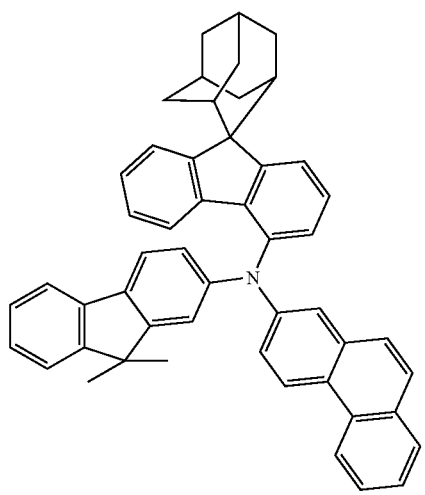
30
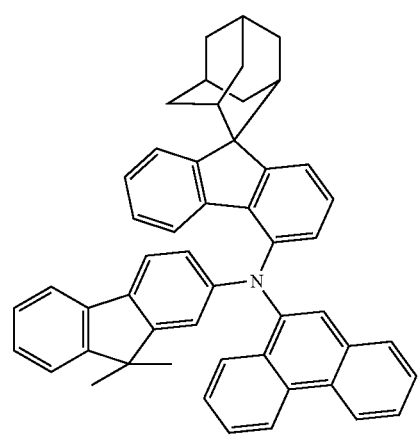
31
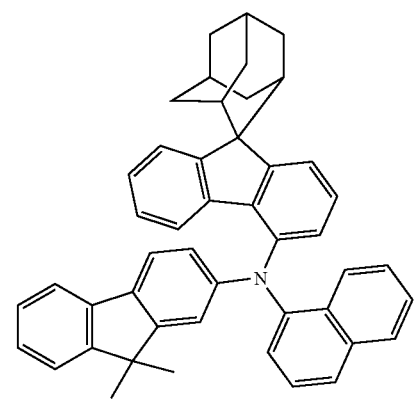
32
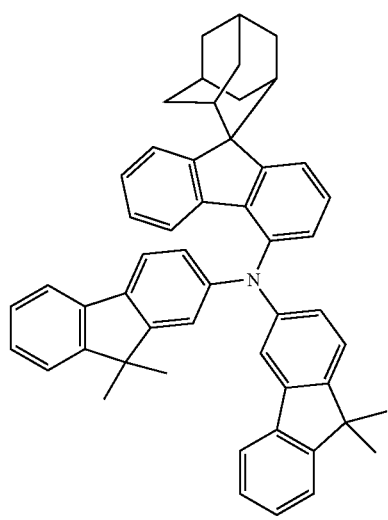
33
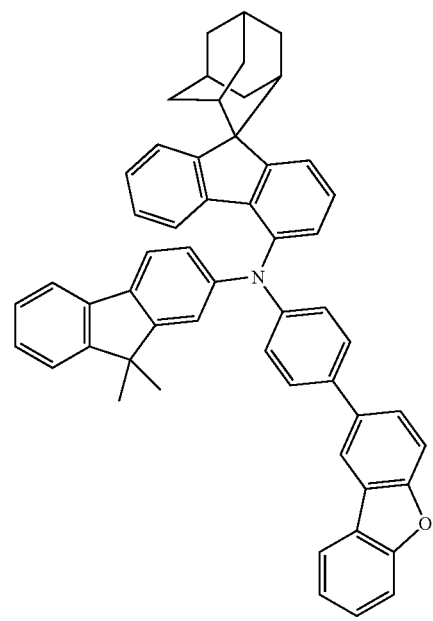
34
35

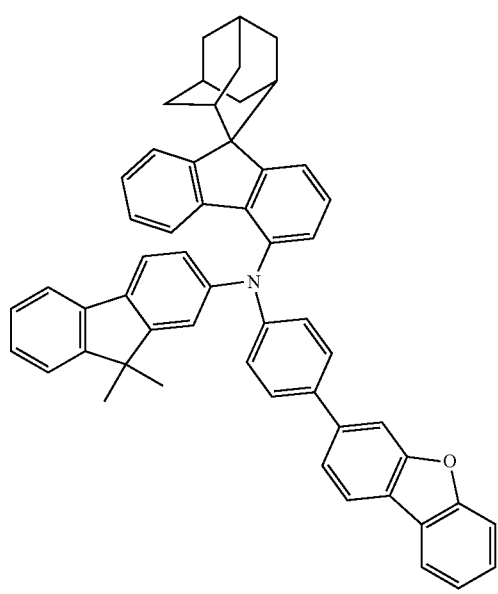
36
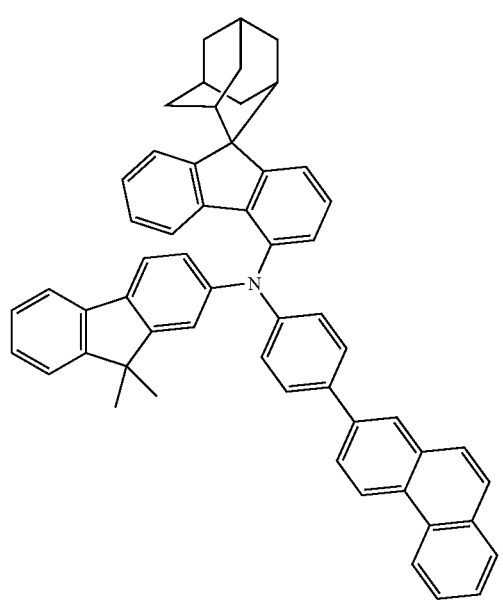
38
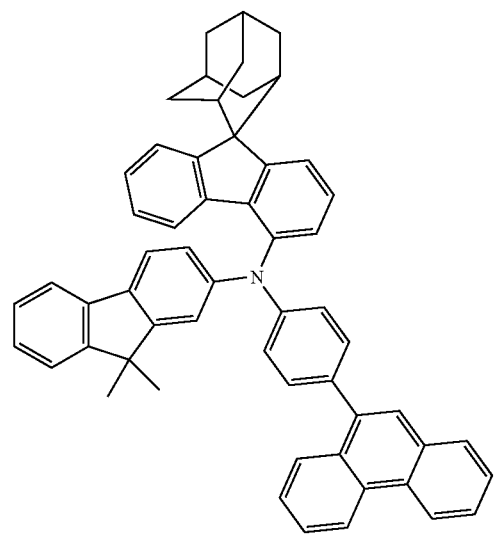
37
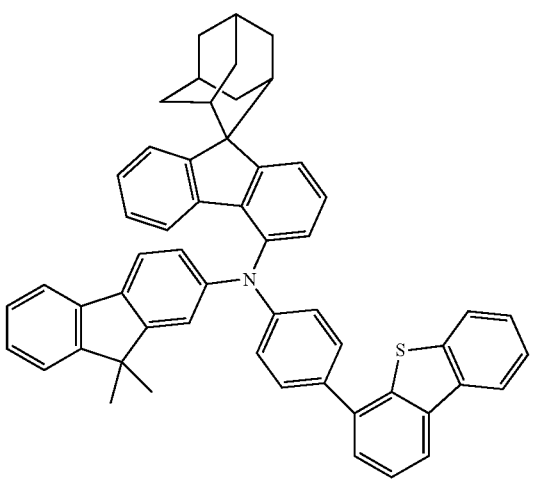
39

40
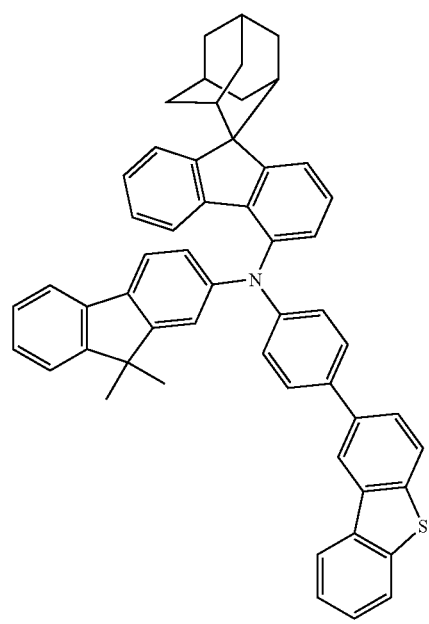
41
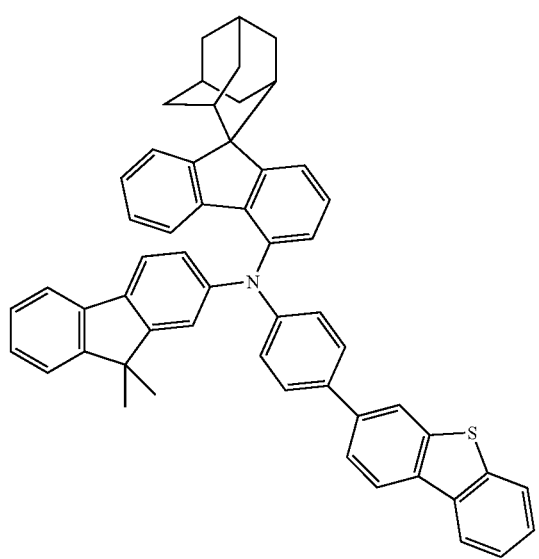
42
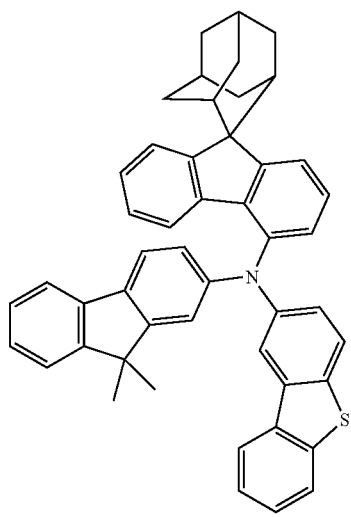
43
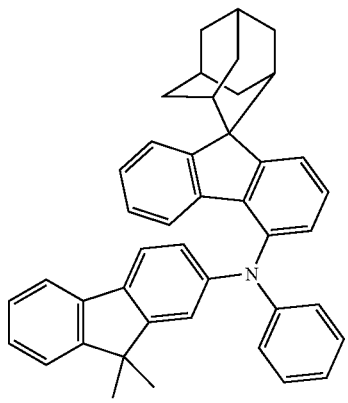
44

45
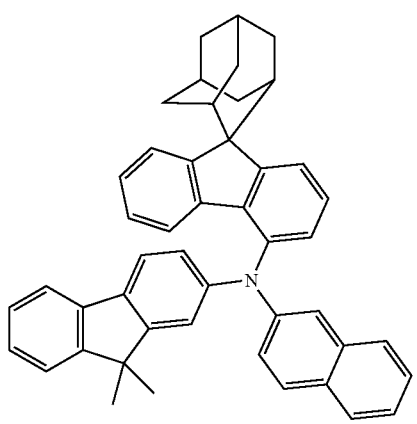
46
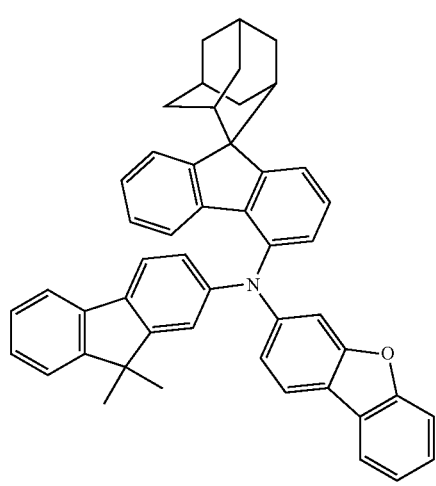
47
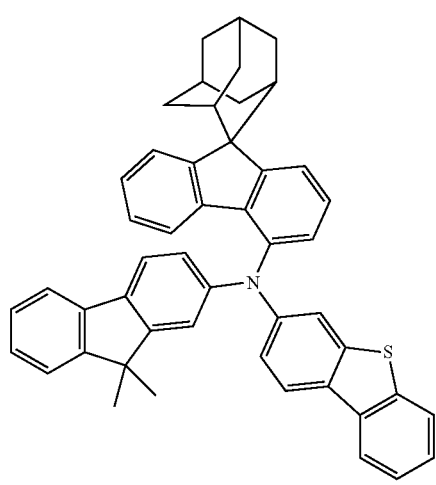
48
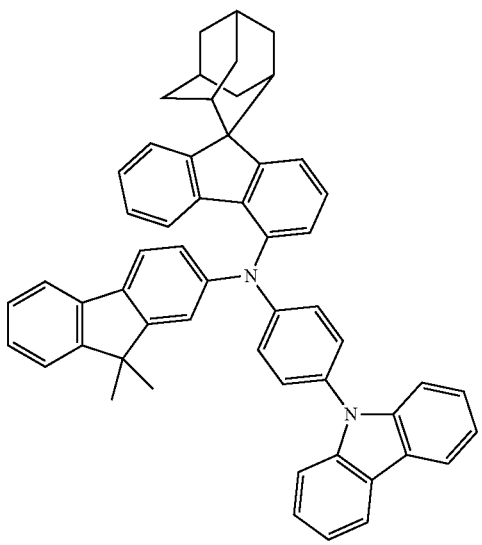
49
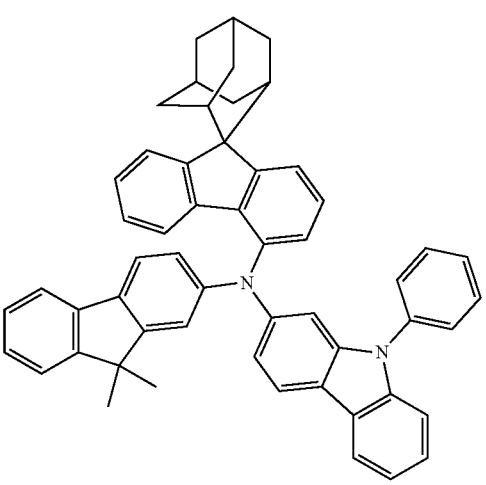
50
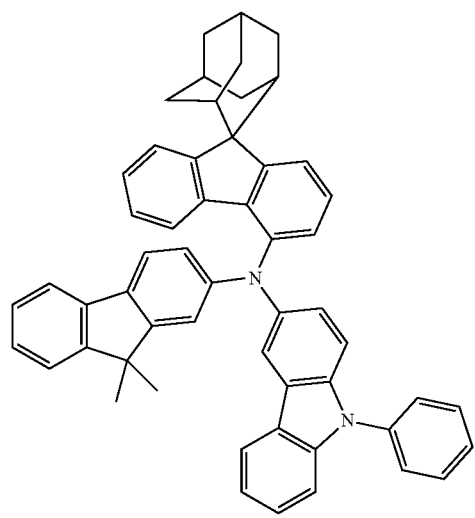

51
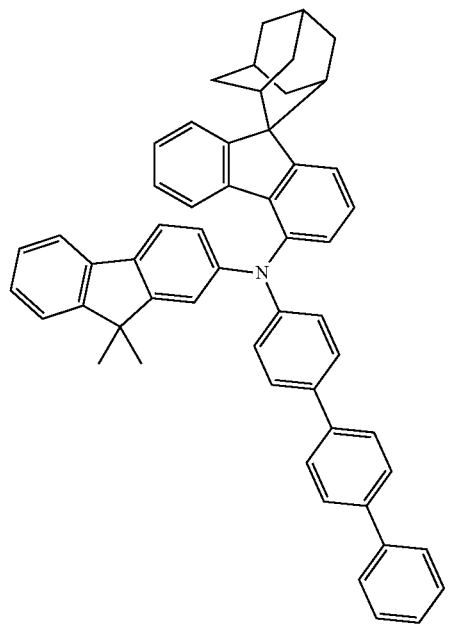
52
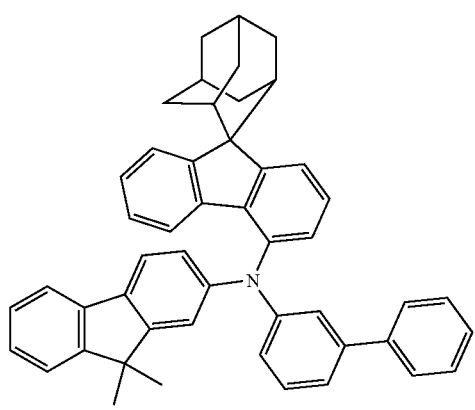
53
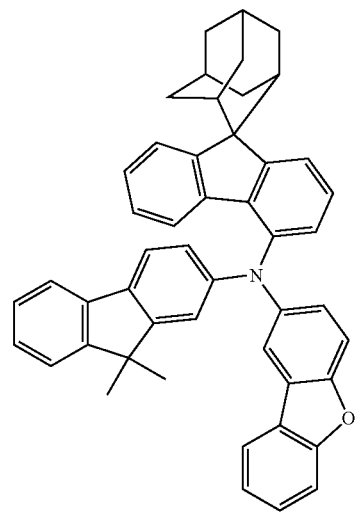
54
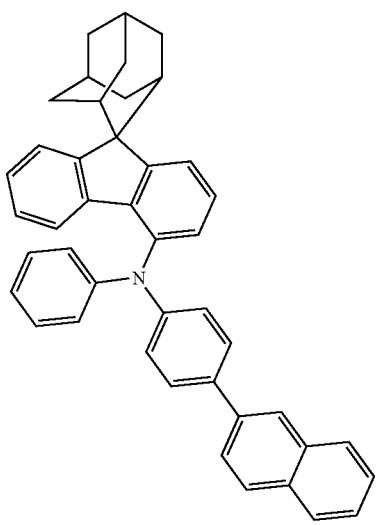
55
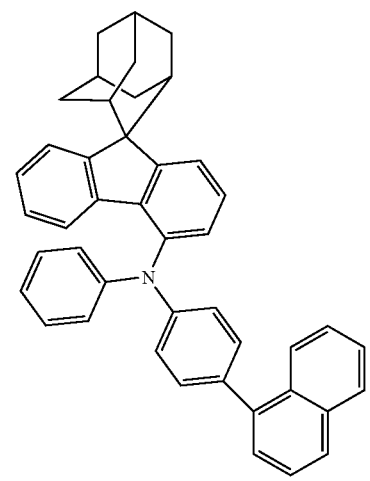
56
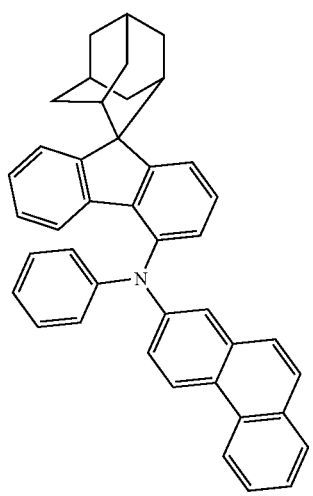

57
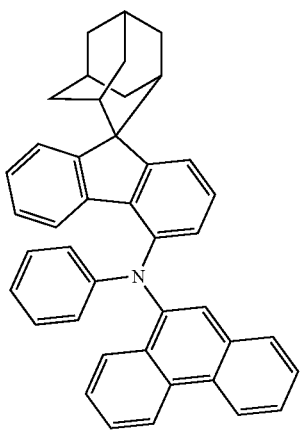
58
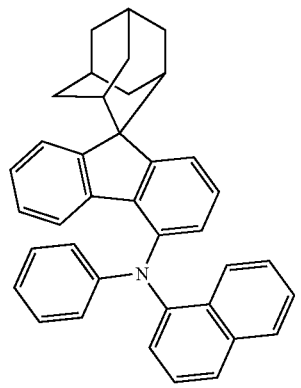
59
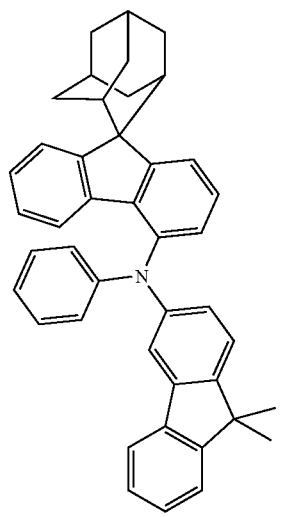
60
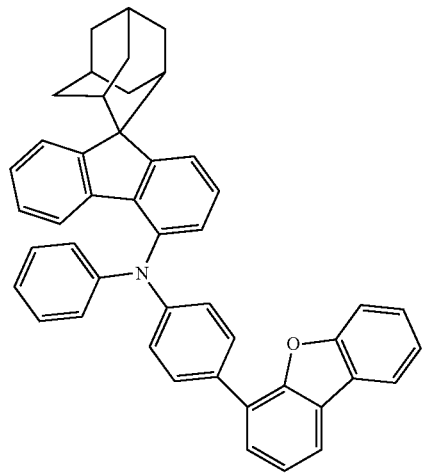
61
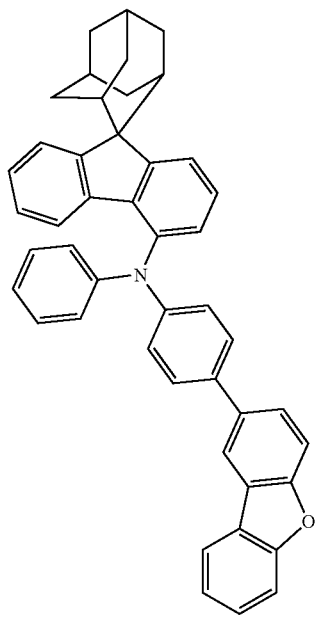
62
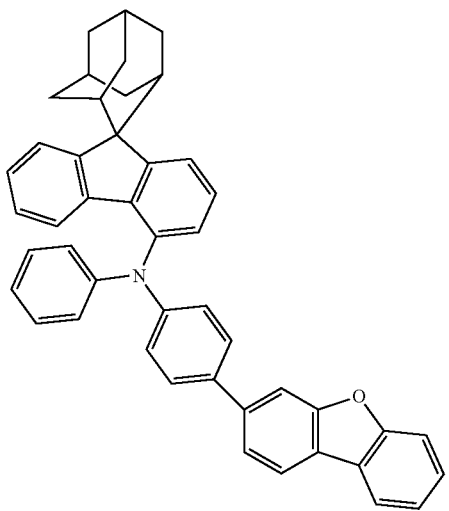

63
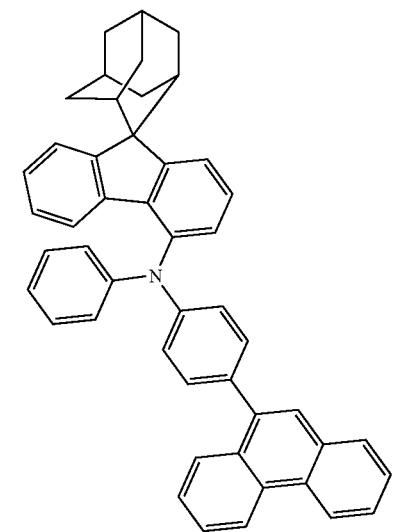
64
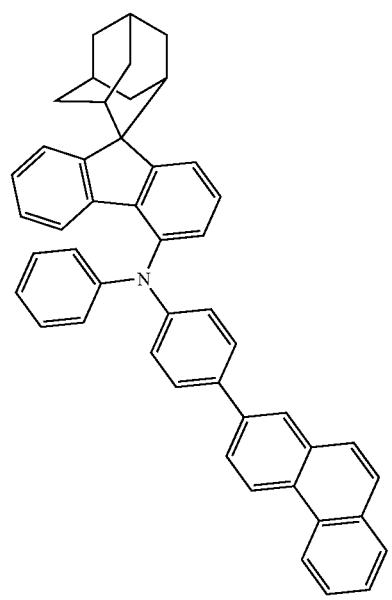
65
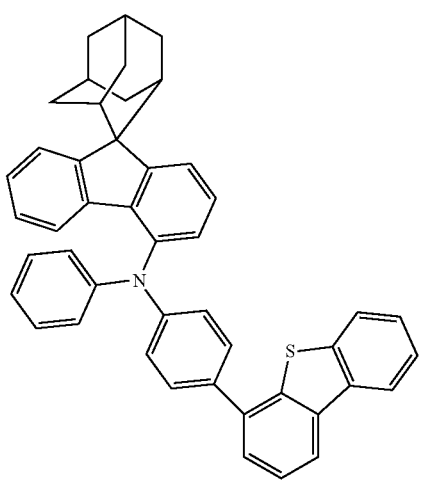
66
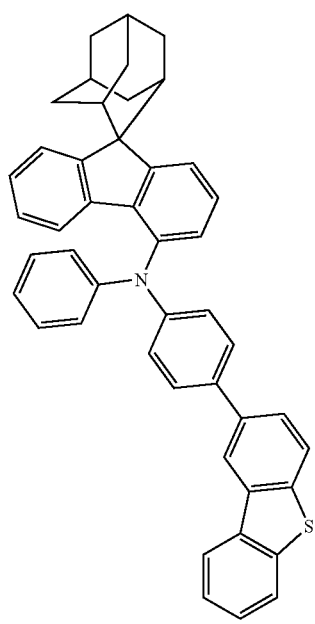
67
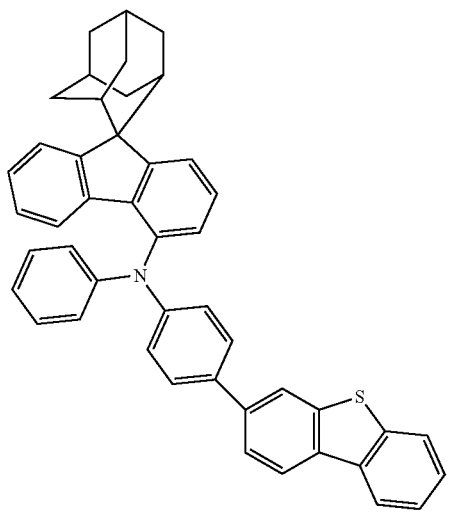
68
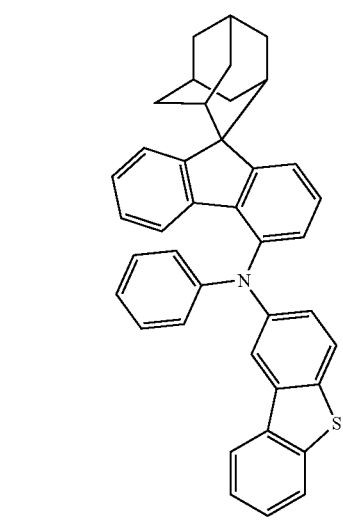

69
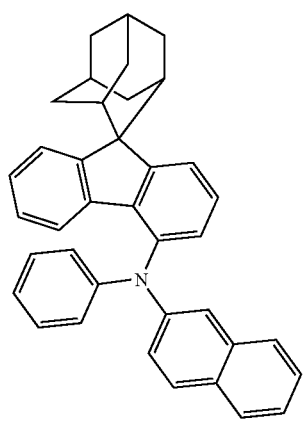
70
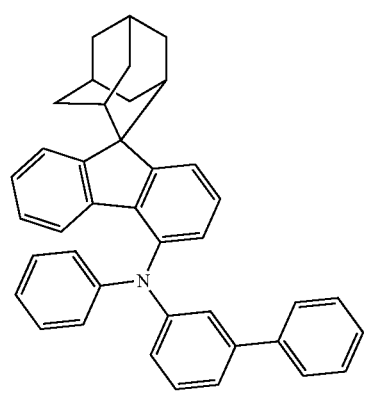
71
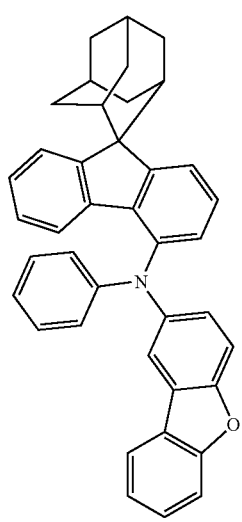
72
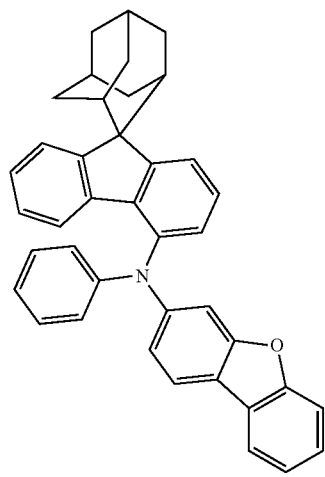
73
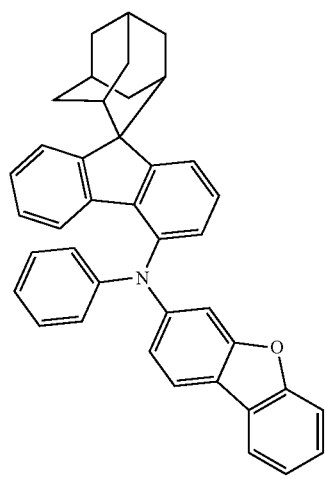
74
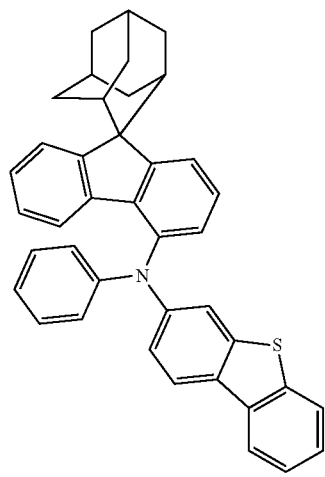

75
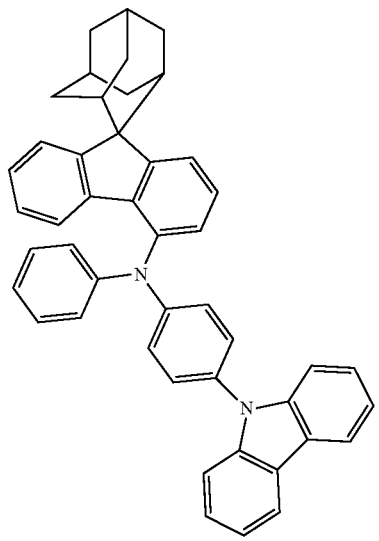
76
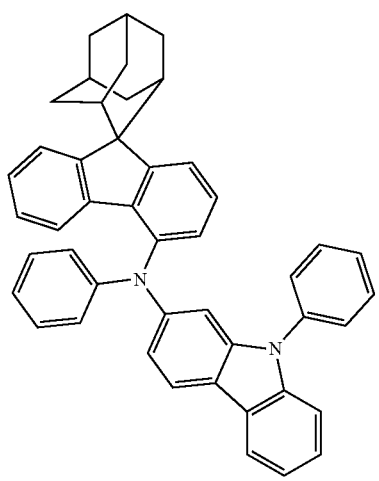
77
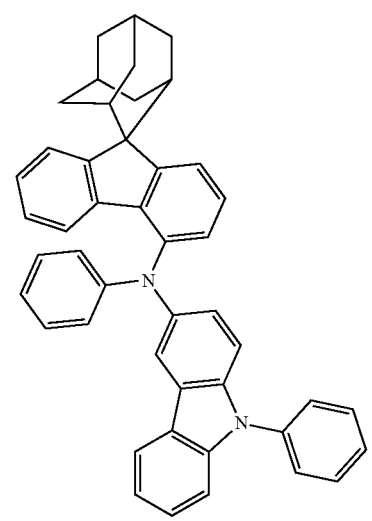
78
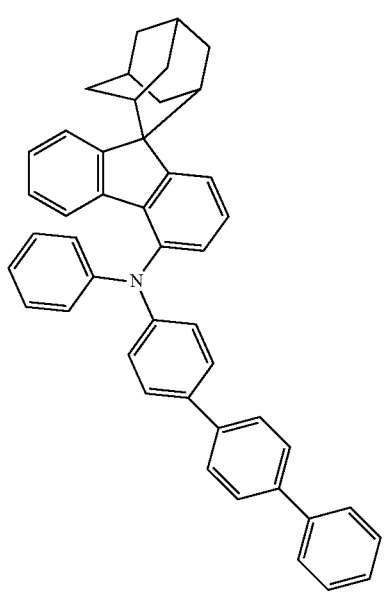
79
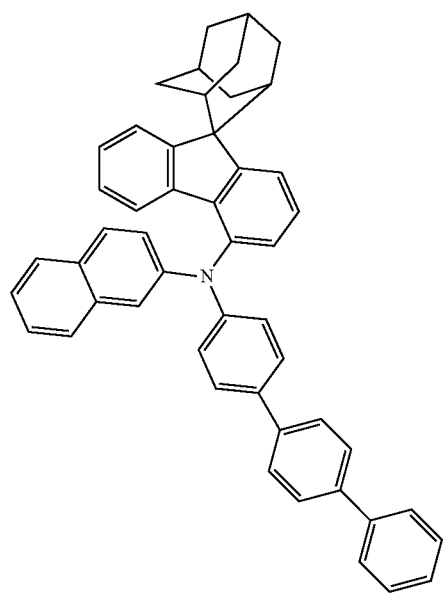
80
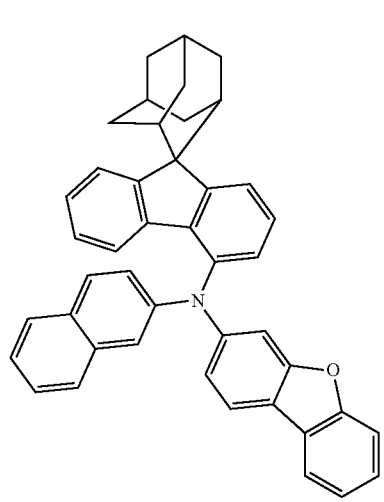

81
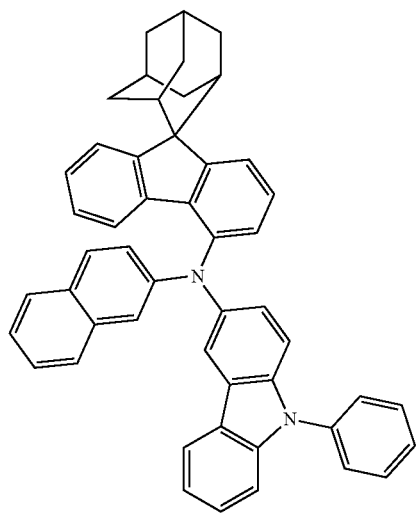
82
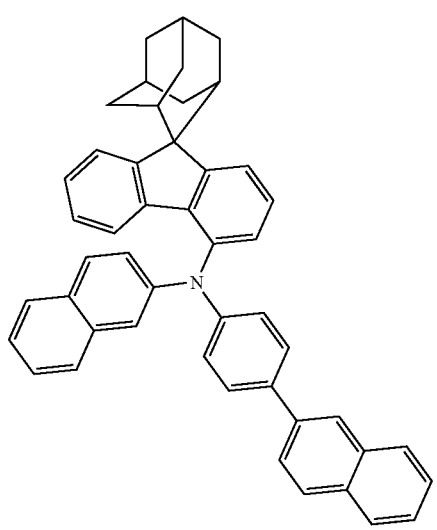
83
84
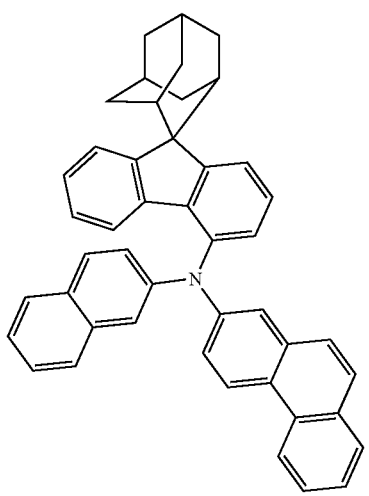
85
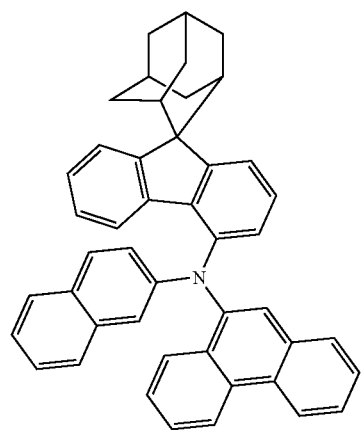
86
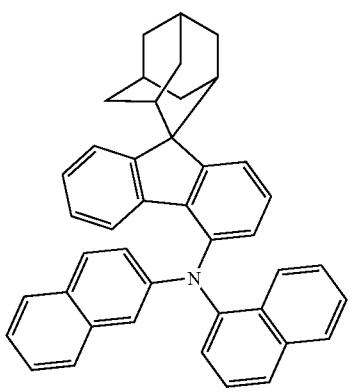

87
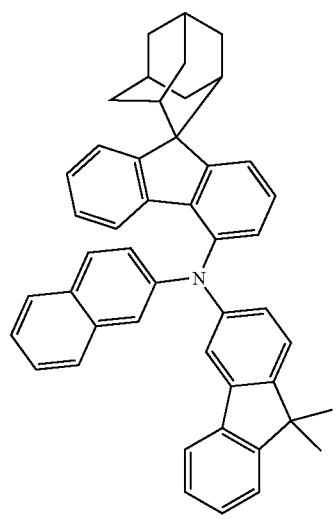
88
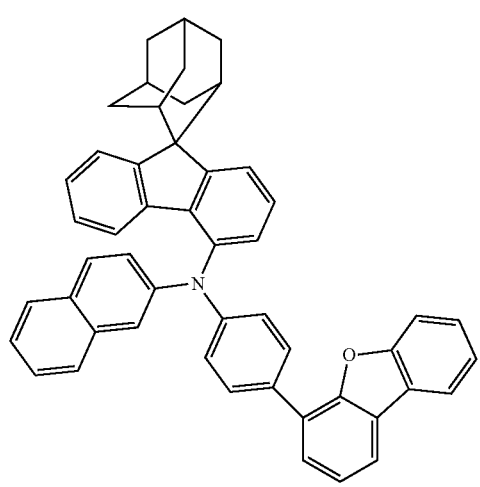
89
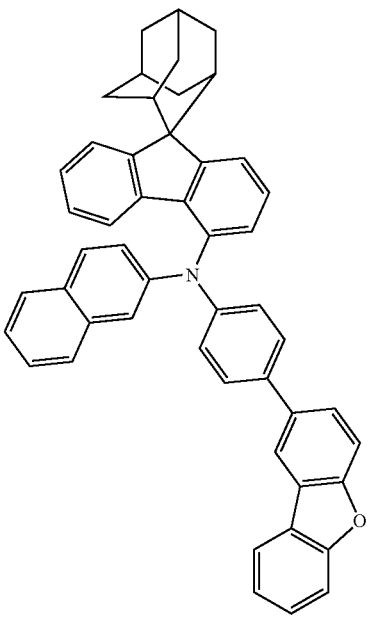
90
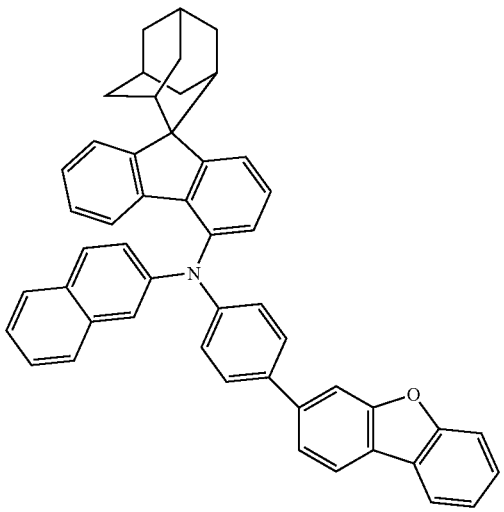
91
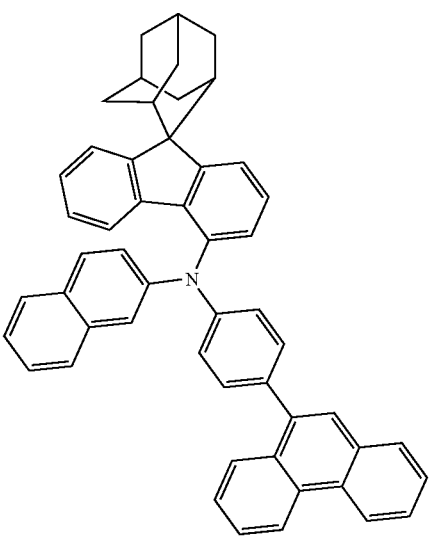
92
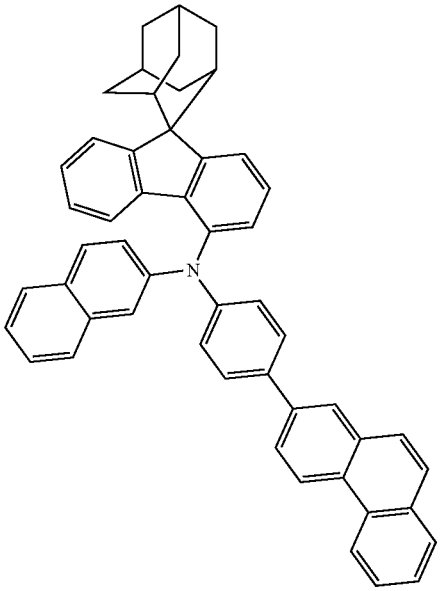

93
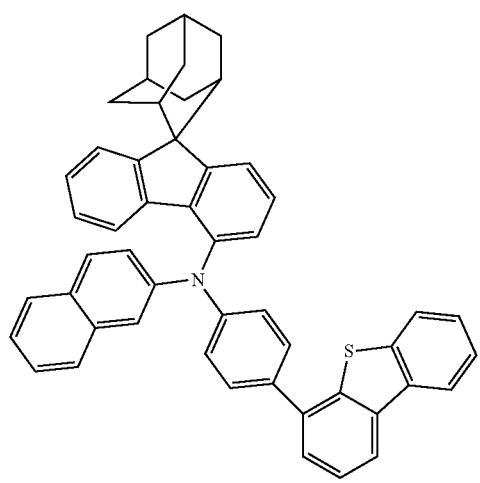
94
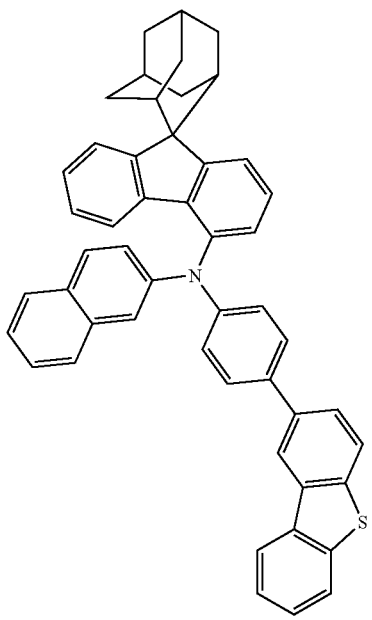
95
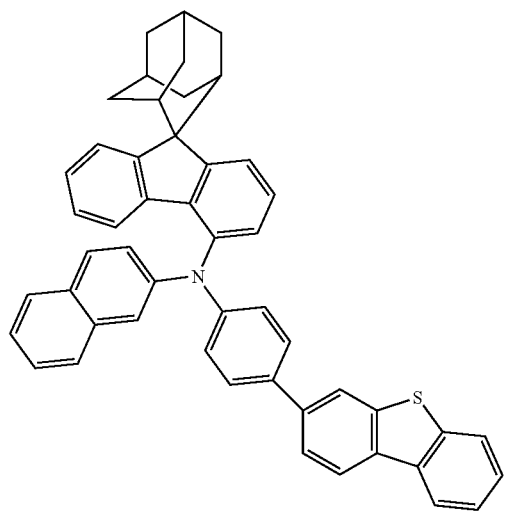
96
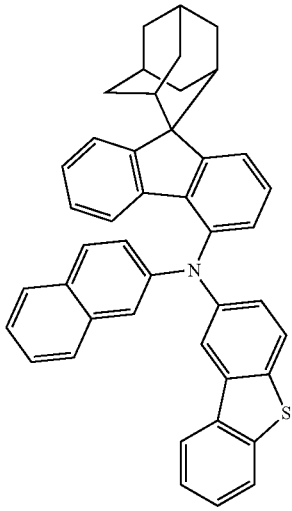
97
98
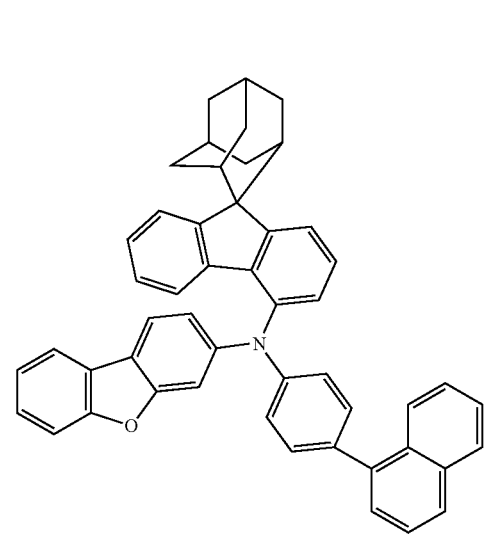

-continued
99
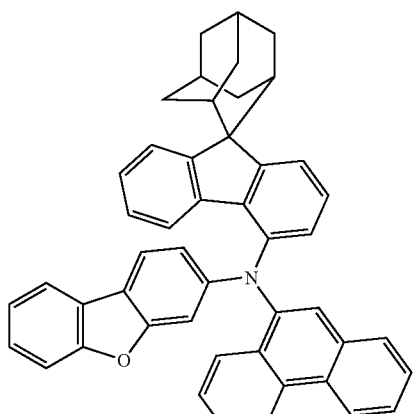
100
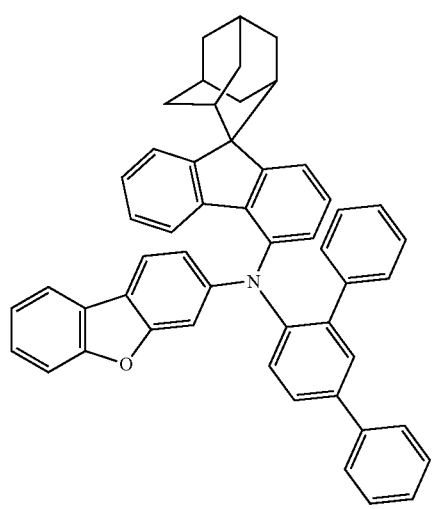
101
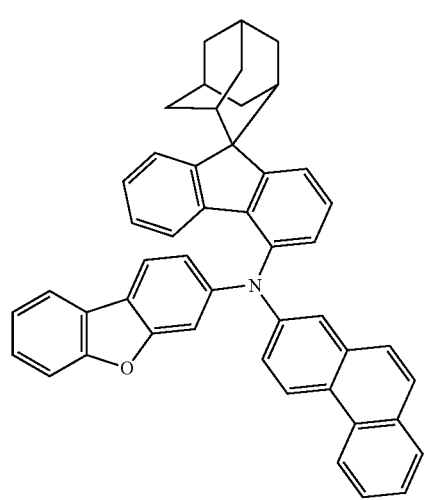
-continued
102
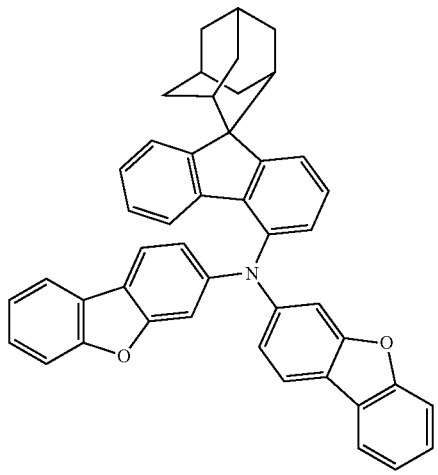
103
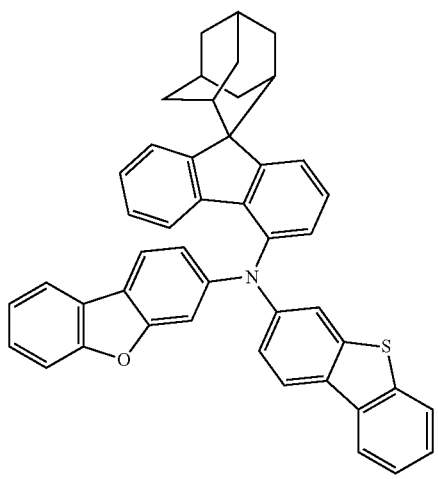
104
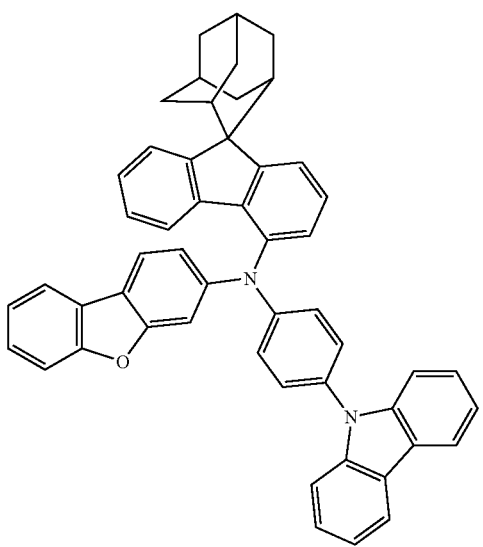

105
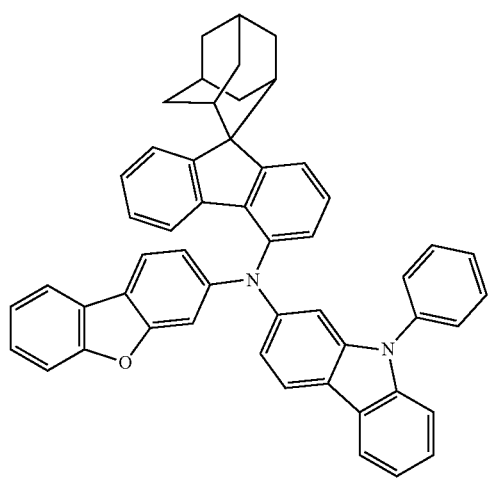
106
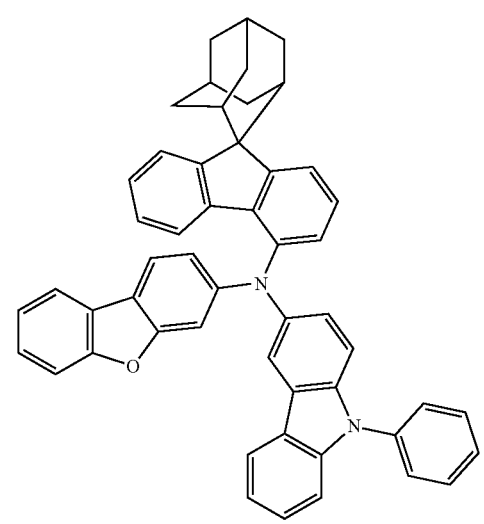
107
108
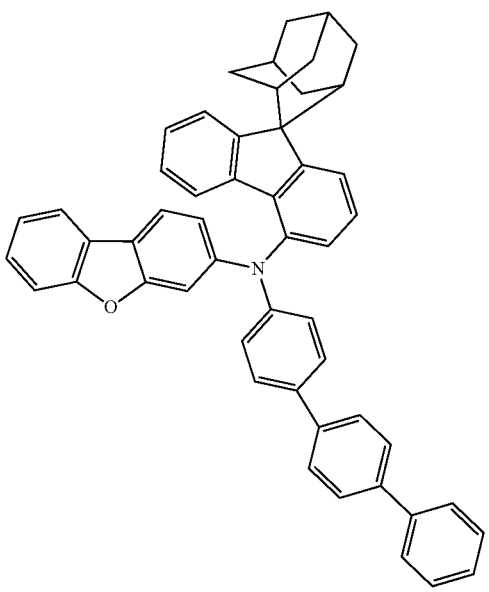
109
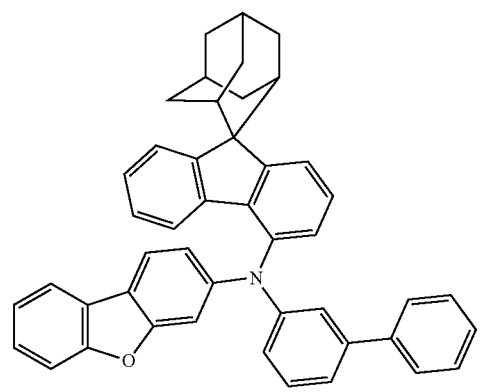
110
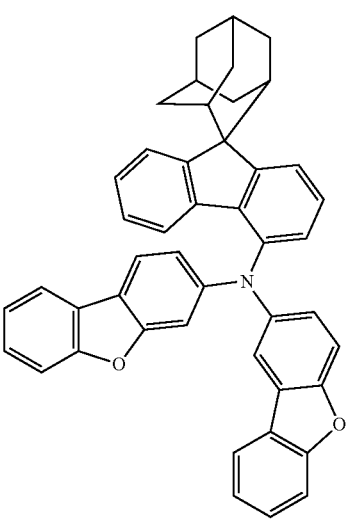

111 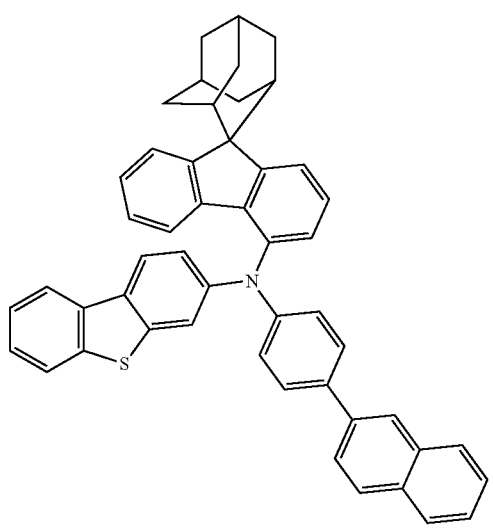
112 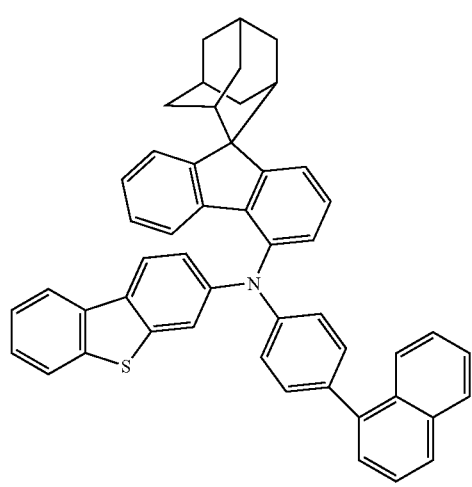
113 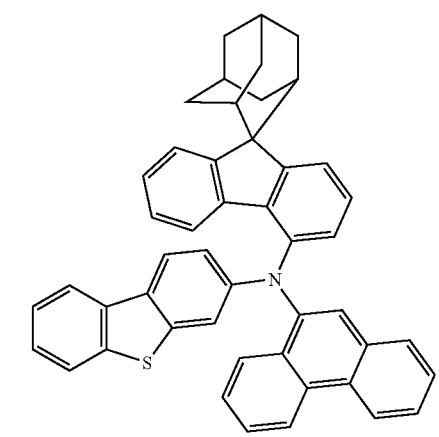
114 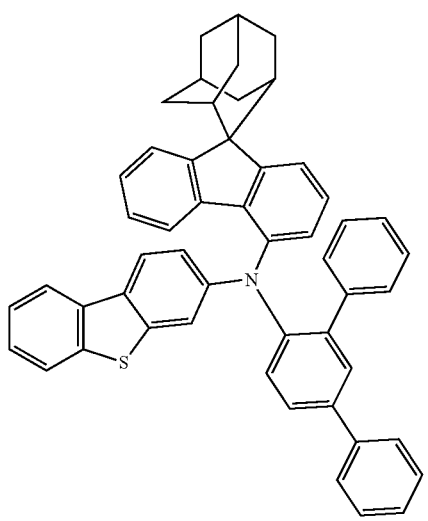
115 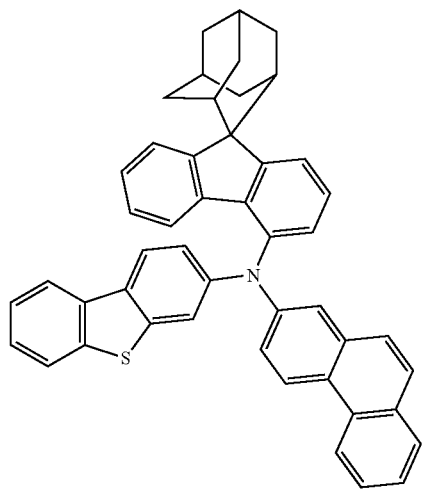
116 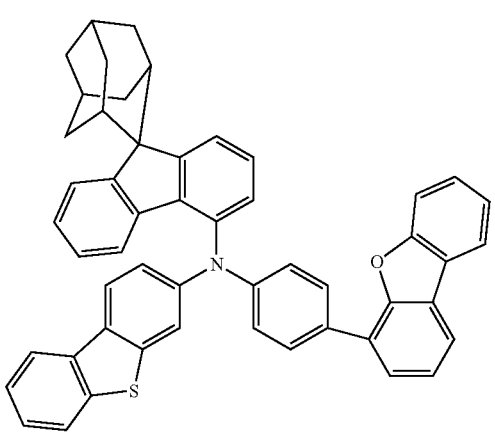

-continued
117
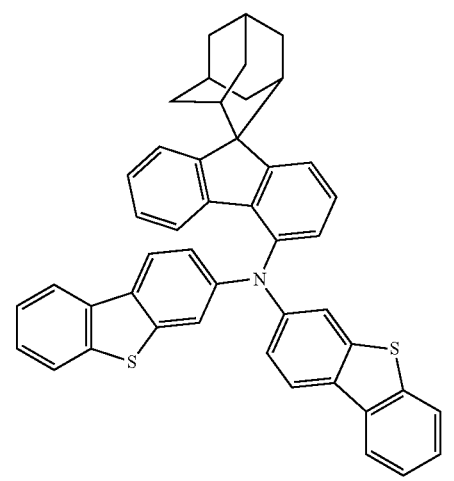
118
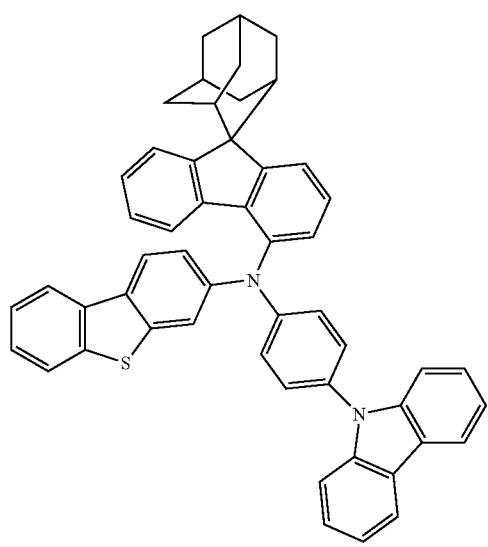
119
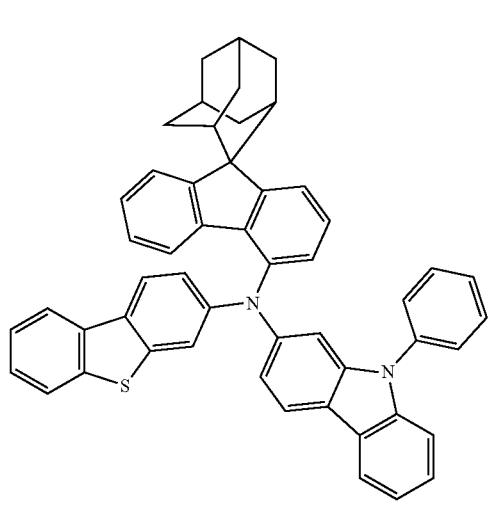
-continued
120
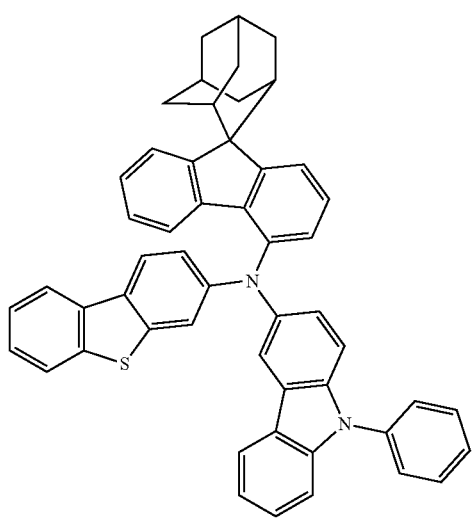
121
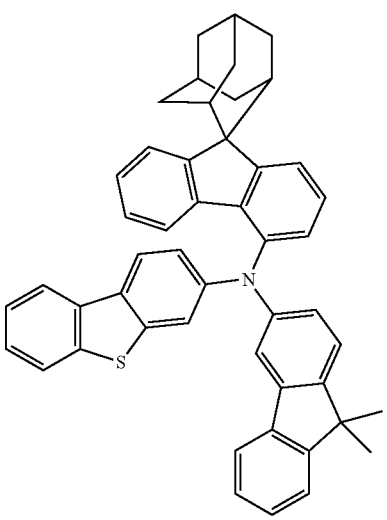
122
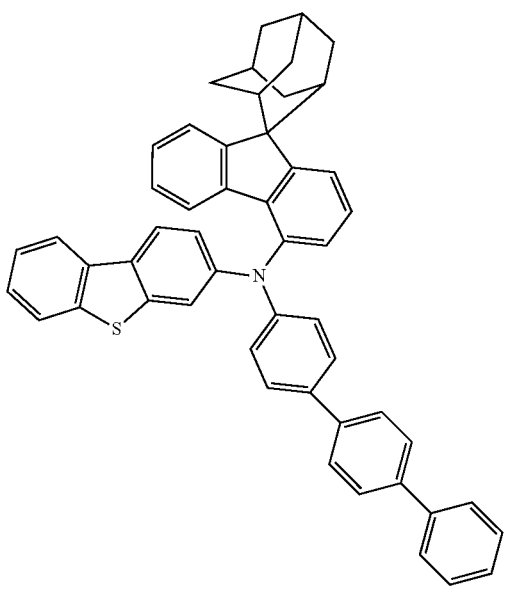

123
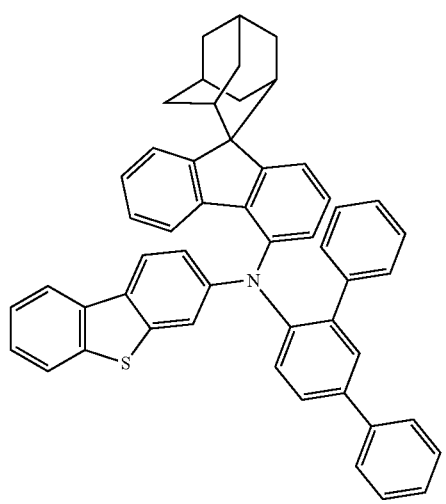
124
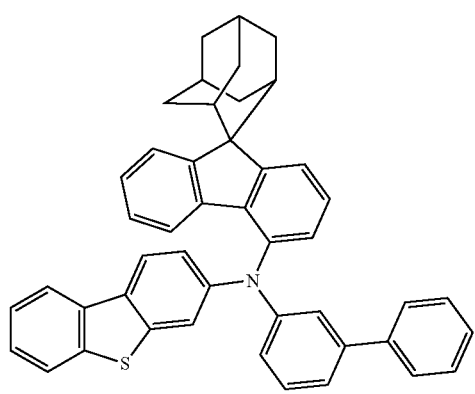
125
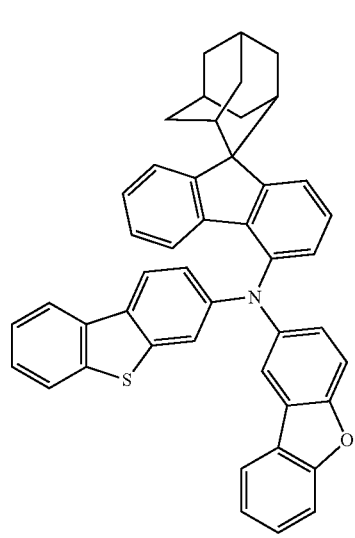
126
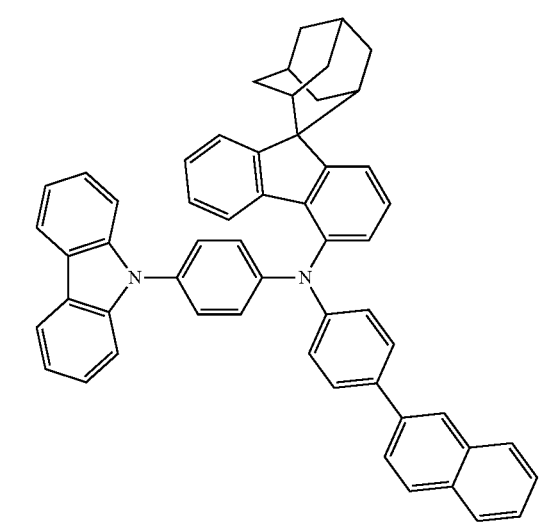
127
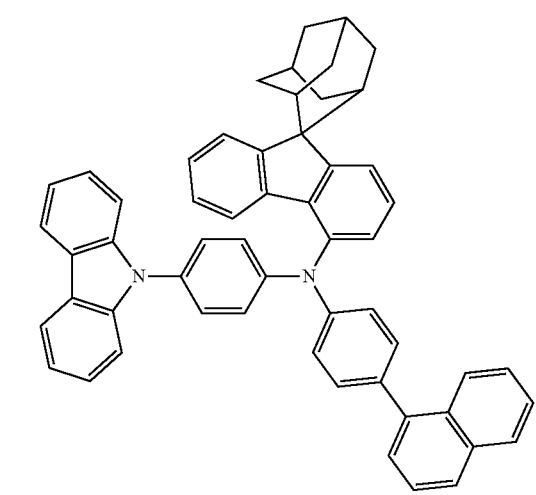
128
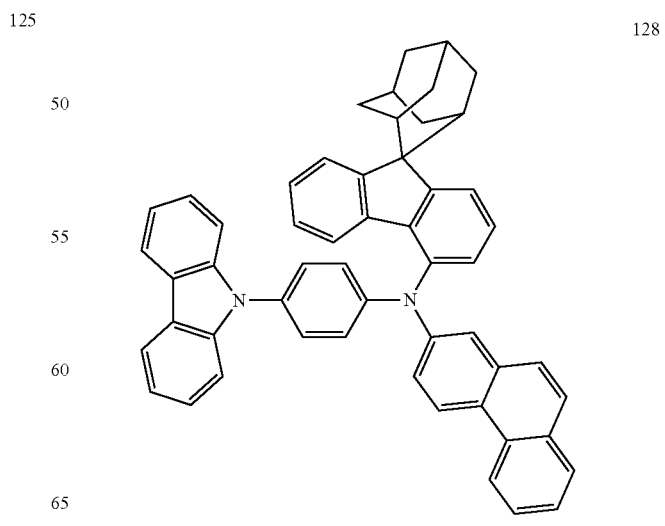

-continued
129
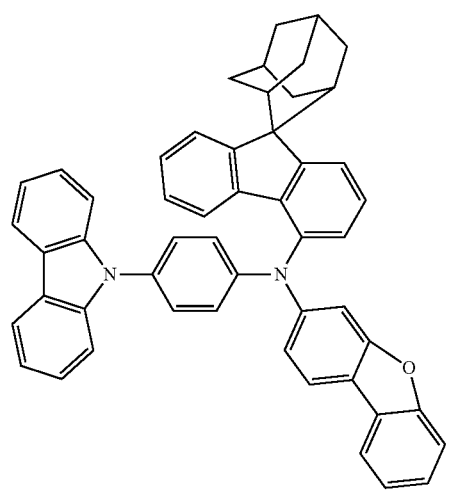
130
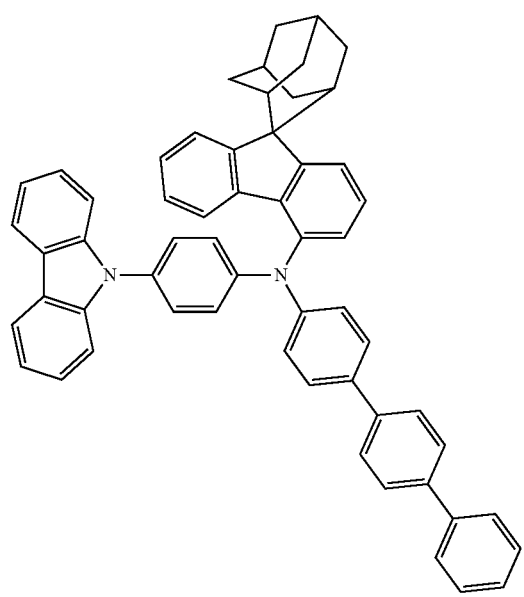
131
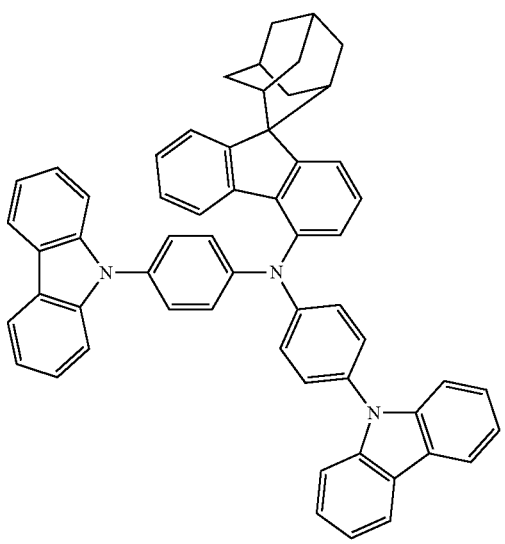
-continued
132
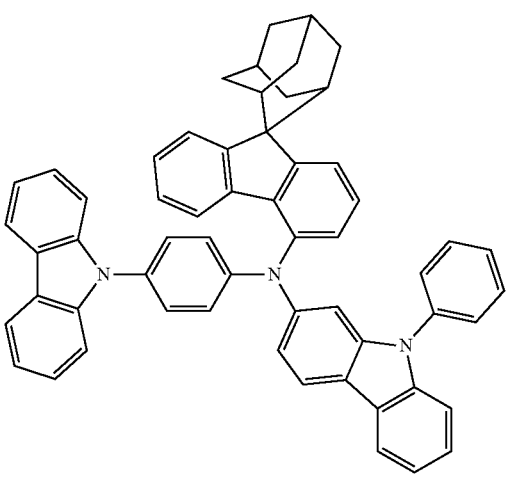
133
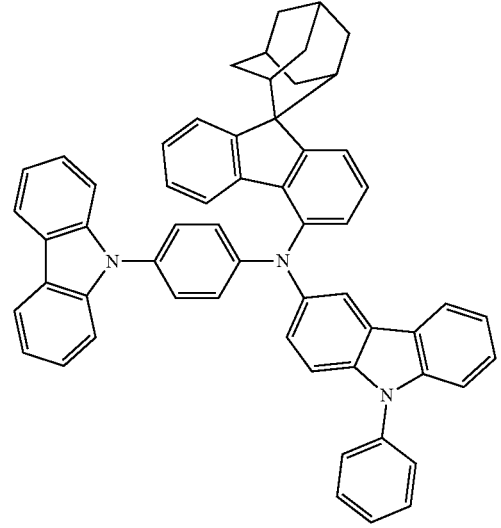
134
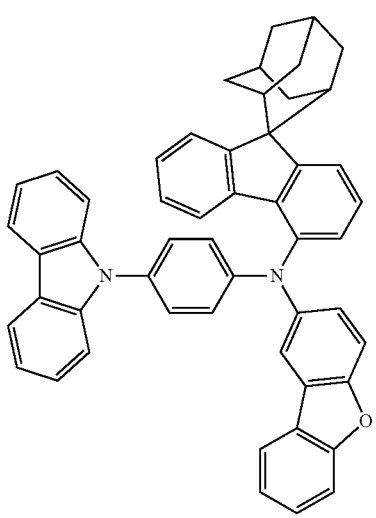

75
-continued
135
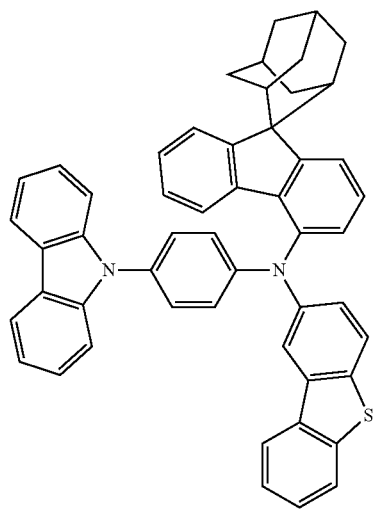
136
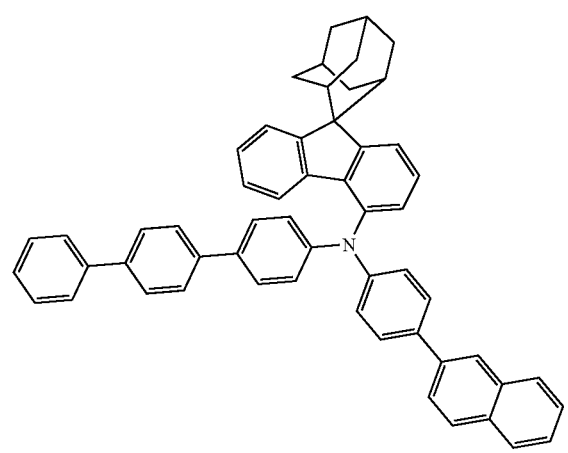
137
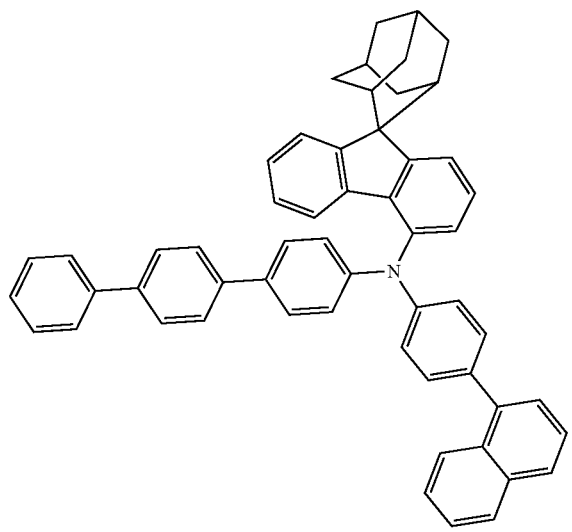
76
-continued
138
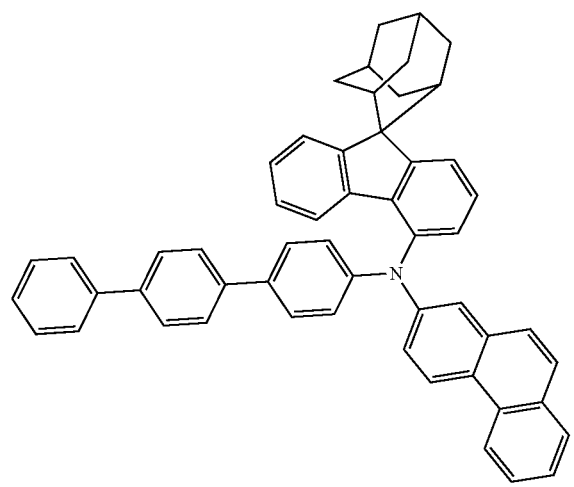
139
140
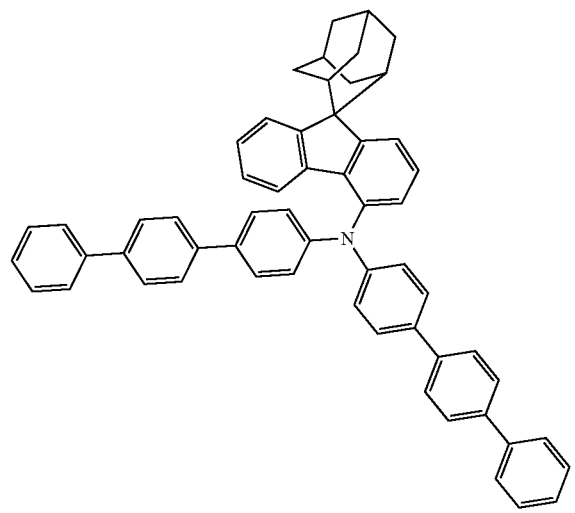

141
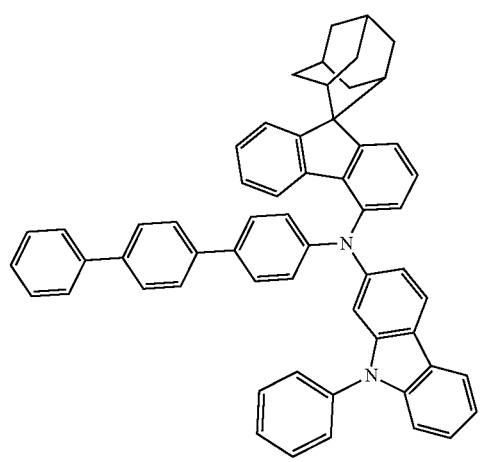
142
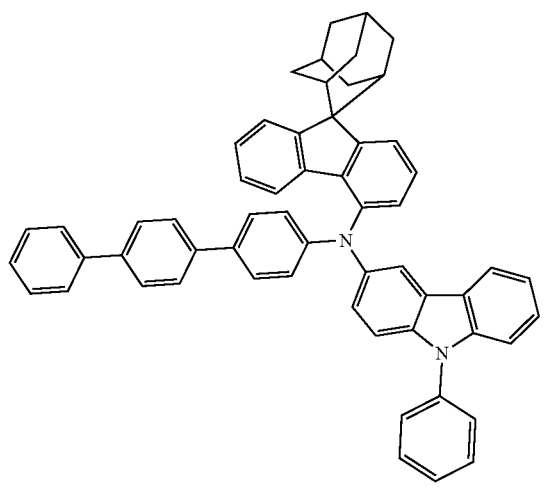
143
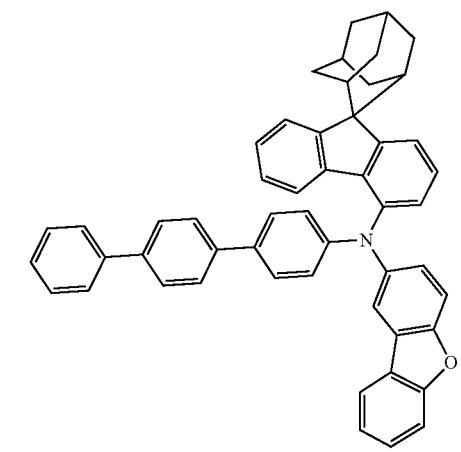
144
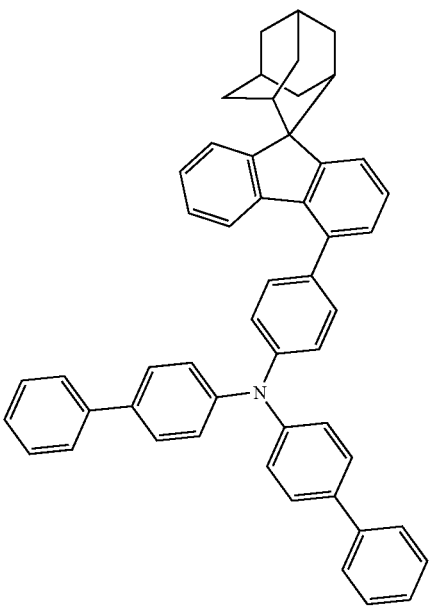
145
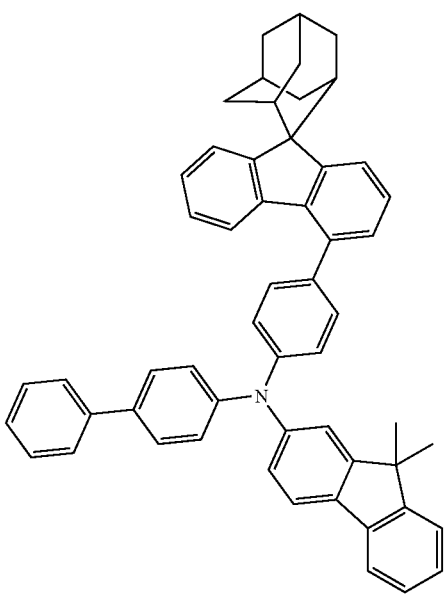

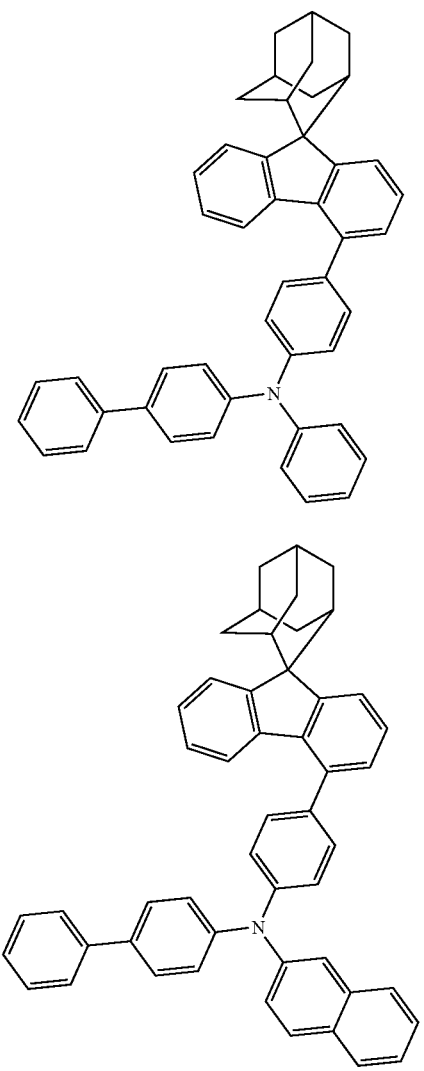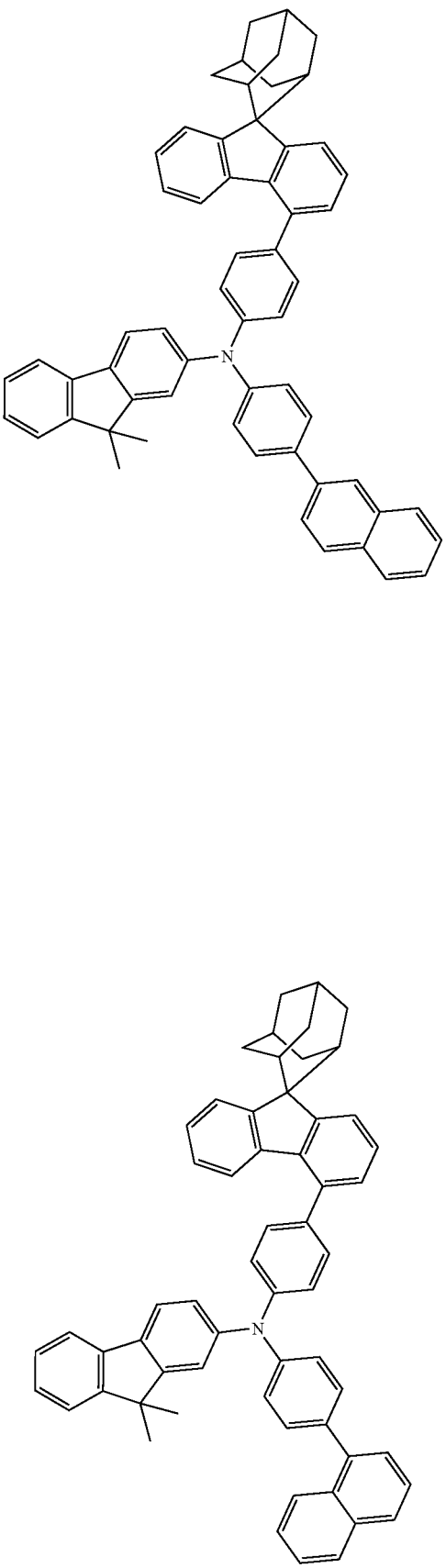

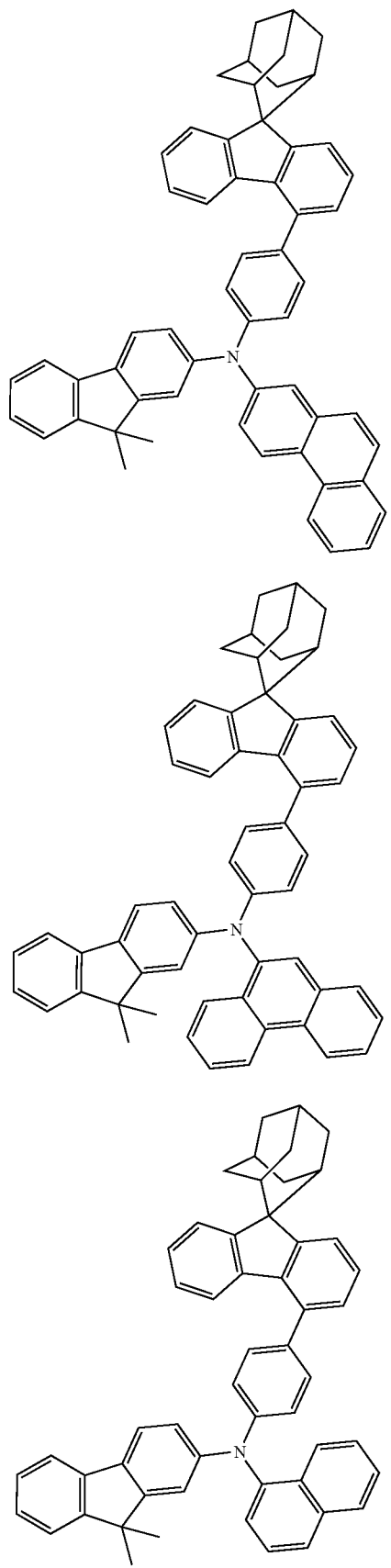

-continued
156
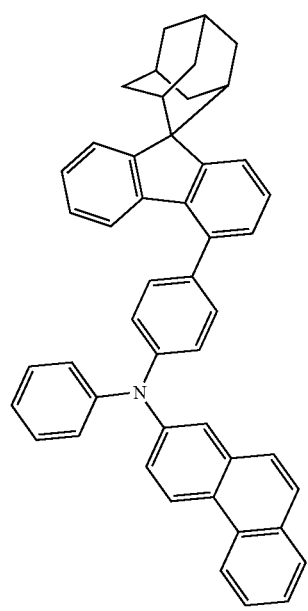
157
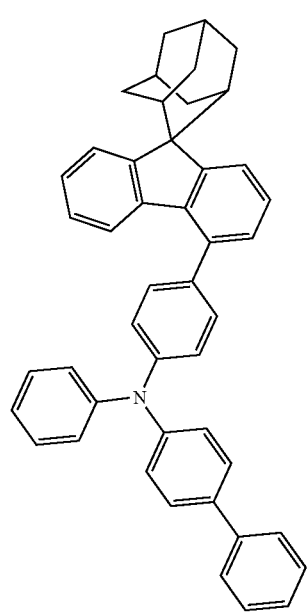
158
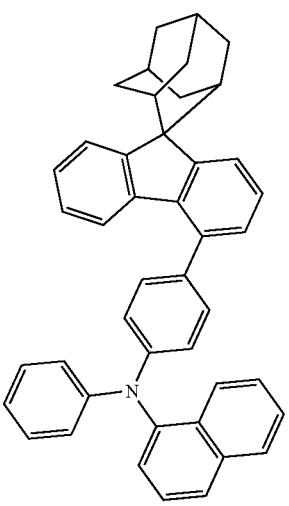
159
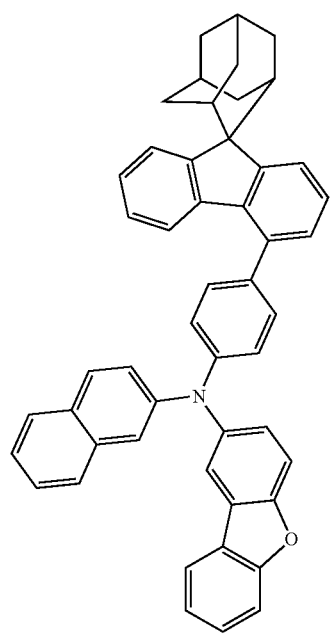
160
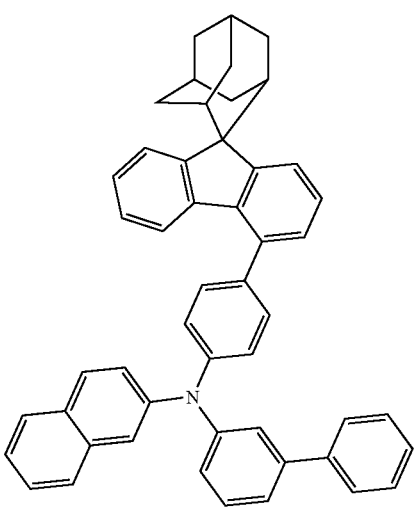

161
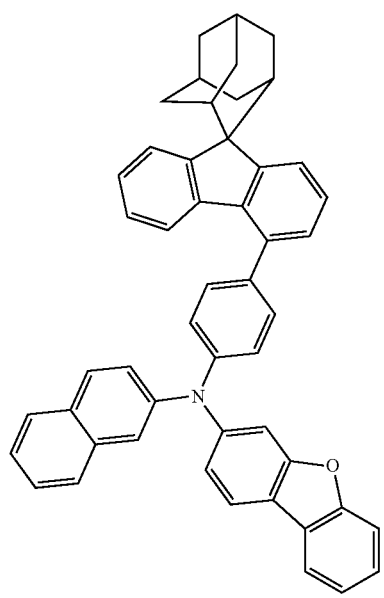
162
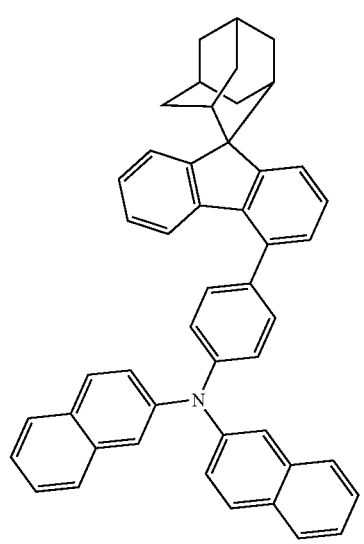
163
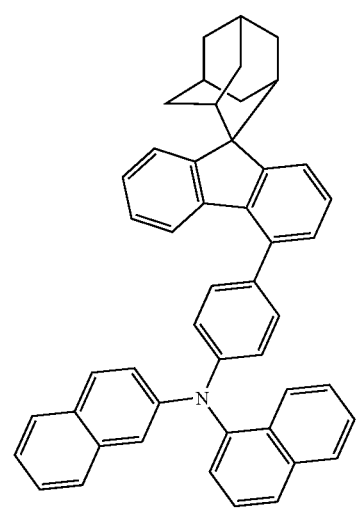
164
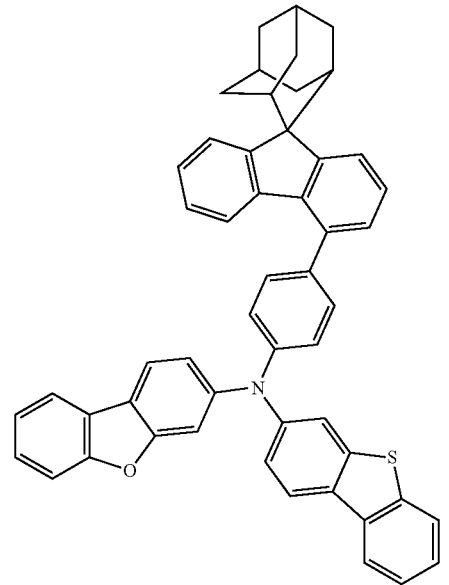
165
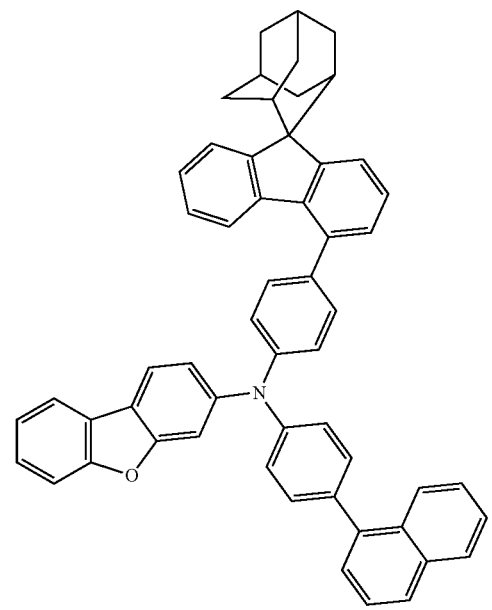

166
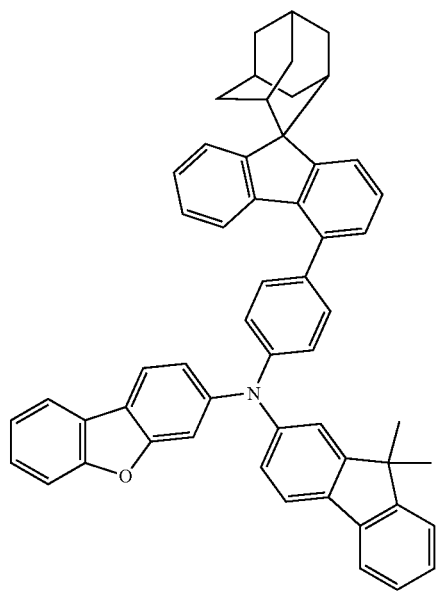
168
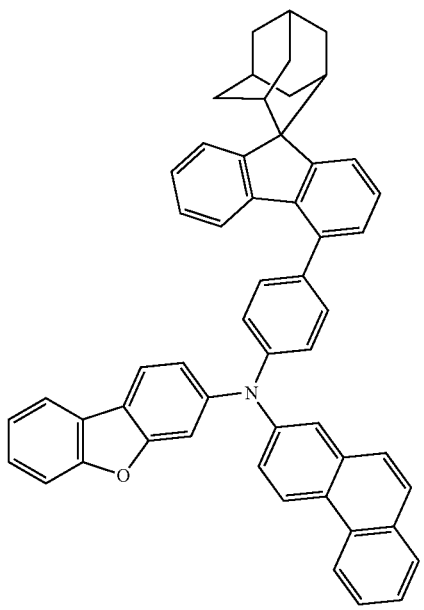
167
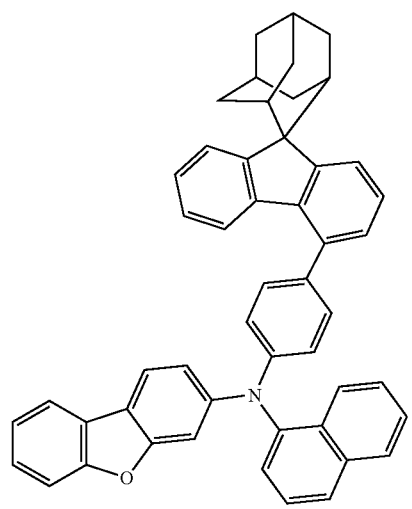
169
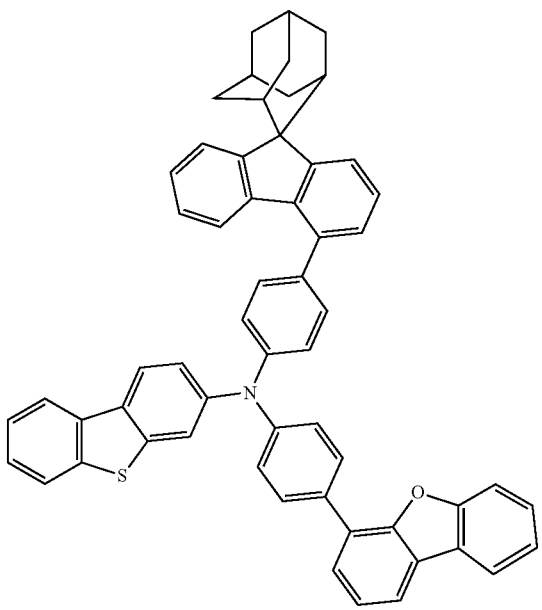

170
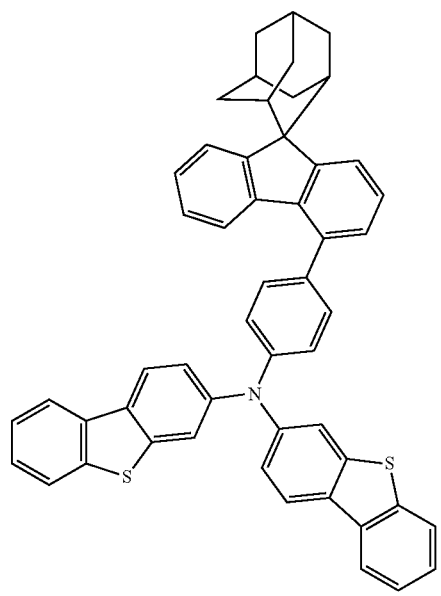
171
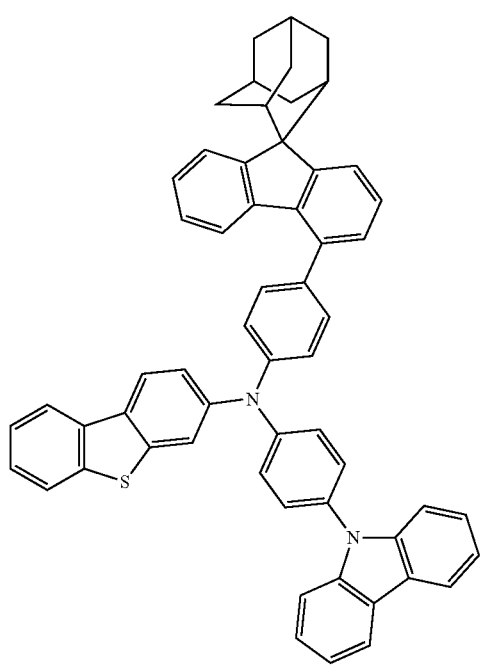
172
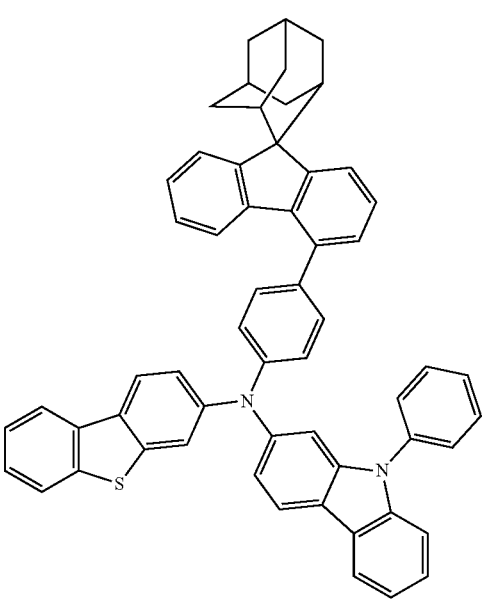
173
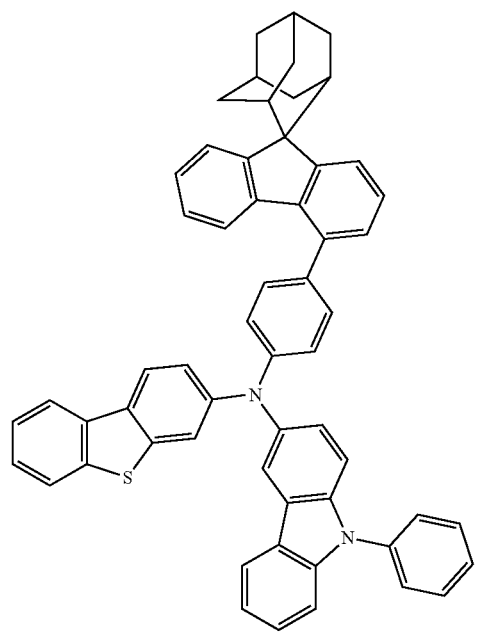

174
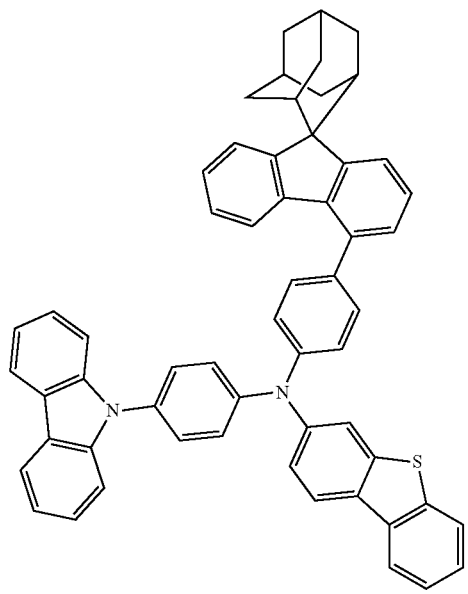
176
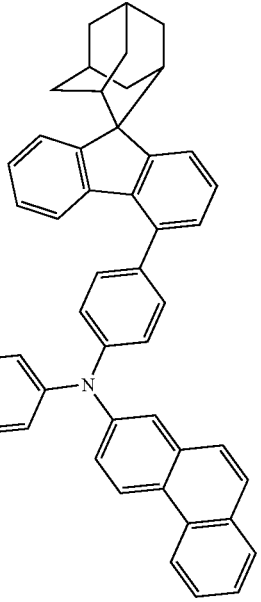
175
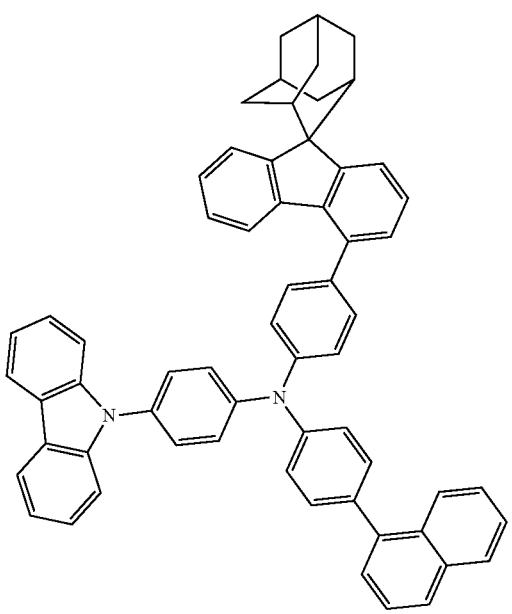
177
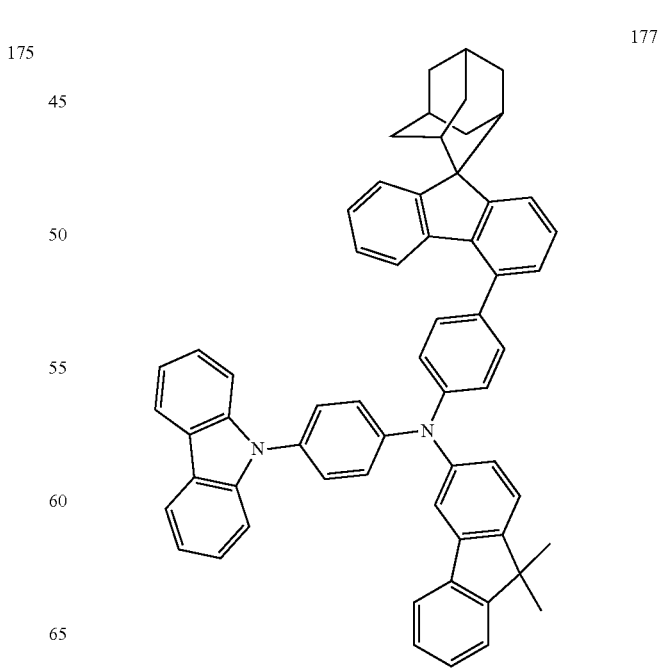

178
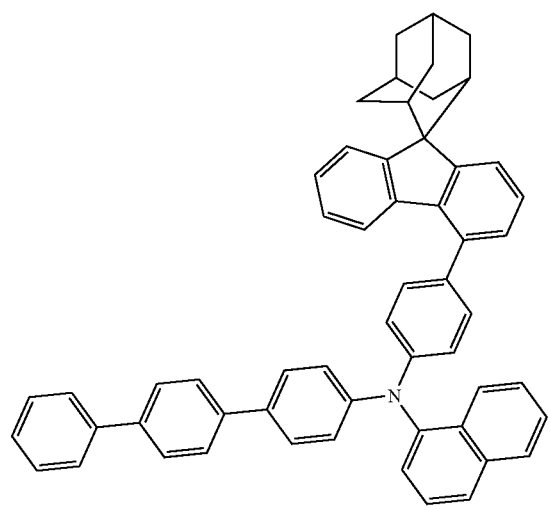
179
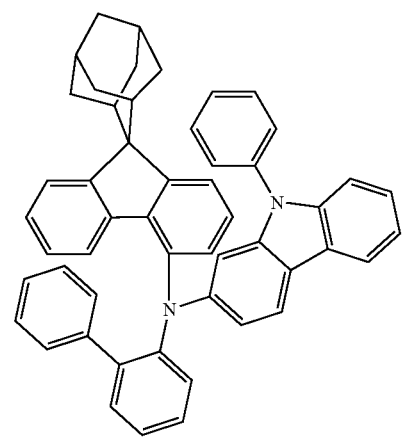
180
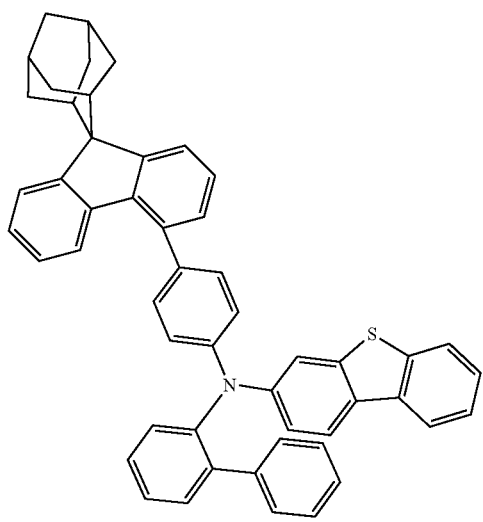
181
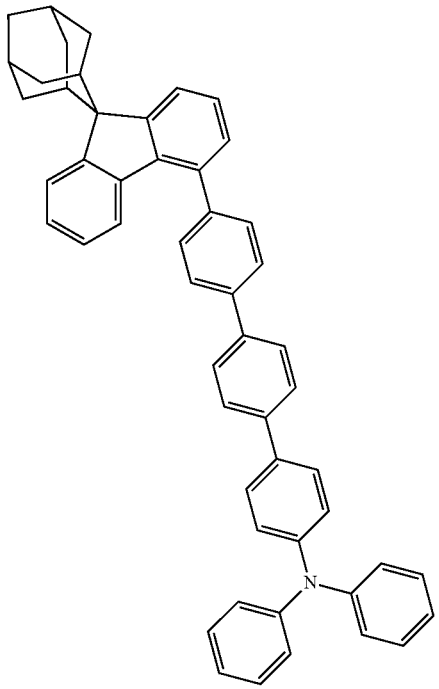
182
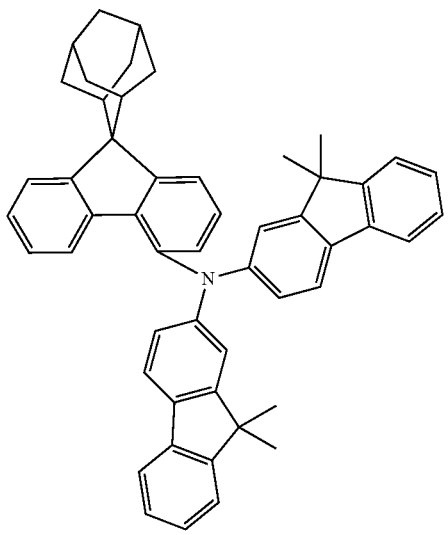

183

184

185

186

187

188

189
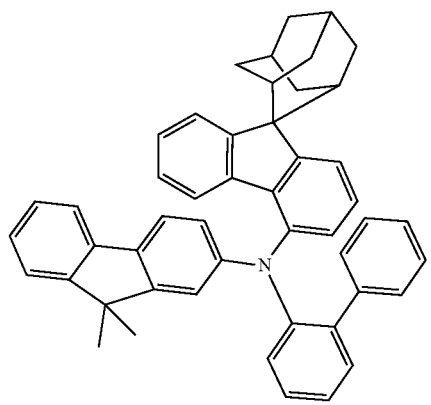
190
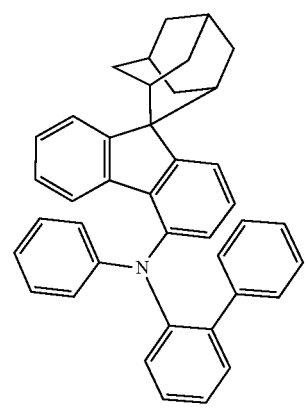
191
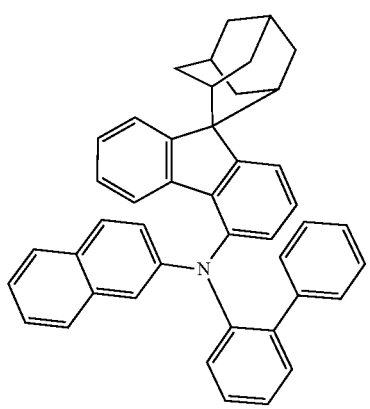
192
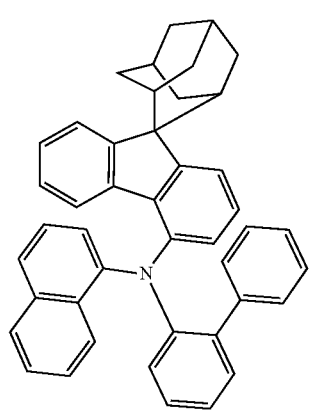
193
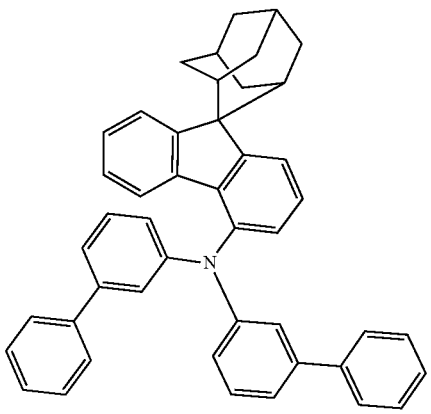
194
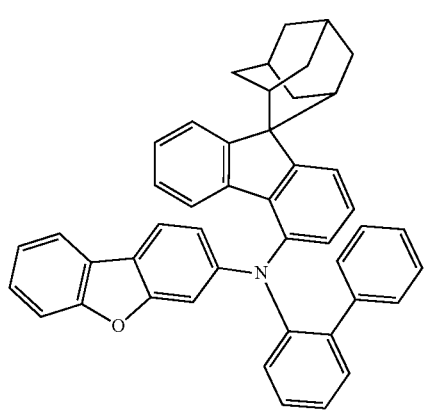
195
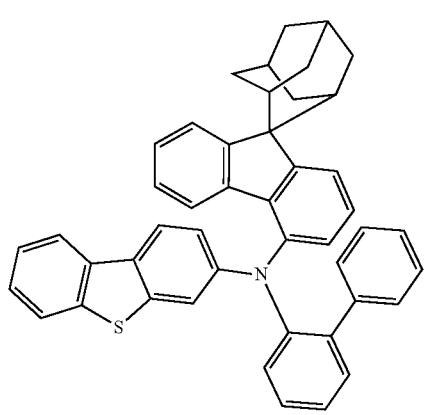
196
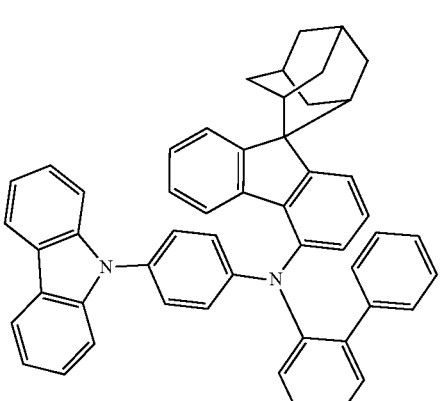

197 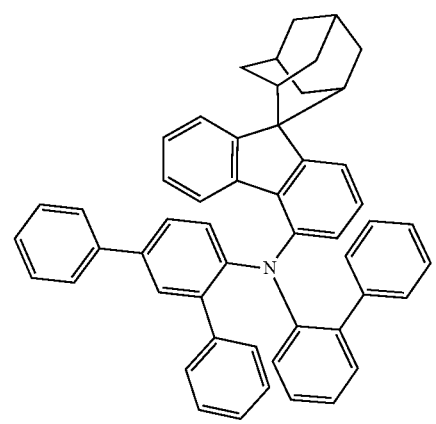
198 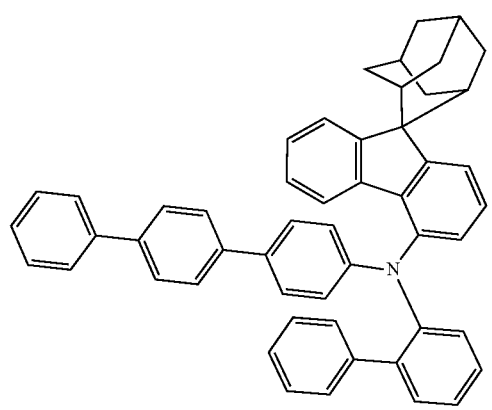
199 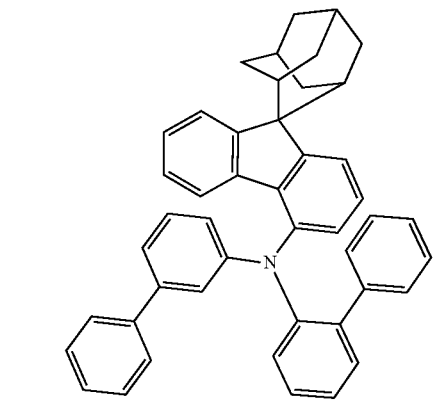
200 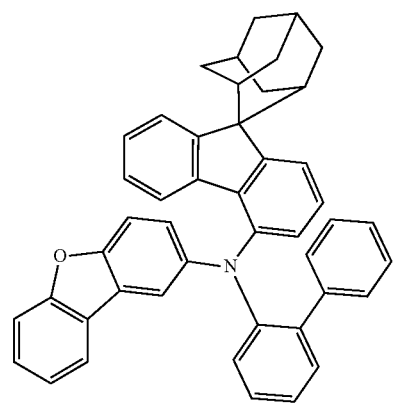
201 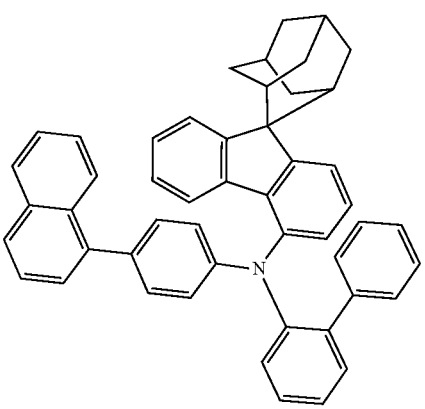
202 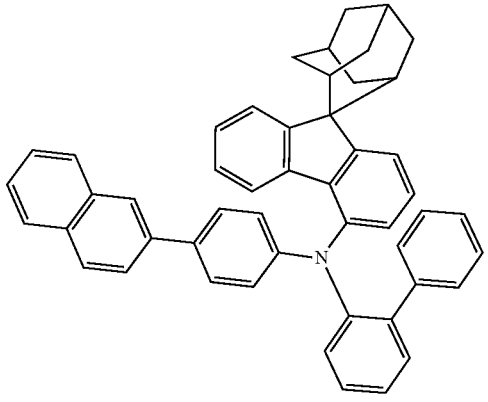
203 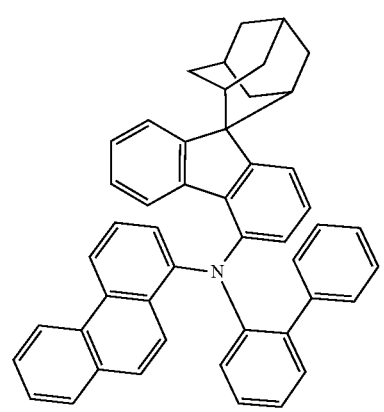
204 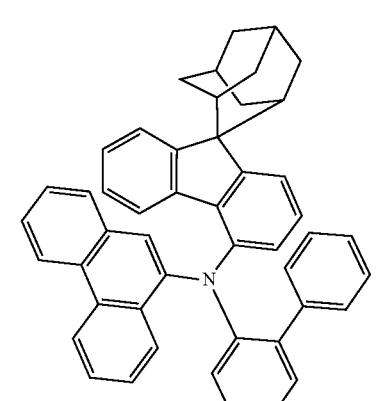

205
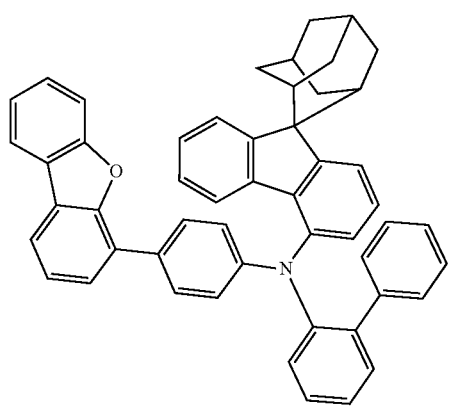
208
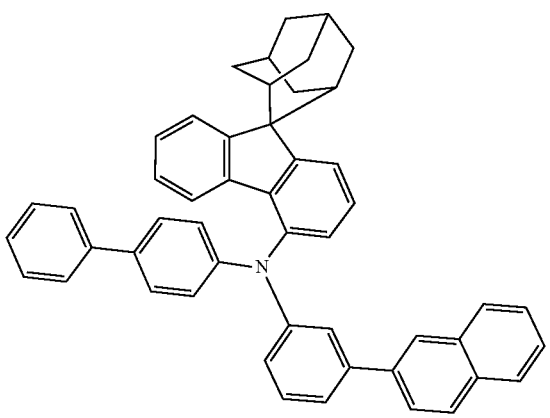
206
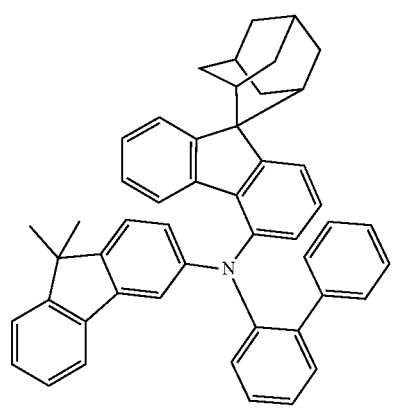
209
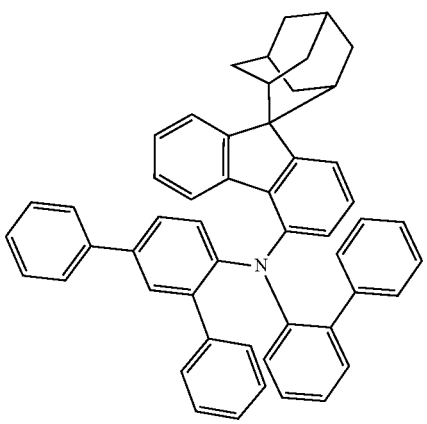
207
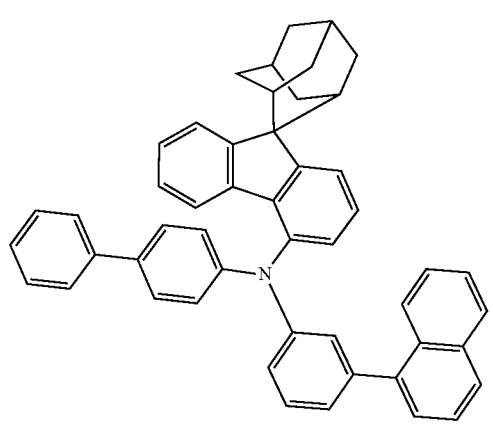
210
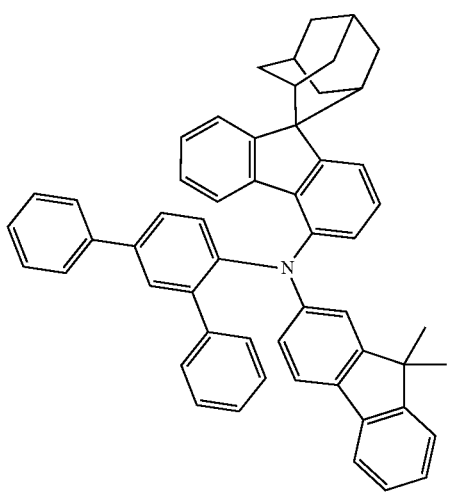

211
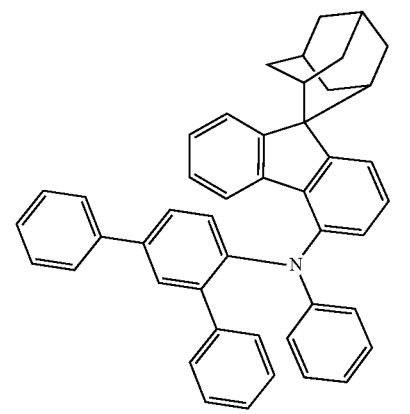
212
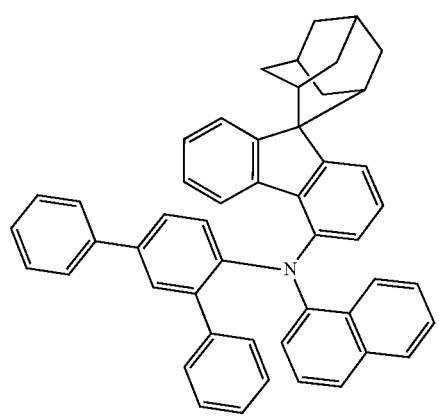
213
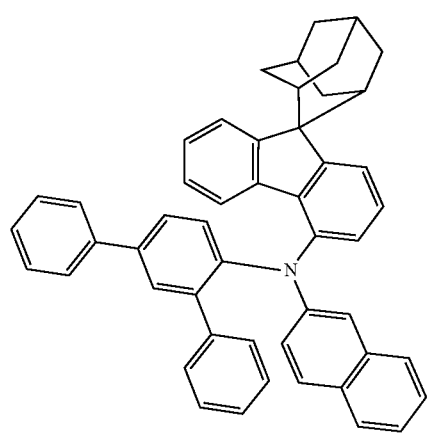
214
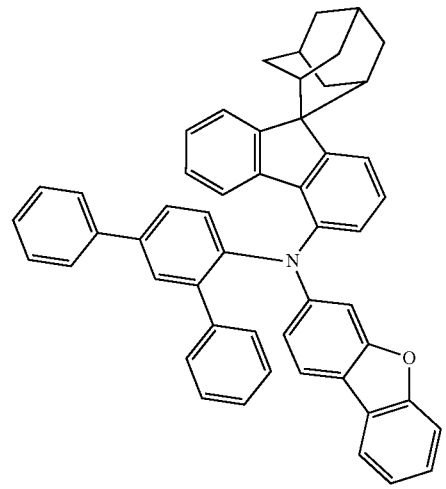
215
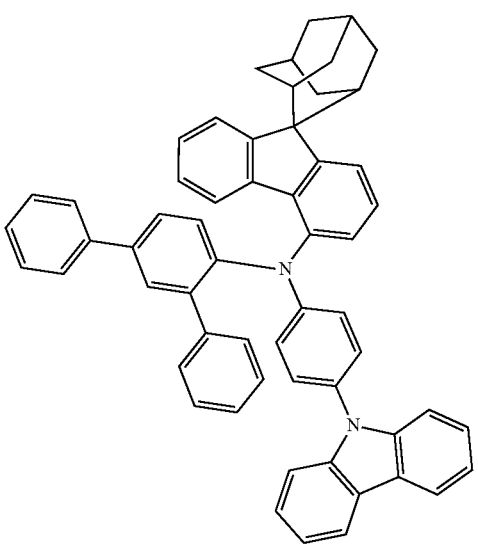
216
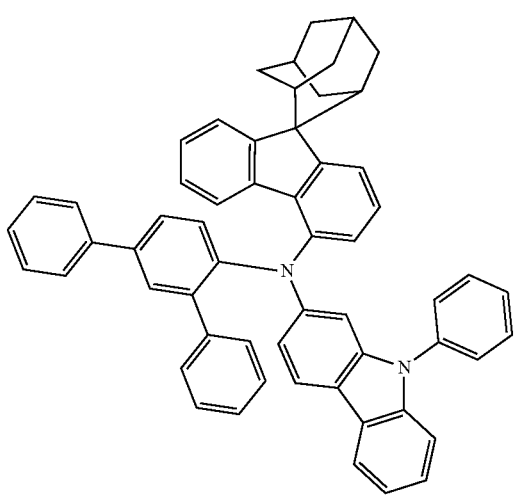

217
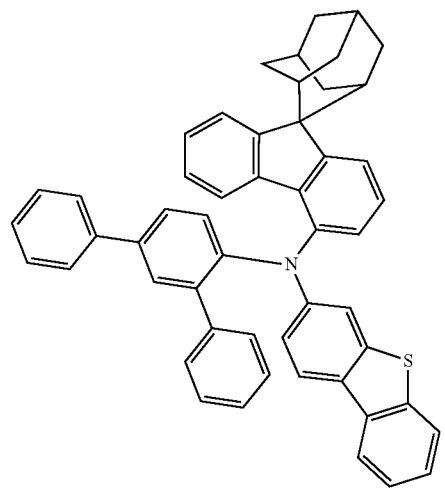
218
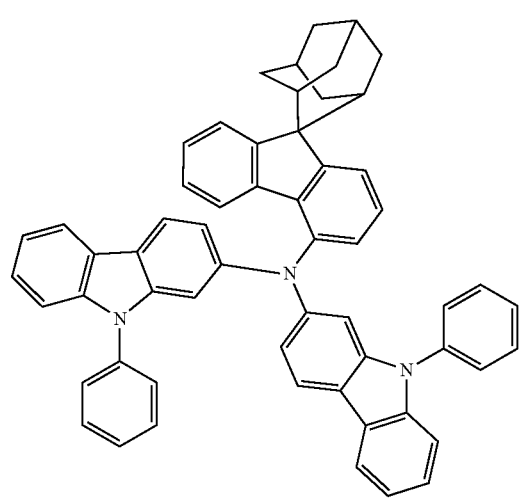
219
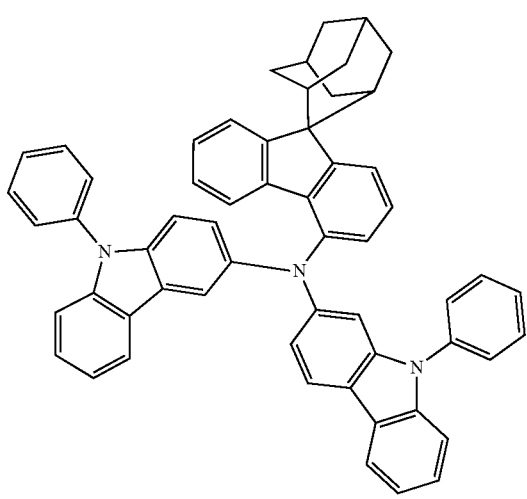
220
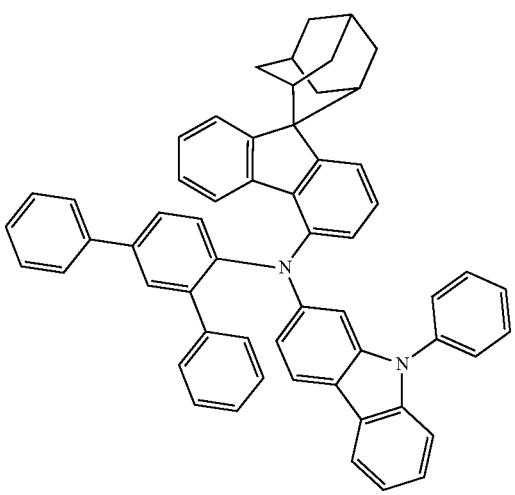
221
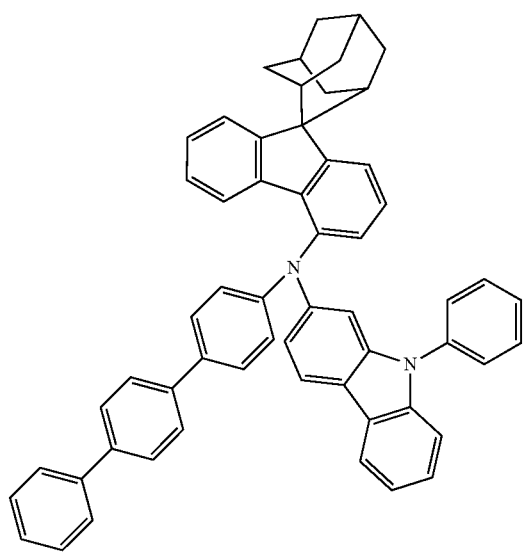
222
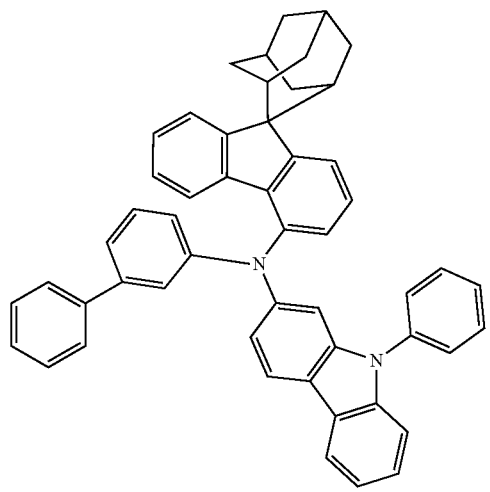

223
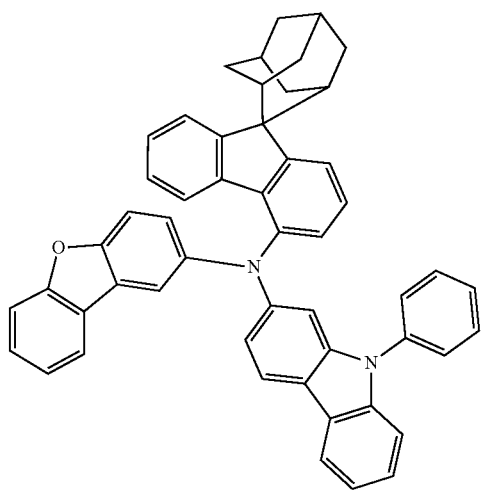
224
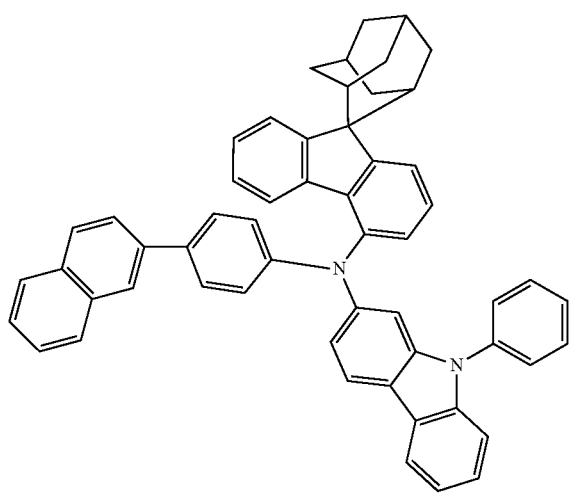
225
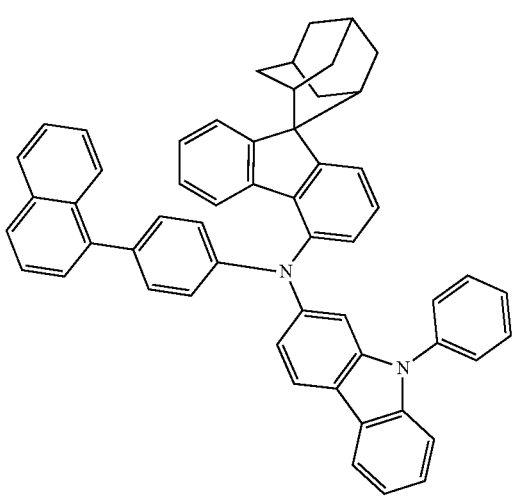
226
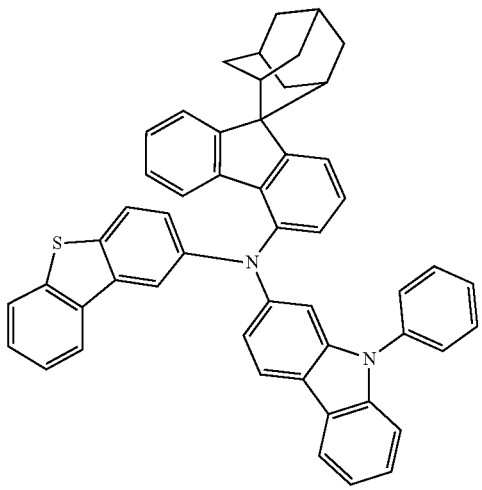
227
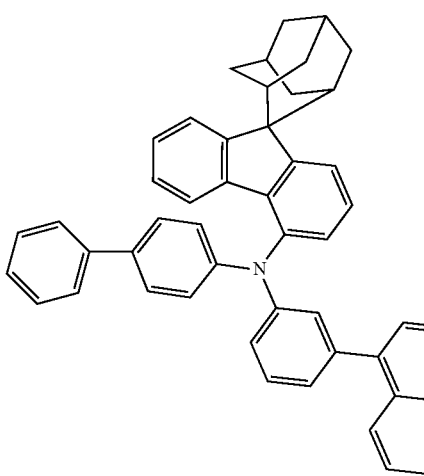
228
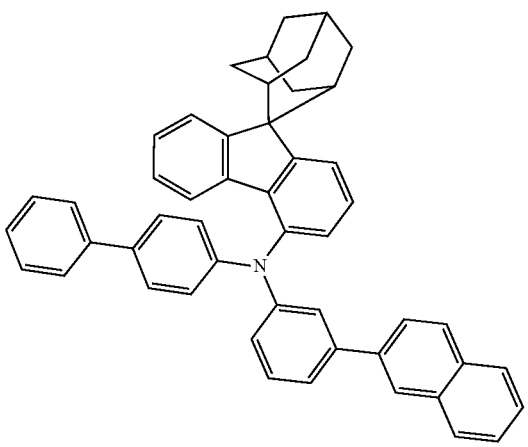

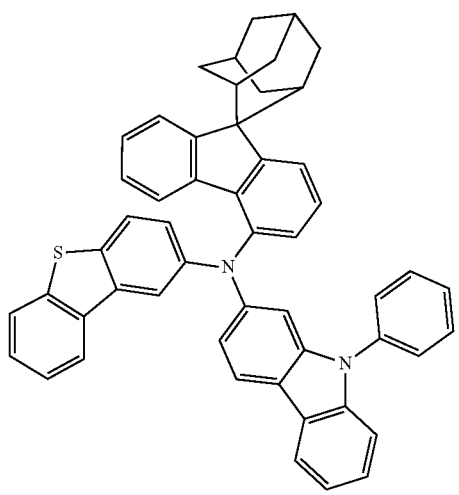
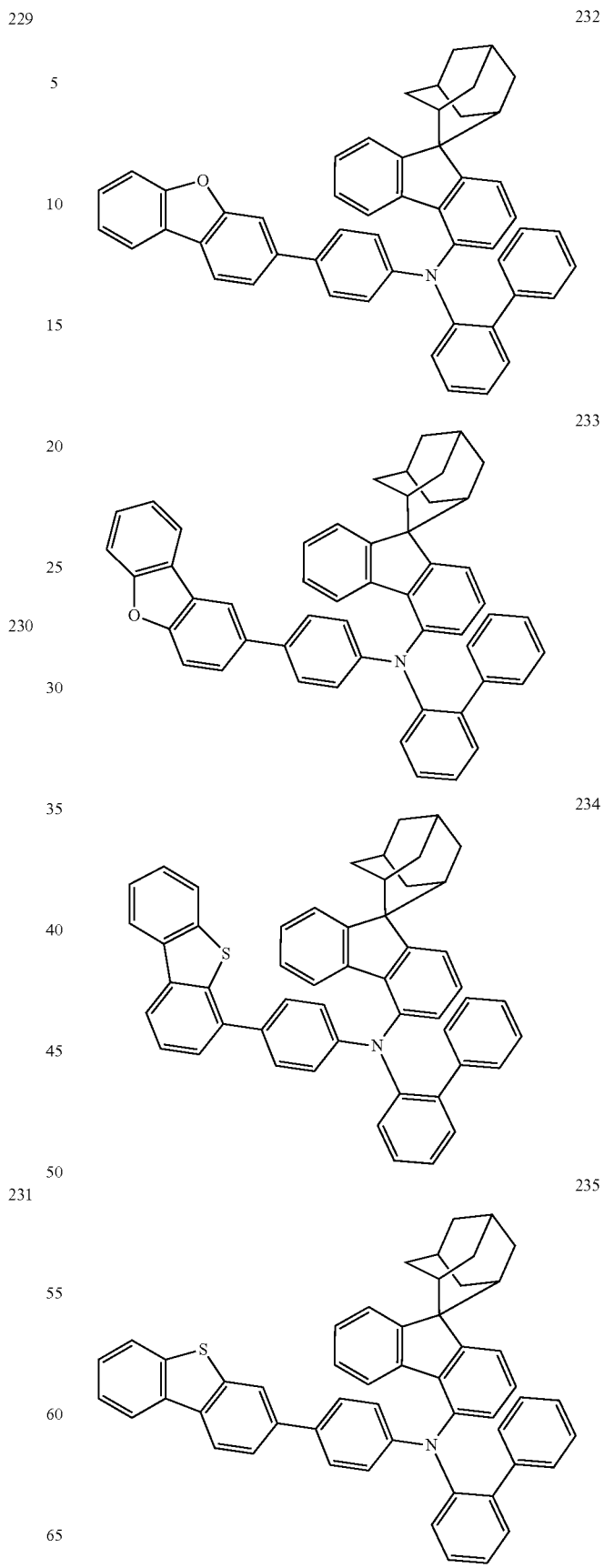

236
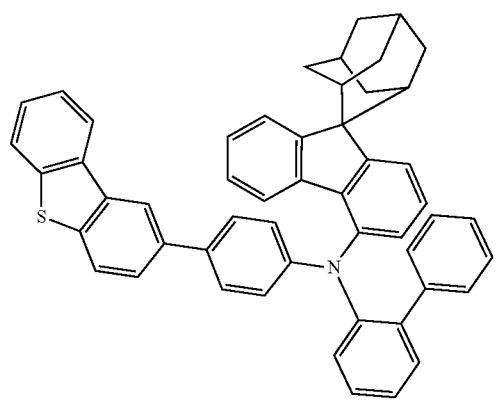
239
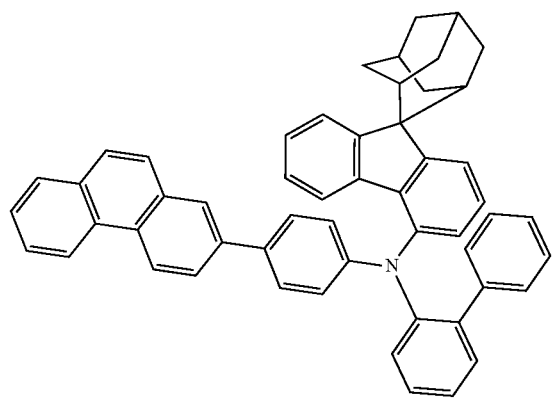
237
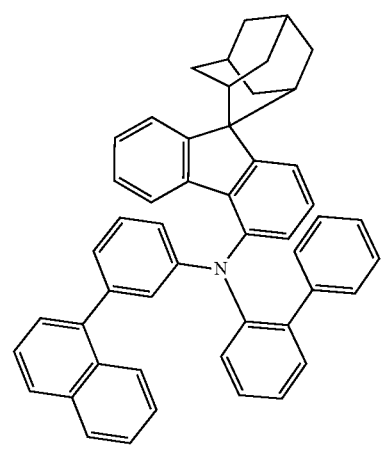
240
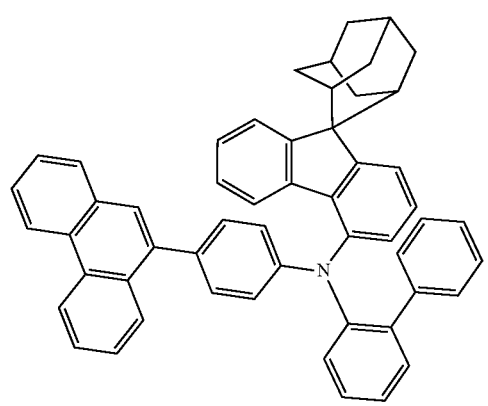
238
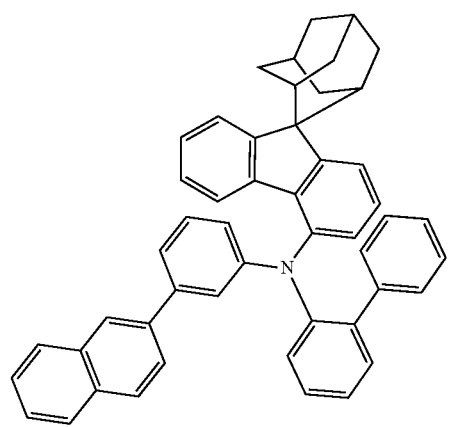
241
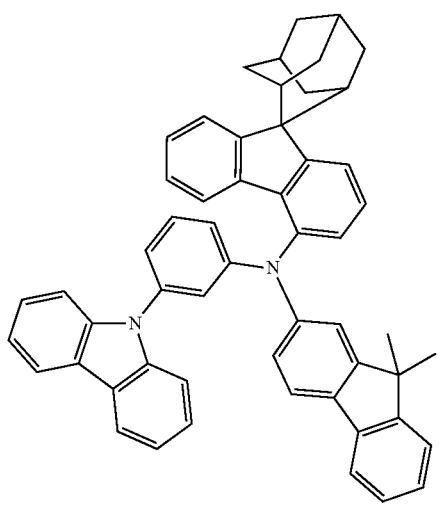

242
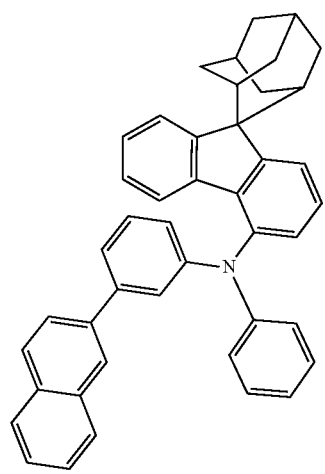
245
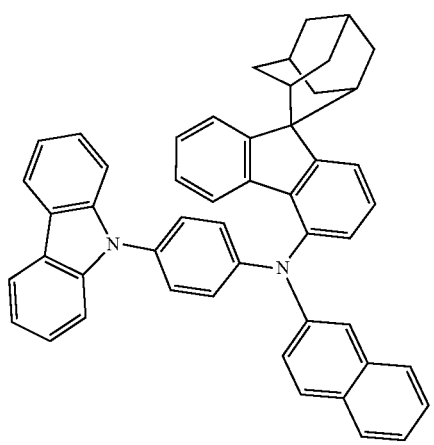
243
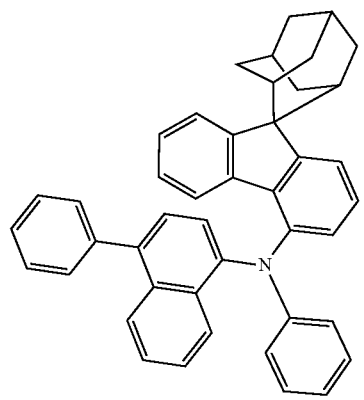
246
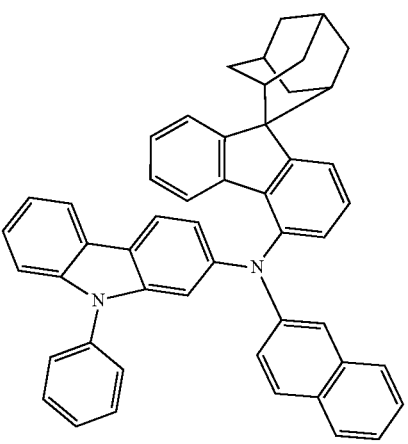
244
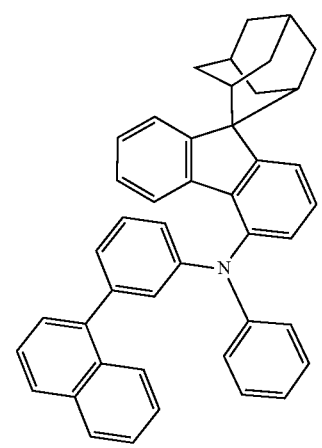
247
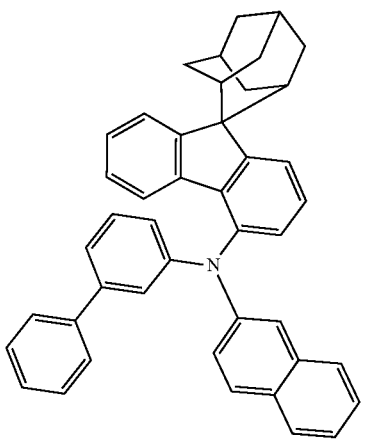

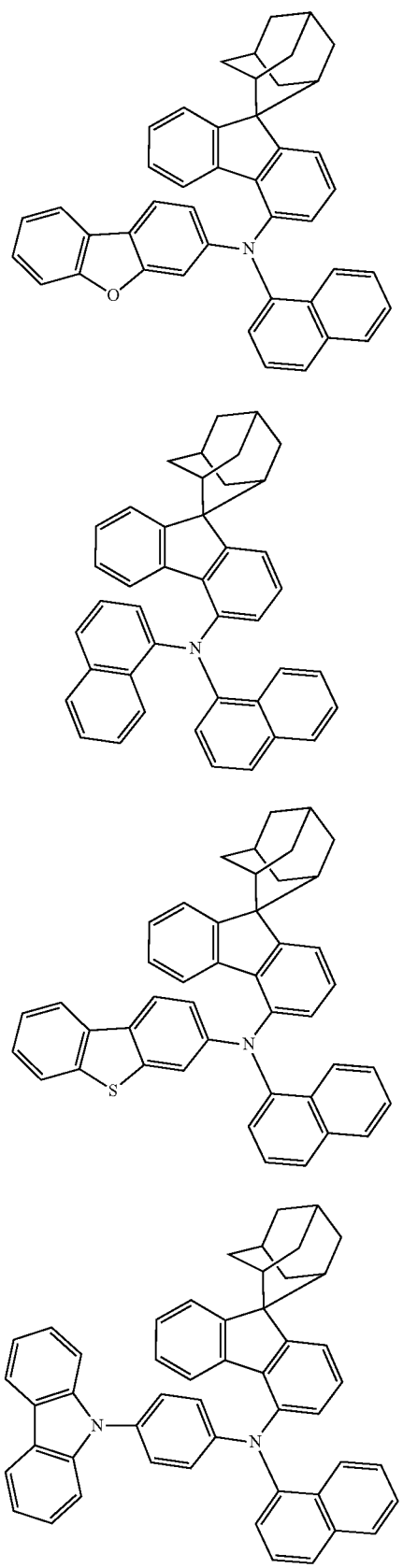
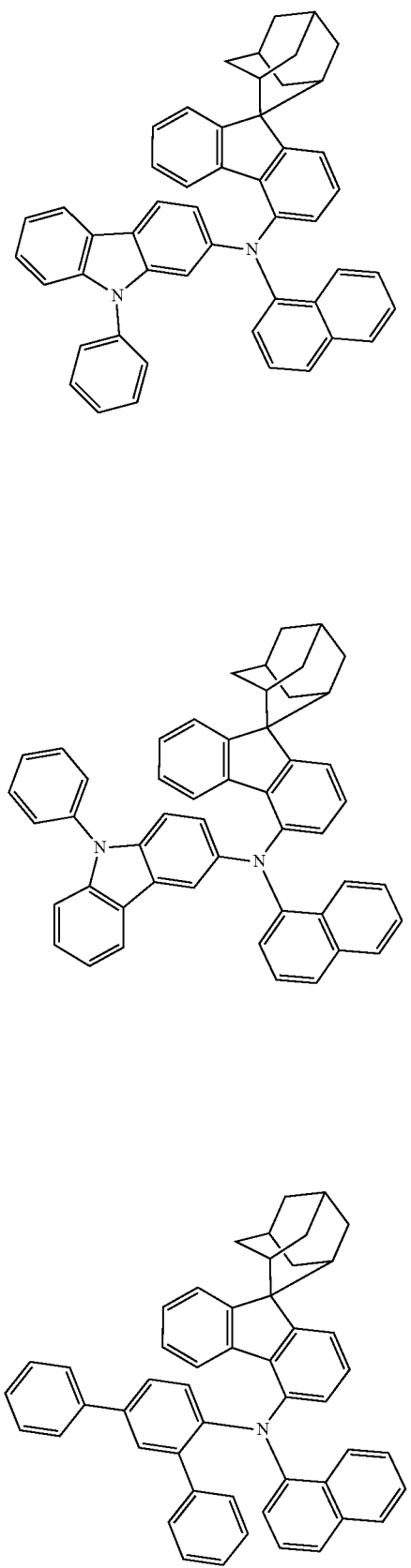

255
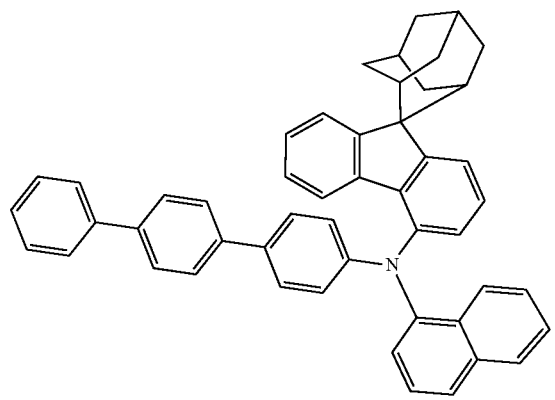
256
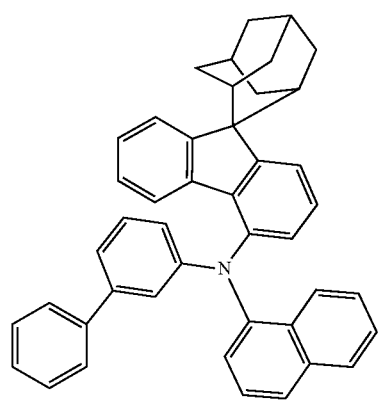
257
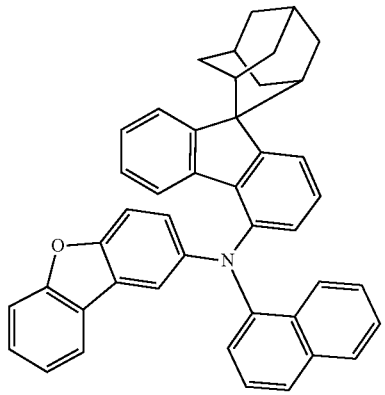
258
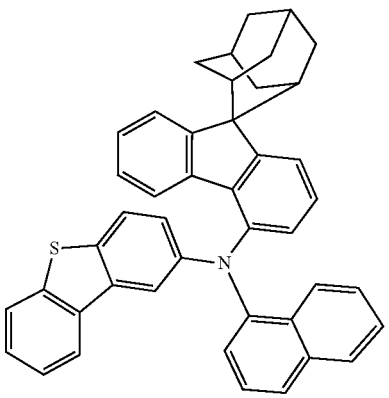
259
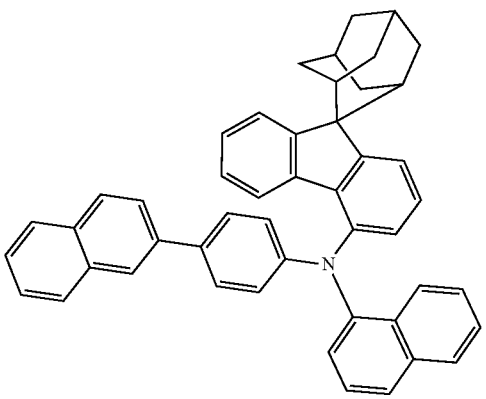
260
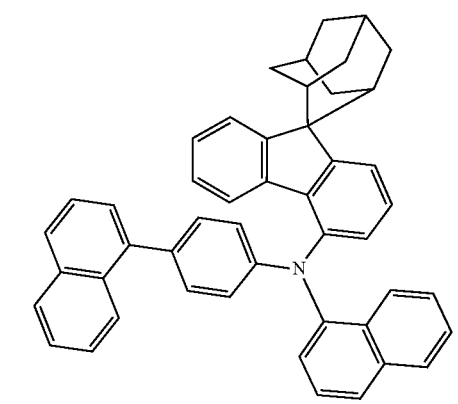
261
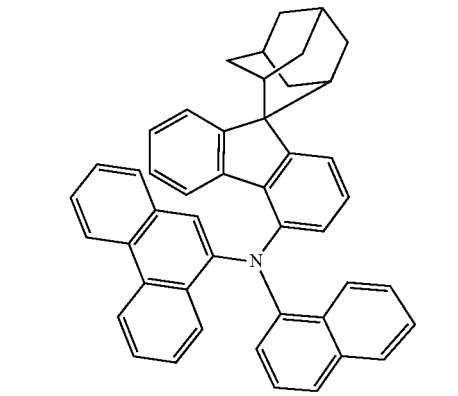
262
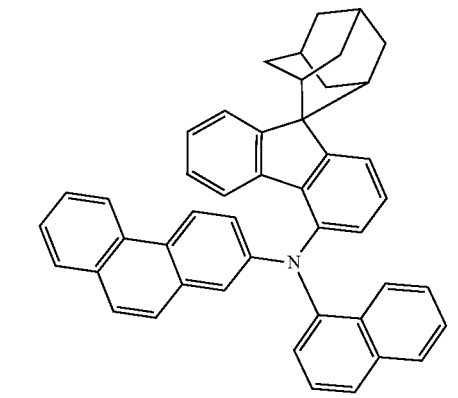

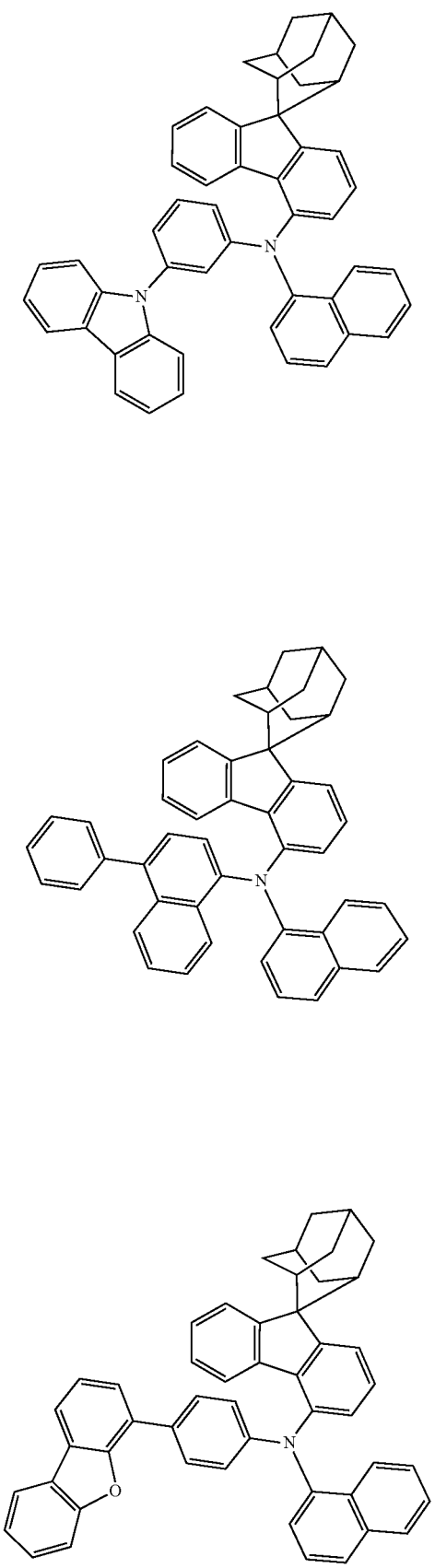
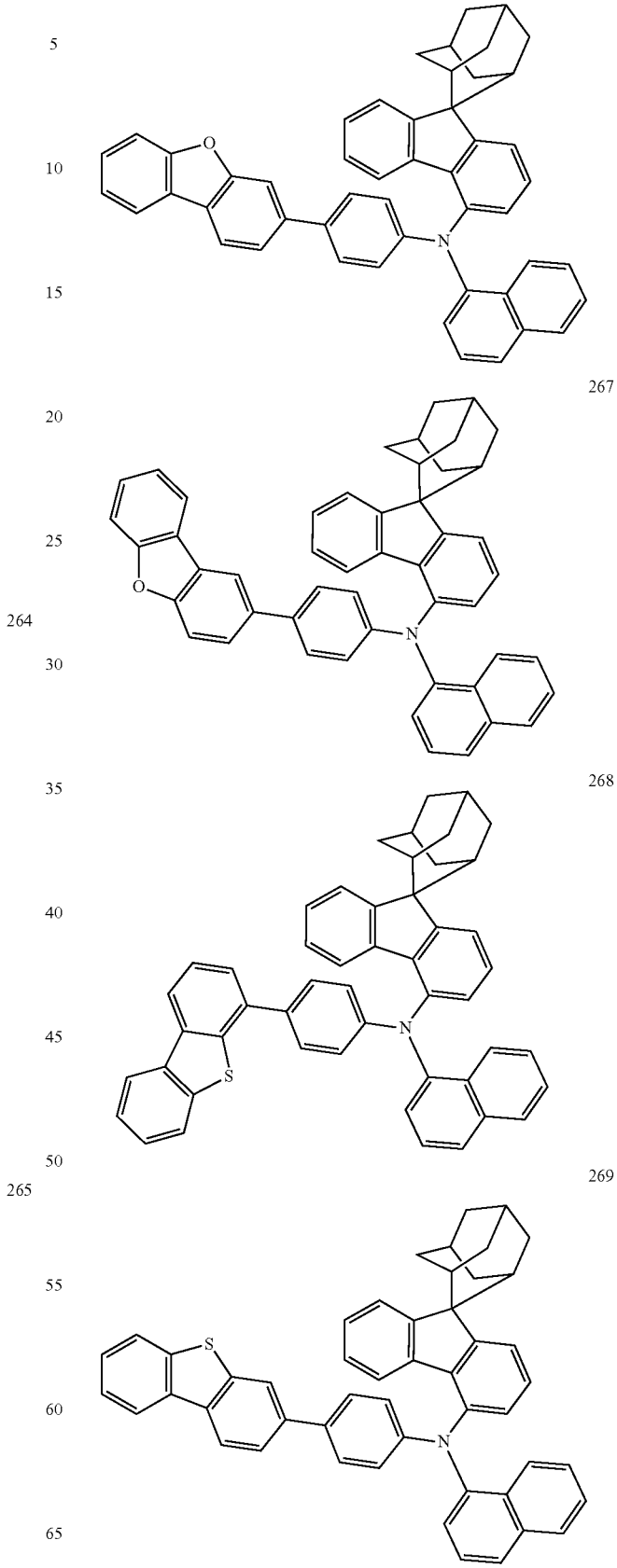

270
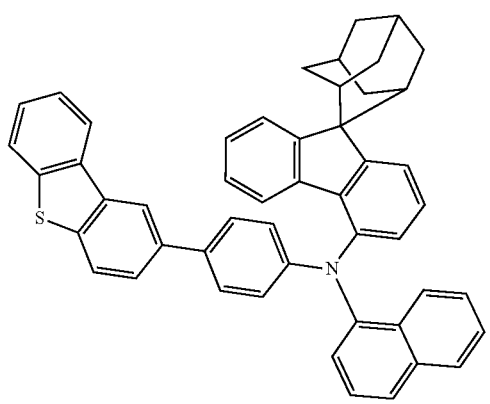
271
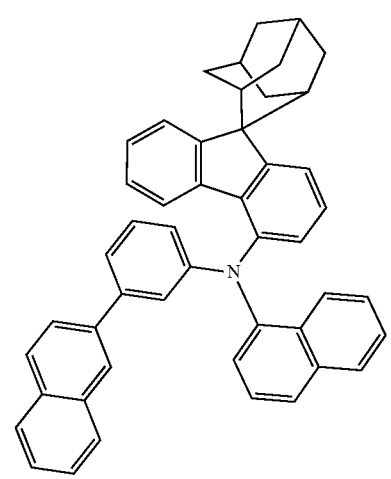
272
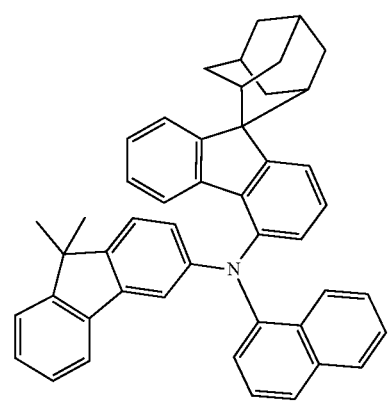
273
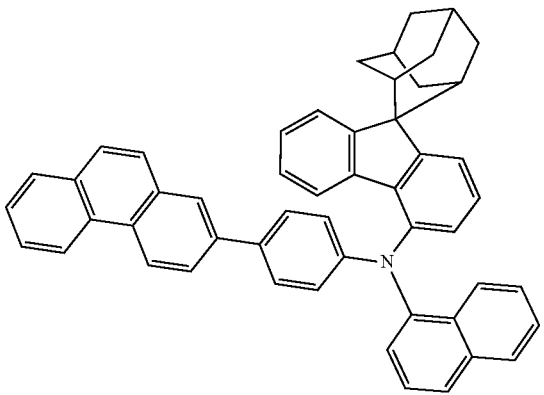
274
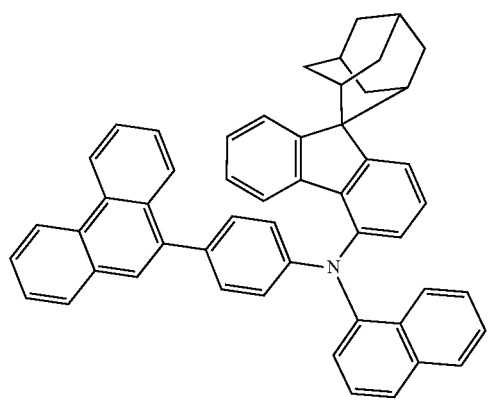
275
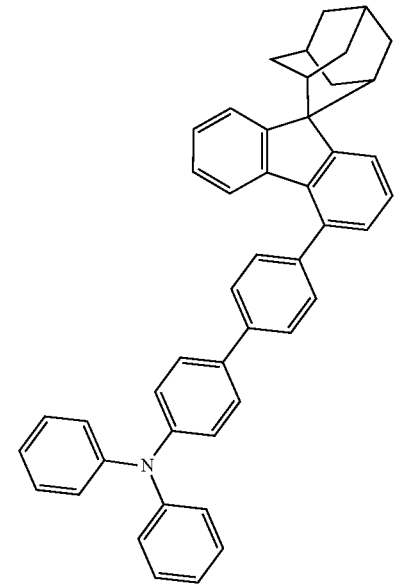

276
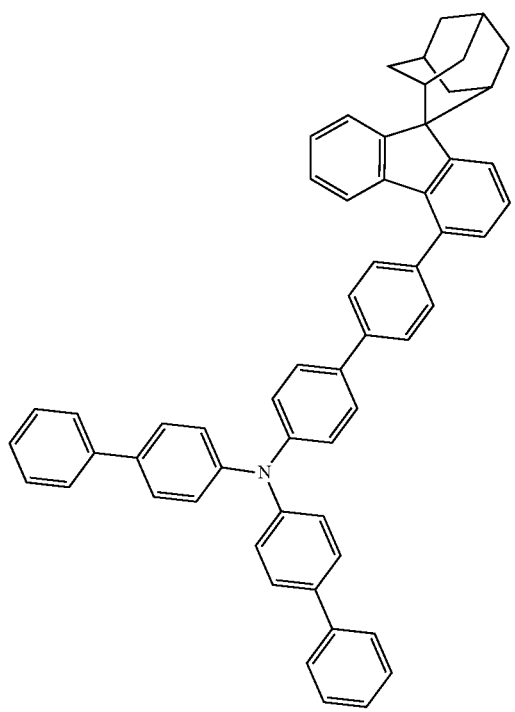
277
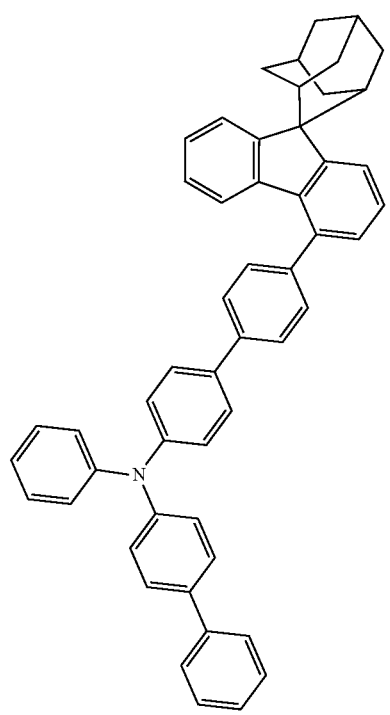
278
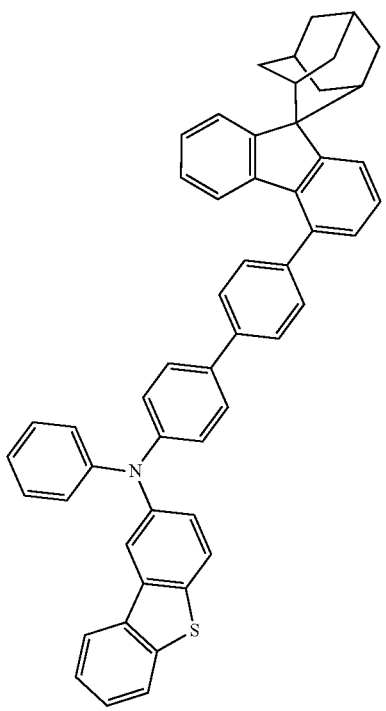
279
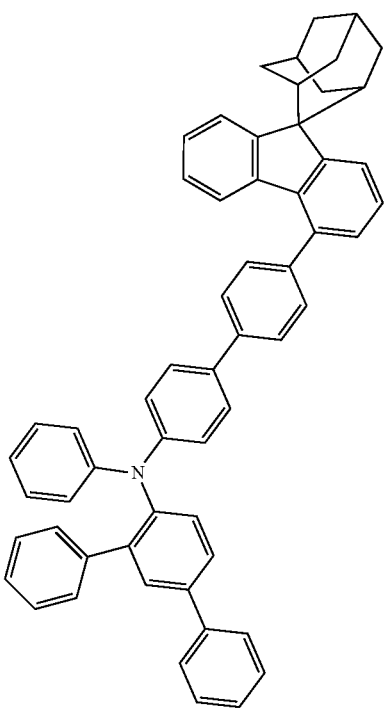

280
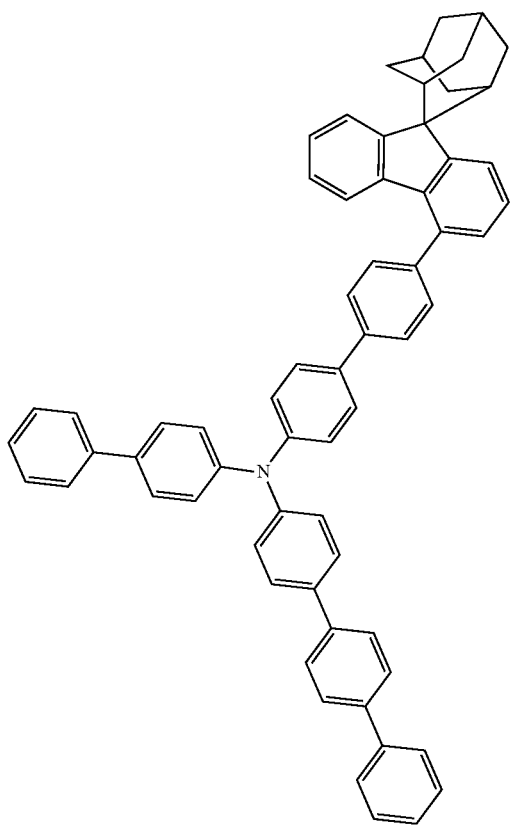
281
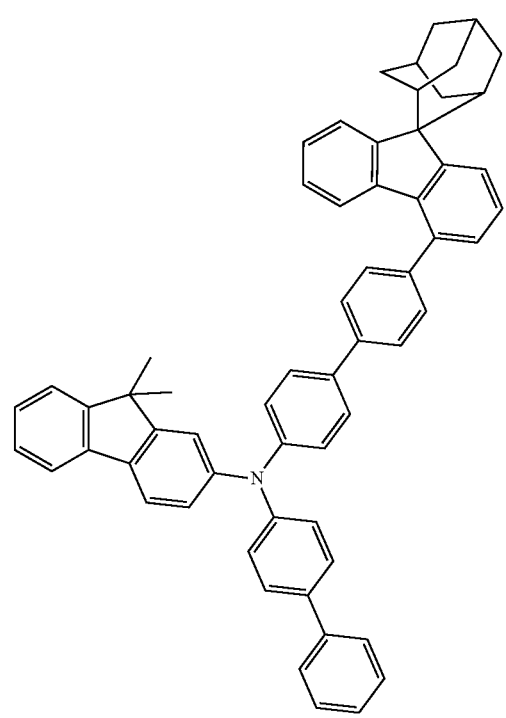
282
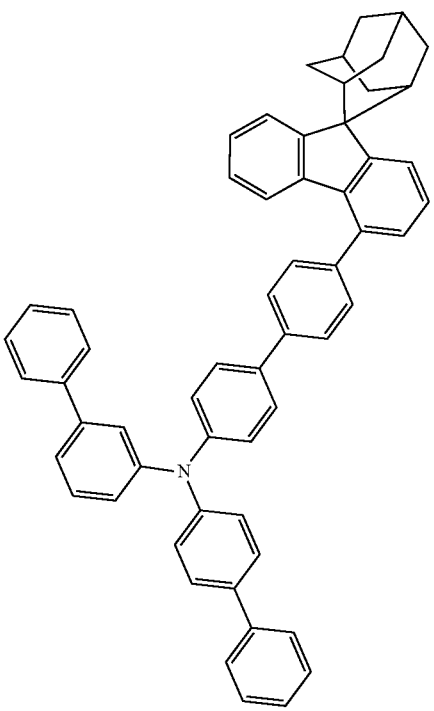
283
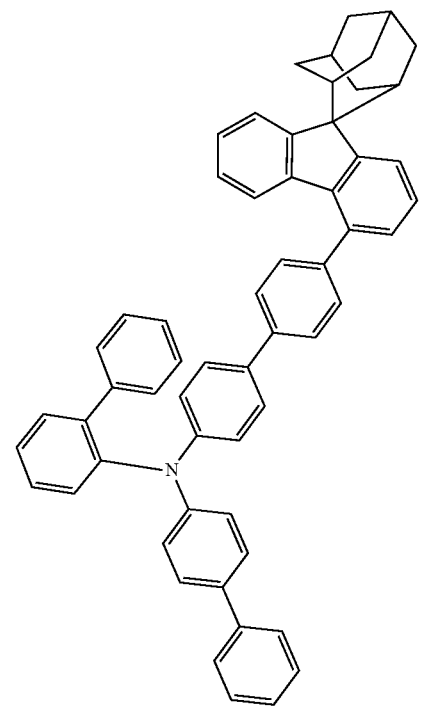

127
-continued
284
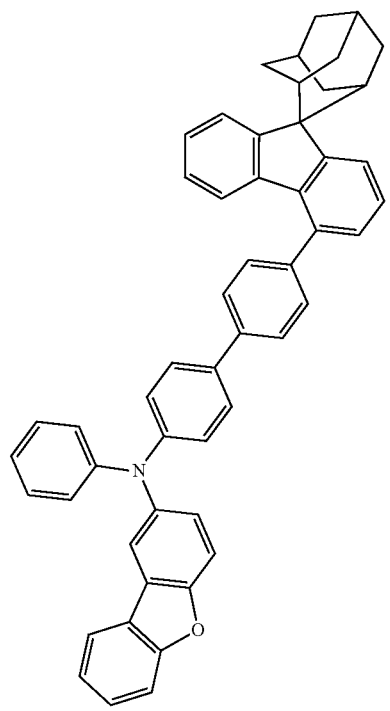
285
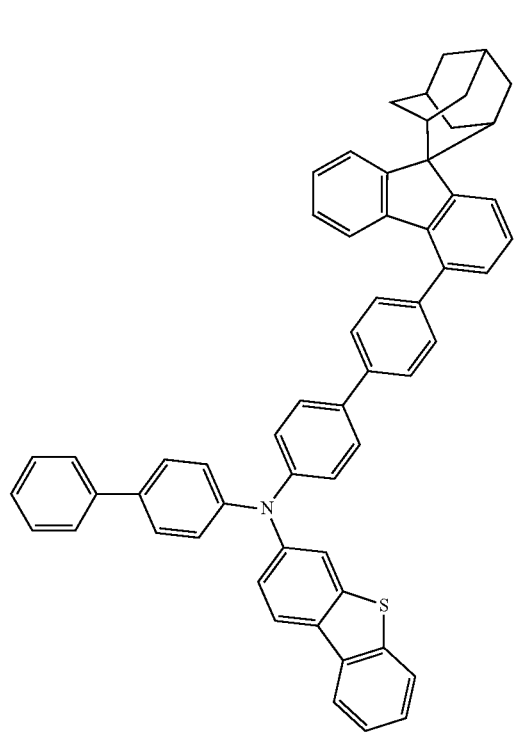
128
-continued
286
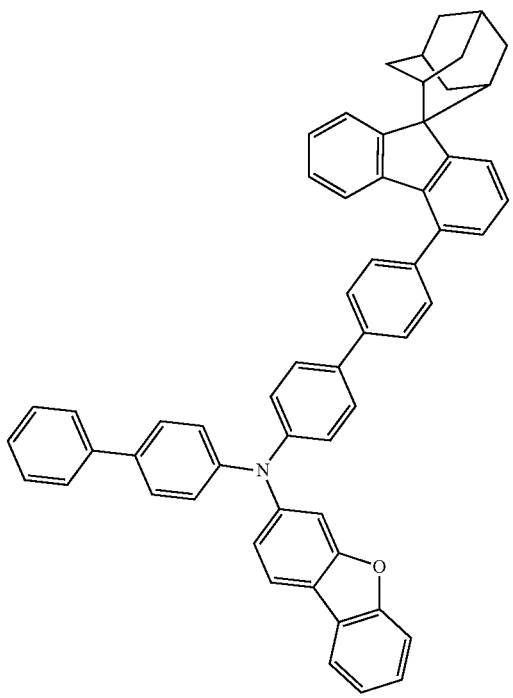
287
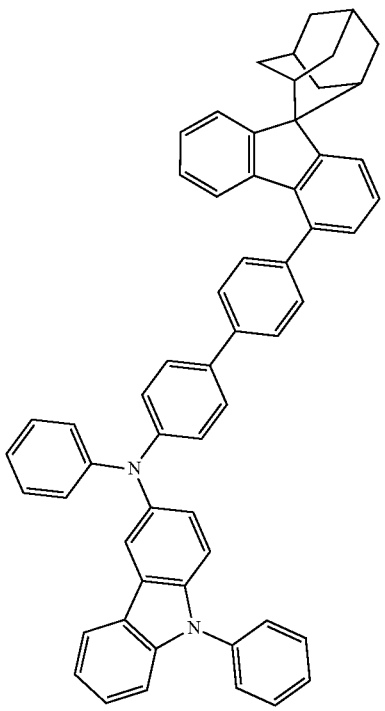

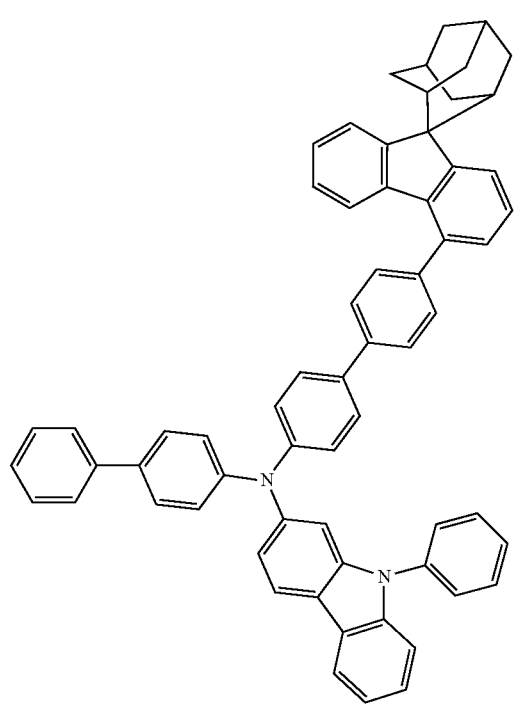
288
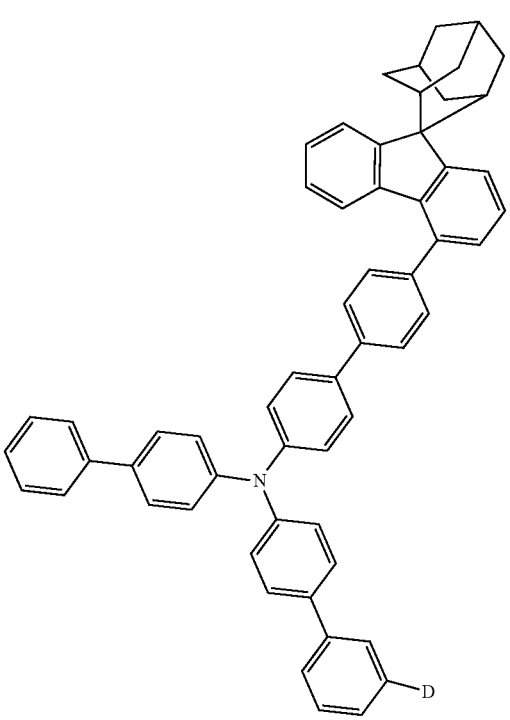
290
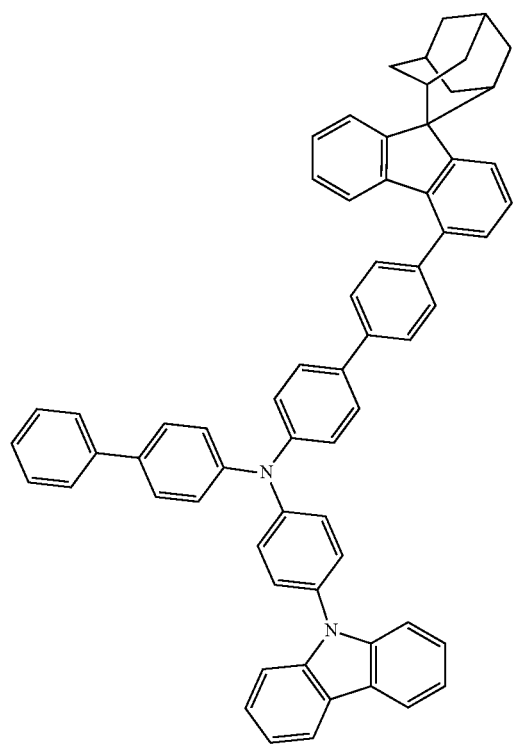
289
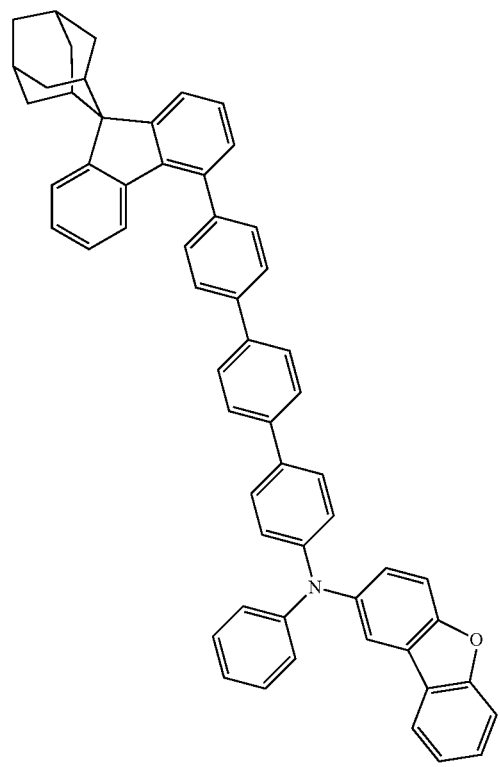
291

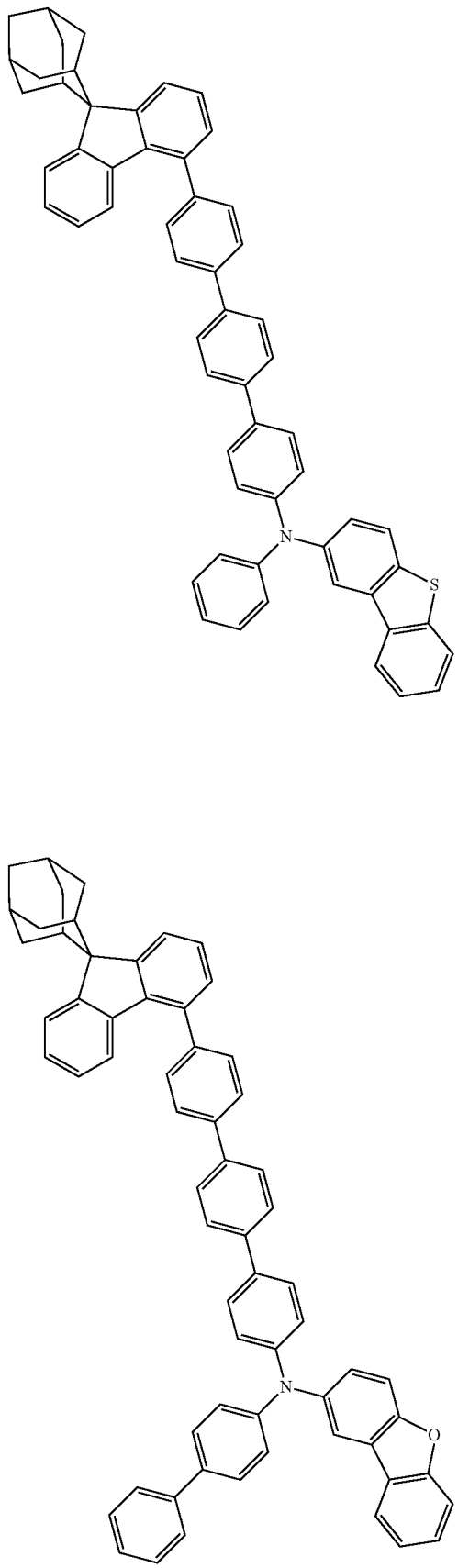
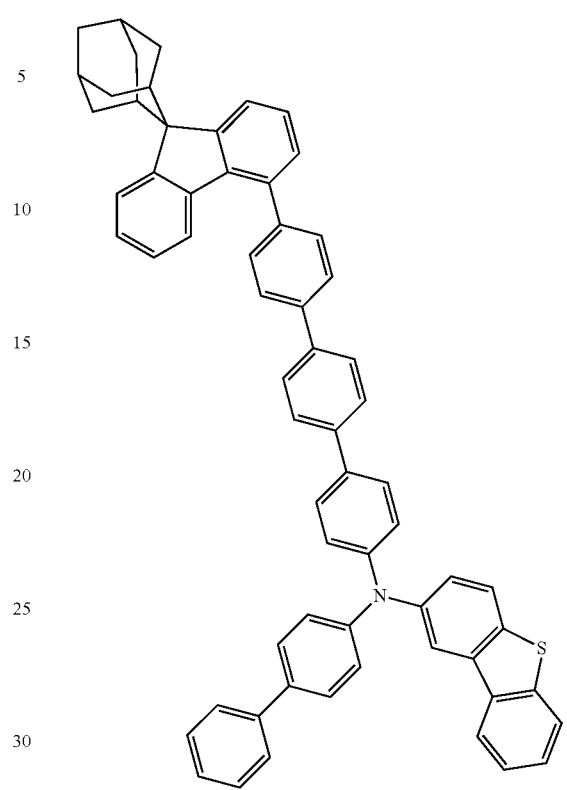
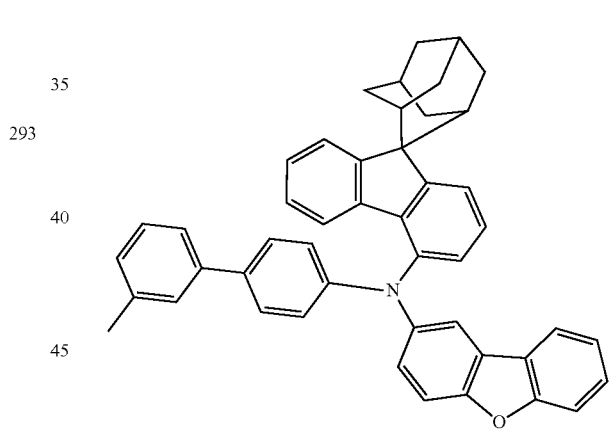
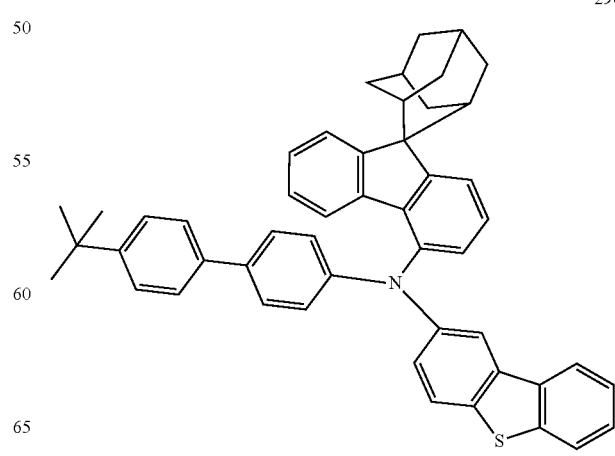

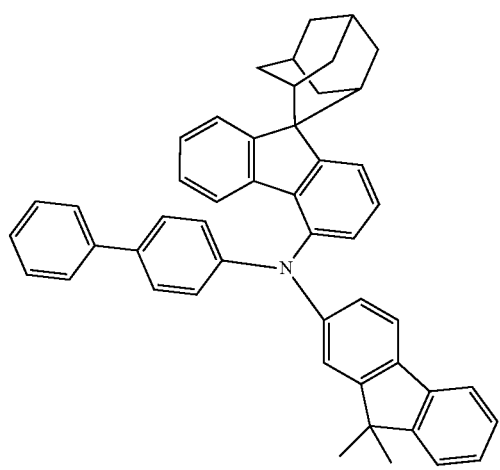
297
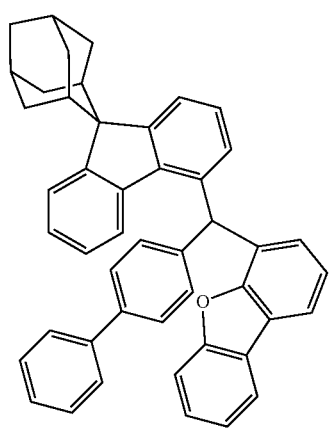
298
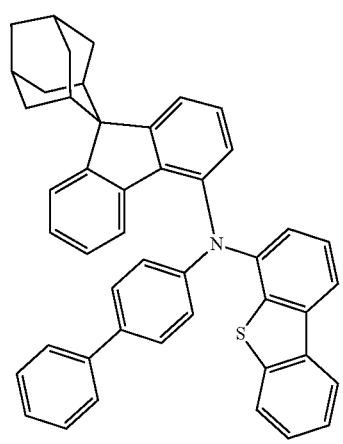
299
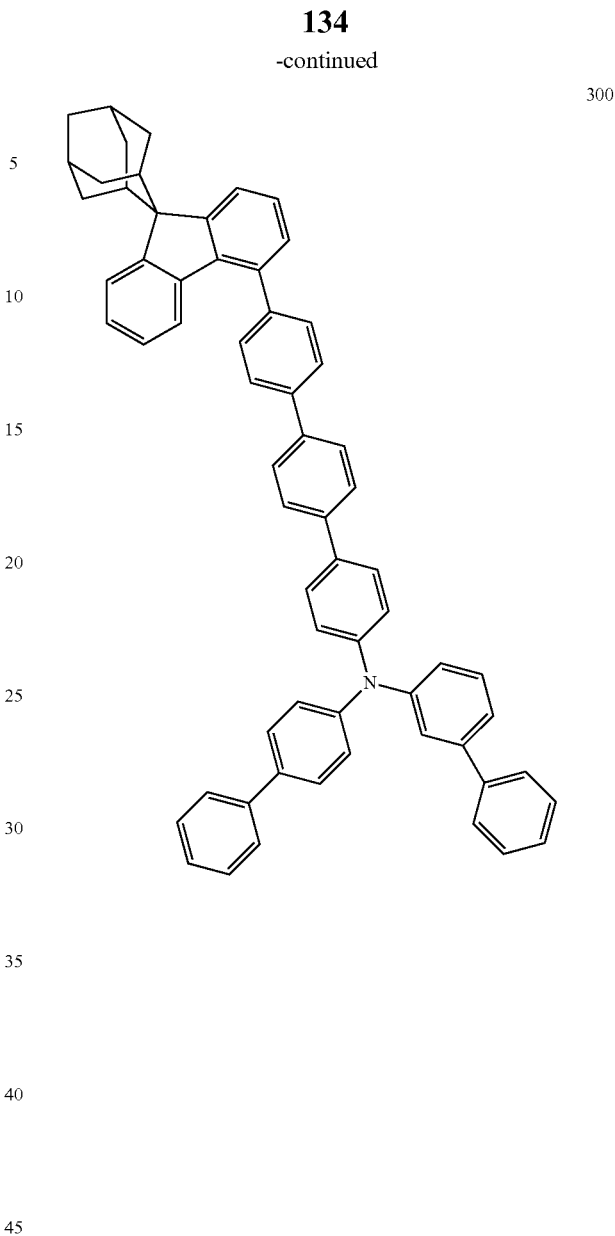
300
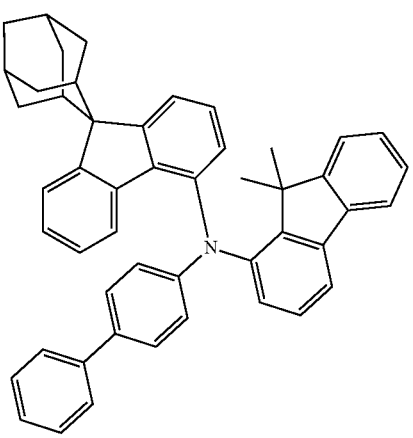
301

302
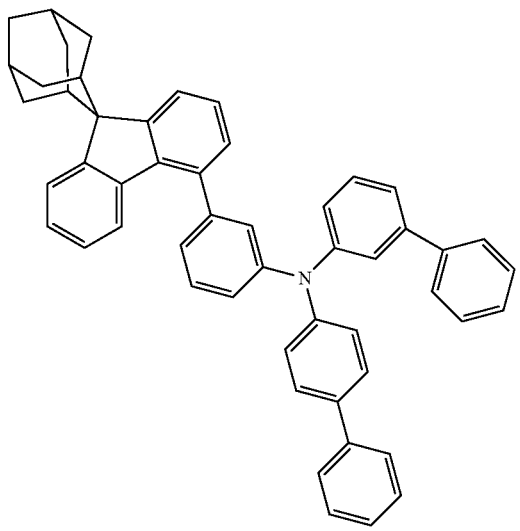
303
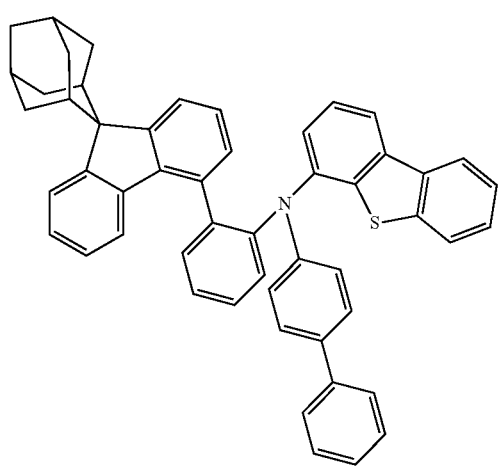
304
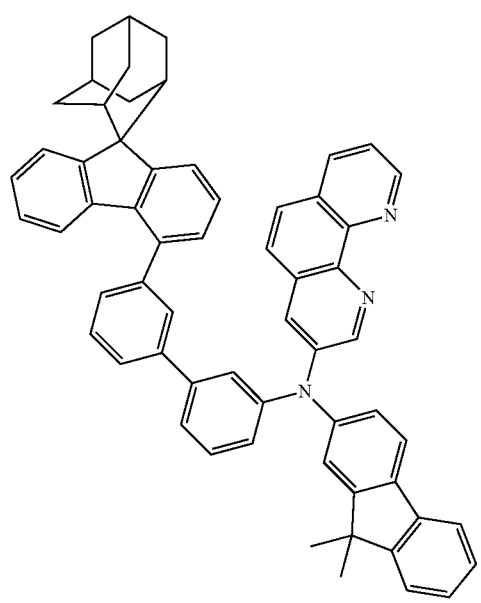
305
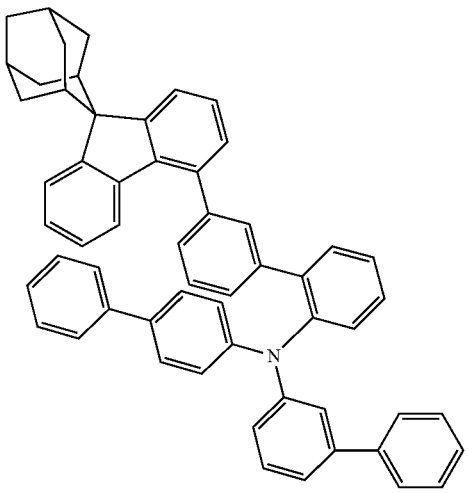
306
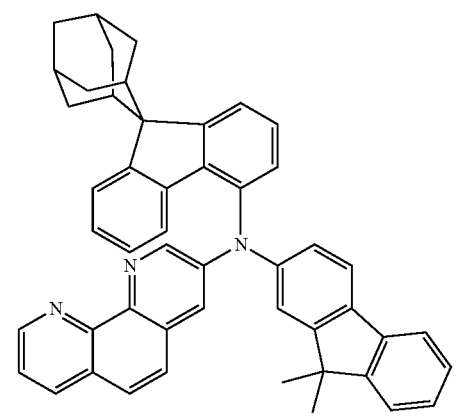
307
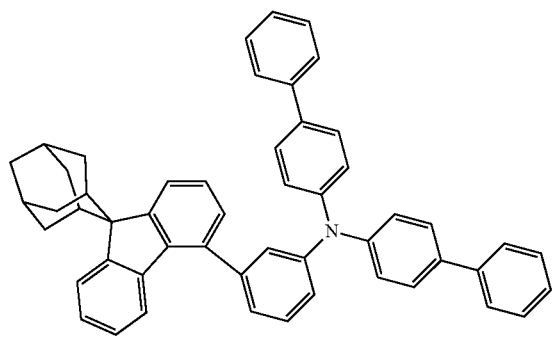

308
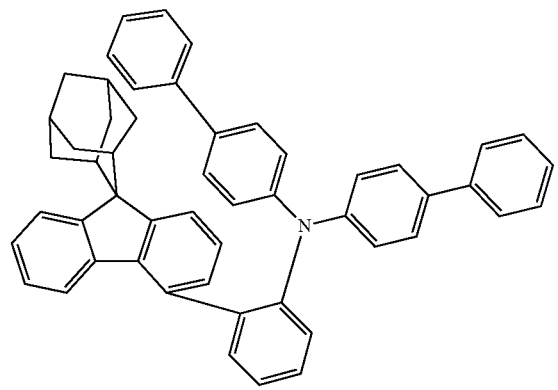
309
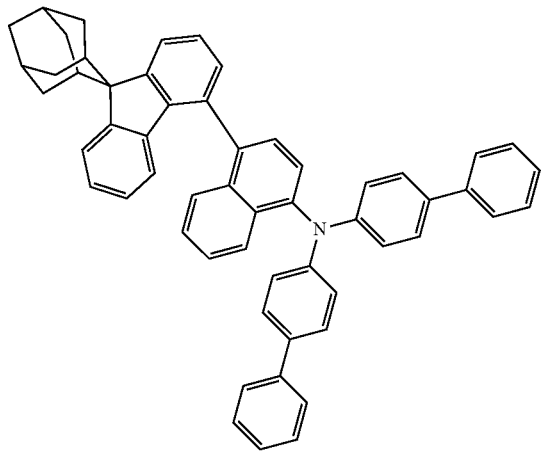
310
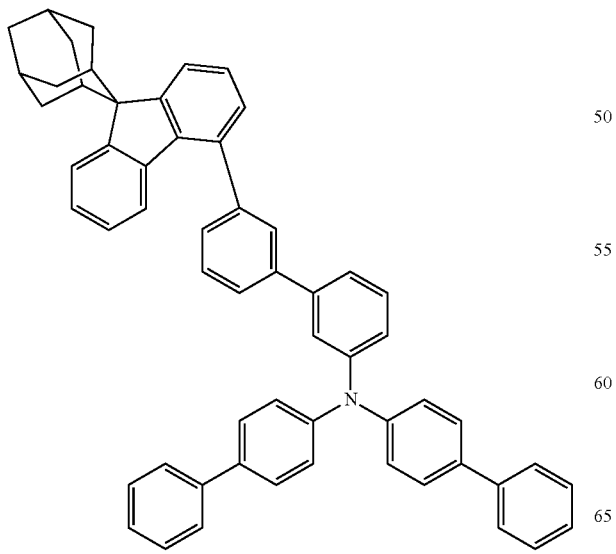
311
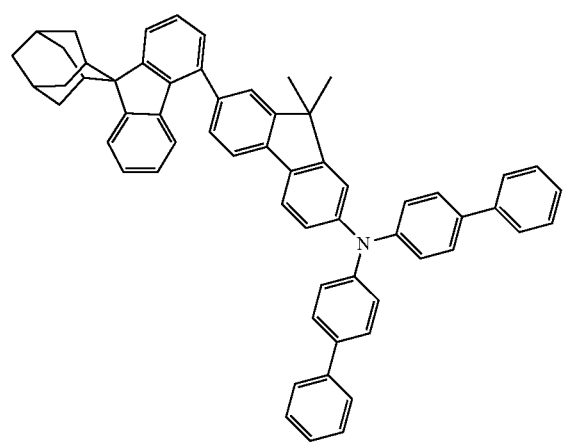
312
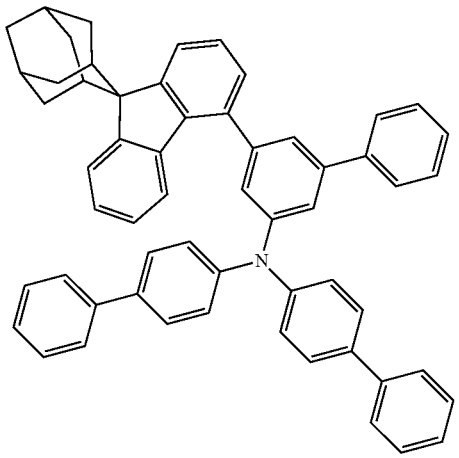
313
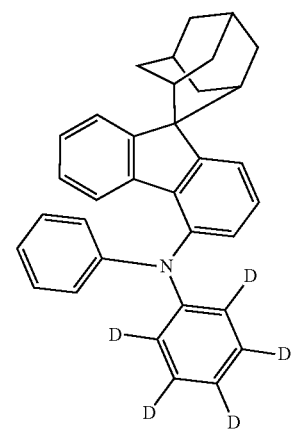

314
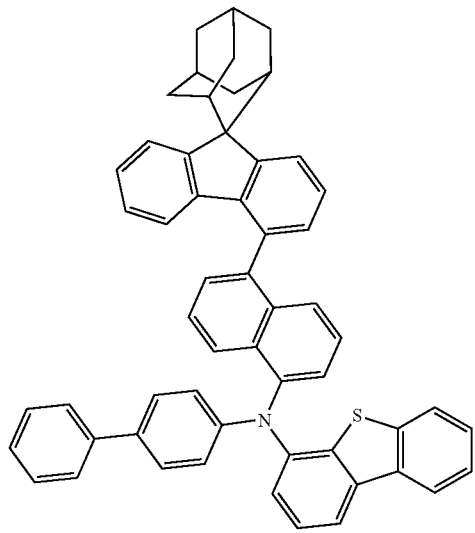
315
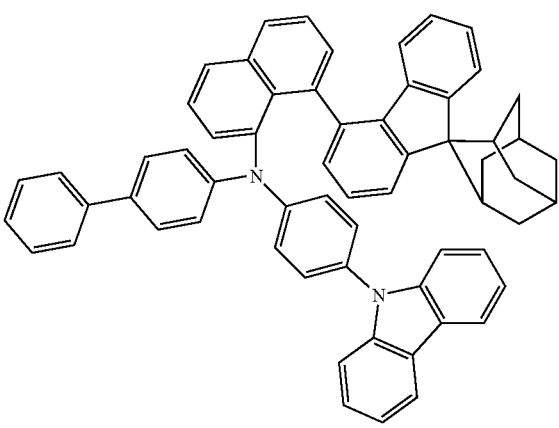
316
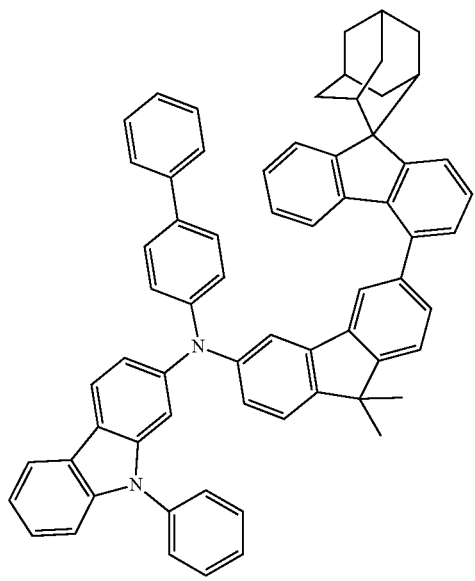
317
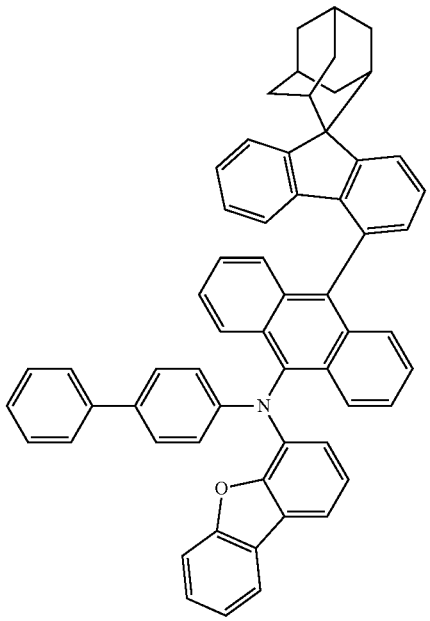
318
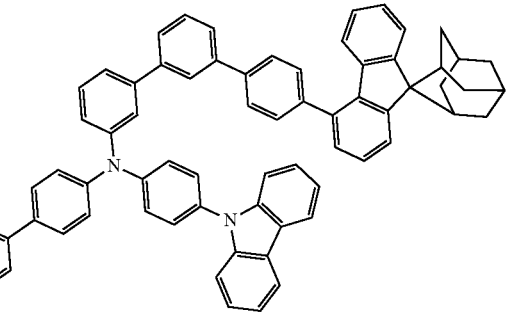
319
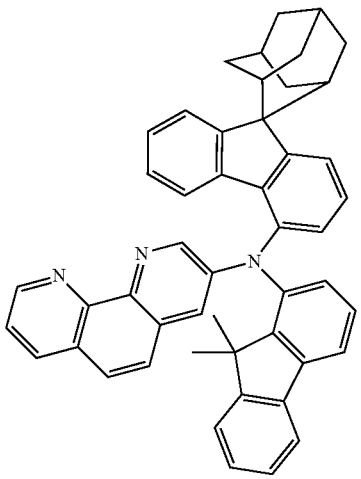

-continued

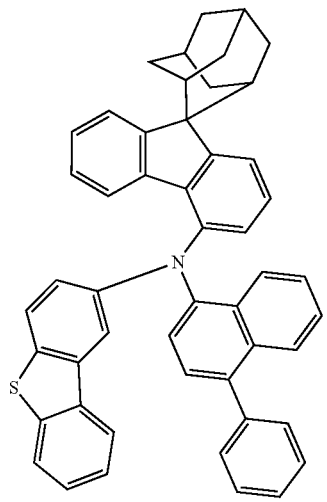
320

The present disclosure also provides an electronic component for implementing photoelectric conversion or electro-optic conversion. The electronic component includes an anode and a cathode disposed opposite to each other, and a functional layer disposed between the anode and the cathode; the functional layer includes the nitrogen-containing compound of the present disclosure.

Alternatively, the functional layer comprises an electron blocking layer comprising the nitrogen-containing compound provided by the present disclosure. The electron blocking layer may be composed of the nitrogen-containing compound provided by the present disclosure, or may be composed of the nitrogen-containing compound provided by the present disclosure and other materials.

For example, the electronic component is an organic electroluminescent device. As shown in FIG. 1, the organic electroluminescent device includes an anode 100 and a cathode 200 disposed opposite to each other, and a functional layer 300 disposed between the anode 100 and the cathode 200; the functional layer 300 includes the nitrogen-containing compound provided by the present disclosure.

Alternatively, the functional layer 300 includes an electron blocking layer 322, and the electron blocking layer 322 includes a nitrogen-containing compound provided by the present disclosure. The electron blocking layer 322 may be composed of the nitrogen-containing compound provided by the present disclosure, or may be composed of the nitrogen-containing compound provided by the present disclosure and other materials.

In one embodiment of the present disclosure, the organic electroluminescent device may include an anode 100, a hole transporting layer 321, an electron blocking layer 322, an organic electroluminescent layer 330 as an energy conversion layer, an electron transporting layer 350 and a cathode 200, which are sequentially stacked. The nitrogen-containing compound provided by the present disclosure can be applied to the electron blocking layer 322 of an organic electroluminescent device, which can effectively improve the luminous efficiency and life of the organic electroluminescent device and reduce the driving voltage of the organic electroluminescent device.

Alternatively, the anode 100 includes the following anode material, which is preferably a material having a large work function that facilitates hole injection into the functional layer. Specific examples of anode materials include: metals such as nickel, platinum, vanadium, chromium, copper, zinc, and gold or their alloys; metal oxides such as zinc oxide, indium oxide, indium tin oxide (ITO), and indium zinc oxide (IZO); combined metals and oxides such as ZnO:Al or $SnO_2$:Sb; or conductive polymers such as poly(3-methylthiophene), poly[3,4-(ethylene-1,2-dioxy)thiophene] (PEDT), polypyrrole and polyaniline, but not limited to this. It preferably includes a transparent electrode containing indium tin oxide (ITO) as the anode.

Alternatively, the hole transporting layer 321 may include one or more hole transporting materials. The hole transporting material may be selected from carbazole polymers, carbazole-linked triarylamine compounds, or other types of compounds, which is not specially limited in the present disclosure. For example, in one embodiment of the present disclosure, the hole transporting layer 321 is composed of the compound NPB.

Alternatively, the organic light-emitting layer 330 may be composed of a single light-emitting material, and may also include a host material and a guest material. Alternatively, the organic light-emitting layer 330 is composed of a host material and a guest material. The holes injected into the organic light-emitting layer 330 and the electrons injected into the organic light-emitting layer 330 may recombine in the organic light-emitting layer 330 to form excitons, and the excitons transfer energy to host material, the host material transfers energy to the guest material, which in turn enables the guest material to emit light.

The host material of the organic light-emitting layer 330 may be a metal chelated oxinoid compound, a bisstyryl derivative, an aromatic amine derivative, a dibenzofuran derivative, or other types of materials, which is not specially limited in the present disclosure. In an embodiment of the present disclosure, the host material of the organic light-emitting layer 330 may be α,β-ADN.

The guest material of the organic light-emitting layer 330 may be a compound having a condensed aryl ring or a derivative thereof, a compound having a heteroaryl ring or a derivative thereof, an aromatic amine derivative or other materials, which is not specially limited in the present disclosure. In an embodiment of the present disclosure, the guest material of the organic light-emitting layer 330 may be BD-1.

The electron transporting layer 350 may have a single layer structure or a multilayer structure, which may include one or more electron transporting materials, and the electron transporting materials may be selected from benzimidazole derivatives, oxadiazole derivatives, quinoxaline derivatives or other electron transporting materials, which are not specifically limited in the present disclosure. For example, in one embodiment of the present disclosure, the electron transporting layer 340 may be composed of DBimiBphen and LiQ.

Alternatively, the cathode 200 includes the following cathode material, which is a material having a small work function that facilitates electron injection into the functional layer. Specific examples of cathode materials include: metals such as magnesium, calcium, sodium, potassium, titanium, indium, yttrium, lithium, gadolinium, aluminum, silver, tin, and lead or their alloys; or multilayer materials such as LiF/Al, Liq/Al, $LiO_2$/Al, LiF/Ca, LiF/Al, and $BaF_2$/Ca, but not limited thereto. It is preferable to include a metal electrode containing aluminum as a cathode.

Alternatively, as shown in FIG. 1, a hole injecting layer 310 may also be provided between the anode 100 and the first hole transporting layer 321 to enhance the ability to inject holes into the first hole transporting layer 321. The hole injecting layer 310 can be selected from benzidine derivatives, starburst arylamine compounds, phthalocyanine derivatives, or other materials, which is not specially limited in the present disclosure. In an embodiment of the present disclosure, the hole injecting layer 310 may be composed of m-MTDATA.

Alternatively, as shown in FIG. 1, an electron injecting layer 360 may also be provided between the cathode 200 and the electron transporting layer 340 to enhance the ability to inject electrons into the electron transporting layer 350. The electron injecting layer 360 may include an inorganic material such as an alkali metal sulfide or an alkali metal halide, or may include a complex compound of an alkali metal and an organic substance. In an embodiment of the present disclosure, the electron injecting layer 360 may include LiQ.

Alternatively, a hole blocking layer 340 may be further provided between the organic electroluminescent layer 330 and the electron transporting layer 350.

Figure 2:
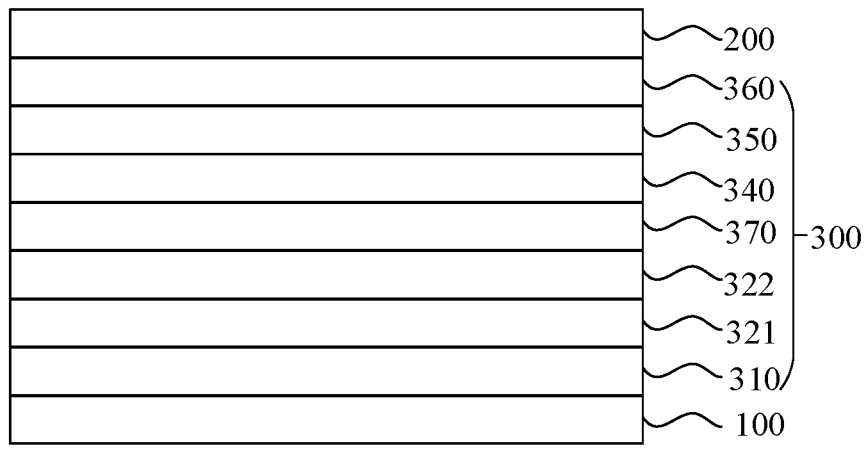
FIG. 2 is a schematic structural diagram of a photoelectric conversion device according to an embodiment of the present disclosure.

For another example, the electronic component may be a photoelectric conversion device. As shown in FIG. 2, the photoelectric conversion device may include an anode 100 and a cathode 200 disposed opposite to each other, and a functional layer 300 disposed between the anode 100 and the cathode 200; the functional layer 300 contains the nitrogen-containing compound provided in the present disclosure.

Alternatively, the functional layer 300 includes an electron blocking layer 322, and the electron blocking layer 322 includes a nitrogen-containing compound provided by the present disclosure. The electron blocking layer 322 may be composed of the nitrogen-containing compound provided by the present disclosure, or may be composed of the nitrogen-containing compound provided by the present disclosure and other materials.

Alternatively, as shown in FIG. 2, the photoelectric conversion device may include an anode 100, a hole transporting layer 321, an electron blocking layer 322, a photoelectric conversion layer 370 as an energy conversion layer, an electron transporting layer 350, and a cathode 200 that are sequentially stacked. The nitrogen-containing compound provided in the present disclosure can be applied to the electron blocking layer 322 of the photoelectric conversion device, which can effectively improve the luminous efficiency and life of the photoelectric conversion device and increase the open circuit voltage of the photoelectric conversion device.

Alternatively, a hole injecting layer 310 may also be provided between the anode 100 and the hole transporting layer 321.

Alternatively, an electron injecting layer 360 may also be provided between the cathode 200 and the electron transporting layer 350.

Alternatively, a hole blocking layer 340 may also be provided between the photoelectric conversion layer 370 and the electron transporting layer 350.

Alternatively, the photoelectric conversion device may be a solar cell, especially an organic thin film solar cell. For example, as shown in FIG. 2, in one embodiment of the present disclosure, the solar cell includes an anode 100, a hole transporting layer 321, an electron blocking layer 322, a photoelectric conversion layer 370, an electron transporting layer 350 and the cathode 200 that are sequentially stacked, wherein the electron blocking layer 322 contains the nitrogen-containing compound of the present disclosure.

An embodiment of the present disclosure further provides an electronic device including any one of the electronic components described in the embodiments of the foregoing electronic component. Since the electronic device has any of the electronic components described in the above-mentioned embodiments of the electronic component, it has the same beneficial effects, which will not be repeated here.

Figure 3:
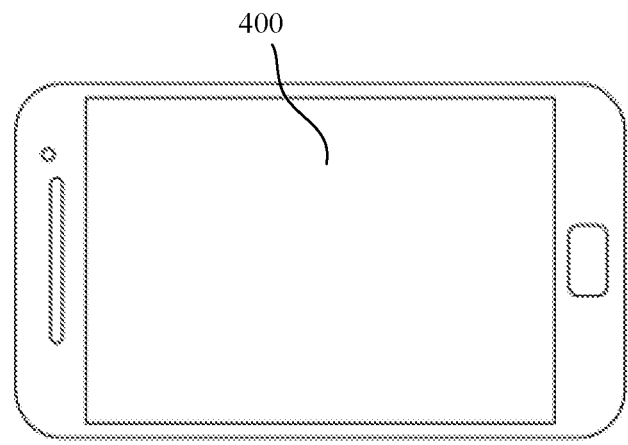
FIG. 3 is a schematic structural diagram of an electronic device according to an embodiment of the present disclosure.

For example, as shown in FIG. 3, the present disclosure provides an electronic device 400. The electronic device 200 includes any organic electroluminescent device described in the above-mentioned embodiments of the organic electroluminescent device. The electronic device 400 may be a display device, a lighting device, an optical communication device, or other types of electronic devices. For example, the electronic device 400 may include, but is not limited to, a computer screen, a mobile phone screen, a television, an electronic paper, an emergency lighting lamp, and an optical module and the like. Since the electronic device 400 has any of the organic electroluminescent devices described in the above-mentioned embodiments of the organic electroluminescent device, it has the same beneficial effects, which will not be repeated here.

Figure 4:
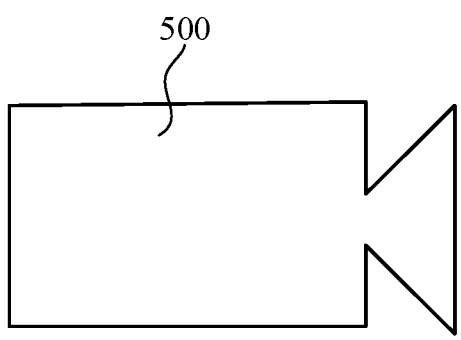
FIG. 4 is a schematic structural diagram of an electronic device according to an embodiment of the present disclosure.

For another example, as shown in FIG. 4, the present disclosure provides an electronic device 500 that includes any photoelectric conversion device described in the above-mentioned embodiments of the photoelectric conversion device. The electronic device 500 may be a solar power generation device, a light detector, a fingerprint recognition device, an optical module, a CCD camera, or other types of electronic devices. Since the electronic device 500 has any one of the photoelectric conversion devices described in the above-mentioned embodiments of the photoelectric conversion device, it has the same beneficial effects, which will not be repeated here.

Hereinafter, the present disclosure will be described in further detail through examples. However, the following embodiments are merely examples of the present disclosure, and do not limit the present disclosure.

Compound Synthesis
Synthesis of Compound 1

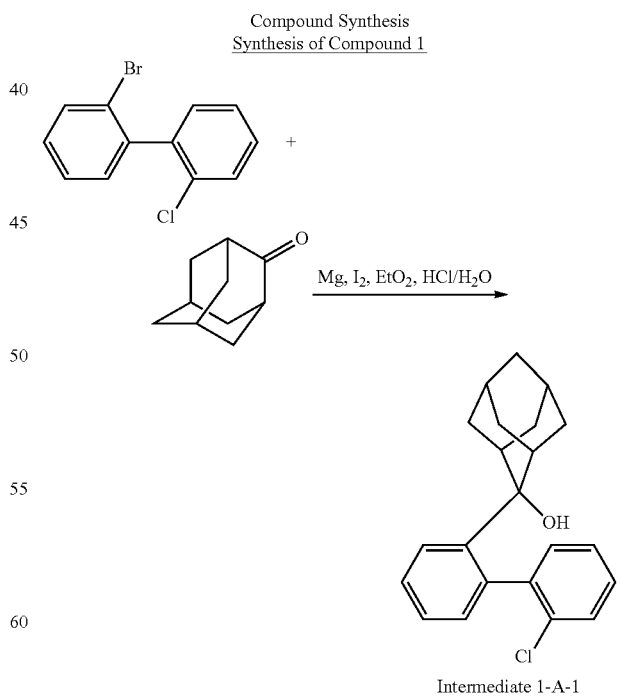

Intermediate 1-A-1

The magnesium bar (13.54 g, 564 mmol) and diethyl ether (100 mL) were placed in a dried round bottom flask under nitrogen gas, and iodine (100 mg) was added. Then, a solution of 2′-bromo-2-chlorobiphenyl (50.00 g, 187.0 mmol) in diethyl ether (200 mL) was slowly dropped into the flask. After the addition was completed, the temperature was raised to 35° C. and the mixture was stirred for 3 hours. The reaction solution was reduced to 0° C., and a solution of amantadone (22.45 g, 149 mmol) in diethyl ether (200 mL) was slowly add. After the addition is complete, the temperature was warmed to 35° C. and the reaction solution was stirred for 6 hours. The reaction solution was cooled to room temperature and 5% hydrochloric acid was added to it to pH<7, and the mixture was stirred for 1 hour. Diethyl ether (200 mL) was added for extraction. Organic phases were combined, and dried over anhydrous magnesium sulfate. After filtration, the solvent was removed under reduced pressure. The resulting crude product was purified by using ethyl acetate/n-heptane (1:2) as the mobile phase through silica gel column chromatography to obtain intermediate I-A-1 as a white solid (43 g, 84.9%).

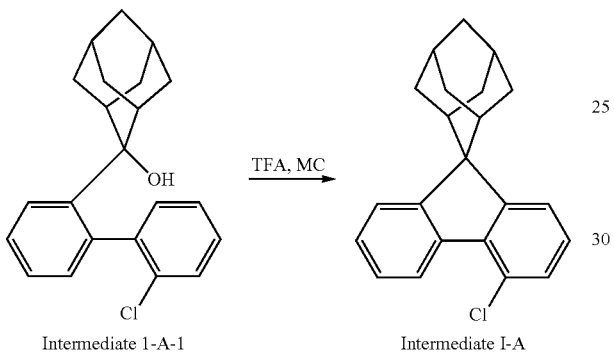

Intermediate 1-A-1           Intermediate I-A

Intermediate I-A-1 (43 g, 126.9 mmol), trifluoroacetic acid (TFA) (36.93 g, 380.6 mmol) and dichloromethane (MC) (300 mL) were added to a round bottom flask and stirred for 2 hours under nitrogen gas. Then a sodium hydroxide aqueous solution was added to the reaction solution to pH=8, and the liquid was separated. The organic phase was dried over anhydrous magnesium sulfate. After filtration, the solvent was removed under reduced pressure. The crude product obtained was purified by using dichloromethane/n-heptane (1:2) through silica gel column chromatography to obtain intermediate I-A as a white solid (39.2 g, 96.3%).

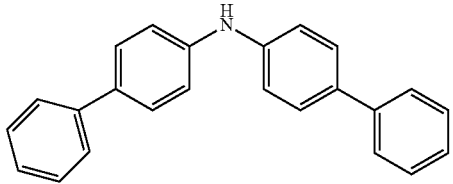

Intermediate II-A 4-bromobiphenyl (5.0 g, 21.45 mmol), 4-aminobiphenyl (3.70 g, 21.87 mmol), tris(dibenzylideneacetone) dipalladium (0.20 g, 0.21 mmol), 2-dicyclohexyl phosphine-2′,4′,6′-triisopropylbiphenyl (0.20 g, 0.43 mmol) and sodium tert-butoxide (3.09 g, 32.18 mmol) were added to toluene (80 mL). The mixture was heated to 108° C. under nitrogen gas, and was stirred for 2 h. Then, after cooling to room temperature, the reaction solution was washed with water and dried over magnesium sulfate. After filtration, the solvent was removed from the filtrate under reduced pressure. The crude product was purified by recrystallization with a dichloromethane/ethyl acetate system to obtain intermediate II-A as a light yellow solid (5.61 g, 81.5%).

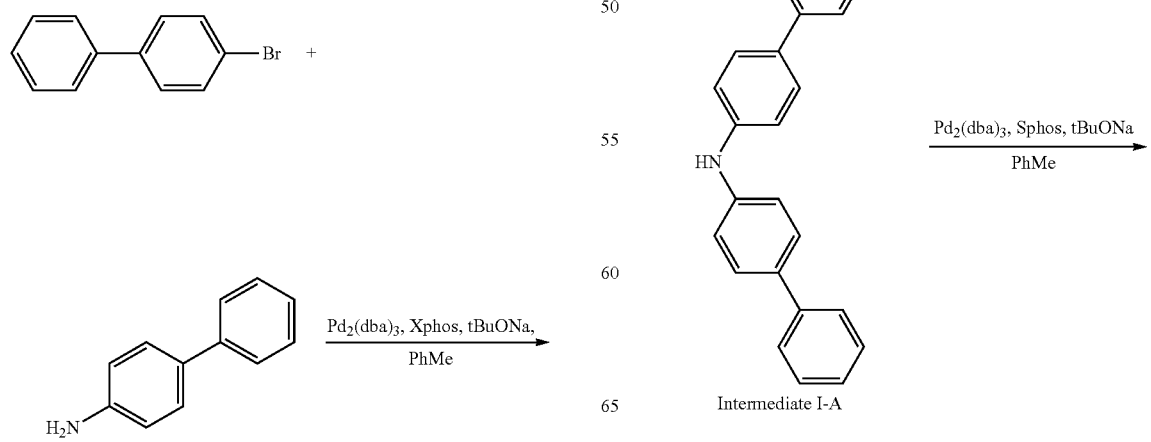

-continued

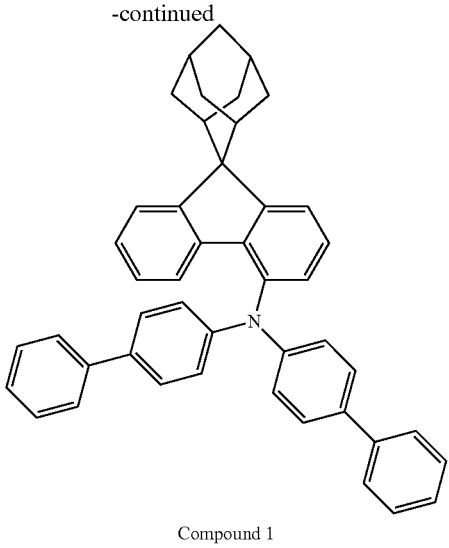

Compound 1

Intermediate I-A (5.6 g, 17.46 mmol), Intermediate II-A (5.61 g, 17.46 mmol), tris(dibenzylideneacetone)dipalladium (0.16 g, 0.17 mmol), 2-dicyclohexylphosphine-2',6'-dimethoxybiphenyl (0.14 g, 0.35 mmol) and sodium tert-butoxide (2.52 g, 26.18 mmol) were added to toluene (40 mL). The mixture was heated to 108° C. under nitrogen gas, and stirred for 3 h. After cooling to room temperature, the reaction solution was washed with water and dried over magnesium sulfate. After filtration, the solvent was removed from the filtrate under reduced pressure. The crude product was purified by recrystallization with a toluene system to obtain compound 1 as a white solid (4.35 g, 41%). Mass spectrum: m/z=606.3[M+H]$^+$.

$^1$H NMR (CDCl$_3$, 400 MHz): 8.17 (d, 1H), 8.15-8.12 (m, 2H), 7.54 (d, 4H), 7.45 (d, 4H), 7.41-7.35 (m, 5H), 7.28 (t, 2H), 7.24-7.17 (m, 7H), 3.03-2.97 (m, 4H), 2.24 (d, 2H), 2.03 (s, 2H), 1.86-1.80 (m, 4H), 1.69 (s, 2H).

Referring to Table 1, the following compounds were prepared in the same synthesis method as Example 1, except that raw material 1 was used to replace 4-aminobiphenyl and raw material 2 was used to replace 4-bromobiphenyl:

TABLE 1
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 2 | 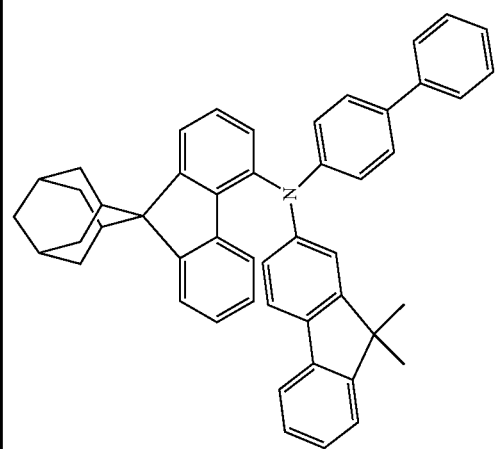 | 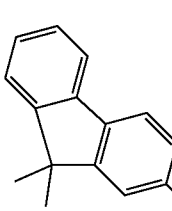 | 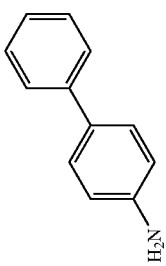 | 67 | 646.3 |

TABLE 1-continued

Raw materials, structure and mass spectrum of some compounds

| Compound Nos | Raw material 1 | Raw material 2 | Product | yield/% | Mass spectrum (m/z)[M + H]+ |
|---|---|---|---|---|---|
| 6 | | (dibromodibenzofuran structure) | (product structure) | 69 | 620.3 |
| 8 | | (bromophenyl carbazole structure) | (product structure) | 67 | 695.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 13 | | 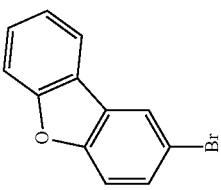 | 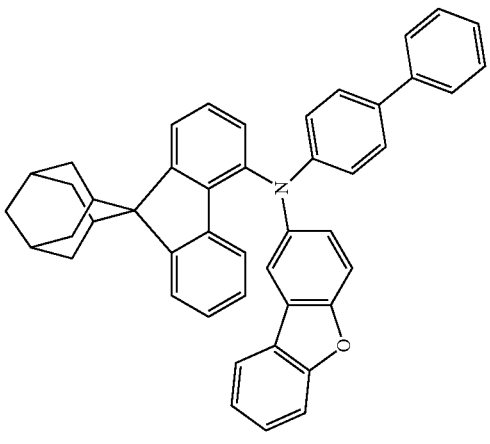 | 72 | 620.3 |
| 19 | | 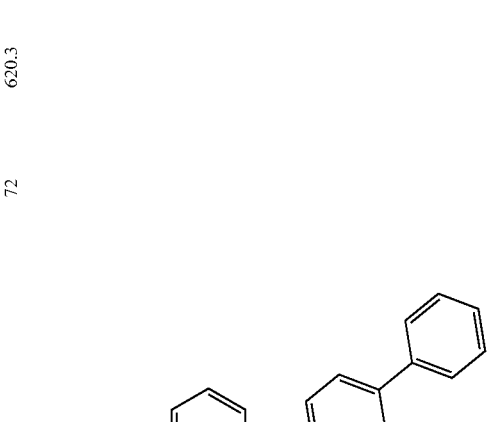 | 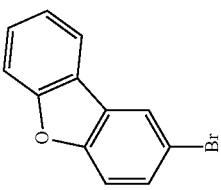 | 54 | 696.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 30 | 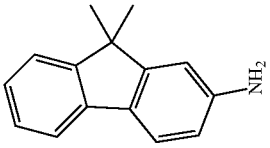 | 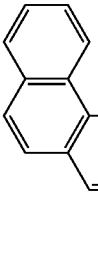 | 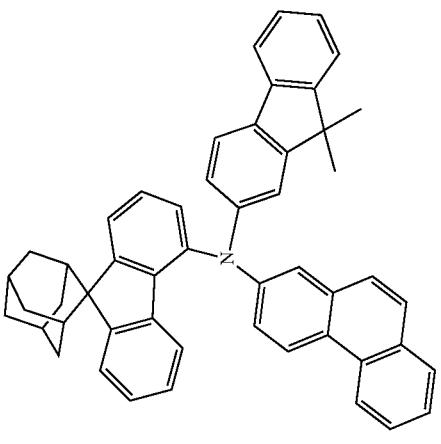 | 49 | 670.3 |
| 47 | | | | 62 | 676.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 58 | 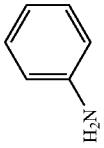 | 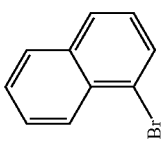 | 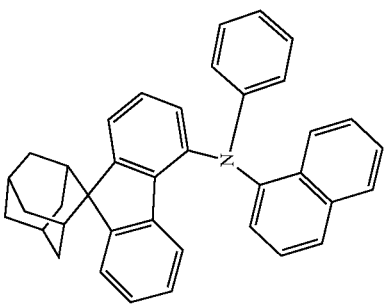 | 53 | 504.3 |
| 63 | | 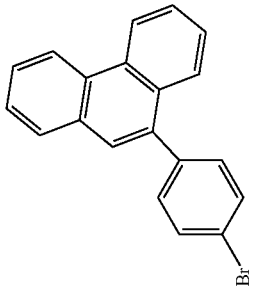 | 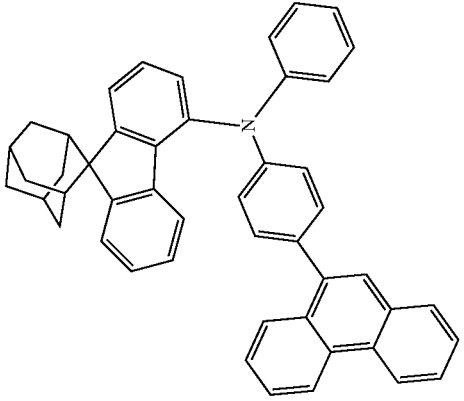 | 69 | 630.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 76 | | 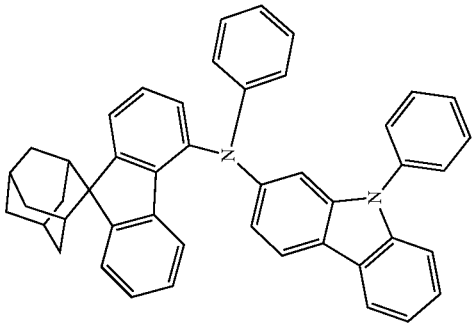 | 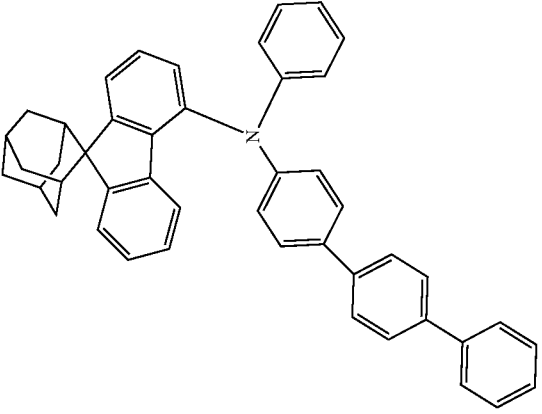 | 55 | 619.3 |
| 78 | | 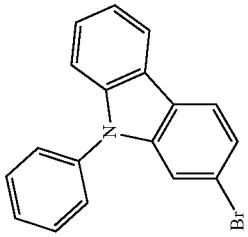 | 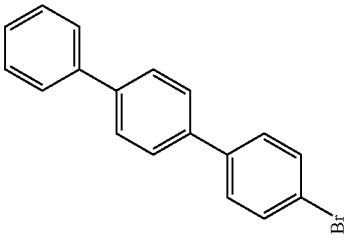 | 67 | 606.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 82 | 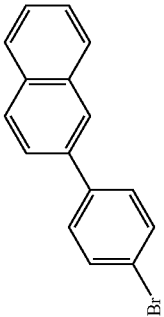 | 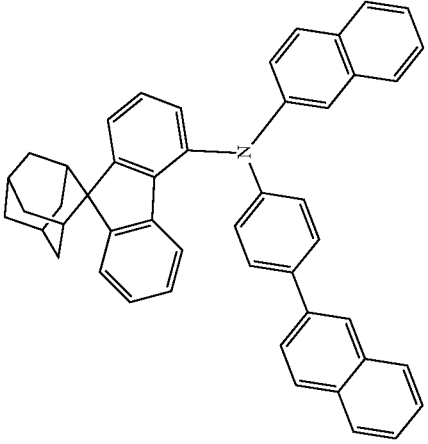 | 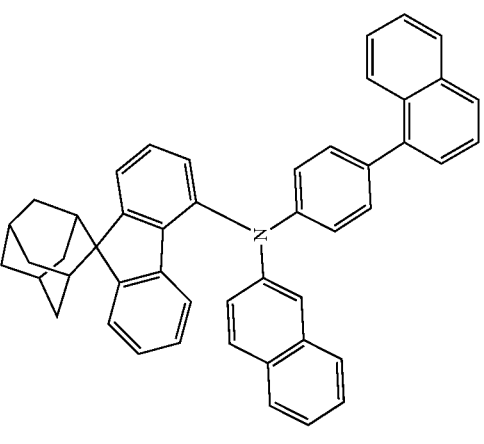 | 50 | 630.3 |
| 83 | | 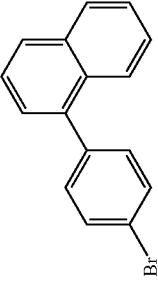 | 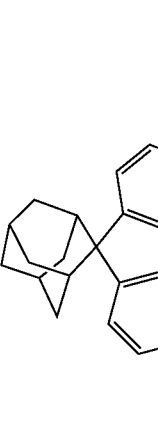 | 43 | 630.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 104 | 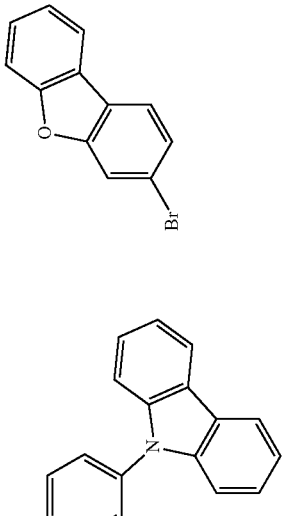 | 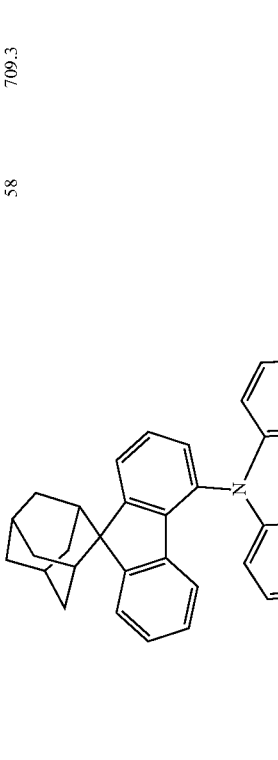 | 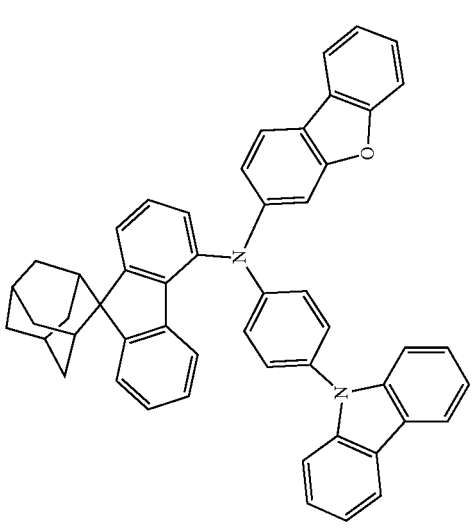 | 58 | 709.3 |
| 182 | 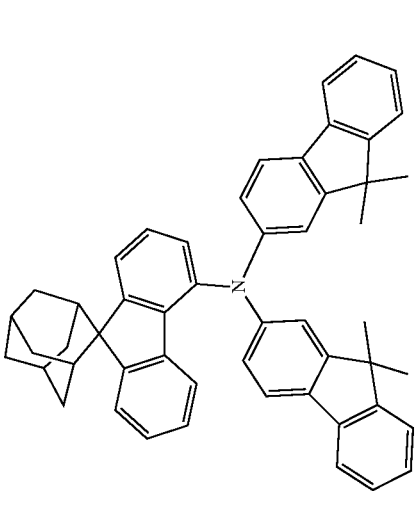 | 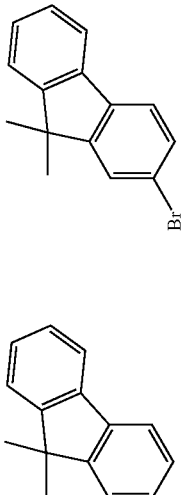 | | 61 | 686.4 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 306 | | 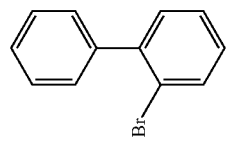 | | 66 | 672.3 |
| 189 | | | | 28 | 656.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 185 | 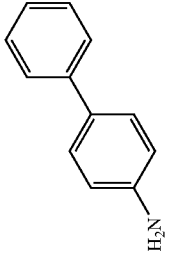 | | 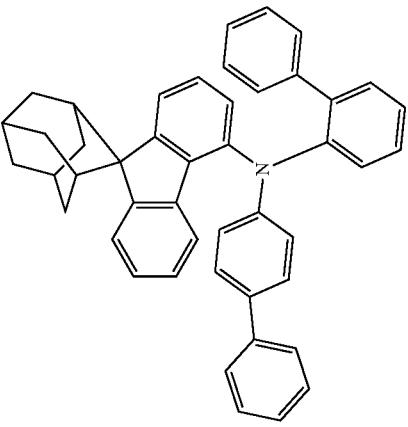 | 34 | 606.3 |
| 194 | 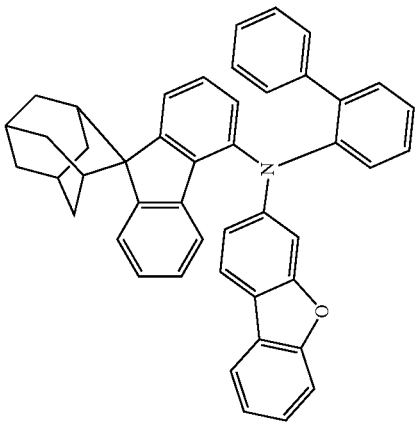 | | 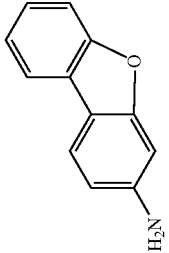 | 37 | 620.3 |

TABLE 1-continued

Raw materials, structure and mass spectrum of some compounds

| Compound Nos | Raw material 1 | Raw material 2 | Product | yield/% | Mass spectrum (m/z)[M + H]⁺ |
|---|---|---|---|---|---|
| 211 | ![H2N-Ph] | ![bromo-terphenyl] | ![product 211] | 49 | 606.3 |
| 313 | | ![bromobenzene-d5] | ![product 313] | 69 | 459.3 |

TABLE 1-continued
Raw materials, structure and mass spectrum of some compounds
| Compound Nos | Raw material 1 | Raw material 2 | Product | yield/% | Mass spectrum (m/z)[M + H]+ |
|---|---|---|---|---|---|
| 299 | 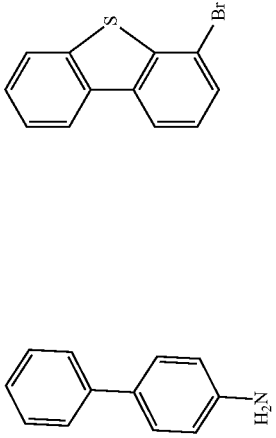 | 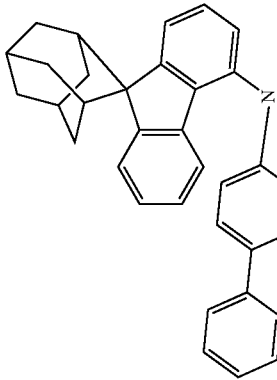 | 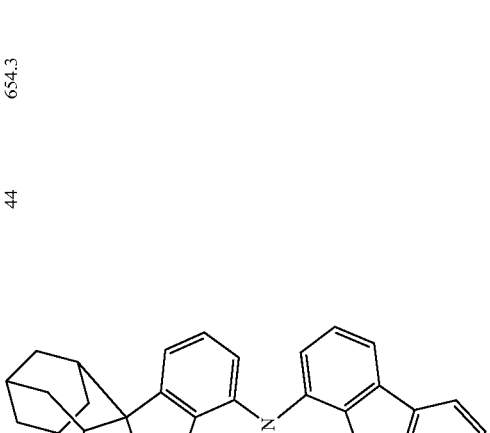 | 44 | 654.3 |

Wherein, the NMR data of compound 2 are:

¹H NMR, 400 MHz (CD$_2$Cl$_2$): 8.17 (d, 1H), 8.11 (t, 2H), 7.59 (d, 1H), 7.56 (d, 2H), 7.47 (d, 2H), 7.52 (d, 1H), 7.41-7.36 (m, 5H), 7.28 (t, 2H), 7.25-7.18 (m, 3H), 7.15-7.11 (m, 3H), 6.93 (d, 1H), 3.02 (d, 2H), 2.96 (d, 2H), 2.23 (d, 2H), 2.03 (s, 2H), 1.87-1.81 (m, 4H), 1.64 (s, 2H), 1.42 (s, 3H), 1.39 (s, 3H)

The NMR data of compound 6 are:

¹H NMR, 400 MHz (CD$_2$Cl$_2$): 8.20 (d, 1H), 8.14-8.12 (m, 2H), 7.83 (d, 1H), 7.77 (d, 1H), 7.56 (d, 2H), 7.50 (d, 2H), 7.46 (d, 1H), 7.42-7.34 (m, 4H), 7.29 (t, 2H), 7.25-7.19 (m, 5H), 7.15-7.13 (m, 2H), 3.02 (d, 2H), 2.98-2.95 (m, 2H), 2.23 (d, 2H), 2.03 (s, 2H), 1.86-1.81 (m, 4H), 1.66 (s, 2H)

The NMR data of compound 182 are:

¹H NMR (CD$_2$Cl$_2$, 400 MHz): 8.16 (d, 1H), 8.09 (d, 2H), 7.58 (d, 2H), 7.49 (d, 2H), 7.46 (s, 2H), 7.39-7.35 (m, 3H), 7.28 (t, 2H), 7.24-7.21 (m, 3H), 7.15 (t, 1H), 7.07 (t, 1H), 6.83 (d, 2H), 3.03 (d, 2H), 2.95 (d, 2H), 2.22 (d, 2H), 2.03 (s, 2H), 1.87-1.80 (m, 4H), 1.63 (s, 2H), 1.42 (s, 6H), 1.39 (s, 6H)

Synthesis of Compound 7

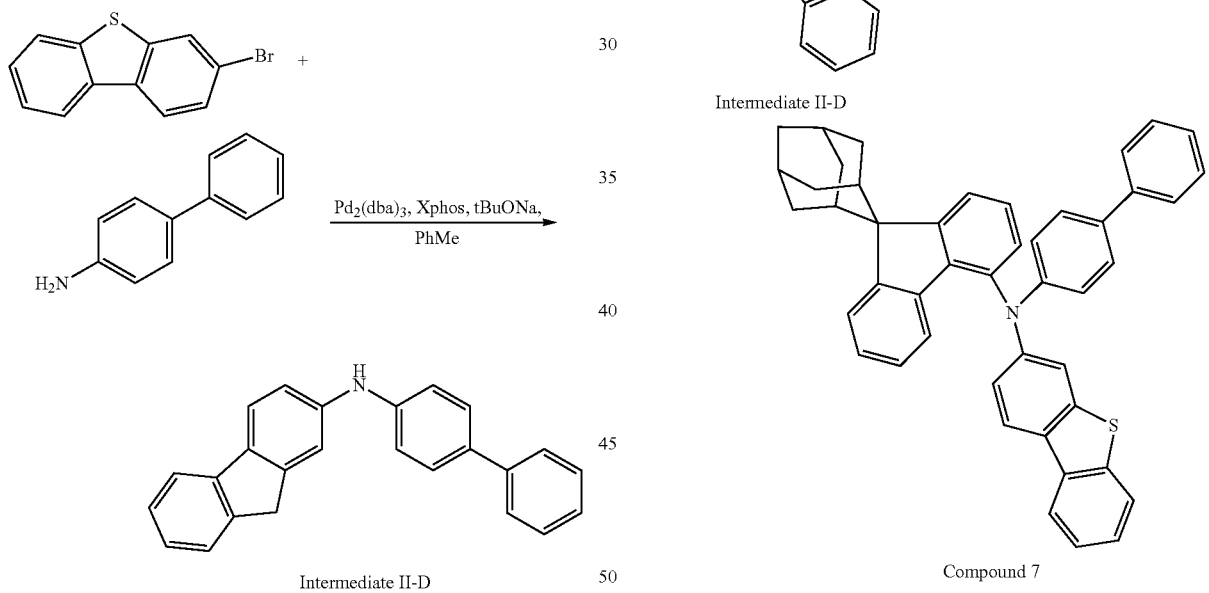

Intermediate II-D

Compound 7

3-bromodibenzothiophene (10.0 g, 38.0 mmol), 4-aminobiphenyl (6.56 g, 38.75 mmol), tris(dibenzylideneacetone)dipalladium (0.35 g, 0.38 mmol), 2-dicyclohexylphosphine-2',4',6'-triisopropylbiphenyl (0.36 g, 0.76 mmol) and sodium tert-butoxide (5.48 g, 57.0 mmol) were added to toluene (80 mL). The mixture was heated to 108° C. under nitrogen, and stirred for 5 h. After cooling to room temperature, the reaction solution was washed with water and then dried with magnesium sulfate. After filtration, the solvent was removed from the filtrate under reduced pressure. The crude product was purified by recrystallization with a dichloromethane/ethyl acetate system to obtain intermediate II-D as a pale yellow solid (11.5 g, yield 86%).

Intermediate I-A (3.5 g, 10.9 mmol), intermediate II-D (3.83 g, 10.9 mmol), tris(dibenzylideneacetone)dipalladium (0.20 g, 0.22 mmol), 2-dicyclohexylphosphine-2',6'-dimethoxybiphenyl (0.18 g, 0.44 mmol) and sodium tert-butoxide (1.58 g, 16.4 mmol) were added to toluene (30 mL). The mixture was heated to 108° C. under nitrogen, and stirred for 6 h. After cooling to room temperature, the reaction solution was washed with water and dried with magnesium sulfate. After filtration, the filtrate was purified by chromatography on a silica gel column with dichloromethane/n-heptane (1/3) as the mobile phase. The solvent was removed from the collected fraction under reduced pressure. The crude product was purified by recrystallization with the toluene system to obtain compound 7 as a white solid (3.35 g, yield 48.3%). Mass spectrum: m/z=636.3 [M+H]⁺.

Synthesis of Compound 179

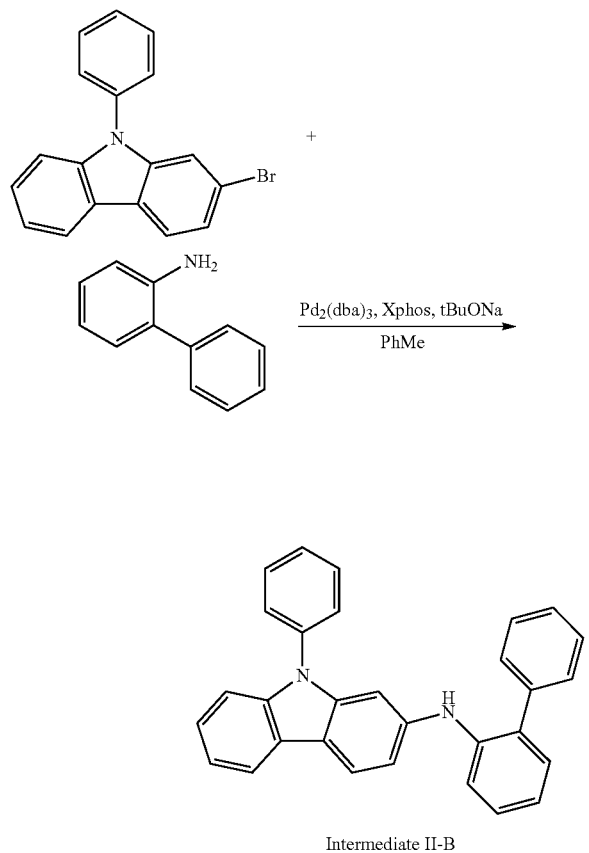

Intermediate II-B 2-bromo-N-phenylcarbazole (10.0 g, 31.0 mmol), 2-aminobiphenyl (5.78 g, 34.1 mmol), tris(dibenzylideneacetone)dipalladium (0.28 g, 0.31 mmol), 2-Dicyclohexylphosphine-2',4',6'-triisopropylbiphenyl (0.30 g, 0.62 mmol) and sodium tert-butoxide (4.47 g, 46.6 mmol) were added to toluene (80 mL). The mixture was heated to 108° C. under nitrogen and stirred for 4 h. After cooling to room temperature, the reaction solution was washed with water and dried with magnesium sulfate. After filtration, the solvent was removed from the filtrate under reduced pressure. The crude product was purified by recrystallization with a dichloromethane/n-heptane system to obtain Intermediate II-B as an orange solid (8.65 g, yield 67.9%).

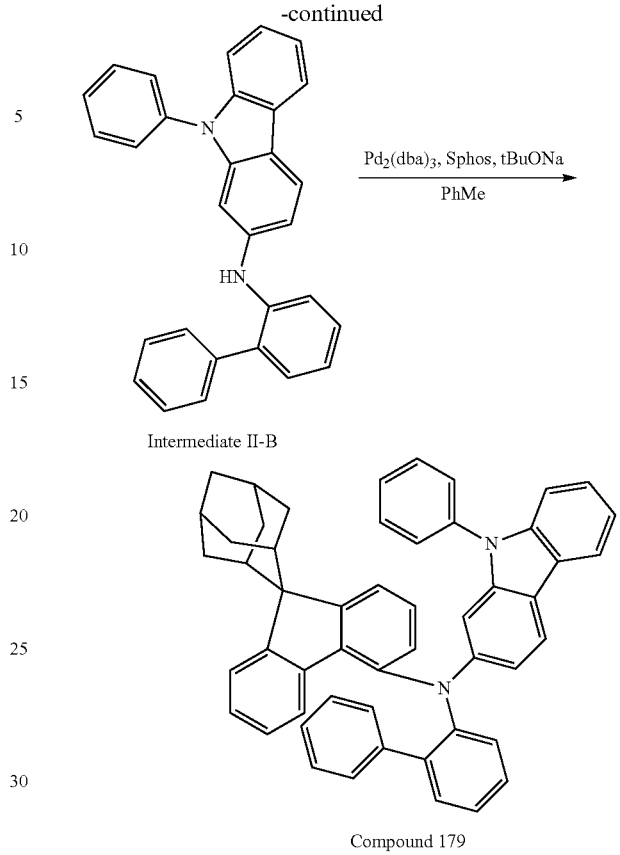

Intermediate II-B

Compound 179

Intermediate I-A (3.5 g, 10.9 mmol), intermediate II-B (4.48 g, 10.9 mmol), tris(dibenzylideneacetone) dipalladium (0.20 g, 0.22 mmol), 2-dicyclohexylphosphine-2',6'-dimethoxybiphenyl (0.18 g, 0.44 mmol) and sodium tert-butoxide (1.57 g, 16.3 mmol) were added to toluene (30 mL). The mixture was heated to 108° C. under nitrogen gas, and stirred for 10 h. After cooling to room temperature, the reaction solution was washed with water and dried with magnesium sulfate. After filtration, the filtrate was purified through a silica gel column chromatography with dichloromethane/n-heptane (1/5) as the mobile phase. The solvent was removed from the collected fraction under reduced pressure. The crude product was purified by recrystallization with the dichloroethane system to obtain compound 179 as a white solid (5.42 g, yield 71.6%). Mass spectrum: m/z=695.3 [M+H]⁺.

Synthesis of Compound 144

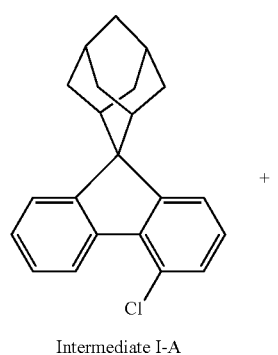

Intermediate I-A

-continued

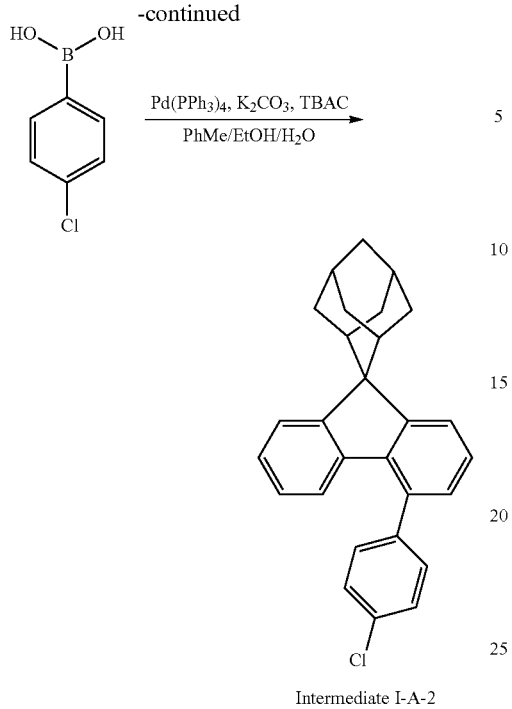

Intermediate I-A-2

Intermediate I-A (10 g, 31.0 mmol), p-chlorophenylboronic acid (3.23 g, 20.7 mmol), tetra(triphenylphosphine) palladium (1.19 g, 1.03 mmol), potassium carbonate (5.71 g, 41.38 mmol), tetrabutylammonium chloride (0.28 g, 1.03 mmol), toluene (80 mL), ethanol (20 mL) and deionized water (20 mL) were added to the round-bottom flask. The mixture was heated to 78° C. under nitrogen gas and stirred for 8 hours. The reaction solution was cooled to room temperature, and toluene (100 mL) was added for extraction. The organic phases were combined, and dried over anhydrous magnesium sulfate. After filtration, the solvent was removed from the filtrate under reduced pressure. The resulting crude product was purified through silica gel column chromatography with n-heptane as the mobile phase, and then was purified by recrystallization with the dichloromethane/ethyl acetate system to obtain intermediate I-A-2 as a white solid (7.56 g, yield 92%).

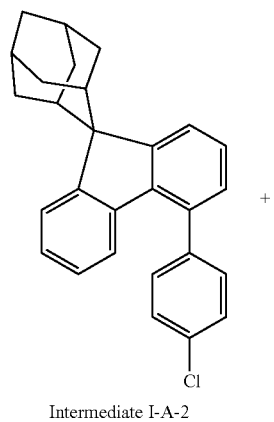

+

Intermediate I-A-2

-continued

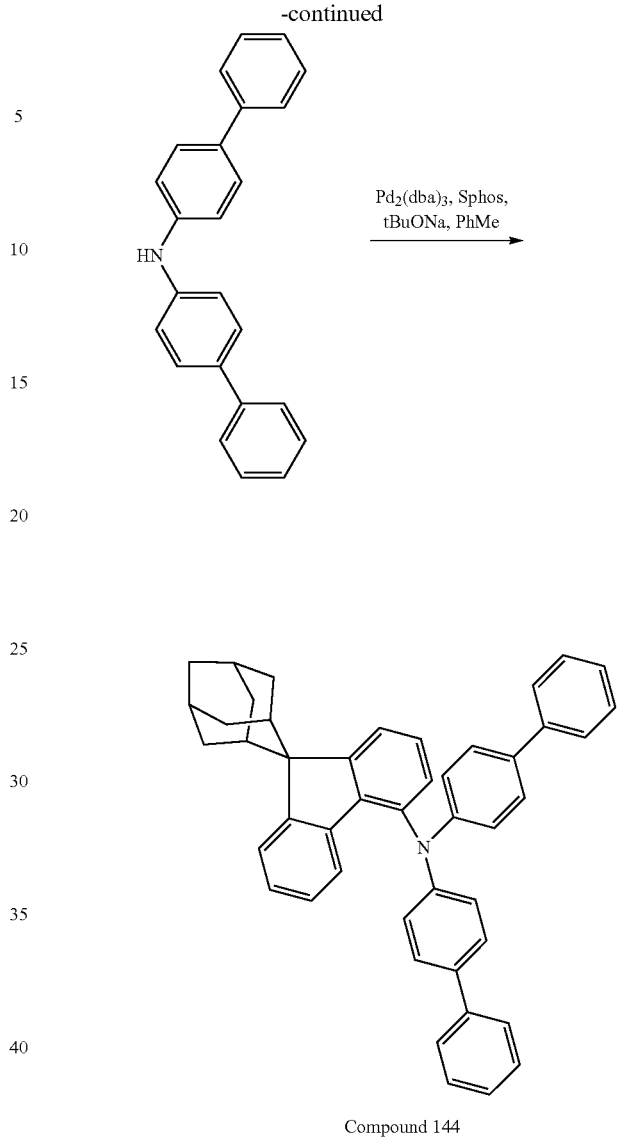

Compound 144

The intermediate I-A-2 (3 g, 7.6 mmol), di-(4-biphenyl) amine (2.43 g, 7.6 mmol), tris(dibenzylideneacetone) dipalladium (0.14 g, 0.15 mmol), 2-dicyclohexylphosphine-2',6'-dimethoxybiphenyl (0.12 g, 0.30 mmol) and sodium tert-butoxide (1.09 g, 11.33 mmol) were added to toluene (25 mL). The mixture was heated to 108° C. under nitrogen gas, and was stirred for 2 h. After cooling to room temperature, the reaction solution was washed with water and then dried with magnesium sulfate. After filtration, the filtrate was passed through a short silica gel column. The solvent was removed under reduced pressure. The crude product was purified by recrystallization with a toluene system to obtain compound 144 as a white solid (2.68 g, yield 52%). Mass spectrum: m/z=682.3[M+H]+.

Referring to the synthesis method of intermediate I-A-2, the intermediates shown in the third column of the table below were synthesized, except that the raw materials 3 in the second column of Table 2 below were used to replace p-chlorophenylboronic acid:

TABLE 2

Raw materials and intermediates

| Intermediates No. | Raw material 3 | Intermediate structures | yield (%) |
|---|---|---|---|
| Intermediate I-C | 3-chlorophenylboronic acid | 9-(adamantyl)-4-(3-chlorophenyl)fluorene | 37 |
| Intermediate I-D | 2-chlorophenylboronic acid | 9-(adamantyl)-4-(2-chlorophenyl)fluorene | 41 |
| Intermediate I-E | 4-chloronaphthalen-1-ylboronic acid | 9-(adamantyl)-4-(4-chloronaphthalen-1-yl)fluorene | 44 |

TABLE 2-continued

Raw materials and intermediates

| Intermediates No. | Raw material 3 | Intermediate structures | yield (%) |
|---|---|---|---|
| Intermediate I-F | 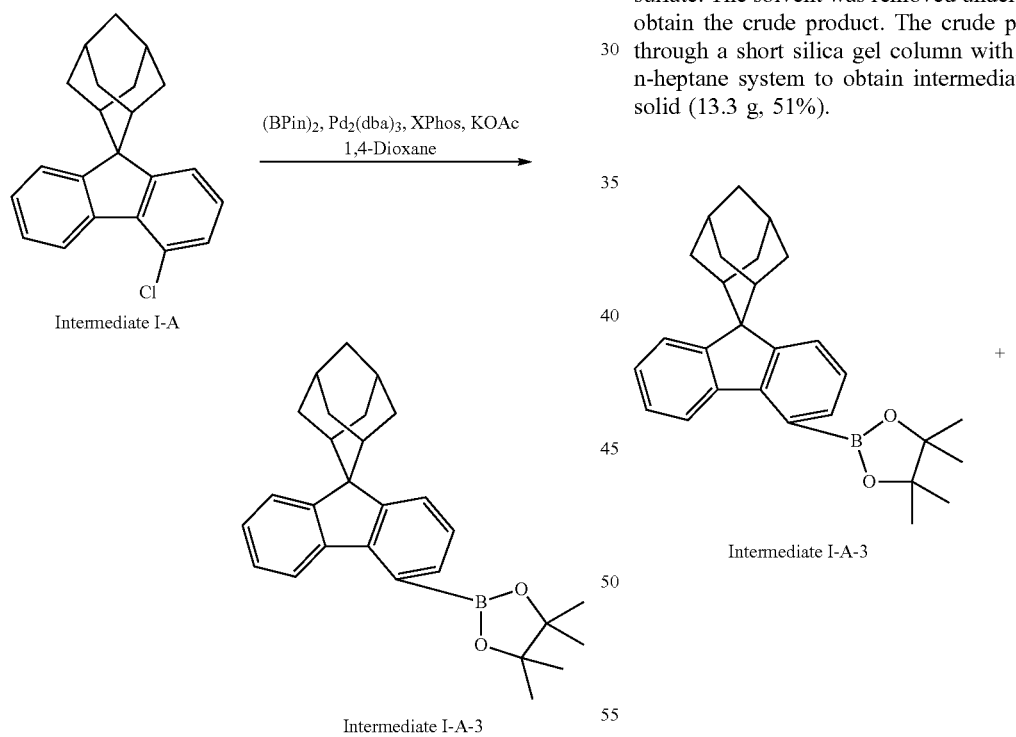 | | 39 | sulfate. The solvent was removed under reduced pressure to obtain the crude product. The crude product was purified through a short silica gel column with a dichloromethane/n-heptane system to obtain intermediate I-A-3 as a white solid (13.3 g, 51%).

Intermediate I-A (20.4 g, 63.7 mmol), pinacol biborate (19.4 g, 76.5 mmol), tris(dibenzylideneacetone) dipalladium (0.6 g, 0.6 mmol), 2-dicyclohexylphosphine-2',4',6'-triisopropylbiphenyl (0.6 g, 1.3 mmol), potassium acetate (12.5 g, 127.4 mmol) and 1,4-dioxane (150 mL) were added to the flask. The mixture was stirred under reflux at 100° C. for 16 hours under nitrogen gas. After cooling to room temperature, dichloromethane and water were added to the reaction solution. After separating the layers, the organic phase was washed with water and dried over anhydrous magnesium

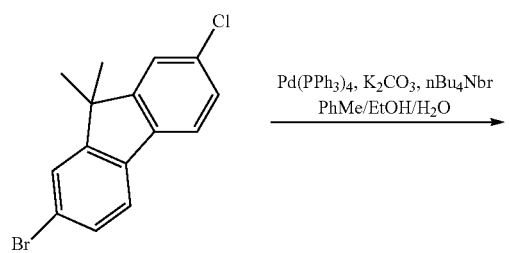

-continued

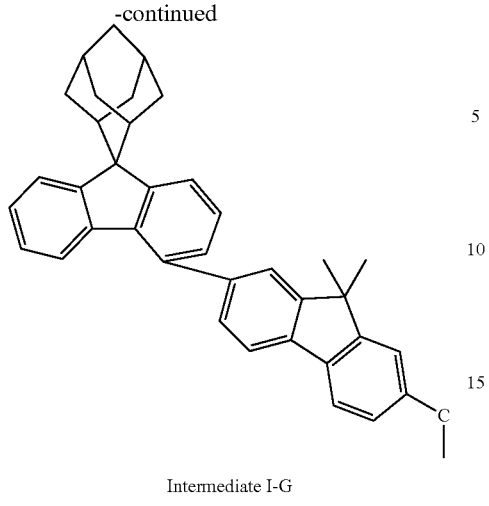

Intermediate I-G

The intermediate I-A-3 (13.3 g, 32.3 mmol), 2-bromo 7-chloro-9,9-dimethylfluorene (7.1 g, 35.5 mmol), tetra(triphenylphosphine) palladium (0.7 g, 0.6 mmol), potassium carbonate (11.1 g, 80.7 mmol), tetrabutylammonium bromide (2.1 g, 6.5 mmol) was added to the flask, and a mixed solvent of toluene (80 mL), ethanol (20 mL) and water (20 mL) was added. Under nitrogen gas, the mixture was heated to 80° C., and was stirred for 24 hours by maintaining the temperature. After cooling to room temperature, the stirring was stopped. After washing with water, the reaction solution was separated to obtain the organic phase. The organic phase was dried over anhydrous magnesium sulfate, and the solvent was removed under reduced pressure to obtain the crude product. The crude product was purified through a short silica gel column with a dichloromethane/n-heptane system as the mobile phase to obtain the intermediate I-G as a white solid product (9.0 g, 69%).

Referring to the synthesis method of intermediate I-G, the intermediates shown in the third column of the table below were synthesized, except that the raw materials 41 in the second column of Table 3 below were used to replace 2-bromo 7-chloro-9,9-dimethylfluorene:

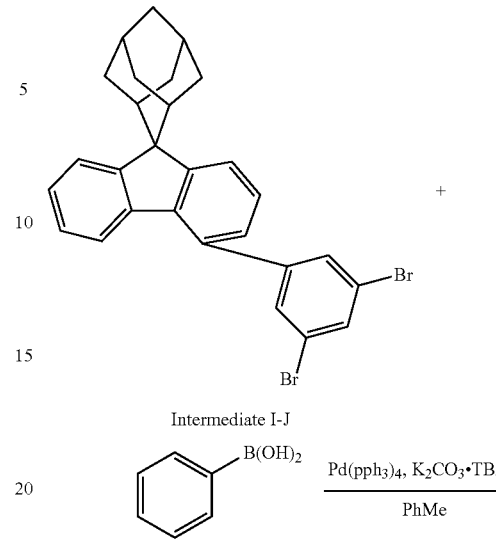

Intermediate I-J

Pd(pph3)4, K2CO3·TBAC
PhMe

Intermediate I-J-1

TABLE 3

Raw materials and intermediates

| Intermediate No. | Raw material 41 | Intermediate structure | yield (%) |
|---|---|---|---|
| Intermediate I-J | Br-phenyl-Br,Br structure | adamantyl-fluorene-phenyl(Br,Br) structure | 31 |

The intermediate I-J (30 g, 112.05 mmol), phenylboronic acid (22.50 g, 112.05 mmol), tetra(triphenylphosphine)palladium (6.47 g, 5.60 mmol), potassium carbonate (46.39 g, 336.7 mmol), tetrabutyl Ammonium chloride (1.56 g, 5.60 mmol), toluene (240 mL), ethanol (120 mL) and deionized water (60 mL) were added to a three-necked flask. The mixture was heated to 78° C. under nitrogen gas and stirred for 8 hours. The reaction solution was cooled to room temperature, and toluene (150 mL) was added for extraction. The organic phases were combined, and dried over anhydrous magnesium sulfate. After filtration, a filtrate was obtained. The filtrate was concentrated under reduced pressure to obtain a crude product. The obtained crude product was purified through silica gel column chromatography with n-heptane as the mobile phase. After that, it was purified by recrystallization with a dichloromethane/ethyl acetate system (1:3) to obtain intermediate I-J-1 (34.8 g, yield 80%).

Referring to the synthesis method of compound 1, the compounds shown in the fourth column of Table 4 were prepared with the intermediates shown in the third column of Table 4 below, which were used to replace intermediate I-A, and intermediate II-A. The specific compound number, structure, raw materials, and the synthesis yield of the final step and characterization data, etc. are shown in Table 4.

TABLE 4

Compound number, structure, preparation and characterization data

| Compound No. | Intermediate No. | Intermediate structure | Compound structure | yield (%) | Mass spectrometry (m/z) [M + H]+ |
|---|---|---|---|---|---|
| 307 | Intermediate I-C | | 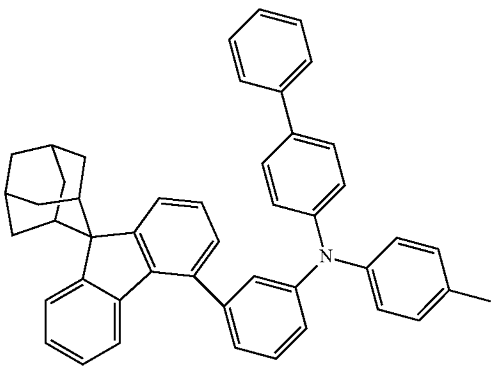 [SMILES: Cc1ccc(N(c2ccc(-c3ccccc3)cc2)c2cccc(-c3cccc4c3-c3ccccc3C43C4CC5CC(C4)CC3C5)c2)cc1] | 61 | 682.3 |
| 308 | Intermediate I-D | | 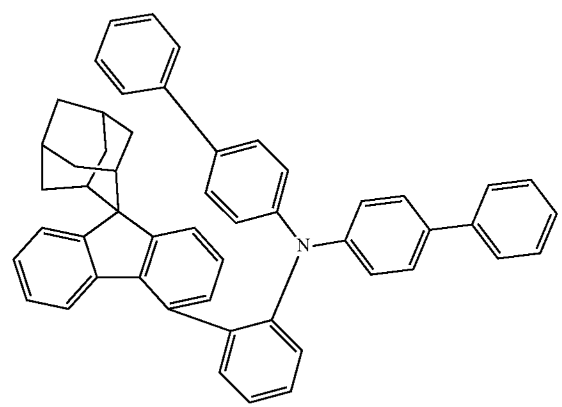 [SMILES: c1ccc(-c2ccc(N(c3ccc(-c4ccccc4)cc3)c3ccccc3-c3cccc4c3-c3ccccc3C43C4CC5CC(C4)CC3C5)cc2)cc1] | 57 | 682.3 |

TABLE 4-continued

Compound number, structure, preparation and characterization data

| Compound No. | Intermediate No. | Intermediate structure | Compound structure | yield (%) | Mass spectrometry (m/z) [M + H]+ |
|---|---|---|---|---|---|
| 309 | Intermediate I-E | | 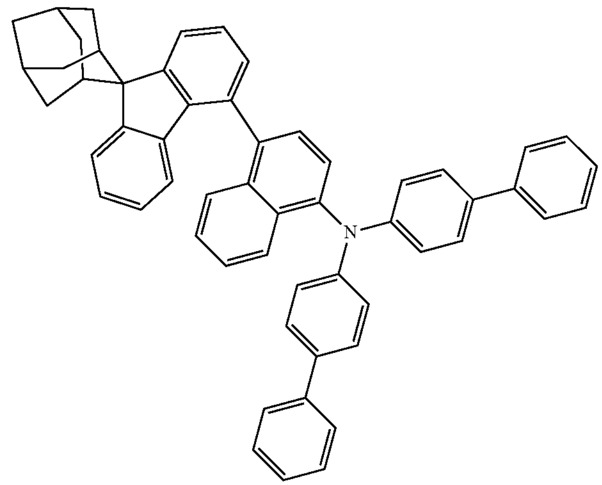 [SMILES: c1ccc(-c2ccc(N(c3ccc(-c4ccccc4)cc3)c3ccc(-c4cccc5c4-c4ccccc4C54C5CC6CC(C5)CC4C6)c4ccccc34)cc2)cc1] | 69 | 732.4 |
| 310 | Intermediate I-F | | 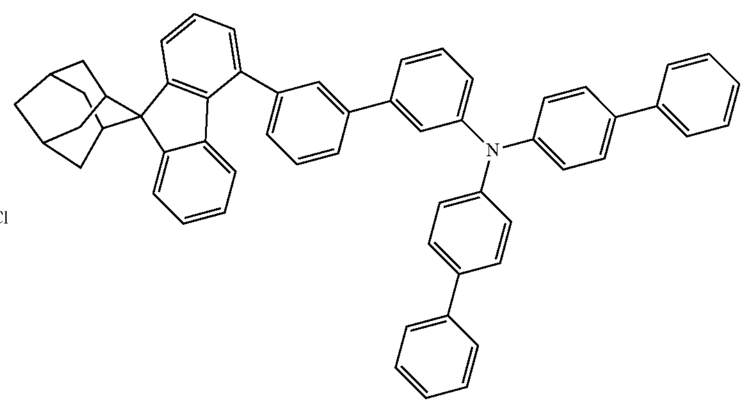 | 54 | 758.4 |

TABLE 4-continued

Compound number, structure, preparation and characterization data

| Compound No. | Intermediate No. | Intermediate structure | Compound structure | yield (%) | Mass spectrometry (m/z) [M + H]+ |
|---|---|---|---|---|---|
| 311 | Intermediate I-G | | 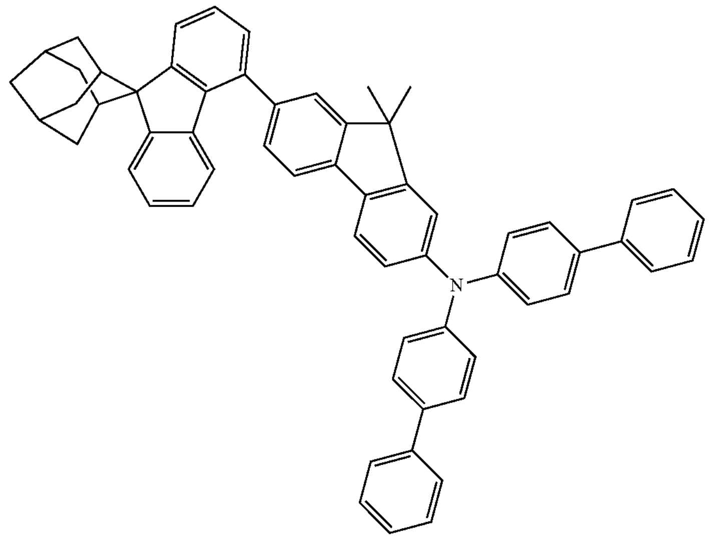 [SMILES: CC1(C)c2cc(-c3cccc4c3-c3ccccc3C43C4CC5CC(C4)CC3C5)ccc2-c2ccc(N(c3ccc(-c4ccccc4)cc3)c3ccc(-c4ccccc4)cc3)cc21] | 49 | 798.4 |
| 312 | Intermediate I-J-1 | | 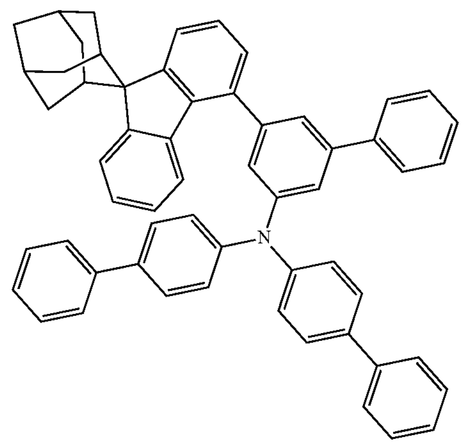 [SMILES: c1ccc(-c2ccc(N(c3ccc(-c4ccccc4)cc3)c3cc(-c4ccccc4)cc(-c4cccc5c4-c4ccccc4C54C5CC6CC(C5)CC4C6)c3)cc2)cc1] | 49 | 758.4 |

Synthesis of Compound 276

Compound 276 was prepared by the same synthetic method as in Compound 144, except that 4'-chlorobiphenyl 4-boronic acid was used to replace p-chlorophenylboronic acid. Mass spectrum: m/z=758.4 [M+H]+.

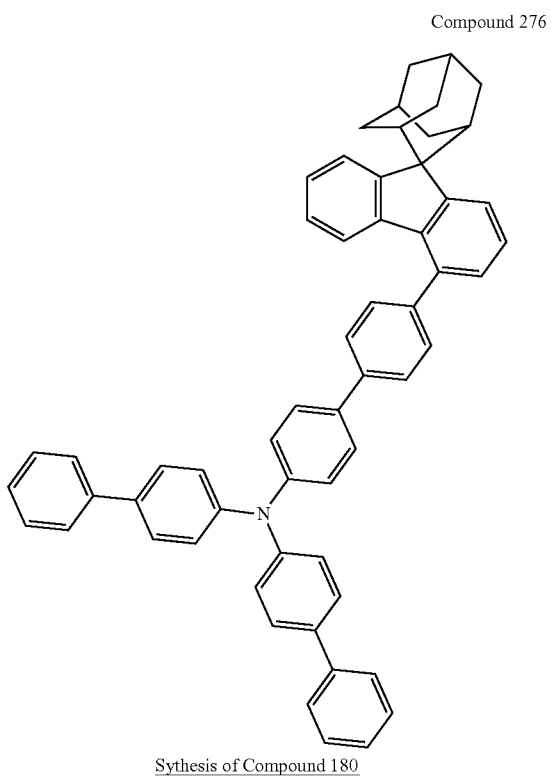

Sythesis of Compound 180

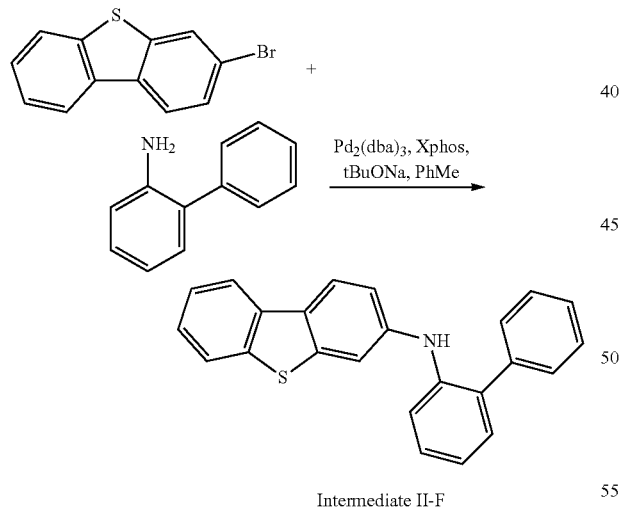

3-bromodibenzothiophene (10.0 g, 38.0 mmol), 2-aminobiphenyl (7.07 g, 41.8 mmol), tris(dibenzylideneacetone) dipalladium (0.35 g, 0.38 mmol), 2-dicyclohexylphosphine-2',4',6'-triisopropylbiphenyl (0.36 g, 0.76 mmol) and sodium tert-butoxide (5.48 g, 57.0 mmol) were added to toluene (80 mL). The mixture was heated to 108° C. under nitrogen, and stirred for 1.5 h. After cooling to room temperature, the reaction solution was washed with water and dried with magnesium sulfate. After filtration, the filtrate was passed through a short silica gel column, and the solvent was removed under reduced pressure. The crude product was purified by recrystallization with dichloromethane/ethyl acetate system to obtain intermediate II-F as a white solid (11.5 g, yield 86%).

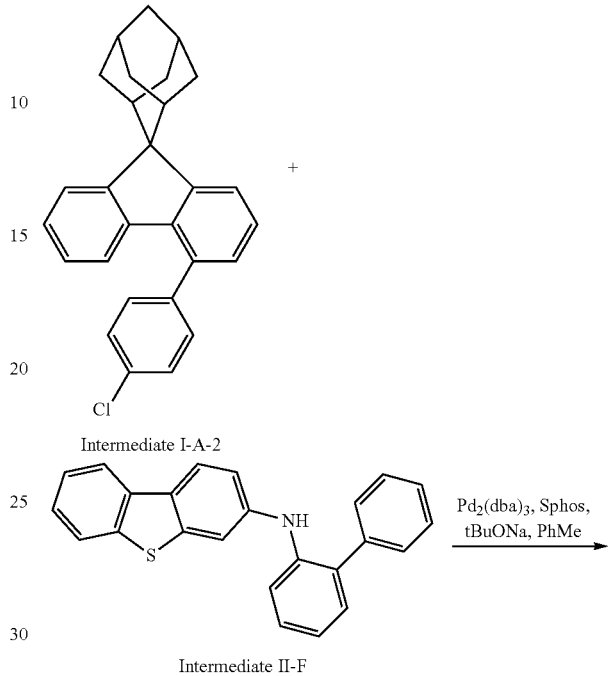

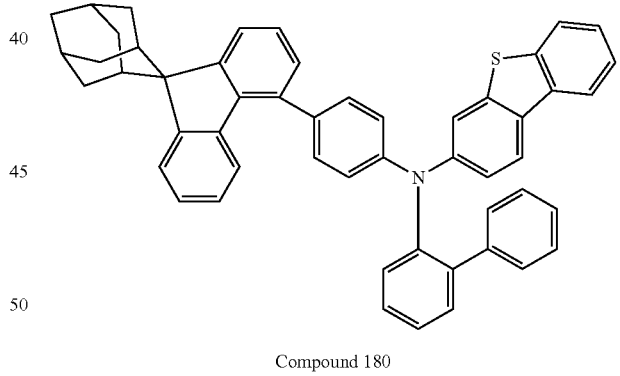

Intermediate I-A-2 (3.0 g, 7.6 mmol), intermediate II-F (2.63 g, 7.6 mmol), tris(dibenzylideneacetone) dipalladium (0.14 g, 0.15 mmol), 2-dicyclohexylphosphine-2',6'-dimethoxybiphenyl (0.12 g, 0.30 mmol) and sodium tert-butoxide (1.09 g, 11.33 mmol) were added to toluene (25 mL). The mixture was heated to 108° C. under nitrogen gas, and was stirred for 3 h. After cooling to room temperature, the reaction solution was washed with water and dried over magnesium sulfate. After filtration, the filtrate was passed through a short silica gel column and the solvent was removed under reduced pressure. The crude product was purified by recrystallization with a toluene system to obtain compound 180 as a white solid (2.17 g, yield 40%). Mass spectrum: m/z=712.3 [M+H]+.

Synthesis of Compound 181

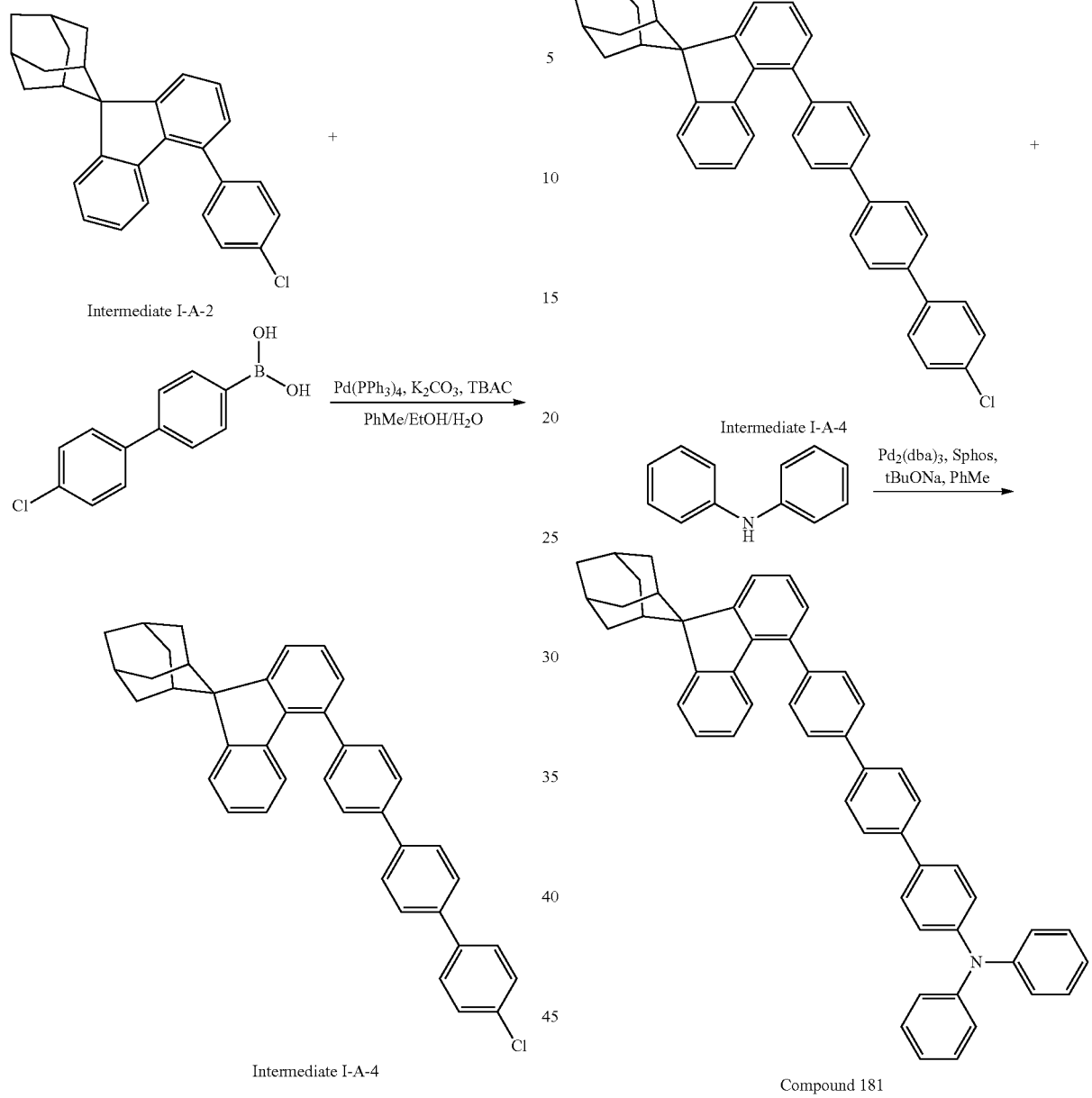

The intermediate I-A-2 (2.03 g, 3.91 mmol), 4'-chlorobiphenyl-4-boronic acid (1.05 g, 3.91 mmol), tetra(triphenylphosphine) palladium (0.09 g, 0.13 mmol), potassium carbonate (1.74 g, 12.6 mmol), tetrabutylammonium chloride (0.13 g, 0.31 mmol), toluene (25 mL), ethanol (6 mL) and deionized water (6 mL) were added to the round bottom flask. The mixture was heated to 78° C. under nitrogen gas, and was stirred for 19 hours. Cooling to room temperature, toluene (30 mL) was added to the reaction solution for extraction. The organic phases were combined, and dried with anhydrous magnesium sulfate. After filtration, the solvent was removed under reduced pressure. The obtained crude product was purified through silica gel column chromatography with n-heptane as the mobile phase. After that, it was purified by recrystallization with dichloromethane/ethyl acetate system to obtain white solid intermediate I-A-4 (0.79 g, yield 37%).

The intermediate I-A-4 (0.79 g, 1.44 mmol), 2-aniline (0.24 g, 1.44 mmol), tris(dibenzylideneacetone) dipalladium (0.01 g, 0.01 mmol), 2-dicyclohexylphosphine-2',6'-dimethoxybiphenyl (0.02 g, 0.02 mmol) and sodium tert-butoxide (0.47 g, 6.6 mmol) were added to toluene (10 mL). The mixture was heated to 108° C. under nitrogen gas, and was stirred for 4 h. After cooling to room temperature, the reaction solution was washed with water, and dried with magnesium sulfate. After filtration, the solvent was removed under reduced pressure. The crude product was purified by recrystallization with a dichloromethane/n-heptane system to obtain compound 181 (0.57 g, yield 58.2%). Mass spectrum: m/z=682.4 [M+H]+.

Synthesis of Compound 157

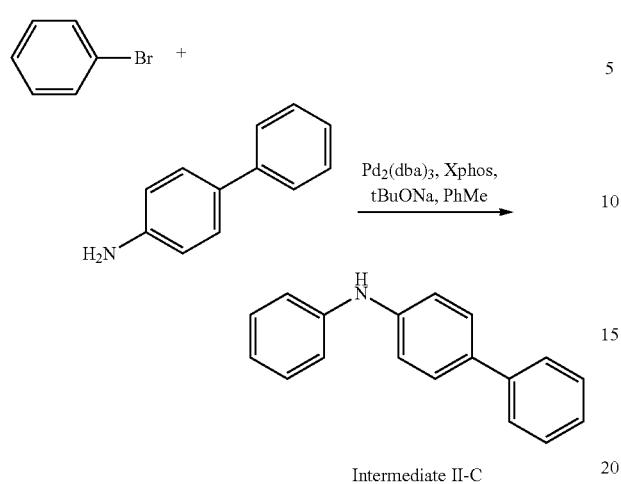

Intermediate II-C

Bromobenzene (10.0 g, 38.0 mmol), 4-aminobiphenyl (7.07 g, 41.8 mmol), tris(dibenzylideneacetone) dipalladium (0.35 g, 0.38 mmol), 2-dicyclohexylphosphine-2',4',6'-triisopropylbiphenyl (0.36 g, 0.76 mmol) and sodium tert-butoxide (5.48 g, 57.0 mmol) were added to toluene (80 mL). The mixture was heated to 108° C. under nitrogen, and was stirred for 2 h. After cooling to room temperature, the reaction solution was washed with water and dried over magnesium sulfate. After filtration, the solvent was removed from the filtrate under reduced pressure. The crude product was purified by recrystallization with a dichloromethane/ethyl acetate system to obtain a light yellow solid intermediate II-C (8.0 g, 86%).

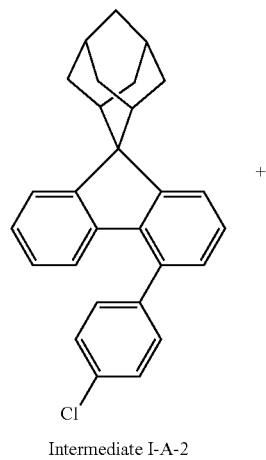

Intermediate I-A-2

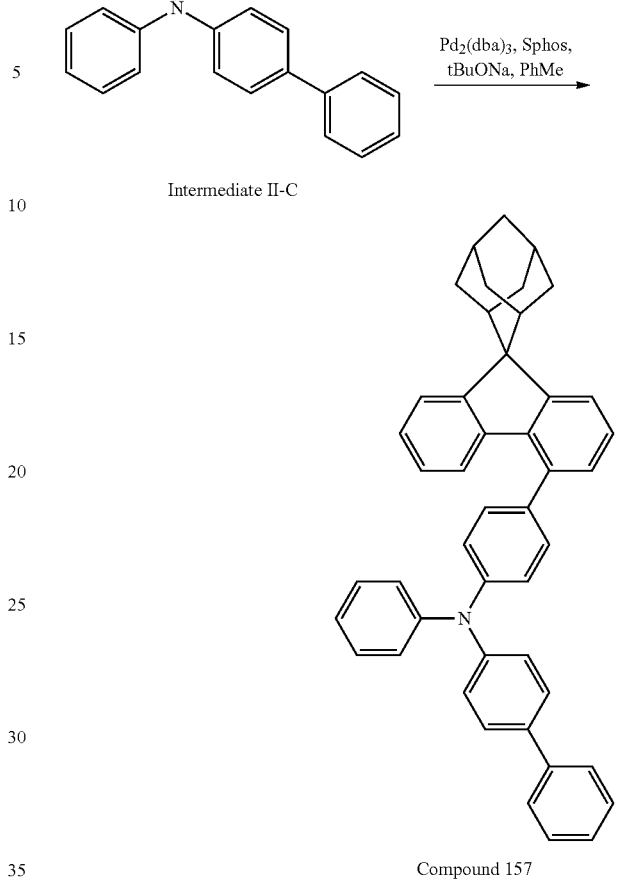

Compound 157

Intermediate I-A-2 (3.50 g, 10.9 mmol), intermediate II-C (3.51 g, 10.9 mmol), tris(dibenzylideneacetone) dipalladium (0.20 g, 0.22 mmol), 2-dicyclohexyl phosphine-2',6'-dimethoxybiphenyl (0.18 g, 0.44 mmol) and sodium tert-butoxide (1.58 g, 16.4 mmol) were added to toluene (30 mL). The mixture was heated to 108° C. under nitrogen gas, and was stirred for 2 h. After cooling to room temperature, the reaction solution was washed with water and dried with magnesium sulfate. After filtration, the solvent was removed from the filtrate under reduced pressure. The crude product was purified by recrystallization with a toluene system to obtain a white solid compound 157 (4.35 g, 65.87%). Mass spectrum: m/z=606.3 [M+H]+

Using the same synthesis method as compound 157, the compounds shown in Table 5 were prepared, except that the raw material 3 was used to replace 4-aminobiphenyl and raw material 4 was used to replace bromobenzene.

TABLE 5
Raw materials, structure and mass spectrum of some compounds
| Compound | Raw material 3 | Raw material 4 | product | yield/% | mass spectrum (m/z) [M + H]⁺ |
|---|---|---|---|---|---|
| 154 | 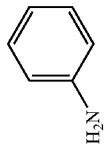 | 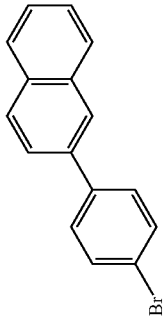 | 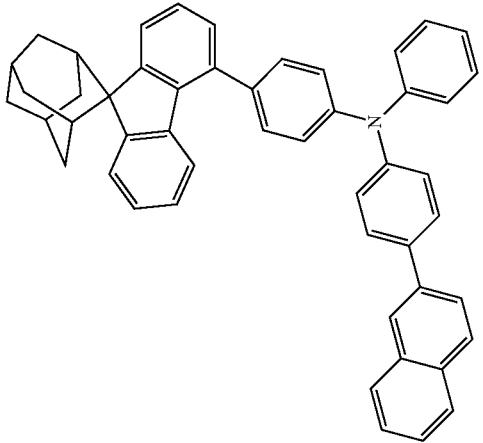 | 63 | 656.3 |

TABLE 5-continued
Raw materials, structure and mass spectrum of some compounds
| Compound | Raw material 3 | Raw material 4 | product | yield/% | mass spectrum (m/z) [M + H]$^+$ |
|---|---|---|---|---|---|
| 166 | 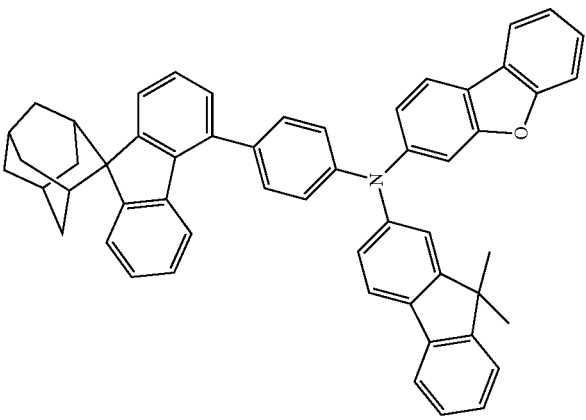 | 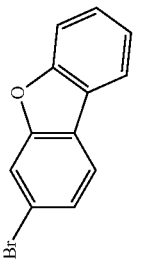 | 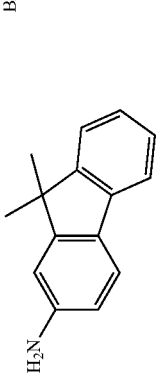 | 54 | 736.4 |

TABLE 5-continued
Raw materials, structure and mass spectrum of some compounds
| Compound | Raw material 3 | Raw material 4 | product | yield/% | mass spectrum (m/z) [M + H]+ |
|---|---|---|---|---|---|
| 184 | 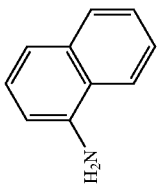 | 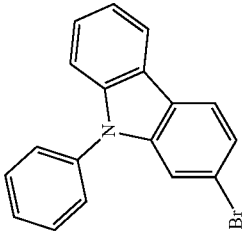 | 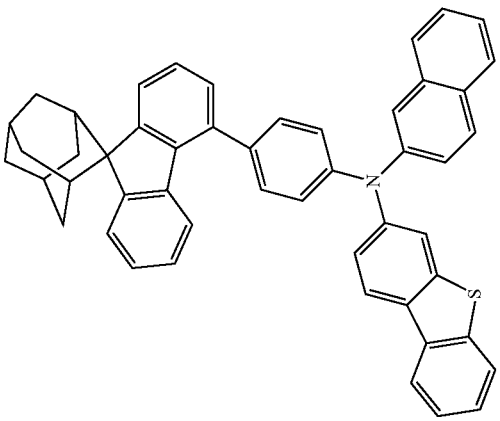 | 41 | 686.3 |

PREPARATION AND EVALUATION OF ORGANIC ELECTROLUMINESCENT DEVICES

Example 1

The green organic electroluminescent device was prepared by the following method The ITO substrate (made by Corning) with an ITO thickness of 1500 Å was cut into a size of 40 mm (length)× 40 mm (width)×0.7 mm (thickness). The photolithography process was used to prepare it with cathode, anode, and insulating layer patterns. The experimental substrate was treated with ultraviolet ozone and $O_2$:$N_2$ plasma to increase the work function of the anode (experimental substrate) and remove scum.

m-MTDATA was vacuum-evaporated on the experimental substrate (anode) to form a hole injecting layer (HIL) with a thickness of 100 Å, and NPB was vacuum-evaporated on the hole injecting layer to form a hole transporting layer with a thickness of 1000 Å.

Compound 1 was evaporated on the hole transporting layer to form an electron blocking layer with a thickness of 100 Å.

α,β-ADN was used as the main body, doping BD-1 at a film thickness ratio of 100:3 at the same time to form a light emitting layer (EML) with a thickness of 200 Å.

DBimiBphen and LiQ were mixed in a weight ratio of 1:1 and evaporated to form an electron transporting layer (ETL) with a thickness of 300 Å. LiQ was evaporated on the electron transporting layer to form an electron injecting layer (EIL) with a thickness of 10 Å. Then, magnesium (Mg) and silver (Ag) were mixed at a vapor deposition rate of 1:9 and vacuum-evaporated on the electron injecting layer to form a cathode with a thickness of 120 Å.

CP-1 with a thickness of 650 Å was vapor-deposited on the cathode to complete the manufacture of a blue organic light-emitting device.

The structures of m-MTDATA, NPB, α,β-ADN, BD-1, DBimiBphen, LiQ, CP-1 are as follows:

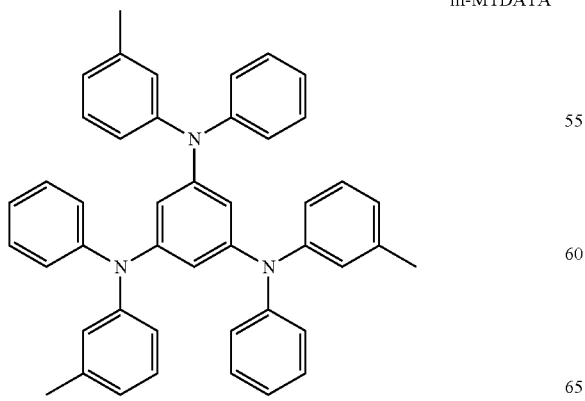

m-MTDATA

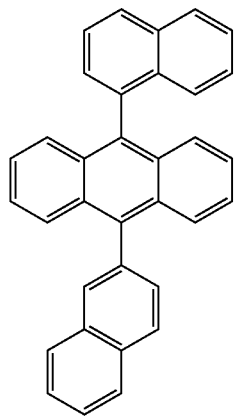

α,β-ADN

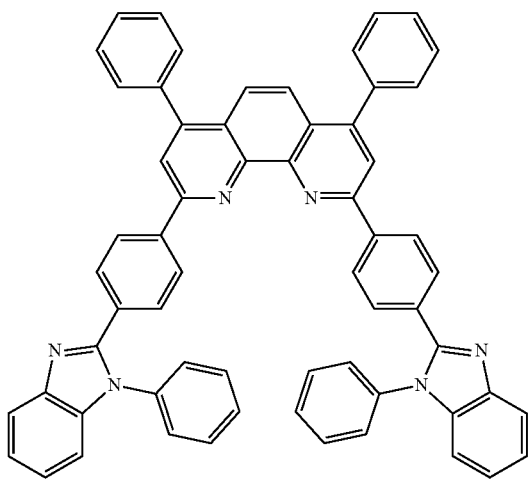

DBimiBphen

LiQ

-continued

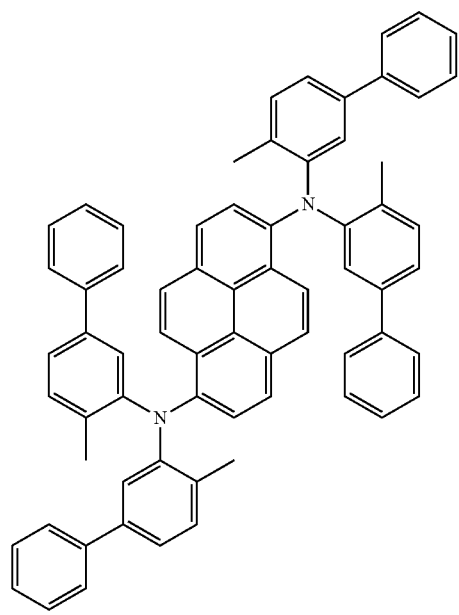
BD-1

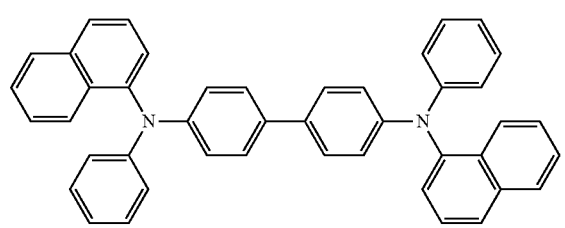
NPB

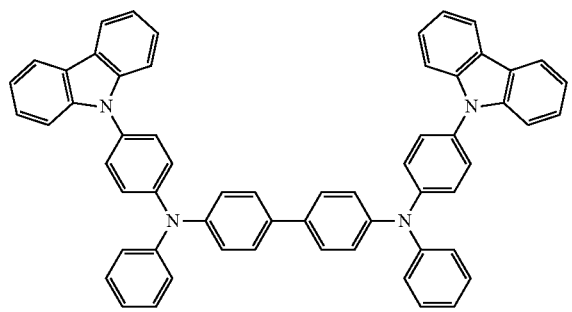
CP-1

Example 2-Example 39

The corresponding blue organic electroluminescent devices were prepared in the same manner as in Example 1, by replacing Compound 1 in Example 1 with the electron blocking layer materials listed in Table 6.

Comparative Example 1

The corresponding blue organic electroluminescent device was prepared in the same manner as in Example 1, by replacing Compound 1 in Example 1 with TCTA. The structure of TCTA is as follows:

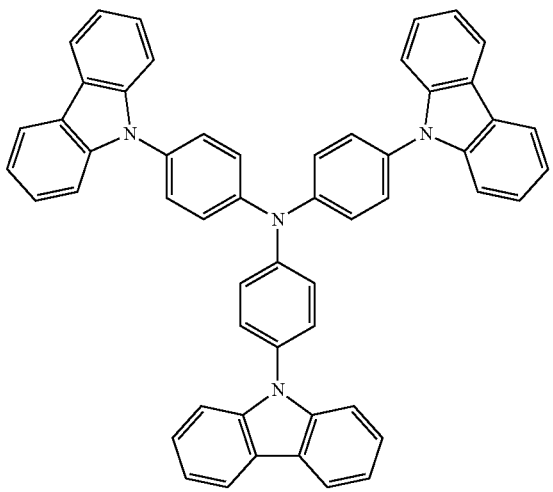
TCTA

Comparative Example 2

The corresponding blue organic electroluminescent device was prepared in the same manner as in Example 1, by replacing Compound 1 in Example 1 with Compound A.

The structure of Compound A is as follows:

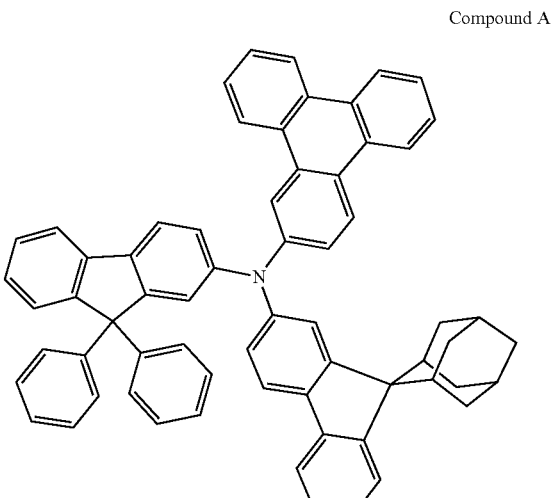
Compound A

Comparative Example 3

The corresponding blue organic electroluminescent device was prepared in the same manner as in Example 1, by replacing Compound 1 in Example 1 with Compound B.

The structure of Compound B is as follows:

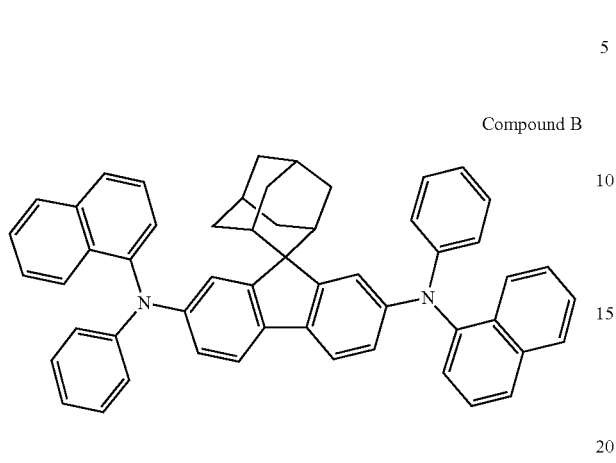

Compound B

The structure of Compound D is as follows:

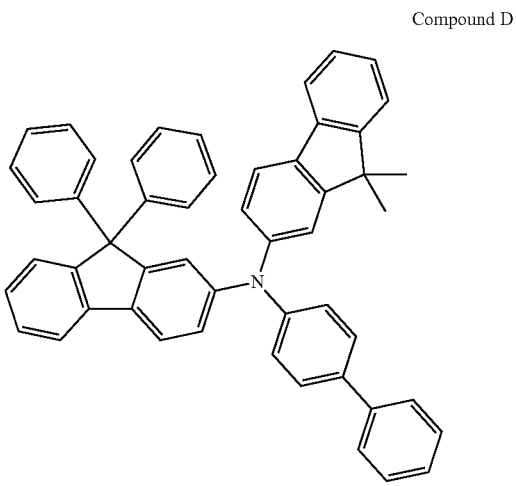 [SMILES: CC1(C)c2ccccc2-c2ccc(N(c3ccc(-c4ccccc4)cc3)c3ccc4c(c3)C(c3ccccc3)(c3ccccc3)c3ccccc3-4)cc21]

Compound D

Comparative Example 4

The corresponding blue organic electroluminescent device was prepared in the same manner as in Example 1, by replacing Compound 1 in Example 1 with Compound C.

The structure of Compound C is as follows:

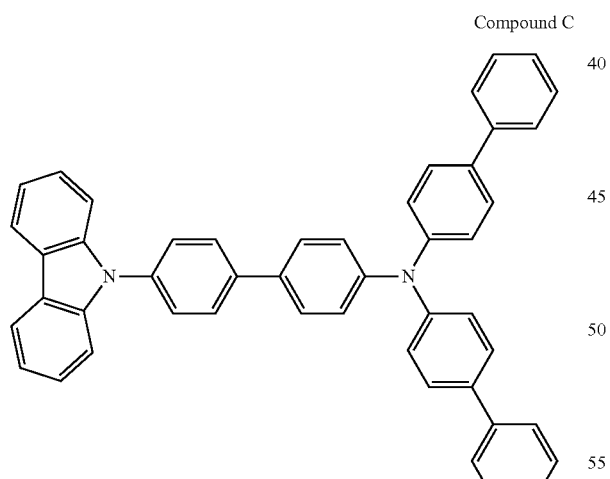

Compound C

Comparative Example 6

The corresponding blue organic electroluminescent device was prepared in the same manner as in Example 1, by replacing Compound 1 in Example 1 with Compound E.

The structure of Compound E is as follows:

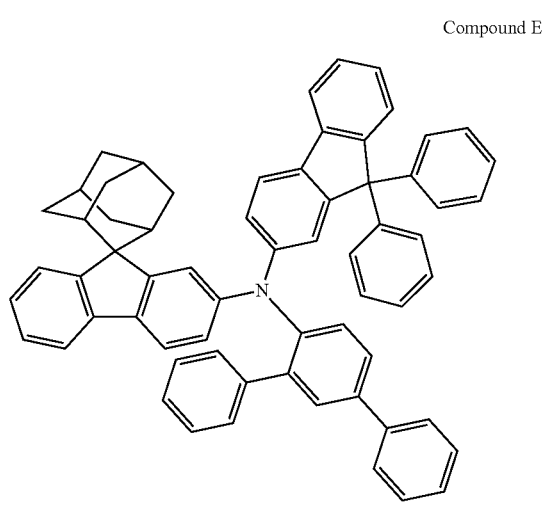 [SMILES: c1ccc(-c2ccc(N(c3ccc4c(c3)C(c3ccccc3)(c3ccccc3)c3ccccc3-4)c3ccc4c(c3)C3(c5ccccc5-4)C4CC5CC(C4)CC3C5)c(-c3ccccc3)c2)cc1]

Compound E

Comparative Example 5

The corresponding blue organic electroluminescent device was prepared in the same manner as in Example 1, by replacing Compound 1 in Example 1 with Compound D.

Comparative Example 7

The corresponding blue organic electroluminescent device was prepared in the same manner as in Example 1, by replacing Compound 1 with Compound F.

Compound F

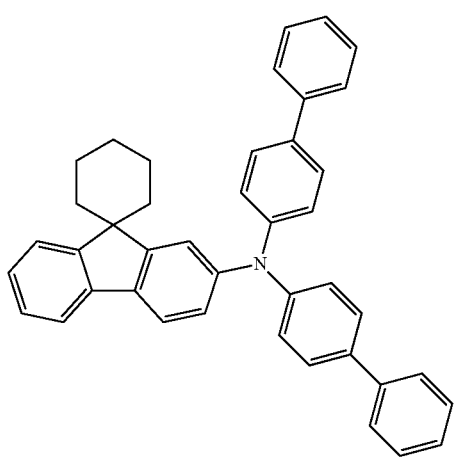

Comparative Example 8

The corresponding blue organic electroluminescent device was prepared in the same manner as in Example 1, by replacing Compound 1 with Compound G.

Compound G

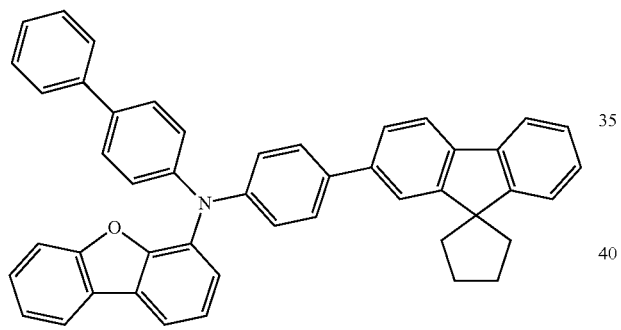

Comparative Example 9

The corresponding blue organic electroluminescent device was prepared in the same manner as in Example 1, by replacing Compound 1 with Compound H.

Compound H

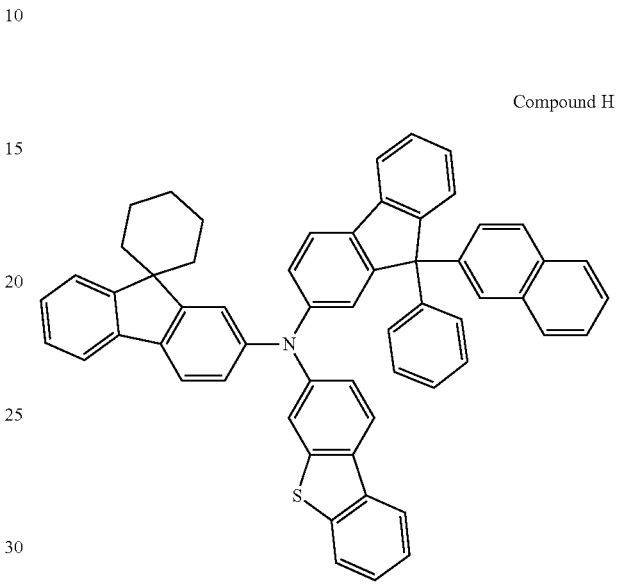

For the blue organic electroluminescent devices prepared in Examples 1 to 39 and Comparative Examples 1 to 9, the driving voltage, current efficiency, color coordinate, and external quantum efficiency of the devices were tested under the conditions of 10 mA/cm$^2$. T95 lifetime of the devices was tested at 20 mA/cm$^2$.

TABLE 6

Performance test results of blue organic electroluminescent devices

| | hole transporting layer material | Electron blocking material | Driving voltage (V) | Current efficiency (Cd/A) | Color coordinates CIEy | External quantum efficiency EQE (%) | T95 lifetime (h) |
|---|---|---|---|---|---|---|---|
| Example 1 | NPB | Compound 1 | 4.01 | 6.3 | 0.047 | 13.0 | 201 |
| Example 2 | NPB | Compound 2 | 4.03 | 6.4 | 0.047 | 13.2 | 203 |
| Example 3 | NPB | Compound 6 | 4.02 | 6.3 | 0.048 | 12.9 | 198 |
| Example 4 | NPB | Compound 7 | 4.03 | 6.4 | 0.047 | 13.0 | 195 |
| Example 5 | NPB | Compound 8 | 4.03 | 6.2 | 0.046 | 12.7 | 205 |
| Example 6 | NPB | Compound 13 | 3.99 | 6.3 | 0.047 | 13.0 | 200 |
| Example 7 | NPB | Compound 30 | 4.00 | 6.4 | 0.046 | 13.3 | 209 |
| Example 8 | NPB | Compound 47 | 3.98 | 6.2 | 0.047 | 12.6 | 190 |

TABLE 6-continued

Performance test results of blue organic electroluminescent devices

| | hole transporting layer material | Electron blocking material | Driving voltage (V) | Current efficiency (Cd/A) | Color coordinates CIEy | External quantum efficiency EQE (%) | T95 lifetime (h) |
|---|---|---|---|---|---|---|---|
| Example 9 | NPB | Compound 58 | 4.01 | 6.3 | 0.047 | 12.9 | 194 |
| Example 10 | NPB | Compound 63 | 3.98 | 6.2 | 0.046 | 12.7 | 197 |
| Example 11 | NPB | Compound 76 | 4.03 | 6.4 | 0.046 | 13.2 | 183 |
| Example 12 | NPB | Compound 78 | 4.01 | 6.3 | 0.047 | 13.0 | 201 |
| Example 13 | NPB | Compound 82 | 4.01 | 6.2 | 0.047 | 12.6 | 206 |
| Example 14 | NPB | Compound 83 | 4.02 | 6.2 | 0.046 | 12.9 | 189 |
| Example 15 | NPB | Compound 104 | 3.98 | 6.1 | 0.047 | 12.5 | 195 |
| Example 16 | NPB | Compound 144 | 3.99 | 6.3 | 0.048 | 12.8 | 205 |
| Example 17 | NPB | Compound 154 | 4.00 | 6.2 | 0.046 | 12.7 | 197 |
| Example 18 | NPB | Compound 157 | 3.98 | 6.4 | 0.047 | 13.0 | 203 |
| Example 19 | NPB | Compound 166 | 3.97 | 6.3 | 0.047 | 12.7 | 195 |
| Example 20 | NPB | Compound 179 | 4.01 | 6.1 | 0.048 | 12.6 | 200 |
| Example 21 | NPB | Compound 180 | 4.03 | 6.3 | 0.047 | 12.8 | 202 |
| Example 22 | NPB | Compound 181 | 4.01 | 6.4 | 0.047 | 13.3 | 192 |
| Example 23 | NPB | Compound 182 | 4.02 | 6.3 | 0.048 | 12.8 | 196 |
| Example 24 | NPB | Compound 184 | 3.98 | 6.4 | 0.047 | 13.0 | 193 |
| Example 25 | NPB | Compound 189 | 4.03 | 6.3 | 0.046 | 12.9 | 197 |
| Example 26 | NPB | Compound 185 | 4.00 | 6.1 | 0.047 | 12.9 | 200 |
| Example 27 | NPB | Compound 194 | 4.01 | 6.2 | 0.048 | 12.6 | 198 |
| Example 28 | NPB | Compound 211 | 4.01 | 6.2 | 0.046 | 12.8 | 195 |
| Example 29 | NPB | Compound 276 | 3.98 | 6.1 | 0.047 | 12.4 | 199 |
| Example 30 | NPB | Compound 19 | 4.01 | 6.3 | 0.046 | 12.5 | 190 |
| Example 31 | NPB | Compound 299 | 4.02 | 6.2 | 0.046 | 13.0 | 197 |
| Example 32 | NPB | Compound 307 | 4.00 | 6.2 | 0.047 | 12.7 | 203 |
| Example 33 | NPB | Compound 308 | 4.00 | 6.3 | 0.048 | 12.6 | 195 |
| Example 34 | NPB | Compound 309 | 3.98 | 6.1 | 0.046 | 12.8 | 200 |
| Example 35 | NPB | Compound 310 | 4.01 | 6.1 | 0.047 | 13.1 | 202 |
| Example 36 | NPB | Compound 311 | 3.99 | 6.3 | 0.046 | 12.8 | 192 |
| Example 37 | NPB | Compound 312 | 3.98 | 6.1 | 0.046 | 12.9 | 197 |
| Example 38 | NPB | Compound 313 | 4.02 | 6.2 | 0.047 | 12.8 | 195 |
| Example 39 | NPB | Compound 306 | 3.97 | 6.2 | 0.046 | 12.9 | 196 |
| Comparative example 1 | NPB | TCTA | 4.43 | 4.9 | 0.047 | 9.8 | 102 |
| Comparative example 2 | NPB | Compound A | 4.41 | 5.5 | 0.047 | 11.4 | 150 |
| Comparative example 3 | NPB | Compound B | 4.42 | 5.2 | 0.047 | 10.8 | 121 |
| Comparative example 4 | NPB | Compound C | 4.46 | 5.2 | 0.046 | 10.3 | 118 |
| Comparative example 5 | NPB | Compound D | 4.41 | 4.7 | 0.047 | 9.5 | 115 |

TABLE 6-continued

Performance test results of blue organic electroluminescent devices

| | hole transporting layer material | Electron blocking material | Driving voltage (V) | Current efficiency (Cd/A) | Color coordinates CIEy | External quantum efficiency EQE (%) | T95 lifetime (h) |
|---|---|---|---|---|---|---|---|
| Comparative example 6 | NPB | Compound E | 4.42 | 4.9 | 0.047 | 9.8 | 120 |
| Comparative example 7 | NPB | Compound F | 4.44 | 5.3 | 0.047 | 10.9 | 125 |
| Comparative example 8 | NPB | Compound G | 4.45 | 5.4 | 0.046 | 11.0 | 127 |
| Comparative example 9 | NPB | Compound H | 4.42 | 4.9 | 0.047 | 10.1 | 138 |

According to the results of Table 6 above, compared to the blue organic electroluminescent devices prepared in Comparative Examples 1-9, the blue organic electroluminescent devices prepared in Examples 1-39 had a lower driving voltage, higher luminous efficiency and higher external quantum efficiency, and the life of the devices was significantly improved. Compared with the blue organic electroluminescent devices prepared in Comparative Examples 1-9, the driving voltage of the blue organic electroluminescent devices prepared in Examples 1-39 was reduced by at least 0.38V, and the luminous efficiency (Cd/A) was increased by at least 10.9%; external quantum efficiency was increased by at least 9.6%; and the life was increased by at least 33 hours and by at least 22%.

Therefore, when the nitrogen-containing compound of the present disclosure is used for preparing an organic electroluminescent device, especially when it is used as an electron blocking layer of the organic electroluminescent device, it can effectively reduce the driving voltage of the electroluminescent devices, improve the external quantum efficiency and extend the life of organic electroluminescent devices.

According to the evaluation results of each device, it can be determined that the nitrogen-containing compound provided in the present disclosure can reduce the operating voltage of the organic electroluminescent device, improve the current efficiency and external quantum efficiency of the organic electroluminescent device, and extend the life of organic electroluminescent devices, when it is used in the organic electroluminescent devices. This indicates that the nitrogen-containing compound of the present disclosure can improve the performance of electronic devices that implement photoelectric conversion or electroluminescent electronic devices. Therefore, the nitrogen-containing compound of the present disclosure can also be applied in photoelectric conversion devices that implement photoelectric conversion, such as solar cells, especially in the electron blocking layer of photoelectric conversion devices.

TABLE 7

Calculated energy levels of some compounds

| Compound No. | HOMO | LUMO | T1 ( First triplet energy level) |
|---|---|---|---|
| Compound 1 | −4.98 | −0.94 | 3.19 |
| Compound 2 | −4.84 | −0.94 | 3.13 |
| Compound A | −4.76 | −1.08 | 2.86 |
| Compound F | −4.74 | −0.93 | 2.90 |

It can be seen from Table 7 that Compound 1 and Compound 2 of the present disclosure had a larger HOMO values than Compound A and Compound F of Comparative Examples, thereby reducing the barrier when holes were injected into the body of the light-emitting layer, such that the hole can be injected into the light-emitting layer more smoothly. Thus, when the material was used as an electron transporting layer, the efficiency and life of the blue light emitting device can be improved.

The nitrogen-containing compound provided in the present disclosure introduces the adamantyl structure at the side of the fluorene to increase the electron density of the conjugated system of the fluorene ring and the entire nitrogen-containing compound through the super-conjugation effect, which can enhance the hole conductivity of the nitrogen-containing compound as well as the electronic tolerance. It can also improve the luminous efficiency and life of organic electroluminescent devices, and improve the conversion efficiency and life of photoelectric conversion devices. Moreover, the adamantyl group is introduced between the branches of the triarylamine, which is originally a near-plane structure, rather than at the end. The large steric hindrance of the adamantyl group can finely adjust the bonding angle and conjugation degree of the amine and each aryl group, thereby obtaining HOMO value suitable for the material of the adjacent layer. It reduces the operating voltage of the organic electroluminescent device, and increases the open circuit voltage of the photoelectric conversion device.

In addition, the introduction of adamantyl can also increase the molecular weight of the nitrogen-containing compound and reduce the molecular symmetry, can increase the glass transition temperature and evaporation temperature of the compound of the present disclosure, and can control the crystallinity of the nitrogen-containing compound. When the nitrogen compound is used in mass production, it has better physical and thermal stability, which facilitates the mass production stability of the organic electroluminescent devices and photoelectric conversion devices.

In particular, the 4-position of the fluorene group in the nitrogen-containing compound of the present disclosure is connected to the amine, which greatly increases the steric hindrance of the arylamine structure, thereby increasing the twist angle between the plane of fluorene and the plane of the arylamine (especially the plane of triarylamine), and reducing the degree of conjugation. Thus, the energy band width and triplet energy level of the nitrogen-containing compound are improved, so that the nitrogen-containing compound is particularly suitable for electron blocking layers (also known as hole auxiliary layer, second hole transporting layer, etc.). When the nitrogen-containing compound is used as an electron blocking layer in organic electroluminescent devices and photoelectric conversion devices, the efficiency and life of the organic electroluminescent devices and photoelectric conversion devices are significantly improved.

It should be understood that the present disclosure should not be limited to the detailed structure and arrangement of the components proposed in this specification. The present disclosure can have other embodiments, and can be implemented and executed in various ways. The aforementioned modified forms and modified forms fall within the scope of the present disclosure. It should be understood that the application disclosed and defined in this specification extends to all alternative combinations of two or more individual features mentioned or evident in the text and/or drawings. All of these different combinations constitute multiple alternative aspects of the application. The embodiments described in this specification illustrate the best ways known to implement the present disclosure, and will enable those skilled in the art to utilize the present disclosure.

What is claimed is:

1. A nitrogen-containing compound, having a structure shown in Formula I:

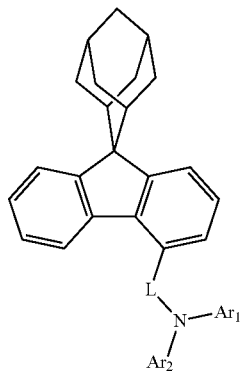

Formula I wherein, L is selected from a single bond, a unsubstituted phenylene, a unsubstituted biphenylene, a unsubstituted terphenylene;

Ar$_1$ and Ar$_2$ are the same or different, and are each independently selected from a unsubstituted phenyl, a unsubstituted naphthyl, a unsubstituted phenanthryl, a unsubstituted biphenyl, a unsubstituted terphenyl, a unsubstituted dimethylfluorenyl, a unsubstituted dibenzothienyl, a unsubstituted dibenzofuranyl, a phenyl substituted by dibenzofuranyl;

or Ar$_1$ and Ar$_2$ are the same or different, and are each independently selected from the group consisting of the following groups:

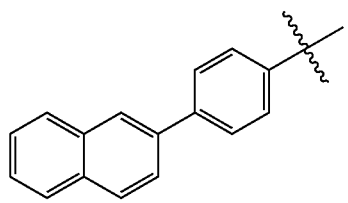

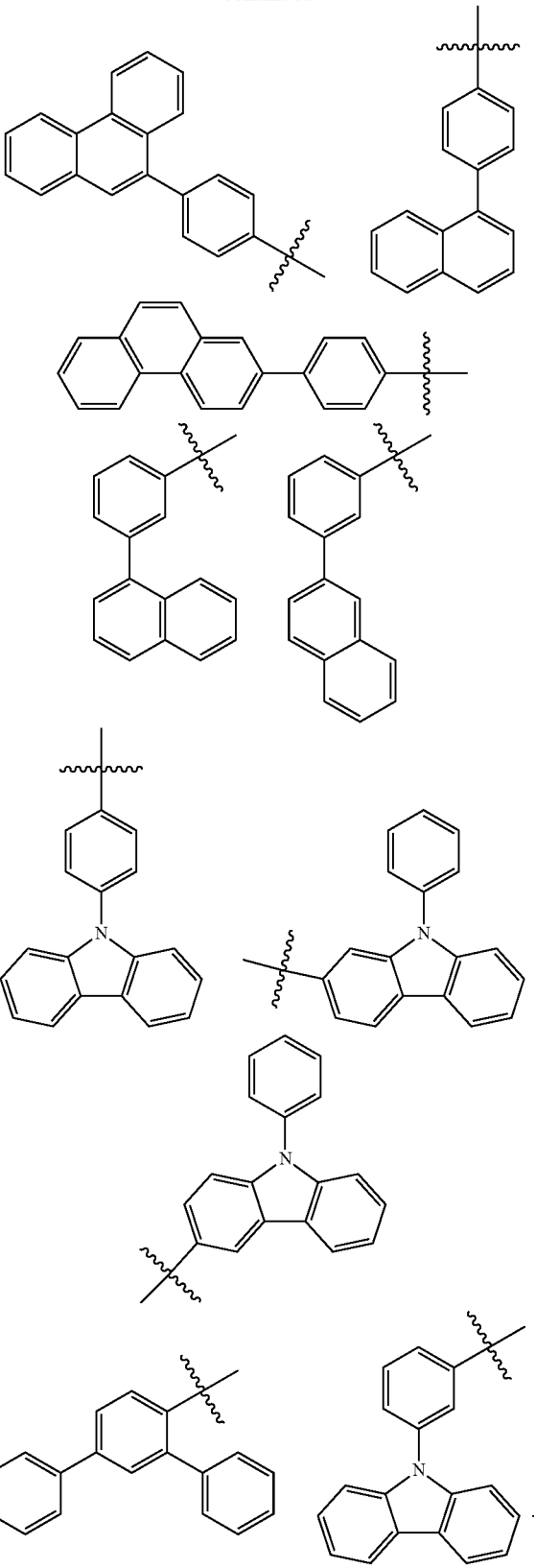

2. The nitrogen-containing compound according to claim 1, wherein the L is selected from a single bond or the group consisting of the following groups:

wherein, * represents the position for L connecting with group

** represents the position for L connecting with group

3. An electronic component, comprising an anode and a cathode disposed opposite to each other, and a functional layer disposed between the anode and the cathode;
  wherein the functional layer comprises the nitrogen-containing compound according to claim 1.

4. The electronic component according to claim 3, wherein the functional layer comprises an electron blocking layer, and the electron blocking layer comprises the nitrogen-containing compound.

5. The electronic component according to claim 3, wherein the electronic component is an organic electroluminescence device or a solar cell.

6. An electronic device comprising the electronic component according to claim 3.

7. A nitrogen-containing compound, having a structure shown in Formula I:

wherein, L is selected from a single bond, a unsubstituted phenylene, a unsubstituted biphenylene, a unsubstituted terphenylene;

$Ar_1$ and $Ar_2$ are the same or different, and are each independently selected from the group consisting of the following groups:

221
-continued
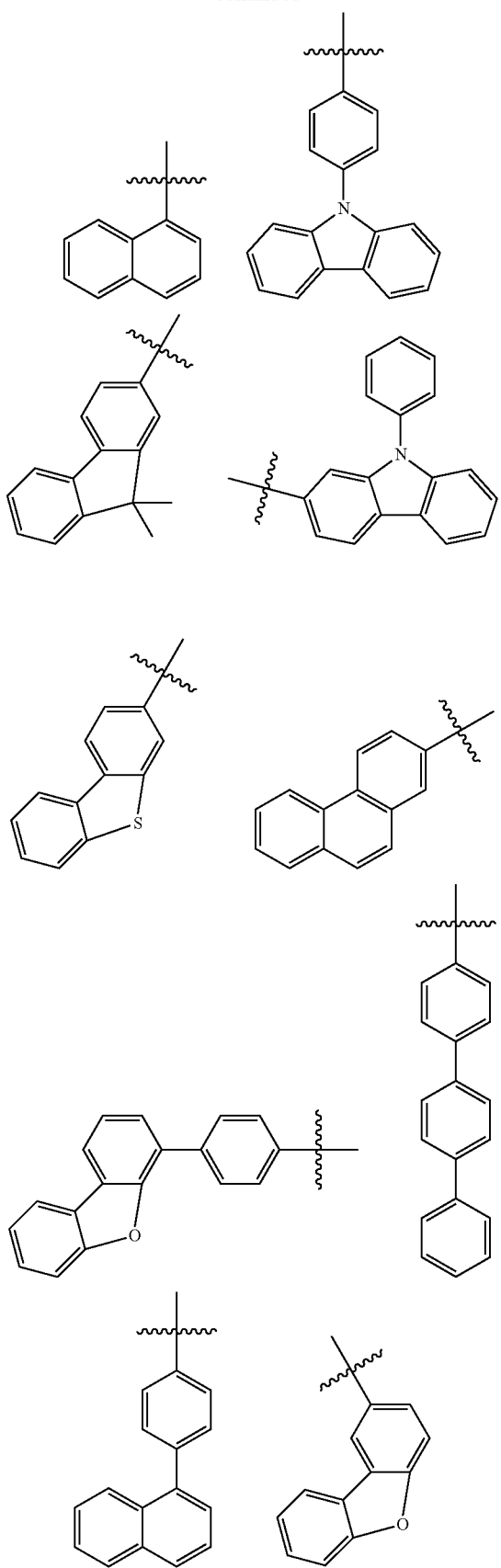
222
-continued
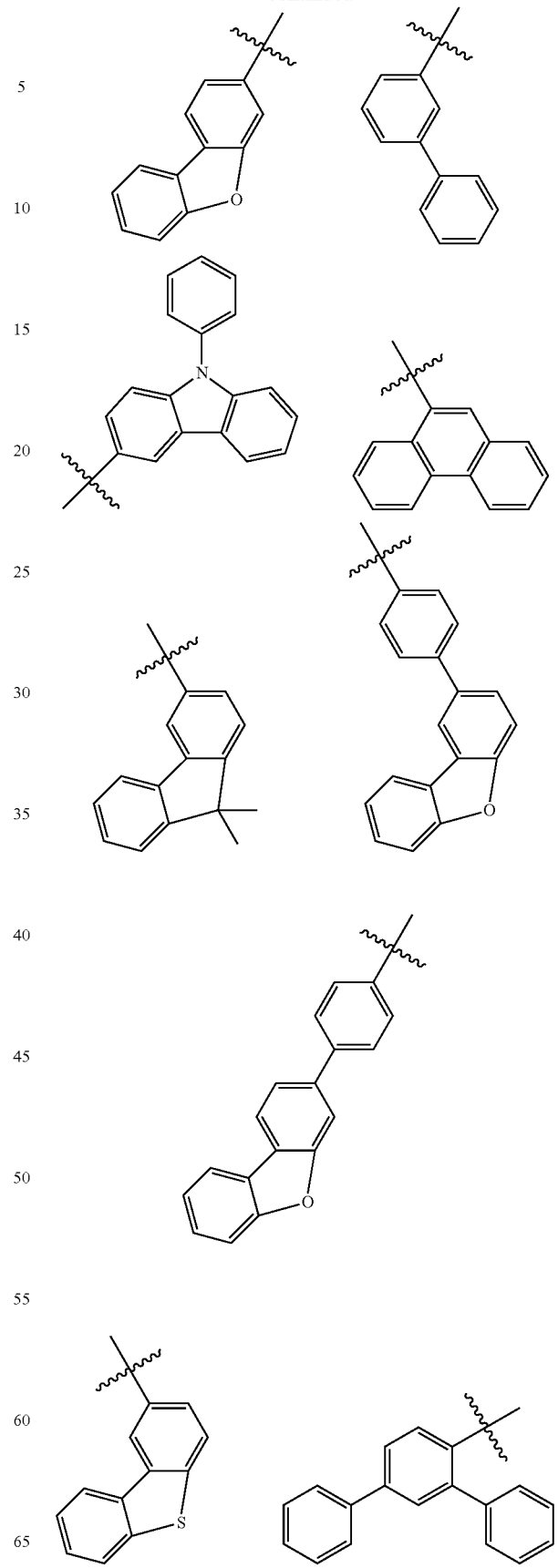

223
-continued
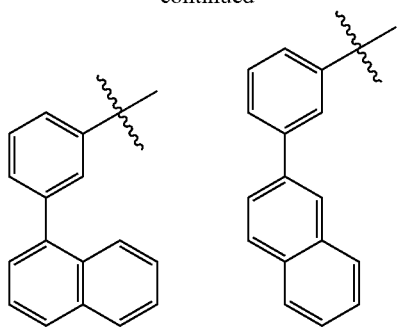
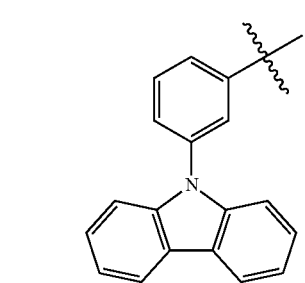
8. A nitrogen-containing compound, wherein the nitrogen-containing compound is selected from the group consisting of the following compounds:
1
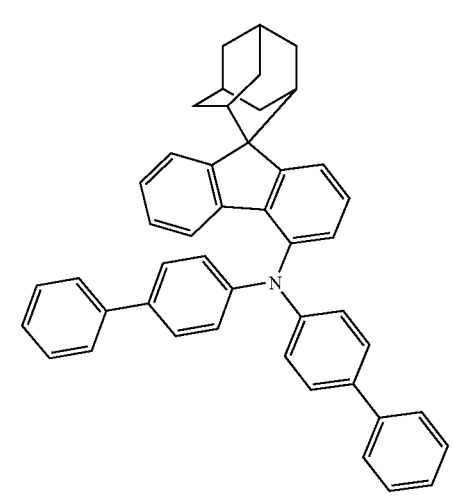
224
-continued
2
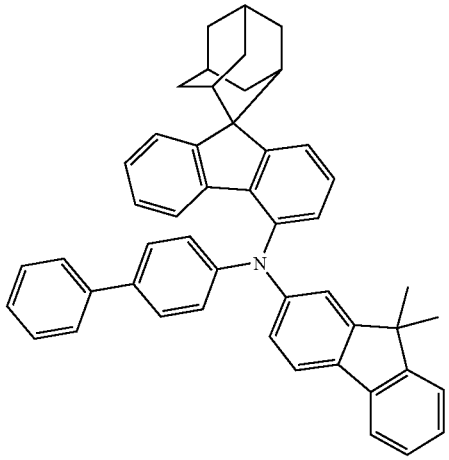
3
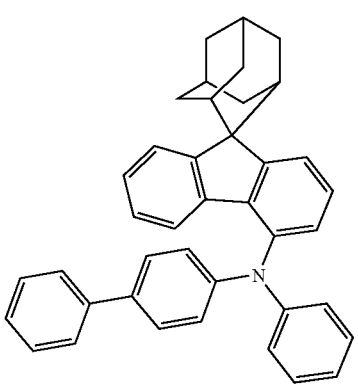
4
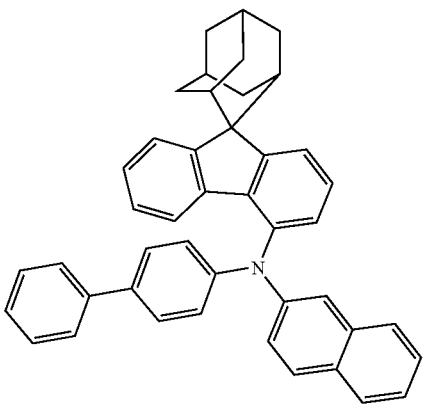
5
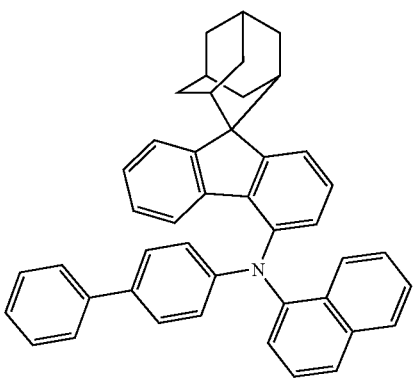

6
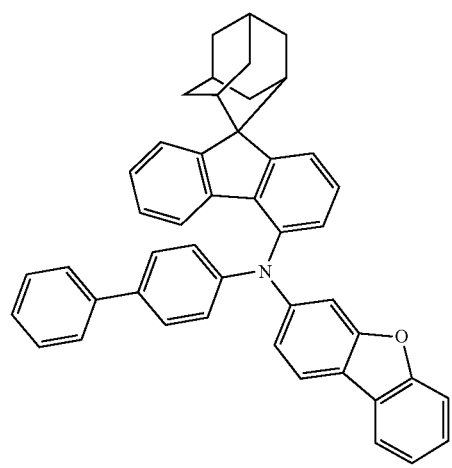
9
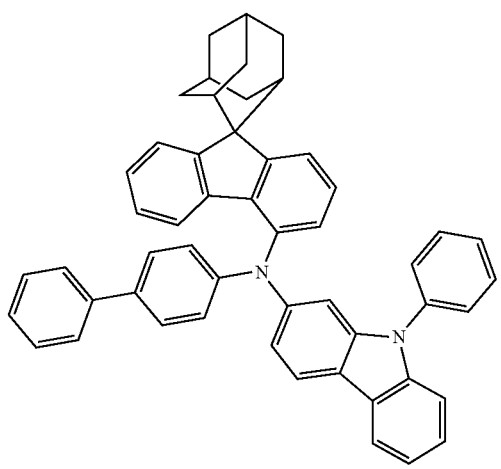
7
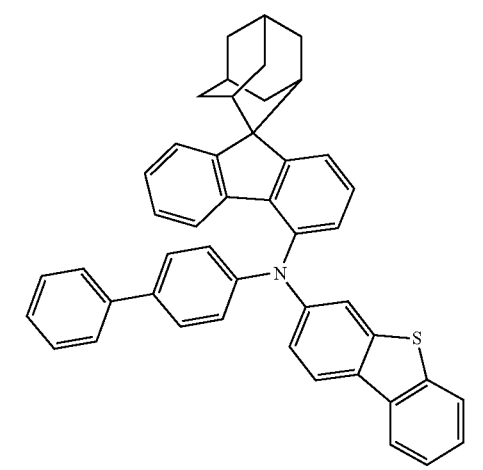
10
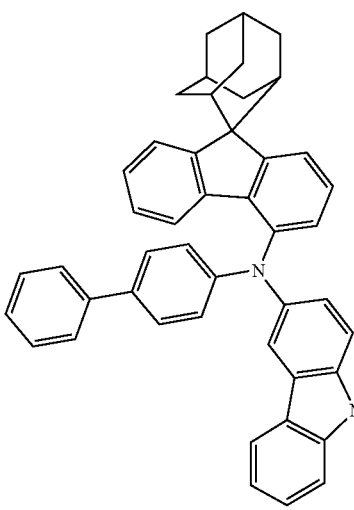
8
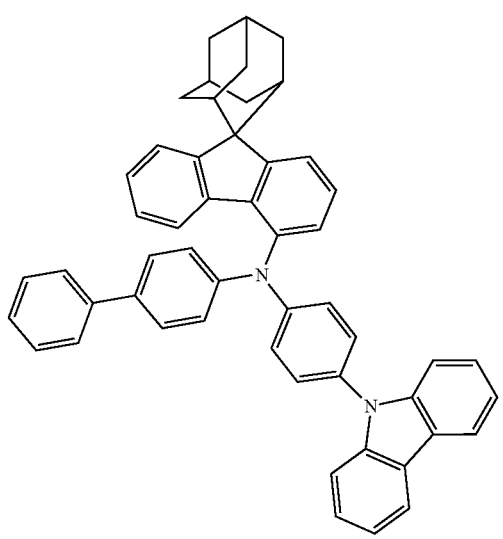
11
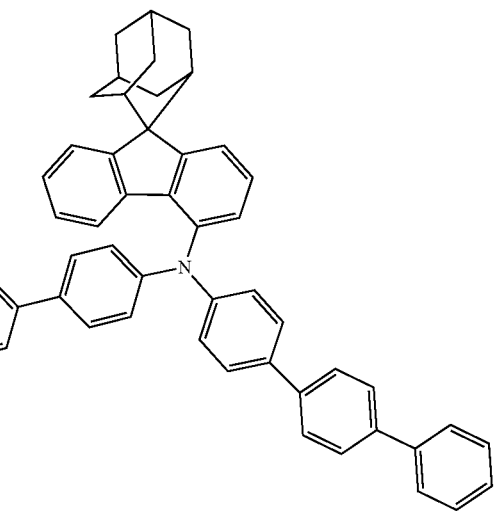

12
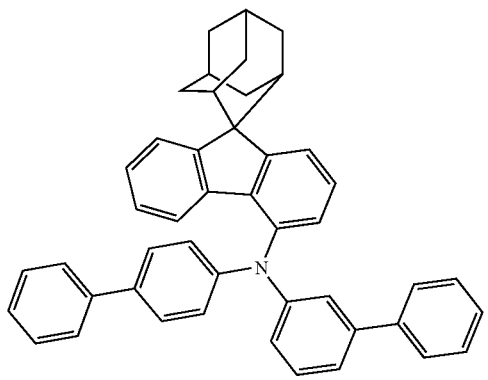
13
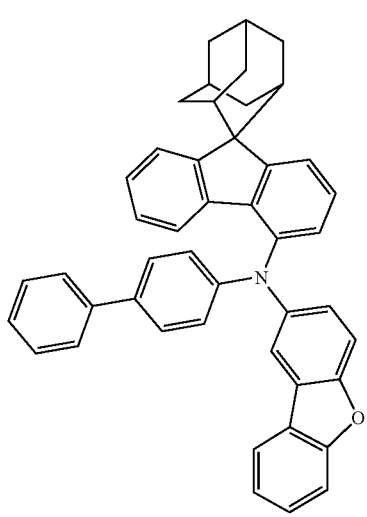
18
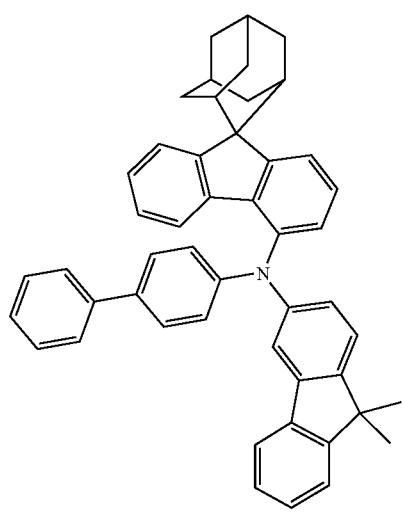
19
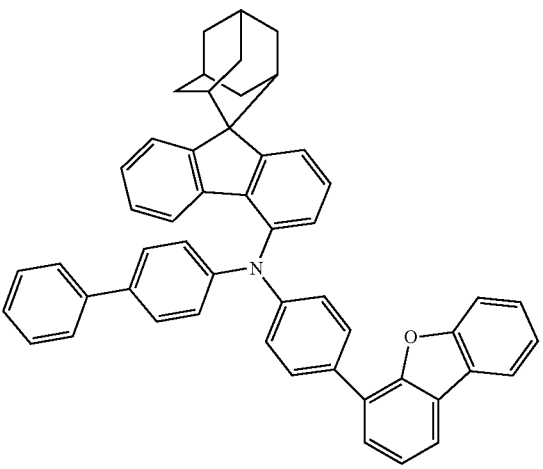
20
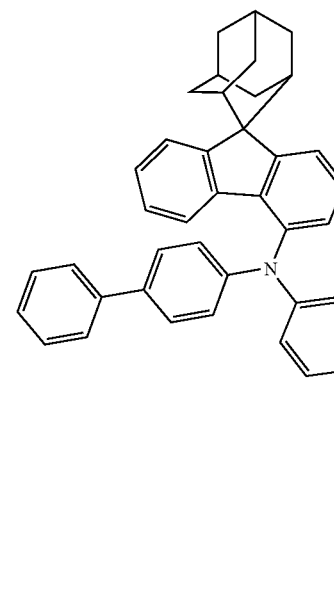
21
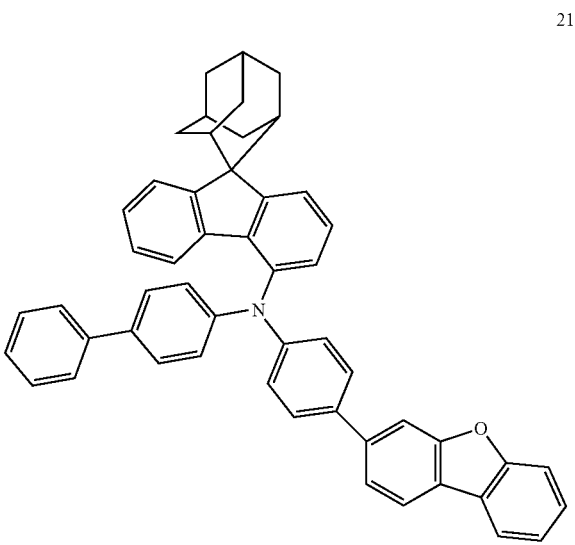

22
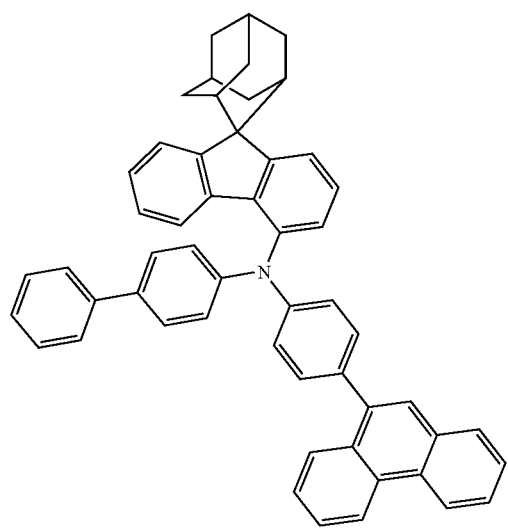
23
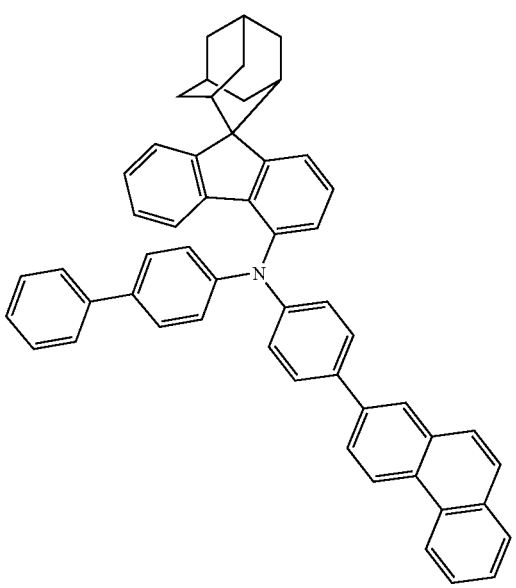
27
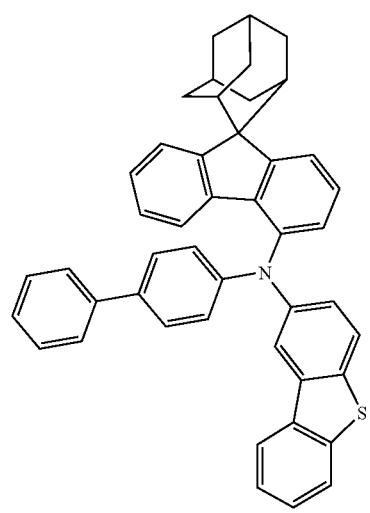
30
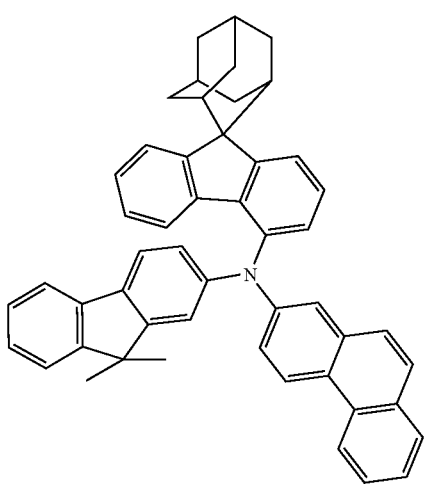
31
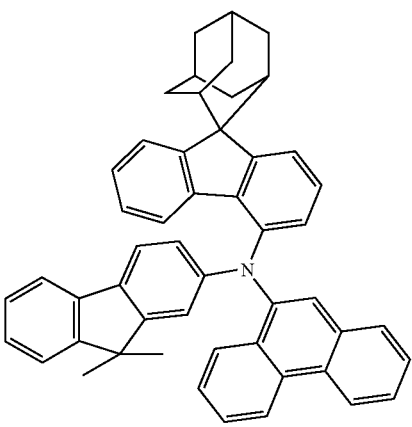
33
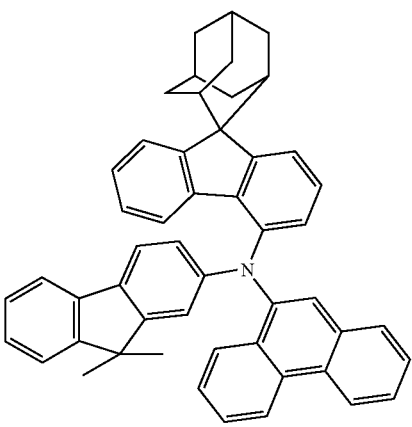

42
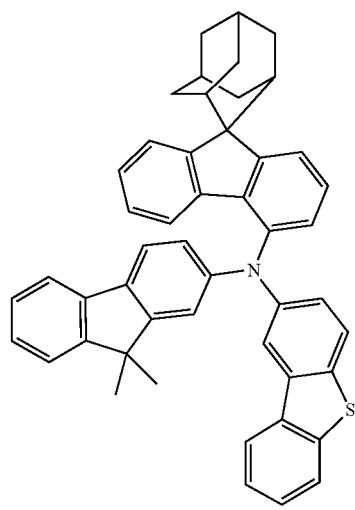
43
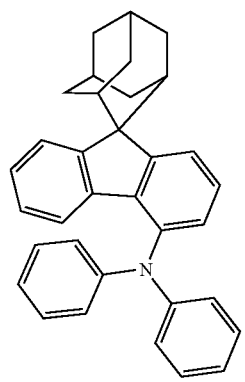
44
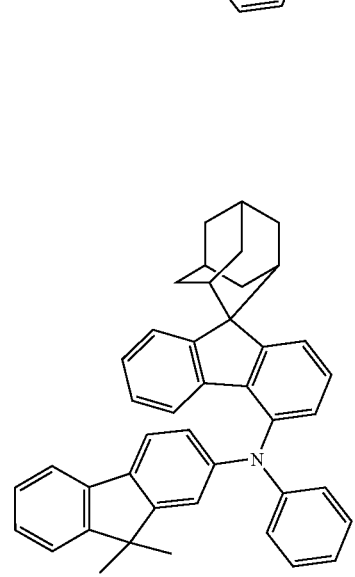
47
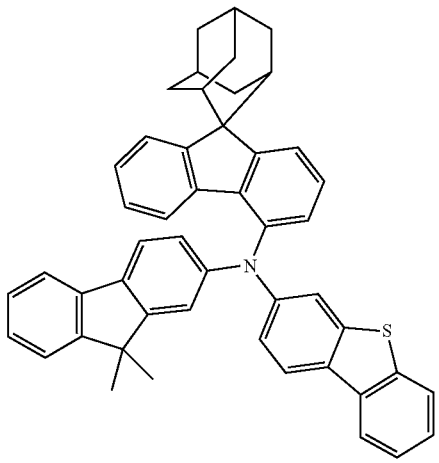
51
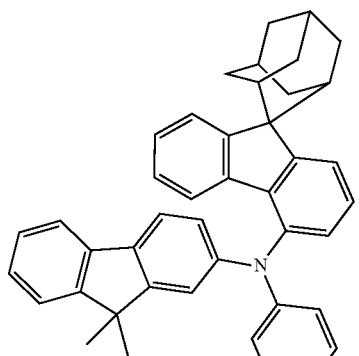
52
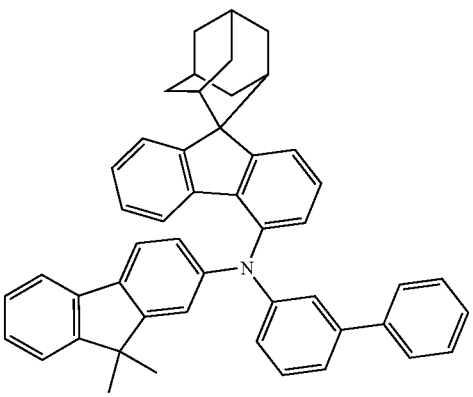

58
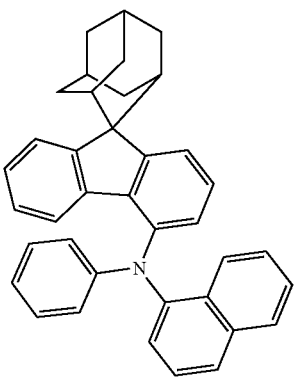
59
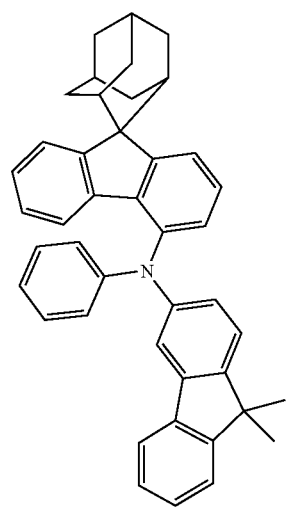
60
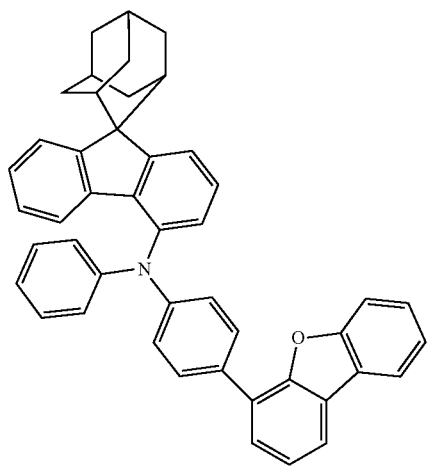
61
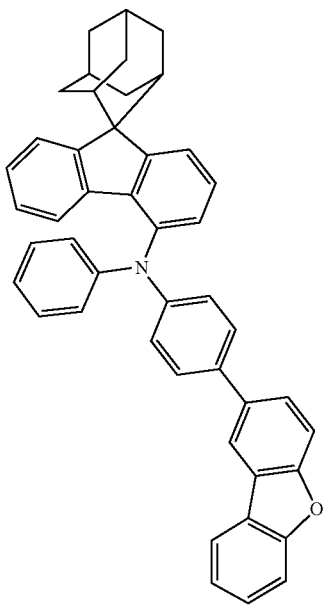
62
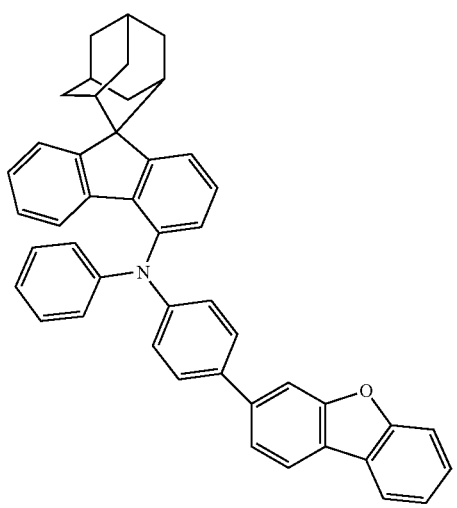
63
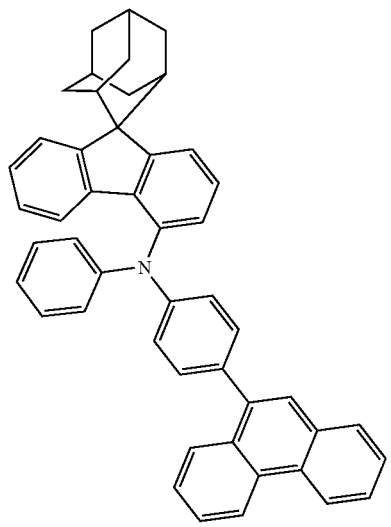

64
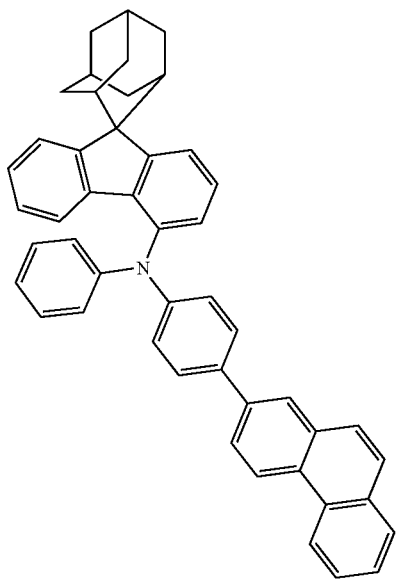
68
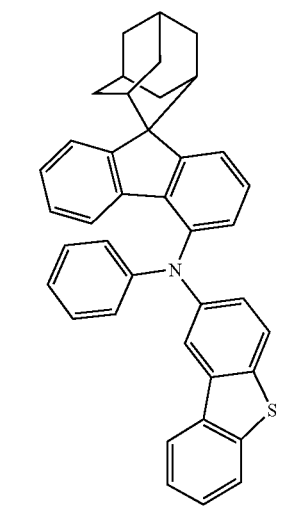
69
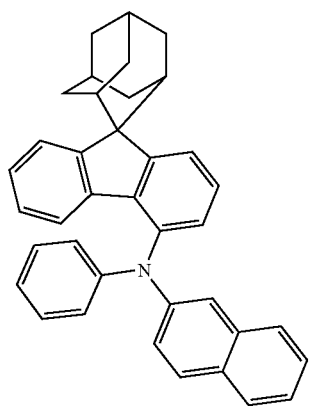
70
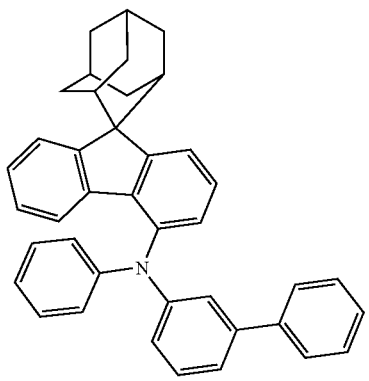
71
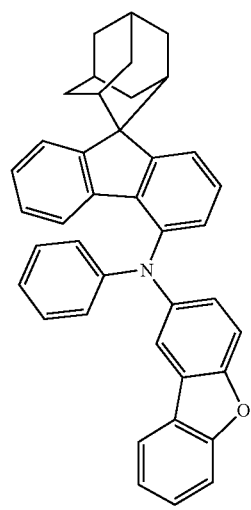
72
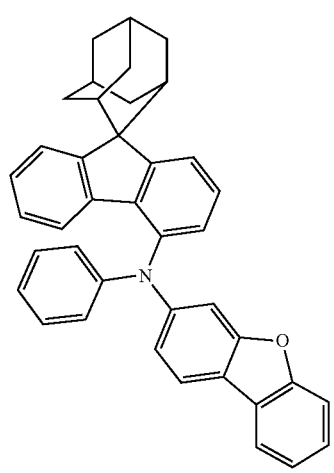

73
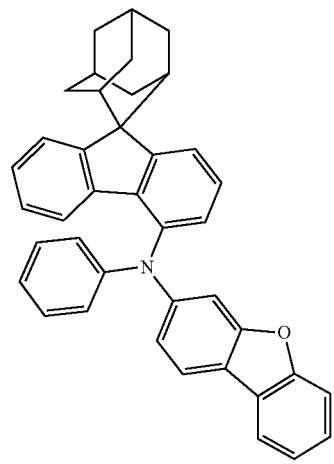
74
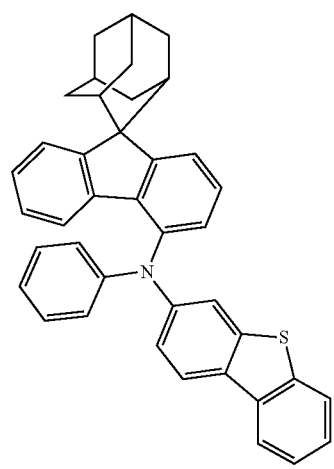
75
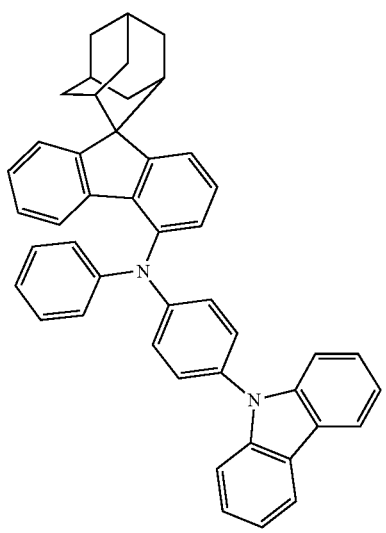
76
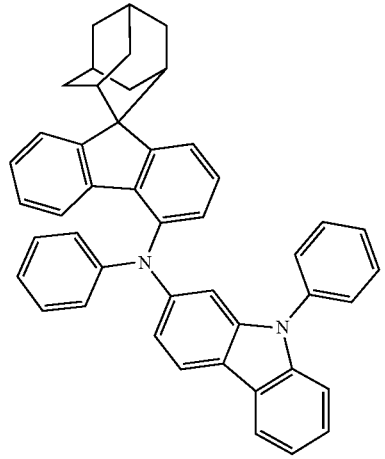
77
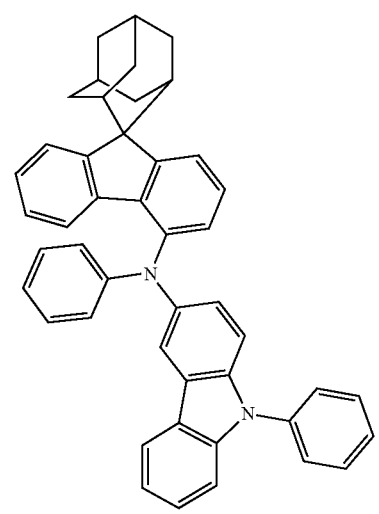
78
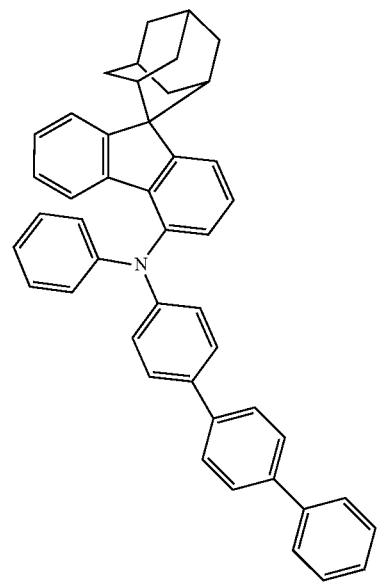

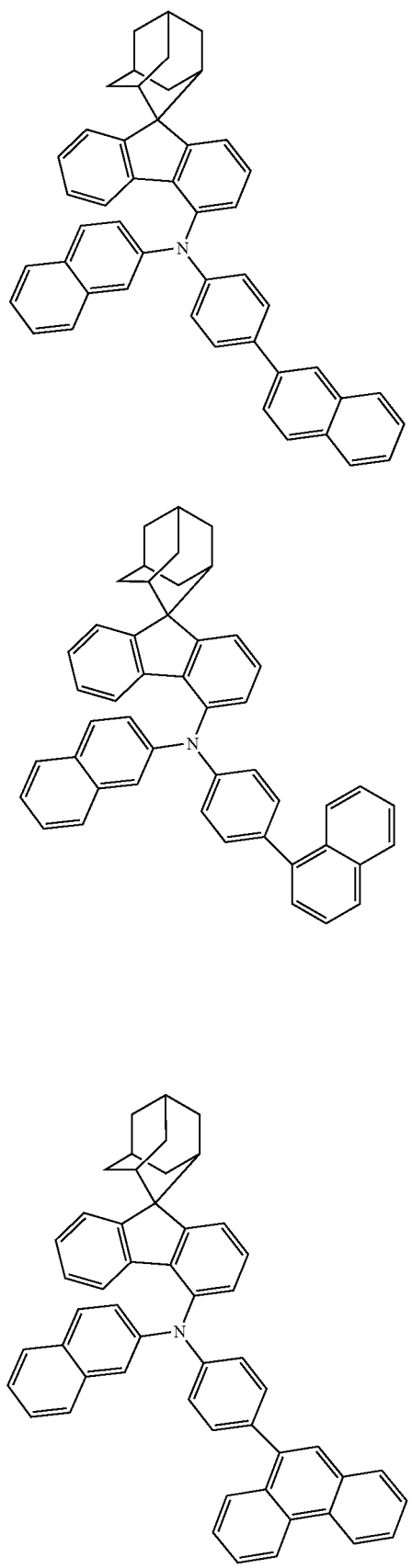
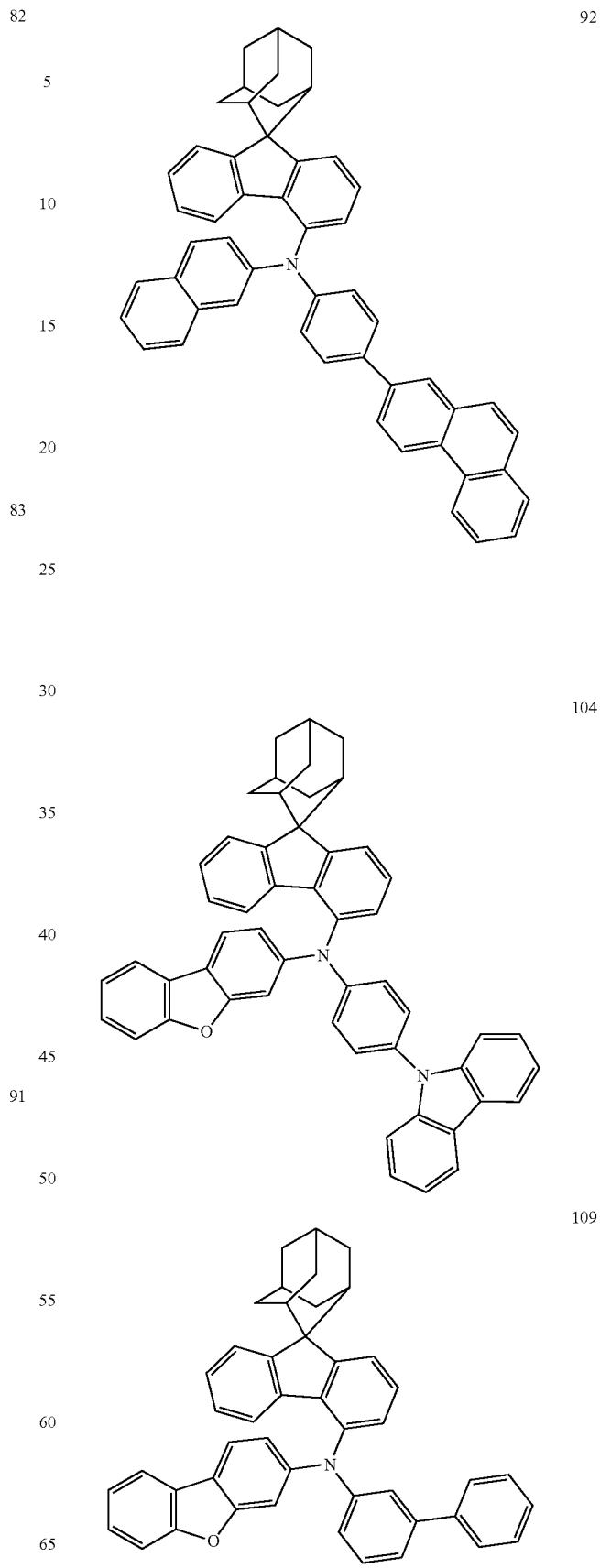

114
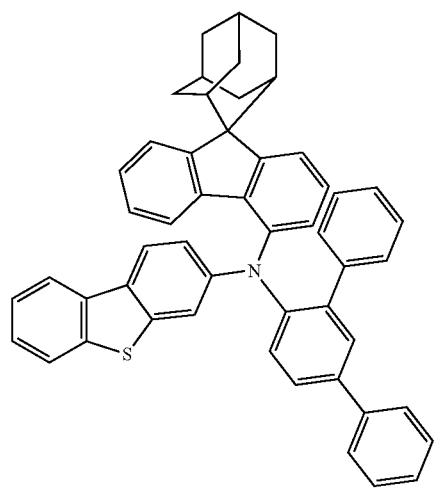
121
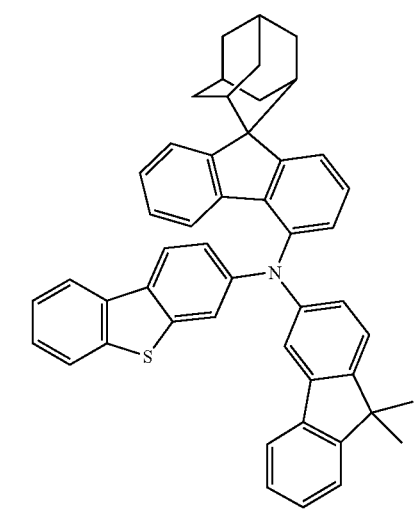
124
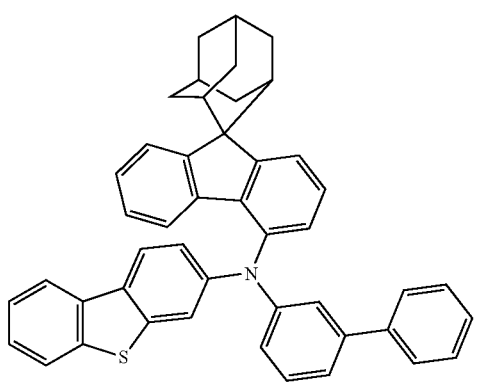
134
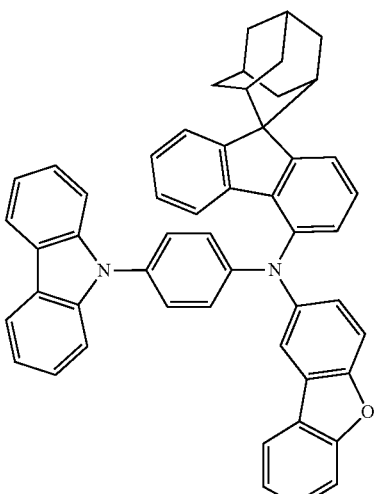
140
144
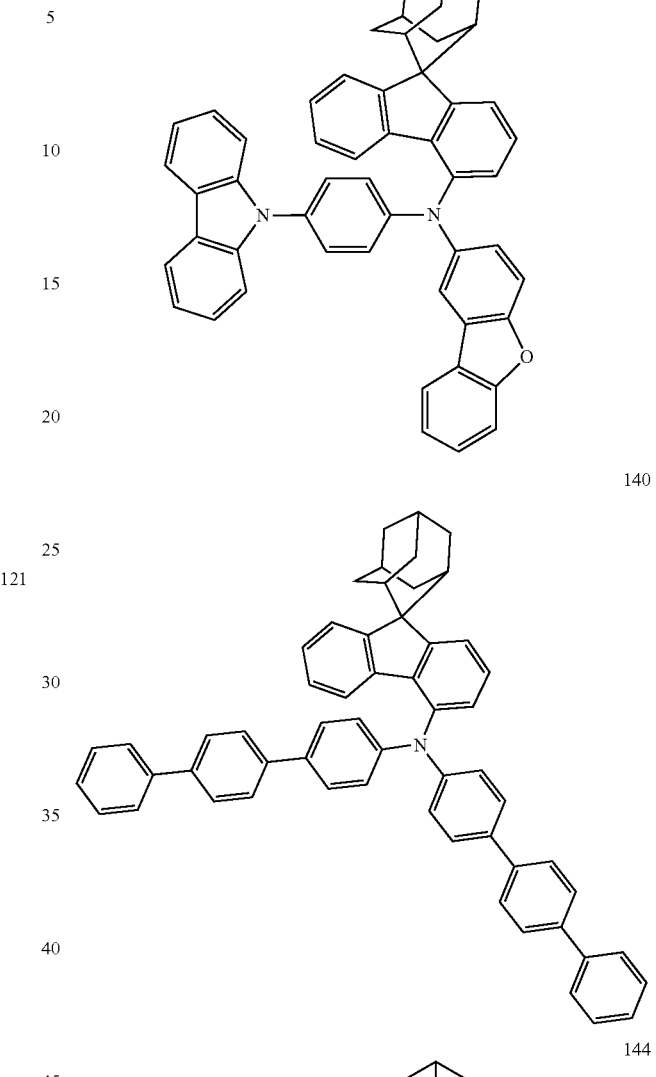

146
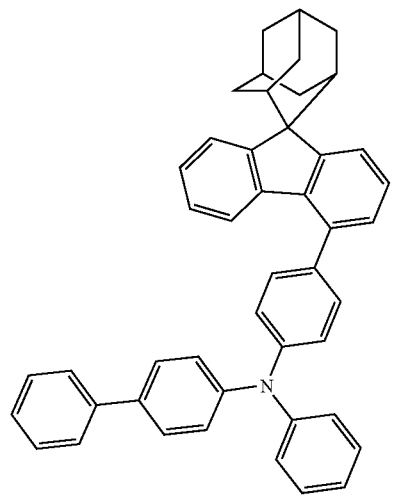
155
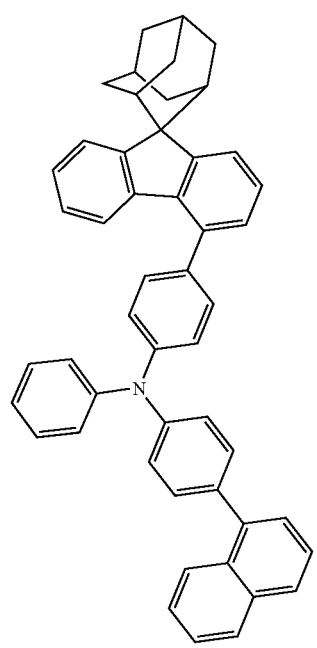
154
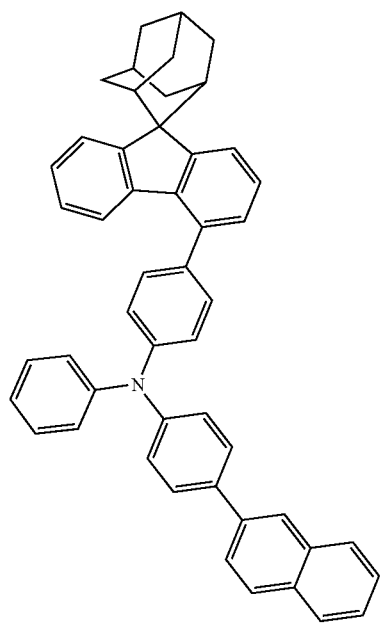
157
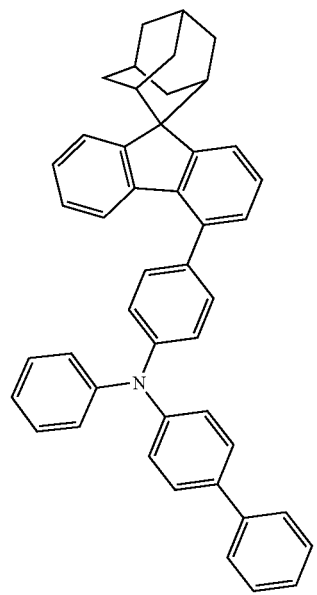

166
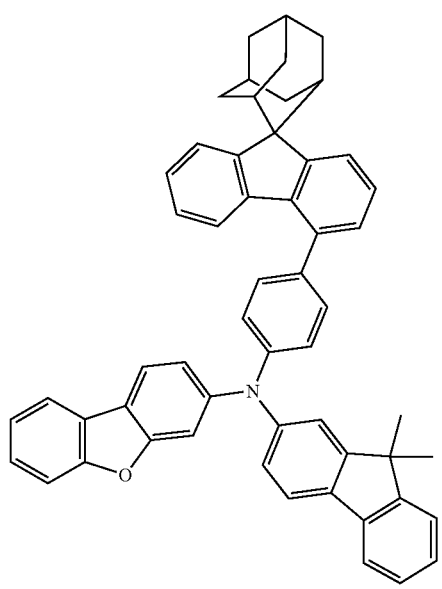
180
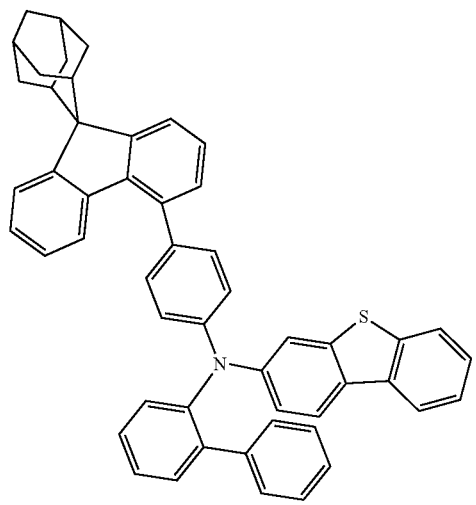
181
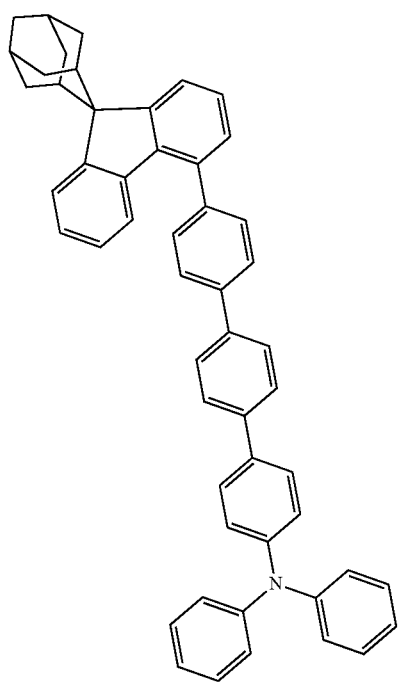
182
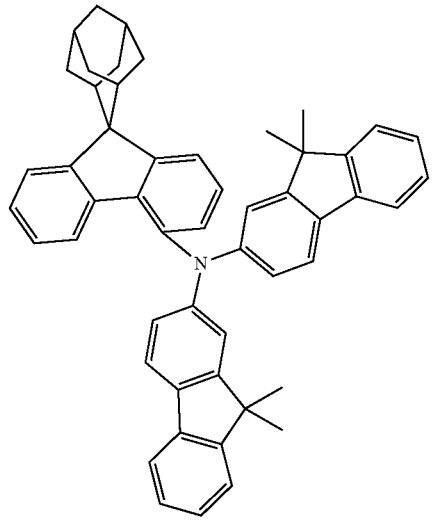

184
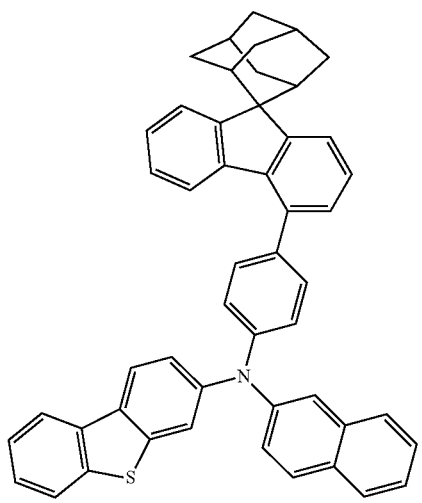
187
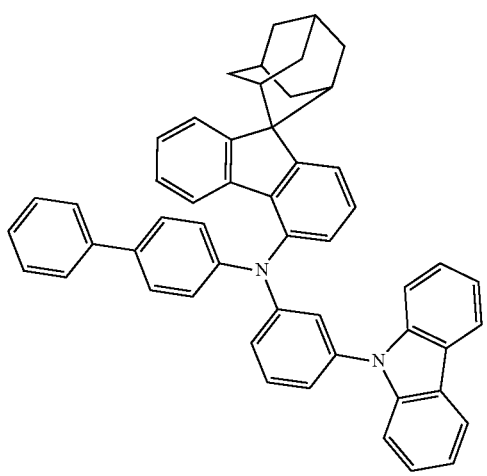
185
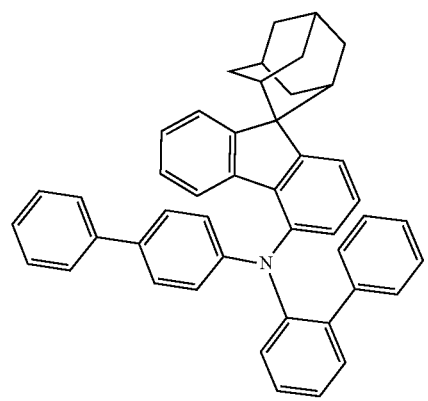
189
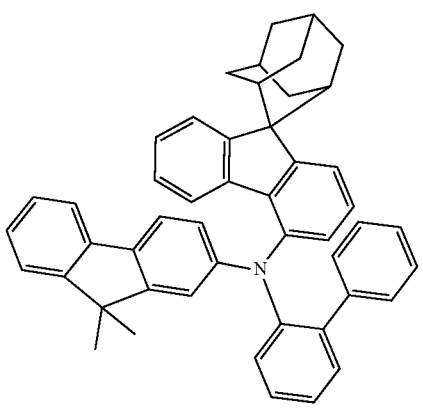
186
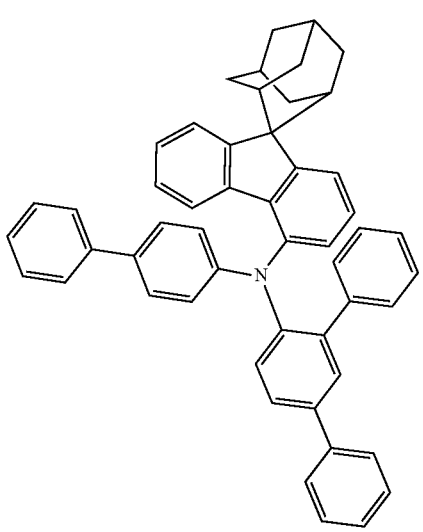
190
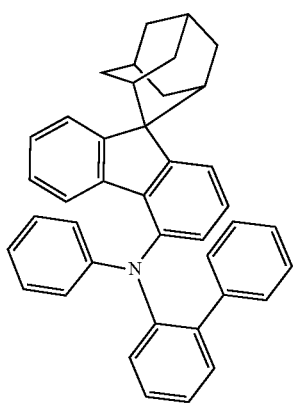

-continued
193
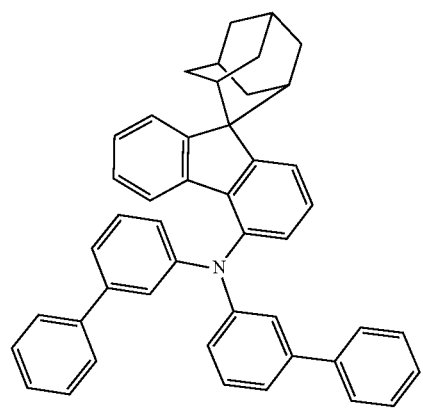
194
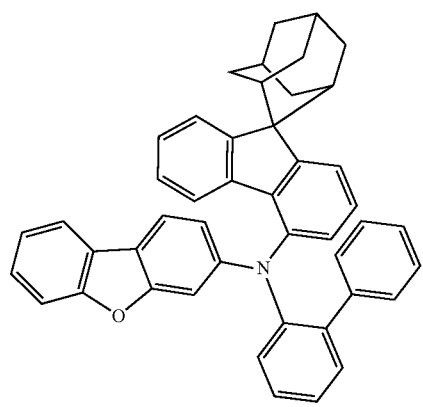
195
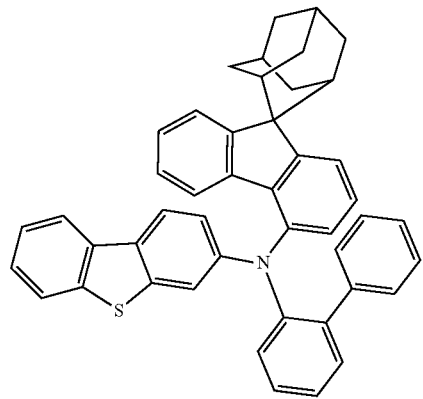
196
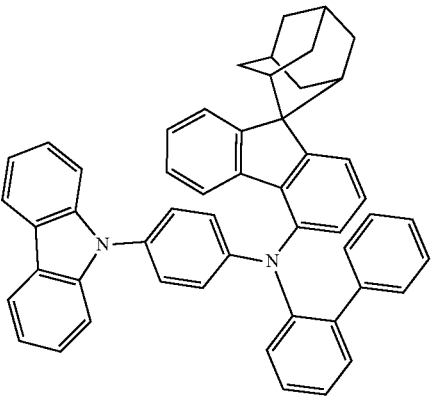
-continued
197
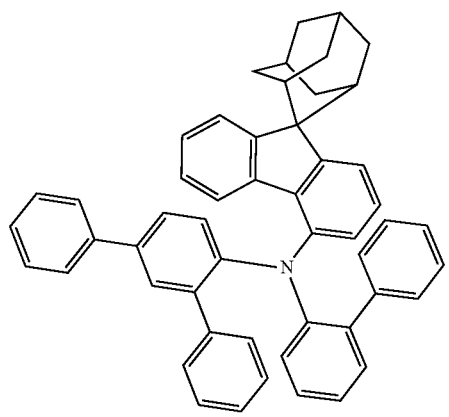
198
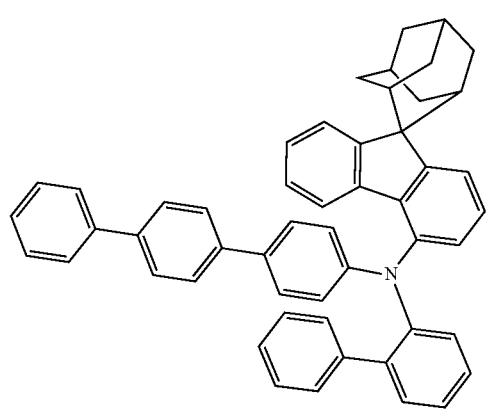
199
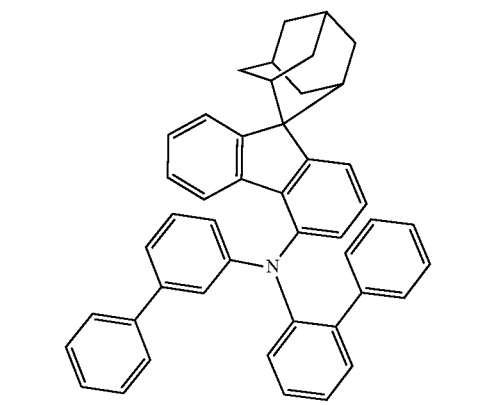
200
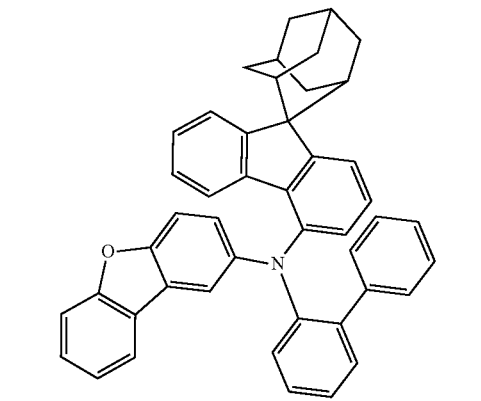

201 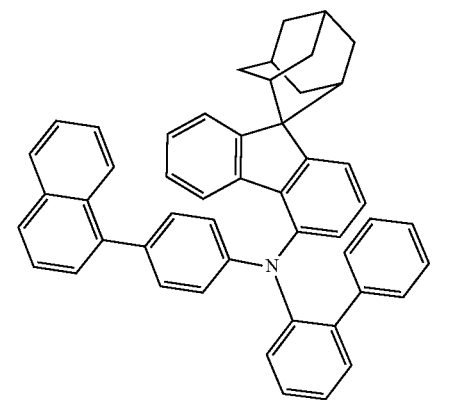
202 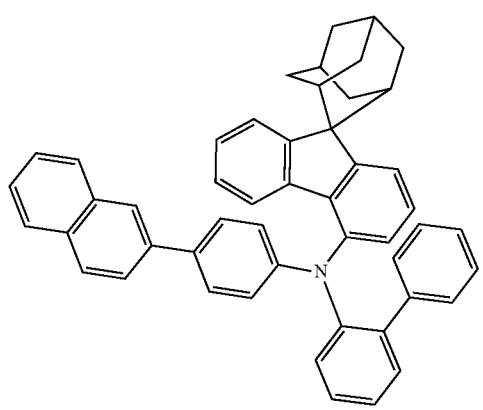
205 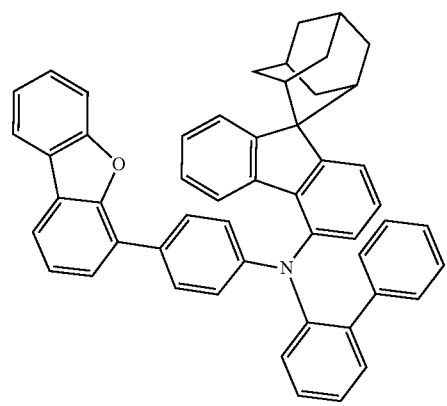
206 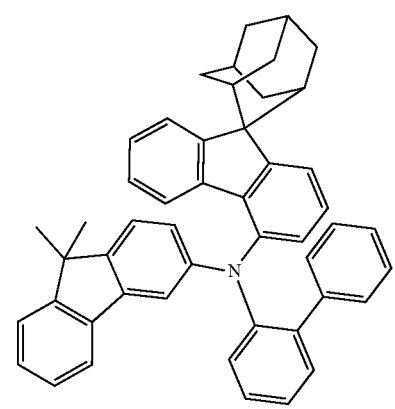
207 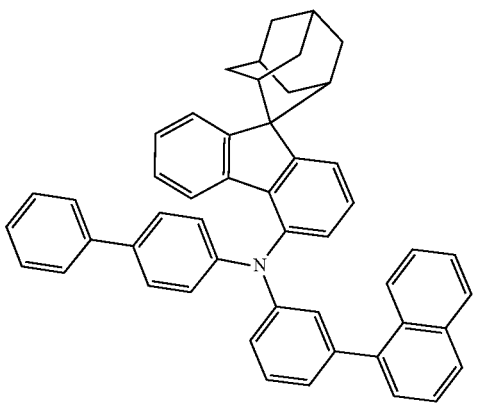
208 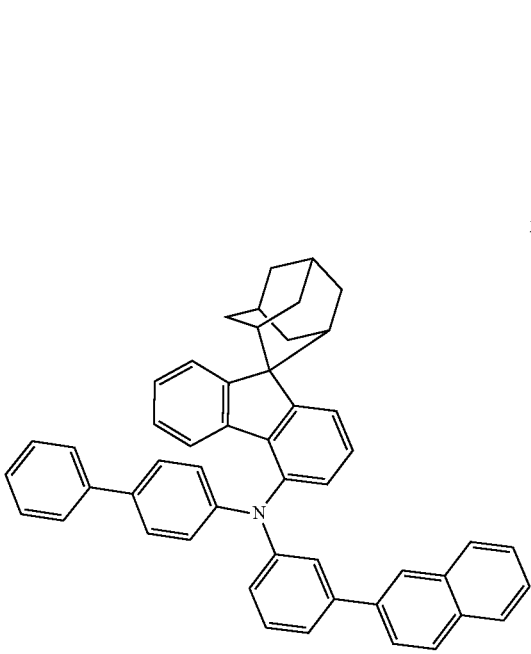
209 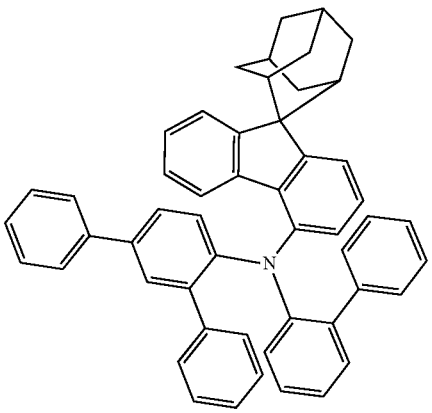

210
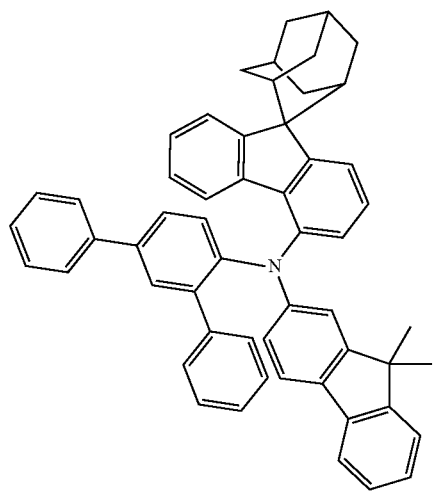
211
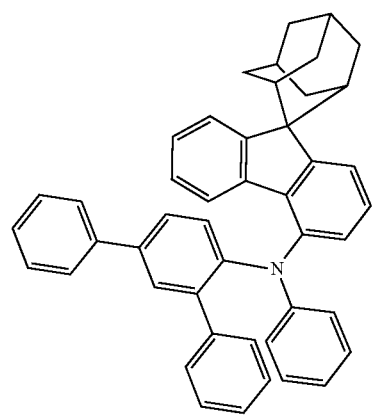
214
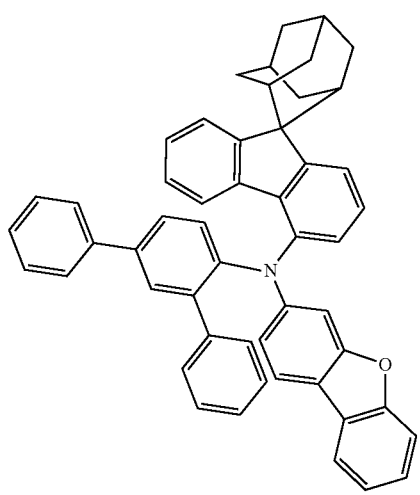
216
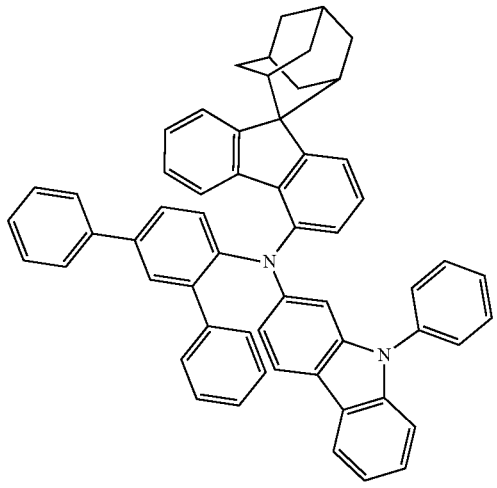
217
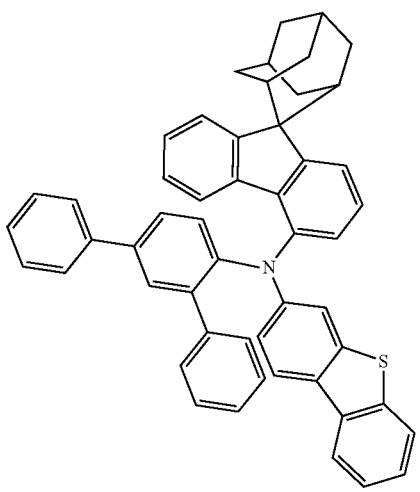
220
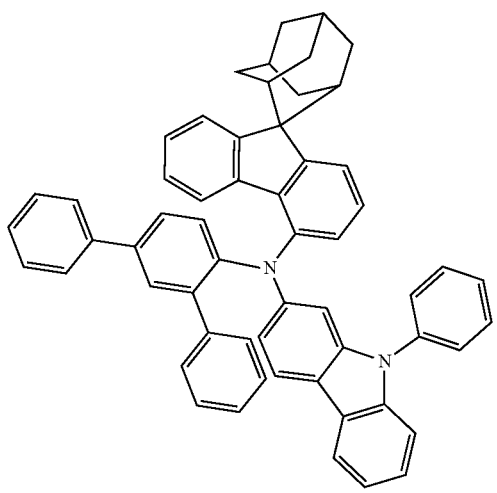

221
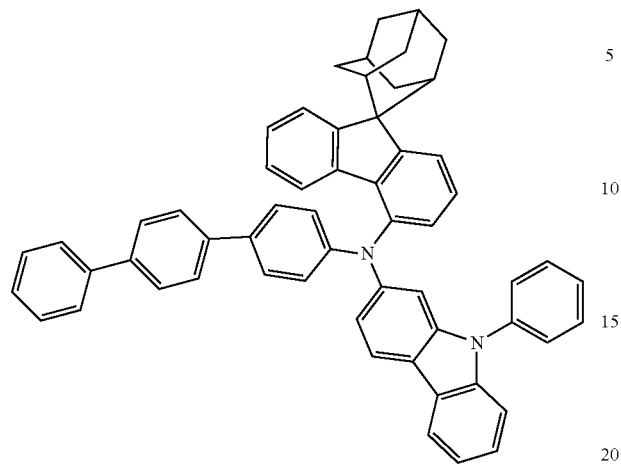
228
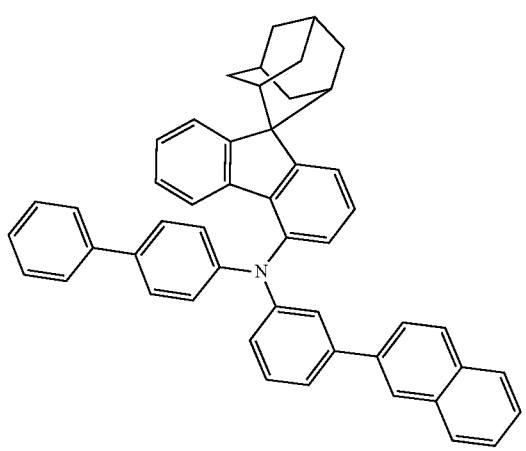
222
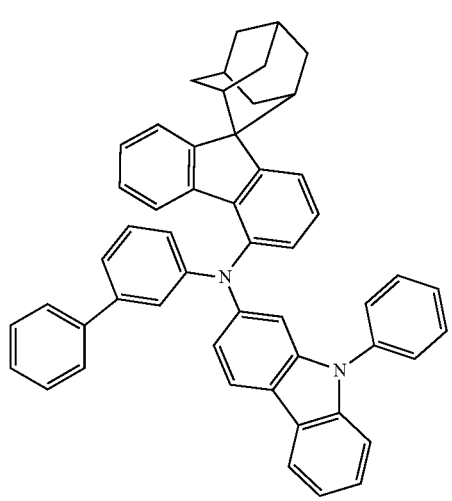
230
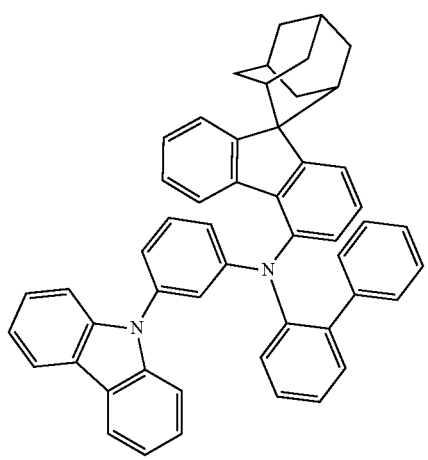
227
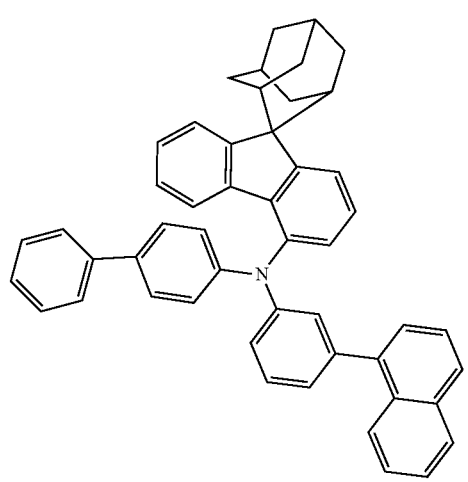
231
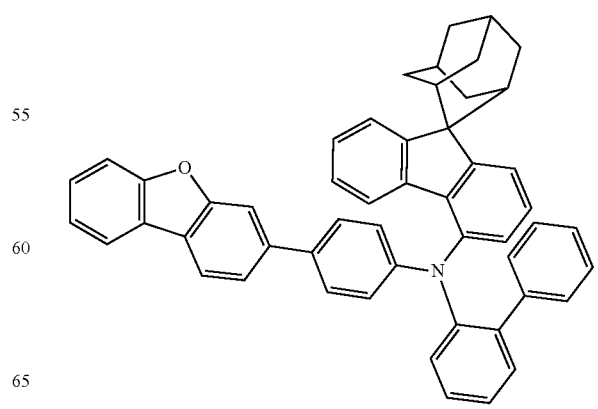

257
-continued
232
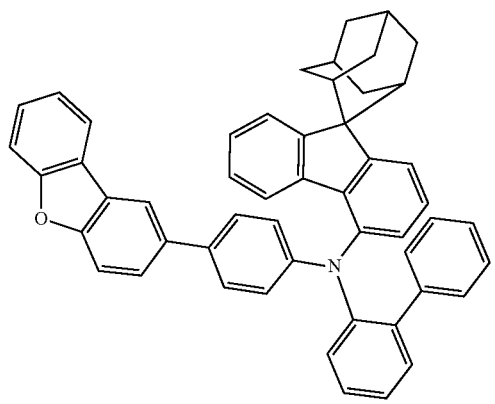
236
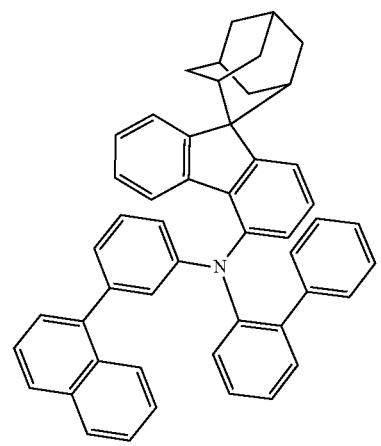
237
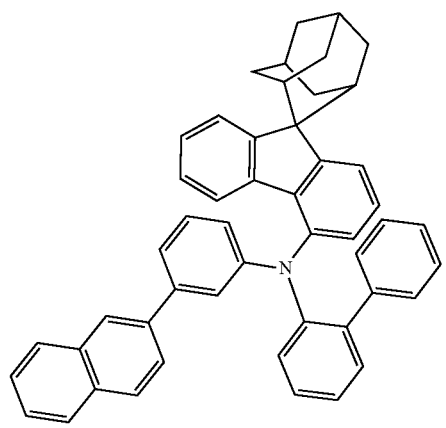
258
-continued
238
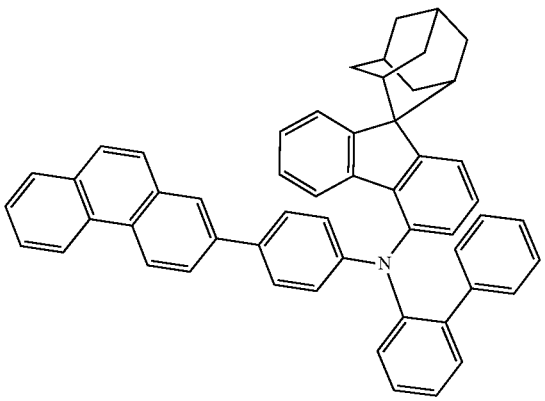
239
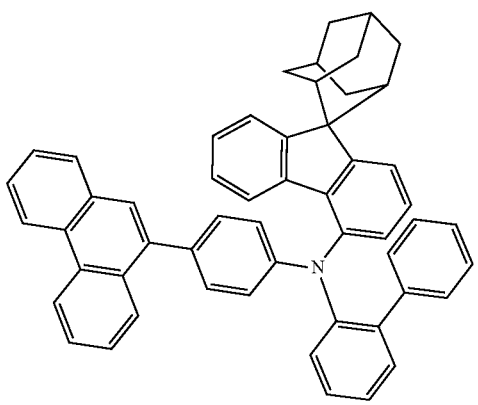
241
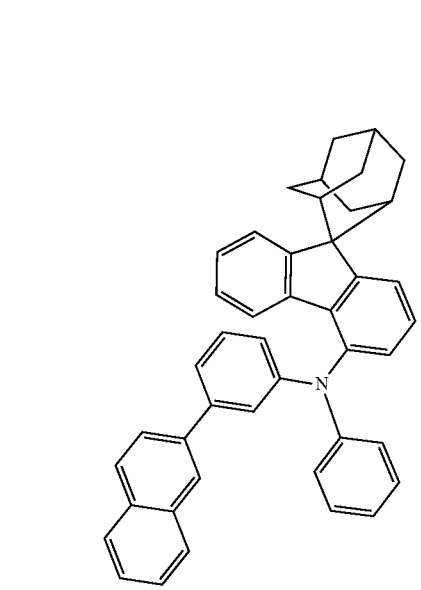

243
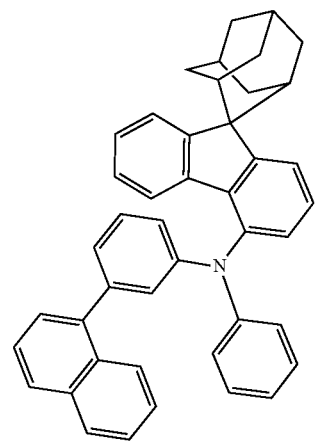
246
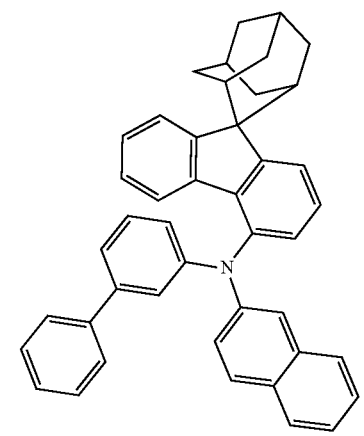
255
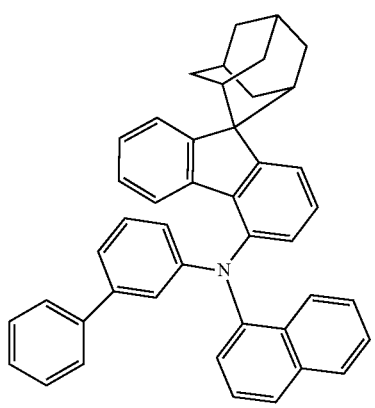
272
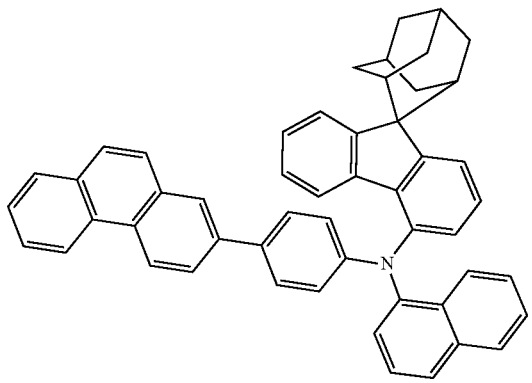
273
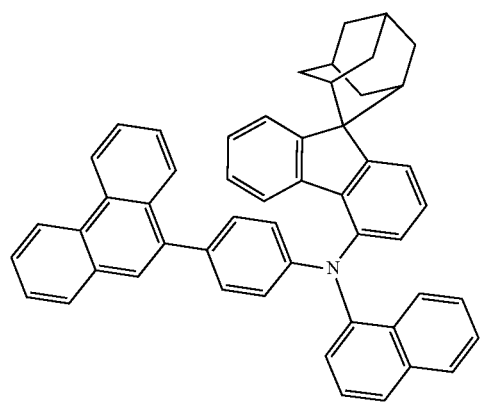

274
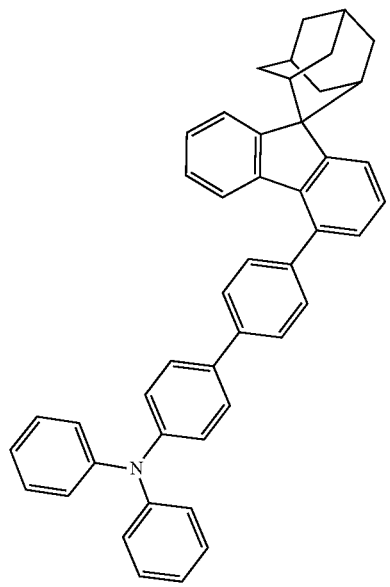
276
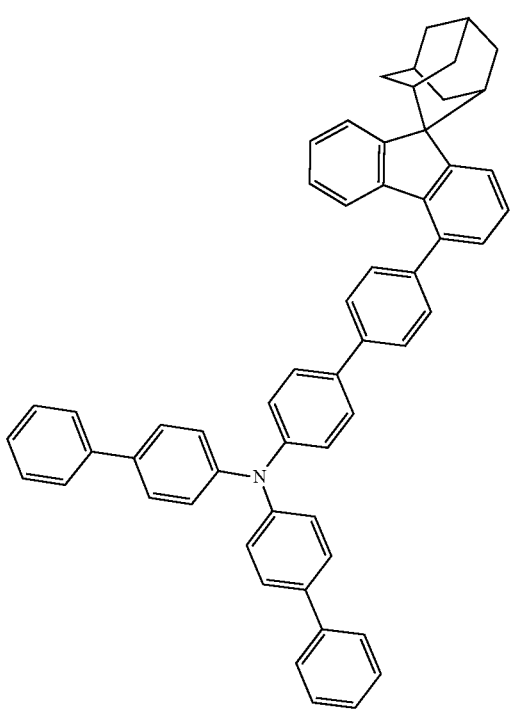
275
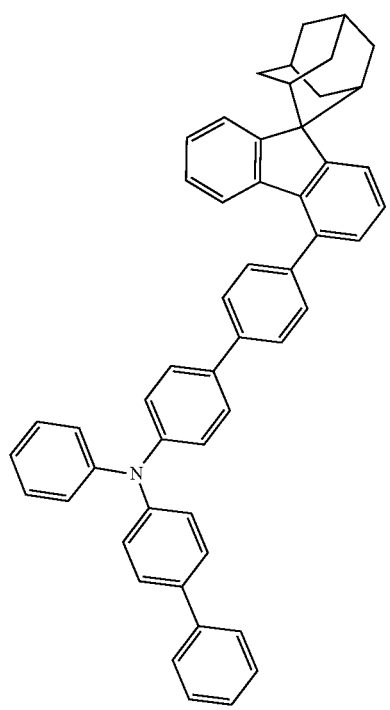
278
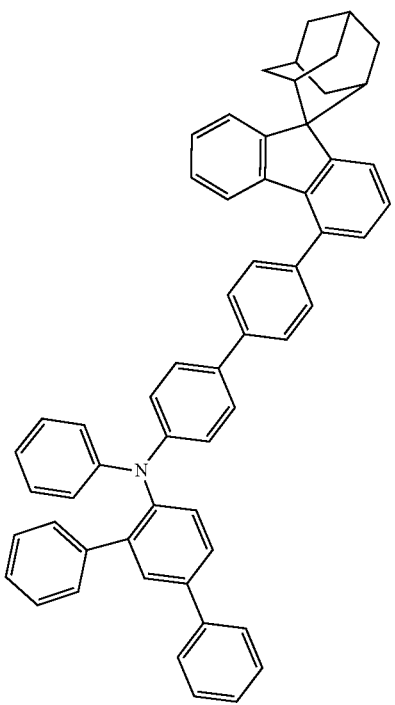

263
-continued
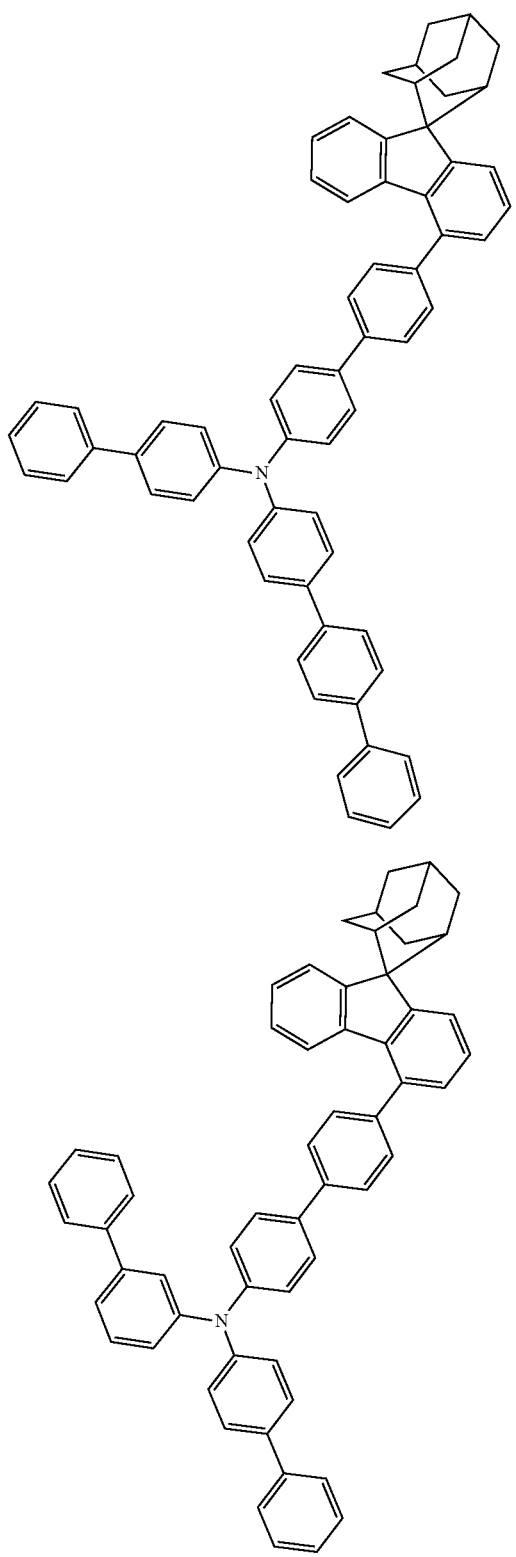
264
-continued
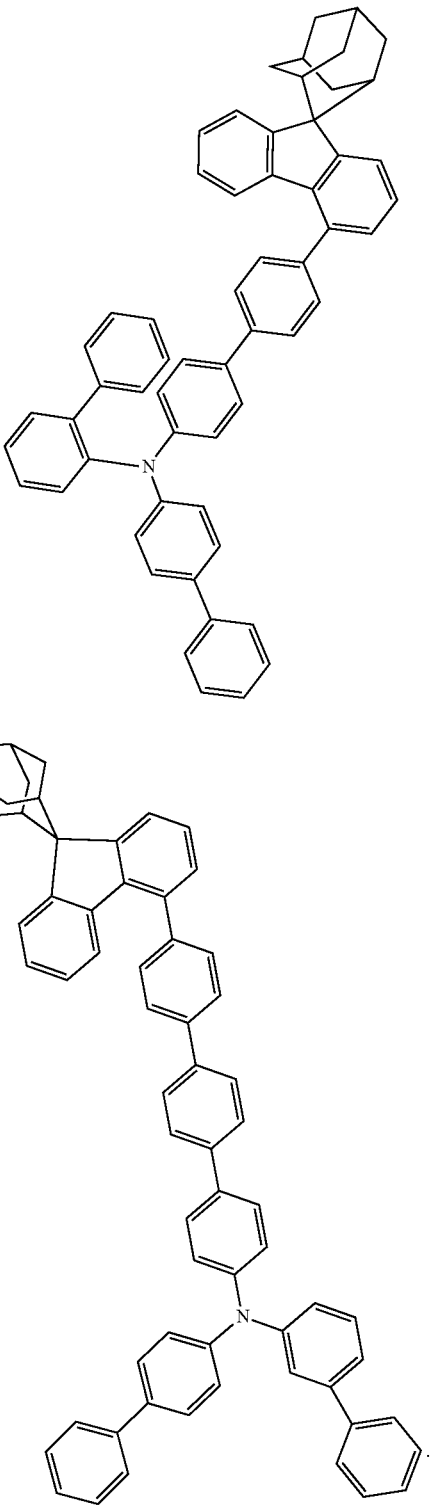
* * * * *